US011800792B2

(12) United States Patent
Yang et al.

(10) Patent No.: US 11,800,792 B2
(45) Date of Patent: Oct. 24, 2023

(54) ORGANIC COMPOUND WITH SPIROCYCLIC ADAMANTANE, AND ELECTRONIC ELEMENT AND ELECTRONIC DEVICE USING SAME

(71) Applicant: Shaanxi Lighte Optoelectronics Material Co., Ltd., Xi'an (CN)

(72) Inventors: Min Yang, Xi'an (CN); Peng Nan, Xi'an (CN)

(73) Assignee: SHAANXI LIGHTE OPTOELECTRONICS MATERIAL CO., LTD., Shaanxi (CN)

(*) Notice: Subject to any disclaimer, the term of this patent is extended or adjusted under 35 U.S.C. 154(b) by 0 days.

(21) Appl. No.: 18/011,754

(22) PCT Filed: Jun. 25, 2021

(86) PCT No.: PCT/CN2021/102557
§ 371 (c)(1),
(2) Date: Dec. 20, 2022

(87) PCT Pub. No.: WO2022/068292
PCT Pub. Date: Apr. 7, 2022

(65) Prior Publication Data
US 2023/0200215 A1 Jun. 22, 2023

(30) Foreign Application Priority Data
Sep. 30, 2020 (CN) .......................... 202011063177.8

(51) Int. Cl.
*H10K 85/60* (2023.01)
*C07C 13/72* (2006.01)
(Continued)

(52) U.S. Cl.
CPC ........... *H10K 85/624* (2023.02); *C07C 13/72* (2013.01); *C07D 307/91* (2013.01);
(Continued)

(58) Field of Classification Search
CPC ............... H10K 85/624; H10K 85/626; H10K 85/6574; H10K 85/6576; H10K 50/11;
(Continued)

(56) References Cited

U.S. PATENT DOCUMENTS 9,145,383 B2 * 9/2015 Bonda .................. A61K 8/4986
9,192,552 B2 * 11/2015 Tanner .................. A61Q 17/04
(Continued)

FOREIGN PATENT DOCUMENTS

CN      106206964 A    12/2016
CN      111018797 A     4/2020
(Continued)

OTHER PUBLICATIONS

International Search Report from corresponding International Application No. PCT/CN2021/102557, dated Aug. 25, 2021, 6 pages with translation.

*Primary Examiner* — Caleb E Henry
(74) *Attorney, Agent, or Firm* — TUCKER ELLIS LLP

(57) ABSTRACT

The present disclosure relates to an organic compound, and an electronic element and electronic device using the same. The organic compound has a structural formula represented by a Formula 1. According to the organic compound provided by the present disclosure, the luminous efficiency of an organic electroluminescent device using the organic compound can be improved, and the conversion efficiency of (Continued)

a photoelectric conversion device using the organic compound can be improved.

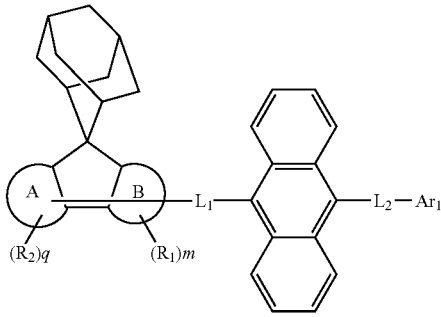

Formula 1

13 Claims, 1 Drawing Sheet

(51) Int. Cl.
*C07D 307/91* (2006.01)
*C07D 333/76* (2006.01)
*C09K 11/06* (2006.01)
*H10K 50/11* (2023.01)

(52) U.S. Cl.
CPC ............ *C07D 333/76* (2013.01); *C09K 11/06* (2013.01); *H10K 85/626* (2023.02); *H10K 85/6574* (2023.02); *H10K 85/6576* (2023.02); *C07C 2603/18* (2017.05); *C07C 2603/24* (2017.05); *C07C 2603/26* (2017.05); *C07C 2603/97* (2017.05); *C09K 2211/1007* (2013.01); *C09K 2211/1011* (2013.01); *C09K 2211/1018* (2013.01); *H10K 50/11* (2023.02)

(58) Field of Classification Search
CPC . C07C 13/72; C07C 2603/18; C07C 2603/24; C07C 2603/26; C07C 2603/97; C07D 307/91; C07D 333/76; C09K 11/06; C09K 2211/1007; C09K 2211/1011; C09K 2211/1018
See application file for complete search history.

(56) References Cited

U.S. PATENT DOCUMENTS

| | | | |
|---|---|---|---|
| 9,271,912 B2* | 3/2016 | Fernandez Prieto | A61Q 19/00 |
| 9,549,891 B2* | 1/2017 | Tanner | A61K 8/894 |
| 9,675,531 B2* | 6/2017 | Gonzales | A61K 8/8117 |
| 9,867,800 B2* | 1/2018 | Bonda | C09B 23/005 |
| 10,285,926 B2* | 5/2019 | Tanner | A61K 8/062 |
| 2004/0062726 A1* | 4/2004 | Bonda | A61K 8/40 424/59 |
| 2009/0105488 A1* | 4/2009 | Cheng | C09K 11/06 548/440 |
| 2012/0194062 A1* | 8/2012 | Osaka | H10K 85/633 585/27 |
| 2015/0236267 A1* | 8/2015 | Hiroaki | H10K 50/156 257/40 |
| 2016/0181542 A1* | 6/2016 | Kawamura | C09K 11/025 585/27 |
| 2018/0309057 A1* | 10/2018 | Ikeda | H10K 50/171 |
| 2018/0309081 A1* | 10/2018 | Ikeda | H10K 50/81 |
| 2019/0010256 A1* | 1/2019 | Lee | C08F 10/02 |
| 2019/0363259 A1* | 11/2019 | Kawakami | C07D 307/77 |

FOREIGN PATENT DOCUMENTS

| | | |
|---|---|---|
| CN | 111377853 A | 7/2020 |
| CN | 111454197 A | 7/2020 |
| CN | 111825518 A | 10/2020 |
| CN | 111848588 A | 10/2020 |
| CN | 111925315 A | 11/2020 |
| CN | 112142548 A | 12/2020 |
| KR | 2020-0107855 A | 9/2020 |
| WO | 2011/010843 A1 | 1/2011 |
| WO | 2020/046049 A1 | 3/2020 |

* cited by examiner

ORGANIC COMPOUND WITH SPIROCYCLIC ADAMANTANE, AND ELECTRONIC ELEMENT AND ELECTRONIC DEVICE USING SAME

CROSS REFERENCE TO RELATED APPLICATIONS

The present application claims the priority of Chinese Patent Application No. CN202011063177.8, filed on Sep. 30, 2020, the contents of which are incorporated herein by reference in their entirety as a part of the present application.

FIELD

The present disclosure belongs to the technical field of organic materials, and in particular provides an organic compound, and an electronic element and electronic device using the same.

BACKGROUND

An organic light-emitting phenomenon refers to a phenomenon in which an organic substance is used to convert an electric energy into a light energy. An organic light-emitting element utilizing the organic light-emitting phenomenon generally has a structure including an anode, a cathode and an organic layer located between them. Among them, in order to improve the efficiency and stability of the organic light-emitting element, the organic layer is often formed in a multilayer structure composed of different substances, and can be composed of, for example, a hole injection layer, a hole transport layer, an organic light-emitting layer, an electron transport layer, an electron injection layer, and the like. For the structure of the organic light-emitting element, if a voltage is applied between the two electrodes, holes are injected from the anode to the organic layer and electrons are injected from the cathode to the organic layer, and when the injected holes and electrons meet, excitons are formed, and light is emitted when the excitons transit to a ground state again.

In the prior art, CN106206964, WO2011010843 and the like disclose organic light-emitting layer materials that can be used in organic electroluminescent devices. However, it is still necessary to continue to develop new materials to further improve the performance of electronic components.

SUMMARY

In view of the above-mentioned problems in the prior art, the present disclosure aims to provide an organic compound, and an electronic element and electronic device using the same. The organic compound can be used as an organic light-emitting layer of an organic electroluminescent device.

In a first aspect, the present disclosure provides an organic compound, having a structural formula represented by a Formula 1:

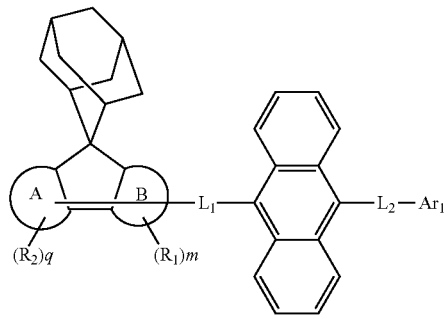

Formula 1

Wherein, ring A and ring B are the same or different, and are each independently selected from a benzene ring or a fused aromatic ring with 10 to 14 ring-forming carbon atoms, and at least one of ring A and ring B is selected from the fused aromatic ring with 10 to 14 ring-forming carbon atoms;

$L_1$ and $L_2$ are the same or different, and are each independently selected from a single bond, substituted or unsubstituted arylene with 6 to 30 carbon atoms, and substituted or unsubstituted heteroarylene with 3 to 30 carbon atoms;

each $R_1$ and $R_2$ are the same or different, and are respectively and independently selected from: hydrogen, deuterium, a halogen group, cyano, haloalkyl with 1 to 10 carbon atoms, alkyl with 1 to 10 carbon atoms, cycloalkyl with 3 to 15 carbon atoms, alkoxy with 1 to 4 carbon atoms, alkylthio with 1 to 4 carbon atoms, trialkylsilyl with 3 to 12 carbon atoms, triarylsilyl with 18 to 24 carbon atoms, aryl with 6 to 12 carbon atoms, heteroaryl with 4 to 12 carbon atoms, and heteroaralkyl with 5 to 13 carbon atoms;

m represents the number of $R_1$, q represents the number of $R_2$; m and q are respectively and independently selected from 1, 2, 3, 4, 5, 6, 7 or 8;

$Ar_1$ is selected from substituted or unsubstituted aryl with 6 to 30 carbon atoms, and substituted or unsubstituted heteroaryl with 3 to 30 carbon atoms;

substituents in the $L_1$, $L_2$ and $Ar_1$ are the same or different, and are each independently selected from: deuterium, a halogen group, cyano, heteroaryl with 3 to 20 carbon atoms, aryl with 6 to 20 carbon atoms which can be optionally substituted by 0, 1, 2, 3, 4, or 5 substituents independently selected from deuterium, fluorine, cyano, methyl, and tert-butyl, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, trialkylsilyl with 3 to 12 carbon atoms, triarylsilyl with 18 to 24 carbon atoms, and phosphinyloxy with 6 to 18 carbon atoms.

In a second aspect, the present disclosure provides an electronic element, comprising an anode and a cathode which is arranged oppositely to the anode, and a functional layer disposed between the anode and the cathode, and the functional layer comprises the organic compound of the first aspect of the present disclosure;

preferably, the functional layer comprises an organic light-emitting layer, and the organic light-emitting layer comprises the organic compound;

more preferably, the organic light-emitting layer comprises a host material and a guest material, and the host material comprises the organic compound.

In a third aspect, the present disclosure provides an electronic device, comprising the electronic element of the second aspect of the present disclosure.

The organic compound provided by the present disclosure has a molecular structure in which an anthryl group is bonded to benzofluorene spiro adamantyl group. On one hand, the molecular structure increases the electron density, charge carrier transfer rate, and triplet energy level of the whole molecule, and thus the organic compound is suitable for use as a host material for an organic light-emitting layer; and introduction of a spirocyclic adamantane structure into the molecular structure can improve the performance of a film, and then improve the service life of the film. On the other hand, the molecular structure has a large molecular weight, the glass transition temperature of the material can be effectively improved, and an aromatic group introduced on a benzo structure and rigid conjugated planar anthryl can increase steric hindrance, thus, the structure is adjusted, the film-forming properties of the material are increased, and the molecule is less likely to crystallize in an amorphous state, thus improving the luminous efficiency of an organic electroluminescent device using the organic compound, and improving the conversion efficiency of a photoelectric conversion device using the organic compound.

Other features and advantages of the present disclosure will be described in detail in the following detailed description.

BRIEF DESCRIPTION OF THE DRAWINGS

The accompanying drawings are intended to provide a further understanding of the present disclosure, and constitute a part of the description, and are used to explain the present disclosure together with the following specific embodiments, but do not constitute a limitation on the present disclosure. In the drawings.

Figure 1:
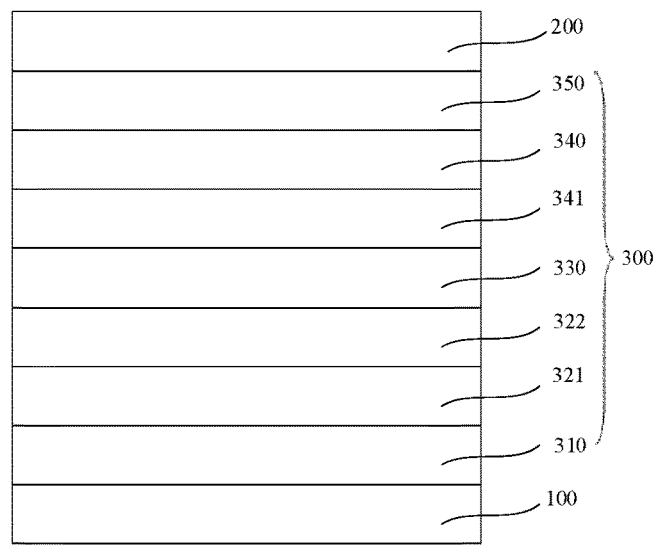
FIG. 1 is a structural schematic diagram of an organic electroluminescent device according to one embodiment of the present disclosure.

DESCRIPTION OF REFERENCE SIGNS 100, anode; 200, cathode; 300, functional layer; 310, hole injection layer; 321, hole transport layer; 322, electron blocking layer; 330, organic light-emitting layer; 341, hole blocking layer, 340, electron transport layer; 350, electron injection layer; 400, first electronic device; and 500, second electronic device.

DETAILED DESCRIPTION

Specific embodiments of the present disclosure will be described in detail below with reference to the accompanying drawings. It should be understood that the specific embodiments described herein are only used to illustrate and explain the present disclosure and are not intended to limit the present disclosure.

In a first aspect, the present disclosure provides an organic compound, having a structural formula represented by a Formula 1:

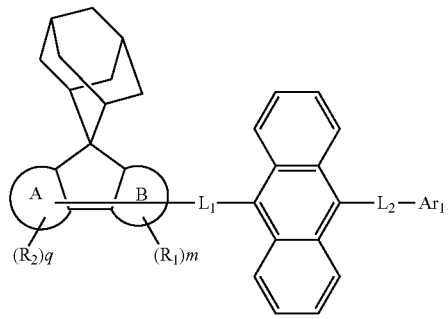

Formula 1 wherein ring A and ring B are the same or different, and are each independently selected from a benzene ring or a fused aromatic ring with 10 to 14 ring-forming carbon atoms, and at least one of ring A and ring B is selected from the fused aromatic ring with 10 to 14 ring-forming carbon atoms;

$L_1$ and $L_2$ are the same or different, and are each independently selected from a single bond, substituted or unsubstituted arylene with 6 to 30 carbon atoms, and substituted or unsubstituted heteroarylene with 3 to 30 carbon atoms;

each $R_1$ and $R_2$ are the same or different, and are respectively and independently selected from: hydrogen, deuterium, a halogen group, cyano, haloalkyl with 1 to 10 carbon atoms, alkyl with 1 to 10 carbon atoms, cycloalkyl with 3 to 15 carbon atoms, alkoxy with 1 to 4 carbon atoms, alkylthio with 1 to 4 carbon atoms, trialkylsilyl with 3 to 12 carbon atoms, triarylsilyl with 18 to 24 carbon atoms, aryl with 6 to 12 carbon atoms, heteroaryl with 4 to 12 carbon atoms, and heteroaralkyl with 5 to 13 carbon atoms;

m represents the number of $R_1$, q represents the number of $R_2$; m and q are respectively and independently selected from 1, 2, 3, 4, 5, 6, 7 or 8;

$Ar_1$ is selected from substituted or unsubstituted aryl with 6 to 30 carbon atoms, and substituted or unsubstituted heteroaryl with 3 to 30 carbon atoms;

substituents in the $L_1$, $L_2$ and $Ar_1$ are the same or different, and are each independently selected from: deuterium, a halogen group, cyano, heteroaryl with 3 to 20 carbon atoms, aryl with 6 to 20 carbon atoms which can be optionally substituted by 0, 1, 2, 3, 4, or 5 substituents independently selected from deuterium, fluorine, cyano, methyl, and tert-butyl, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, trialkylsilyl with 3 to 12 carbon atoms, triarylsilyl with 18 to 24 carbon atoms, and phosphinyloxy with 6 to 18 carbon atoms.

In the present disclosure, "aryl with 6 to 20 carbon atoms which can be optionally substituted by 0, 1, 2, 3, 4, or 5 substituents independently selected from deuterium, fluorine, chlorine, cyano, methyl, and tert-butyl" means that the aryl may be substituted by one or more of deuterium, fluorine, chlorine, cyano, methyl, and tert-butyl, or may not substituted by deuterium, fluorine, chlorine, cyano, methyl, or tert-butyl, and when the number of substituents on the aryl is greater than or equal to 2, the substituents may be the same or different.

The organic compound provided by the present disclosure has a molecular structure in which an anthryl group is bonded to spiro-(benzoadamantane-fluorene). On one hand, the molecular structure increases the electron density, charge carrier transport rate, and triplet energy level of the whole molecule, so that the compound is suitable for use as a host material for an organic light-emitting layer; and on the other hand, the molecular structure has a large molecular weight, the glass transition temperature of the material can be effectively improved. An aromatic group introduced on a benzoadamantane structure and rigid conjugated planar anthryl can increase steric hindrance, thus, the structure is adjusted, the film-forming properties of the material are increased, and the molecule is less likely to crystallize in an amorphous state, thus improving the luminous efficiency of an organic electroluminescent device using the organic compound, and improving the conversion efficiency of a photoelectric conversion device using the organic compound.

In one specific embodiment of the present disclosure, the ring A and ring B are the same or different, and are each independently selected from a benzene ring, a naphthalene ring, a phenanthrene ring, or an anthracene ring, and ring A and ring B are not simultaneously the benzene ring.

In one specific embodiment of the present disclosure, the organic compound is selected from a group consisting of structures of the following Formulae 2 to 21:

Formula 2

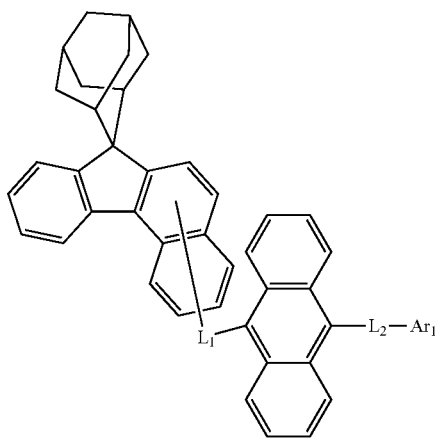

Formula 3

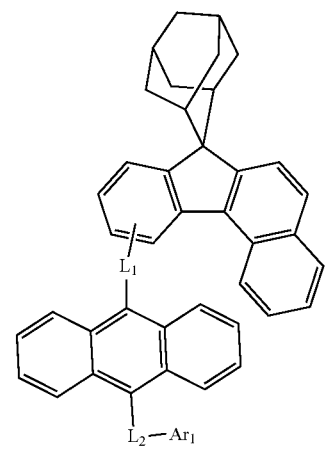

Formula 4

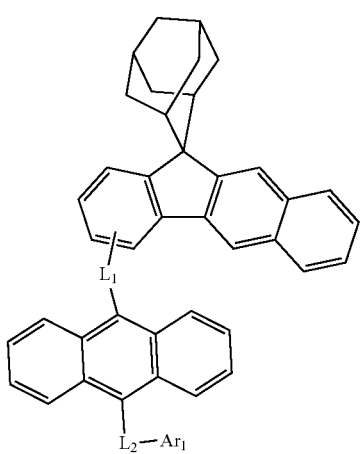

Formula 5

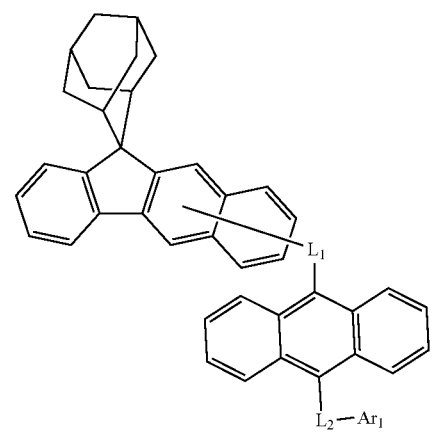

Formula 6

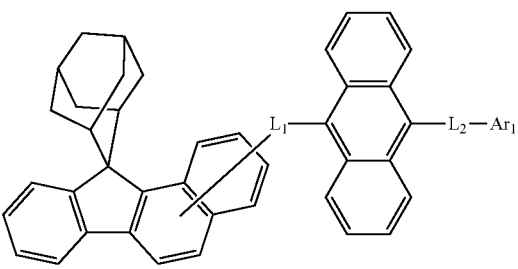

Formula 7

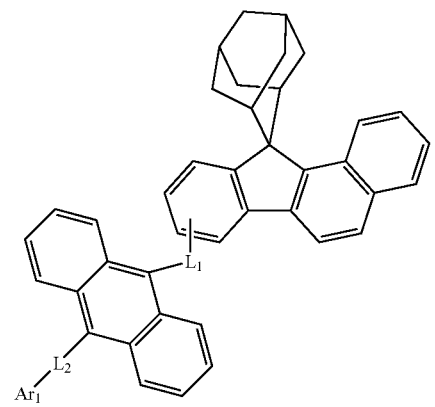

Formula 8
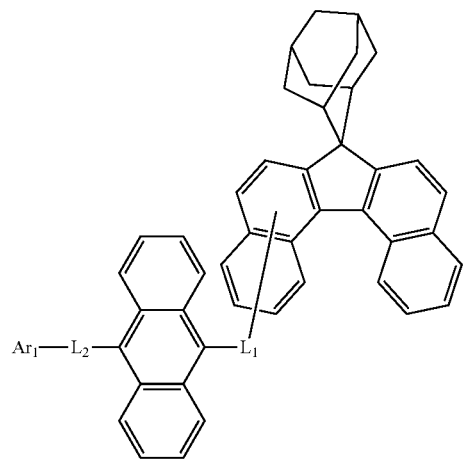
Formula 9
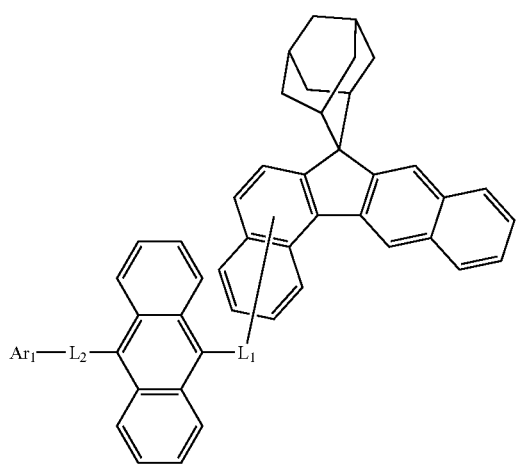
Formula 10
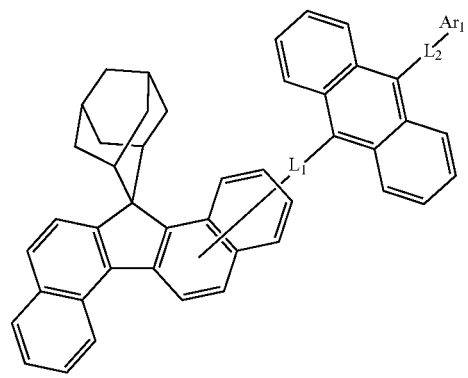
Formula 11
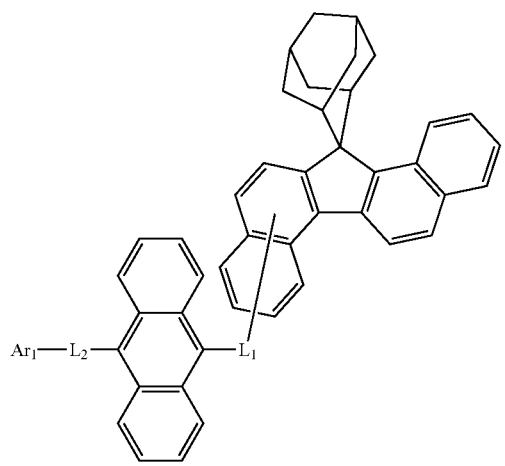
Formula 12
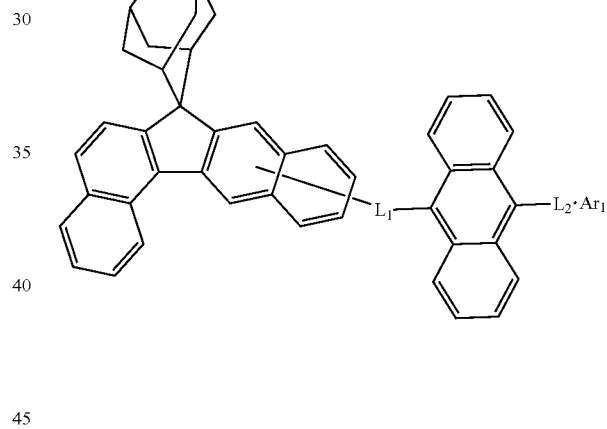
Formula 13
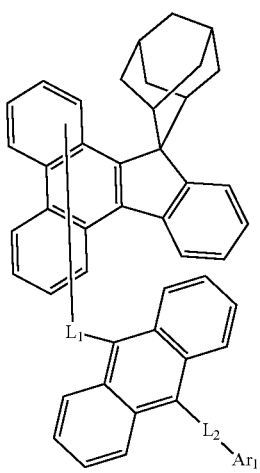

Formula 14
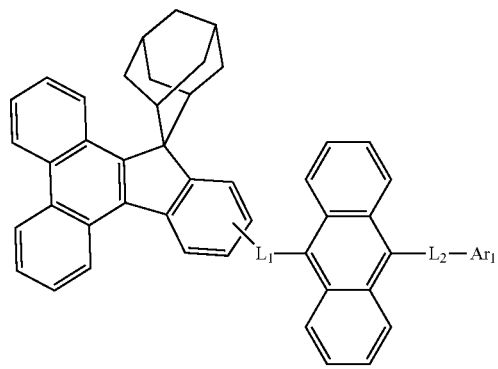
Formula 15
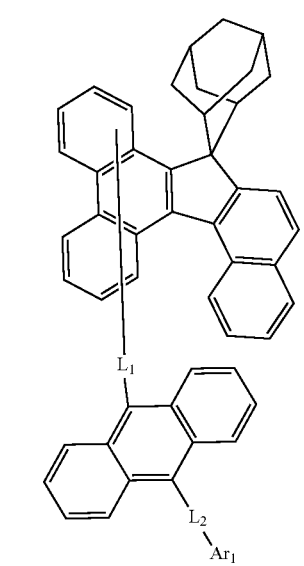
Formula 16
Formula 17
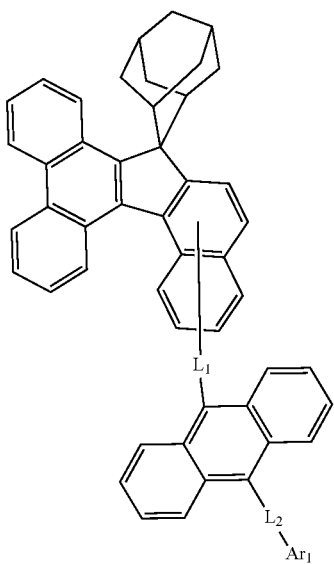
Formula 18
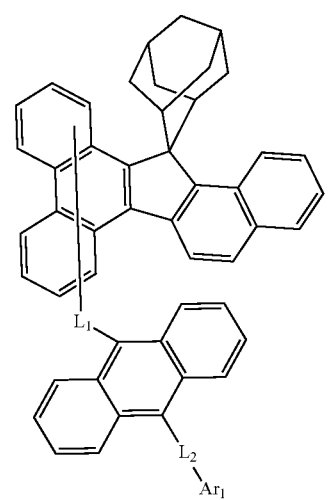
Formula 19
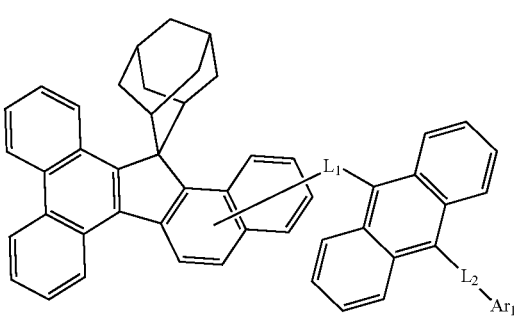

Formula 20

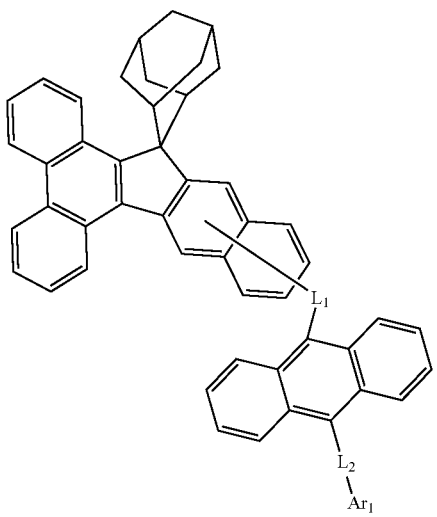

Formula 21

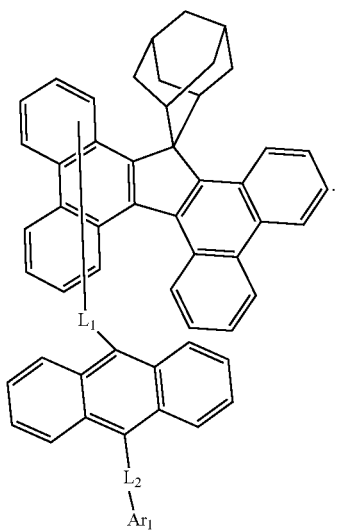

In the present disclosure, adamantane is a three-dimensional structure, and in a compound structure diagram, different planar shapes will present due to different drawing angles, spirocyclic structures formed on cyclopentane in fluorene rings are all adamantane, and the connection positions are also the same. For example, the following structures all belong to a same structure:

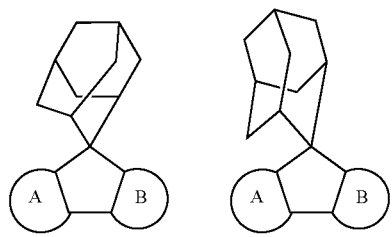

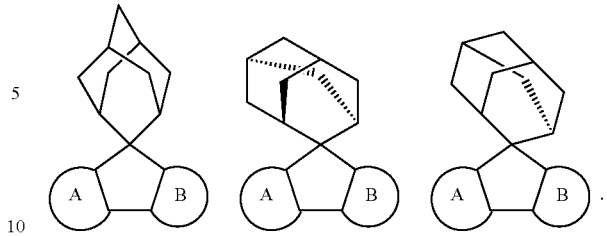

In the present disclosure, the used descriptions modes "each . . . is independently", " . . . is respectively and independently" and " . . . is independently selected from" can be interchanged, which should be understood in a broad sense, and may mean that specific options expressed by a same symbol in different groups do not influence each other, or that specific options expressed by a same symbol in a same group do not influence each other. For example, the meaning of

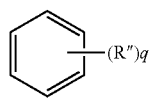   Q-1

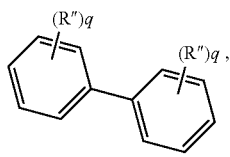   Q-2 where each q is independently 0, 1, 2 or 3 and each R″ is independently selected from hydrogen, deuterium, fluorine, and chlorine", the meaning is as follows: a formula Q-1 represents that q substituents R″ exist on the benzene ring, wherein each R″ can be the same or different, and options of each R″ do not influence each other; and a formula Q-2 represents that each benzene ring of biphenyl has q substituents R″, the number q of the substituents R″ on the two benzene rings can be the same or different, each R″ can be the same or different, and options of each R″ do not influence each other.

In the present disclosure, the term such as "substituted or unsubstituted" means that a functional group described behind the term may or may not have a substituent (the substituent is collectively referred to as Rc hereinafter for ease of description). For example, "substituted or unsubstituted aryl" refers to aryl with a substituent Rc or unsubstituted aryl. The above substituent, i.e. Rc may, for example, be deuterium, a halogen group, cyano, heteroaryl with 3 to 20 carbon atoms, aryl with 6 to 20 carbon atoms which can be optionally substituted by 0, 1, 2, 3, 4, or 5 substituents independently selected from deuterium, fluorine, cyano, methyl, and tert-butyl, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, trialkylsilyl with 3 to 12 carbon atoms, triarylsilyl with 18 to 24 carbon atoms, and phosphinyloxy with 6 to 18 carbon atoms. In the present disclosure, a "substituted" functional group may be substituted by one or two or more substituents in the above Rc; when two substituents Rc are connected to a same atom, the two substituents Rc may independently exist or may be connected to each other to form a ring with the atom; and when two adjacent substituents Rc are present on a functional group, the two adjacent substituents Rc may independently be present or may be fused to a ring with the functional group to which they are connected.

In the present disclosure, the number of carbon atoms of a substituted or unsubstituted functional group refers to the number of all carbon atoms. For example, if $L_1$ is selected from substituted aryl with 30 carbon atoms, the number of all carbon atoms of the aryl and substituents on the aryl is 30.

In the present disclosure, the number of carbon atoms of $L_1$, $L_2$ and $Ar_1$ refers to the number of all carbon atoms. For example: if $L_1$ is substituted arylene with 12 carbon atoms, then the number of all carbon atoms of the arylene and substituents on the arylene is 12. For example: if $Ar_1$ is

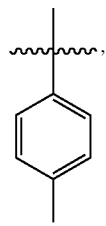

then the number of carbon atoms is 7; and if $L_1$ is

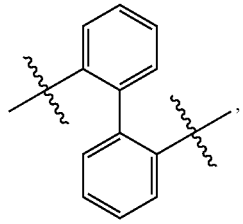 [SMILES: *c1ccccc1-c1ccccc1*]

the number of carbon atoms is 12.

In the present disclosure, aryl refers to an optional functional group or substituent derived from an aromatic carbon ring. The aryl can be monocyclic aryl (e.g., phenyl) or polycyclic aryl, in other words, the aryl can be monocyclic aryl, fused aryl, two or more monocyclic aryl conjugatedly connected by carbon-carbon bond, monocyclic aryl and fused aryl which are conjugatedly connected by a carbon-carbon bond, and two or more fused aryl conjugatedly connected by carbon-carbon bond. That is, unless specified otherwise, two or more aromatic groups conjugatedly connected by carbon-carbon bonds can also be regarded as aryl of the present disclosure. The fused aryl may, for example, include bicyclic fused aryl (e.g., naphthyl), tricyclic fused aryl (e.g., phenanthryl, fluorenyl, and anthryl), and the like. The aryl does not contain heteroatoms such as B, N, O, S, P, Se, and Si. For example, in the present disclosure, phenyl, etc., are aryl. Examples of the aryl can include, but are not limited to, phenyl, naphthyl, fluorenyl, anthryl, phenanthryl, biphenyl, terphenyl, quaterphenyl, quinquephenyl, benzo[9,10]phenanthryl, pyrenyl, benzofluoranthenyl, chrysenyl, and the like.

"Substituted or unsubstituted aryl" in the present disclosure can contain 6 to 30 carbon atoms, in some embodiments, the number of carbon atoms in the substituted or unsubstituted aryl can be 6 to 25, in other embodiments, the number of carbon atoms in the substituted or unsubstituted aryl can be 6 to 18, and in still other embodiments, the number of carbon atoms in the substituted or unsubstituted aryl can be 6 to 13. For example, the number of carbon atoms may be 6, 12, 13, 14, 15, 18, 20, 25, or 30, and of course, the number of carbon atoms may also be other numbers, which will not be listed herein.

In the present disclosure, the related arylene refers to a divalent group formed by further loss of one hydrogen atom of the aryl.

In the present disclosure, a fused aromatic ring refers to a polyaromatic ring formed by two or more aromatic or heteroaromatic rings sharing ring edges, such as naphthalene, anthracene, phenanthrene, and pyrene.

In the present disclosure, substituted aryl can be that one or two or more hydrogen atoms in the aryl are substituted by other groups such as a deuterium atom, a halogen group, cyano, aryl, heteroaryl, trialkylsilyl, alkyl, cycloalkyl, alkoxy, alkylthio, and the like. It should be understood that the number of carbon atoms of the substituted aryl refers to the total number of carbon atoms of the aryl and substituents on the aryl, for example, substituted aryl with 18 carbon atoms means that the total number of carbon atoms of the aryl and substituents is 18.

In the present disclosure, specific embodiments of the substituted aryl include, but are not limited to, phenyl-substituted naphthyl, naphthyl-substituted phenyl, phenanthryl-substituted phenyl, phenyl-substituted biphenyl, dimethylfluorenyl-substituted phenyl, dibenzothienyl-substituted phenyl, carbazolyl-substituted phenyl, phenanthrolinyl-substituted phenyl, and the like.

In the present disclosure, specific embodiments of aryl as a substituent include, but are not limited to, phenyl, naphthyl, phenanthryl, anthryl, dimethylfluorenyl, biphenyl, terphenyl, and the like.

In the present disclosure, the related arylene refers to a divalent group formed by further loss of one hydrogen atom of the aryl.

In the present disclosure, heteroaryl refers to a monovalent aromatic ring containing 1, 2, 3, 4, 5, or 6 heteroatoms in the ring or its derivative, and the heteroatom may be at least one of B, O, N, P, Si, Se, and S. The heteroaryl can be monocyclic heteroaryl or polycyclic heteroaryl, in other words, the heteroaryl can be a single aromatic ring system or a polycyclic of aromatic ring systems conjugatedly connected by carbon-carbon bond, and any one aromatic ring system is one aromatic monocyclic ring or one aromatic fused ring. For example, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolyl, quinazolinyl, quinoxalinyl, phenothiazinyl, phenoxazinyl, phthalazinyl, pyridopyrimidinyl, pyridopyrazinyl, pyrazinopyrazinyl, isoquinolyl, indolyl, carbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, benzothiazolyl, phenothiazinyl, silafluorenyl, dibenzofuranyl, as well as N-arylcarbazolyl (e.g., N-phenylcarbazolyl), N-heteroarylcarbazolyl (e.g., N-pyridylcarbazolyl), N-alkylcarbazolyl (e.g., N-methylcarbazolyl), and the like, but is not limited to this. Thienyl, furyl, phenanthrolinyl, etc. are heteroaryl of the single aromatic ring system, and N-arylcarbazolyl, and N-heteroarylcarbazolyl are heteroaryl of the plurality of aromatic ring systems conjugatedly connected by carbon-carbon bonds.

"Substituted or unsubstituted heteroaryl" in the present disclosure can contain 3 to 30 carbon atoms, in some embodiments, the number of carbon atoms in the substituted or unsubstituted heteroaryl can be 3 to 25, in other embodiments, the number of carbon atoms in the substituted or unsubstituted heteroaryl can be 3 to 20, and in still other embodiments, the number of carbon atoms in the substituted or unsubstituted heteroaryl can be 12 to 20. For example, the number of carbon atoms may be 3, 4, 5, 7, 12, 13, 18, 20, 24, 25 or 30, and of course, the number of carbon atoms may also be other numbers, which will not be listed herein.

In the present disclosure, heteroaryl refers to a monovalent aromatic ring containing at least one heteroatom in the ring or its derivative, and the heteroatom may be at least one of B, O, N, P, Si, Se and S, and the heteroaryl at least has one N.

In the present disclosure, the related heteroarylene refers to a divalent group formed by further loss of one hydrogen atom of the heteroaryl.

In the present disclosure, substituted heteroaryl may be that one or two or more hydrogen atoms in the heteroaryl are substituted by other groups such as a deuterium atom, a halogen group, cyano, aryl, heteroaryl, trialkylsilyl, alkyl, cycloalkyl, alkoxy, alkylthio, and the like. It should be understood that the number of carbon atoms of the substituted heteroaryl refers to the total number of carbon atoms of the heteroaryl and substituents on the heteroaryl.

In the present disclosure, specific examples of heteroaryl as a substituent include, but are not limited to, dibenzofuranyl, dibenzothienyl, N-phenylcarbazolyl, carbazolyl, and the like.

In the present disclosure, alkyl with 1 to 10 carbon atoms can be linear alkyl or branched alkyl. Specifically, the alkyl with 1 to 10 carbon atoms may be linear alkyl with 1 to 10 carbon atoms, or branched alkyl with 3 to 10 carbon atoms. The number of carbon atoms may, for example, be 1, 2, 3, 4, 5, 6, 7, 8, 9, or 10. Specific examples of the alkyl with 1 to 10 carbon atoms include, but are not limited to, methyl, ethyl, n-propyl, isopropyl, n-butyl, isobutyl, tert-butyl, n-pentyl, isopentyl, neopentyl, cyclopentyl, n-hexyl, heptyl, n-octyl, 2-ethylhexyl, nonyl, decyl, 3,7-dimethyloctyl, and the like.

In the present disclosure, the halogen group may be fluorine, chlorine, bromine, or iodine.

In the present disclosure, an unpositioned connecting bond refers to a single bond

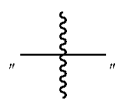

extending from a ring system, which indicates that one end of the connecting bond can be connected to any position in the ring system through which the bond penetrates, and the other end of the connecting bond is connected to the remaining part of a compound molecule.

For example, as shown in the following formula (f), naphthyl represented by the formula (f) is connected to other positions of a molecule through two unpositioned connecting bonds penetrating a dicyclic ring, and its meaning includes any one possible connecting mode represented by formulae (f-1) to (f-10).

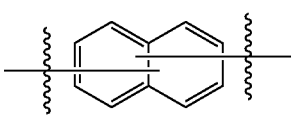 (f)

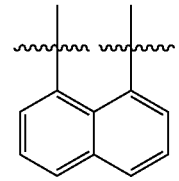 (f-1)

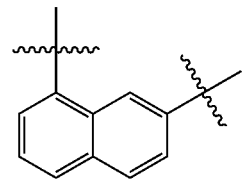 (f-2)

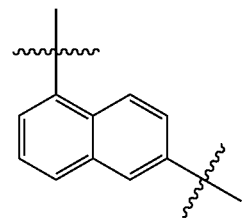 (f-3)

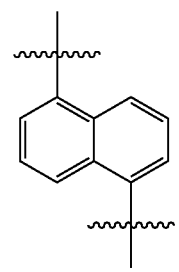 (f-4)

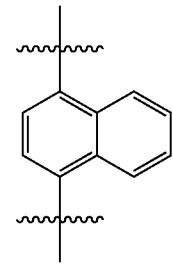 (f-5)

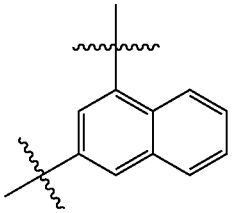 (f-6)

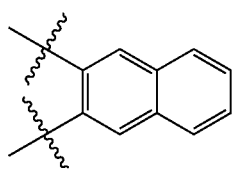 (f-7)

-continued (f-8)
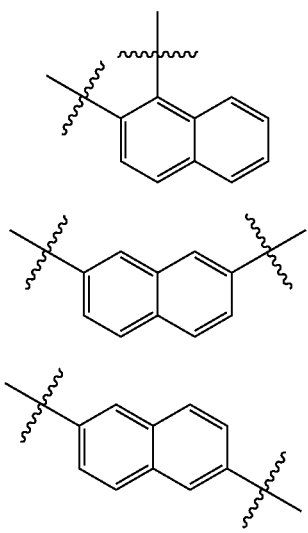

(f-9)

(f-10)

For another example, as shown in the following formula (X'), dibenzofuranyl represented by the formula (X') is connected with other positions of a molecule through one unpositioned connecting bond extending from the middle of a benzene ring on one side, and its meaning includes any possible connecting mode represented by formulae (X'-1) to (X'-4).

(X)

(X'-1)

(X'-2)

(X'-3)

(X'-4)

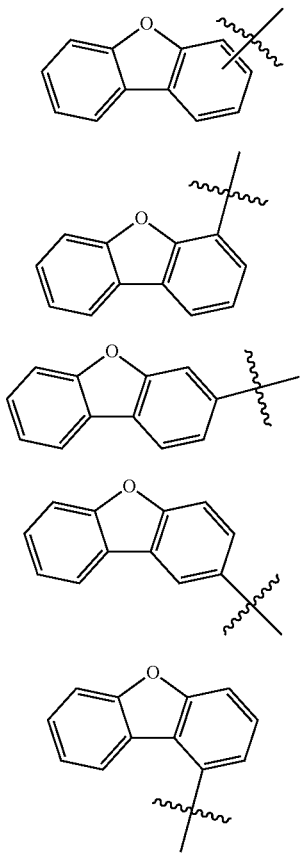

In some embodiments of the present disclosure, in the Formula 1,

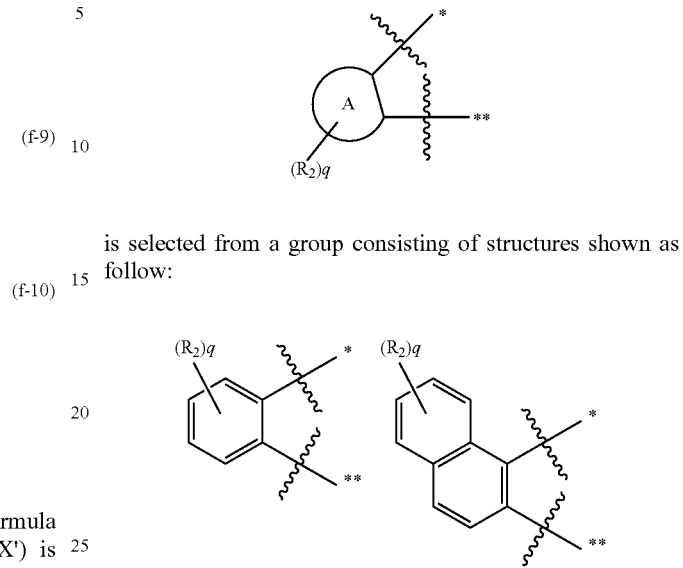

is selected from a group consisting of structures shown as follow:

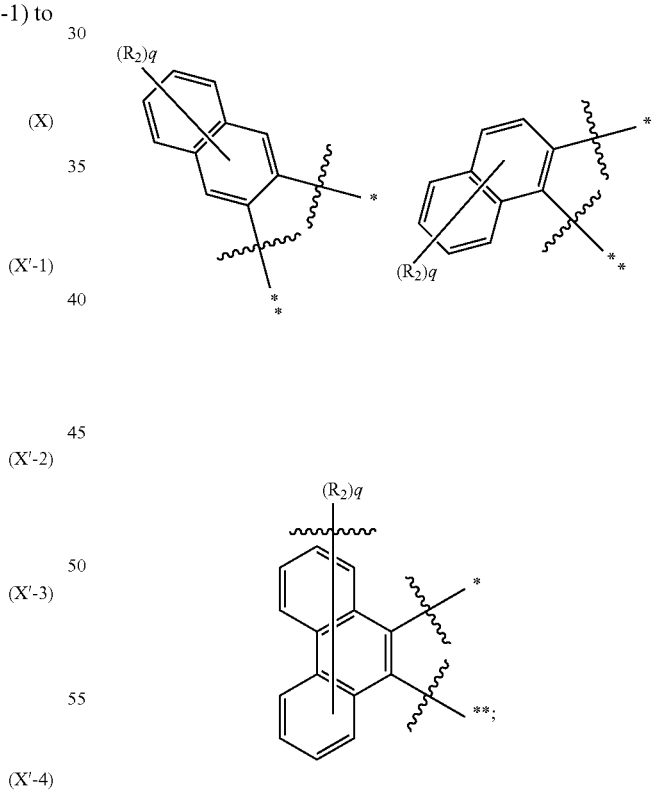

wherein,

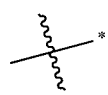

represents a chemical bond for connecting with
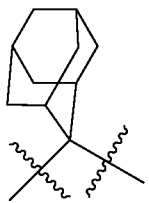 [SMILES: *C1(*)C2CC3CC(C2)CC1C3]
in the above structures, and
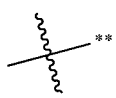
represents a chemical bond for connecting with
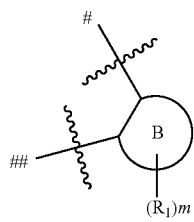
in the above structures.
In some embodiments of the present disclosure, in
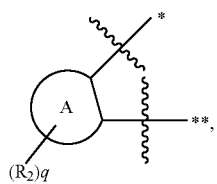
when q is equal to 1,
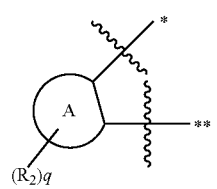
is selected from a group consisting of structures shown as follow:
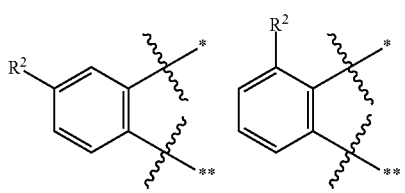
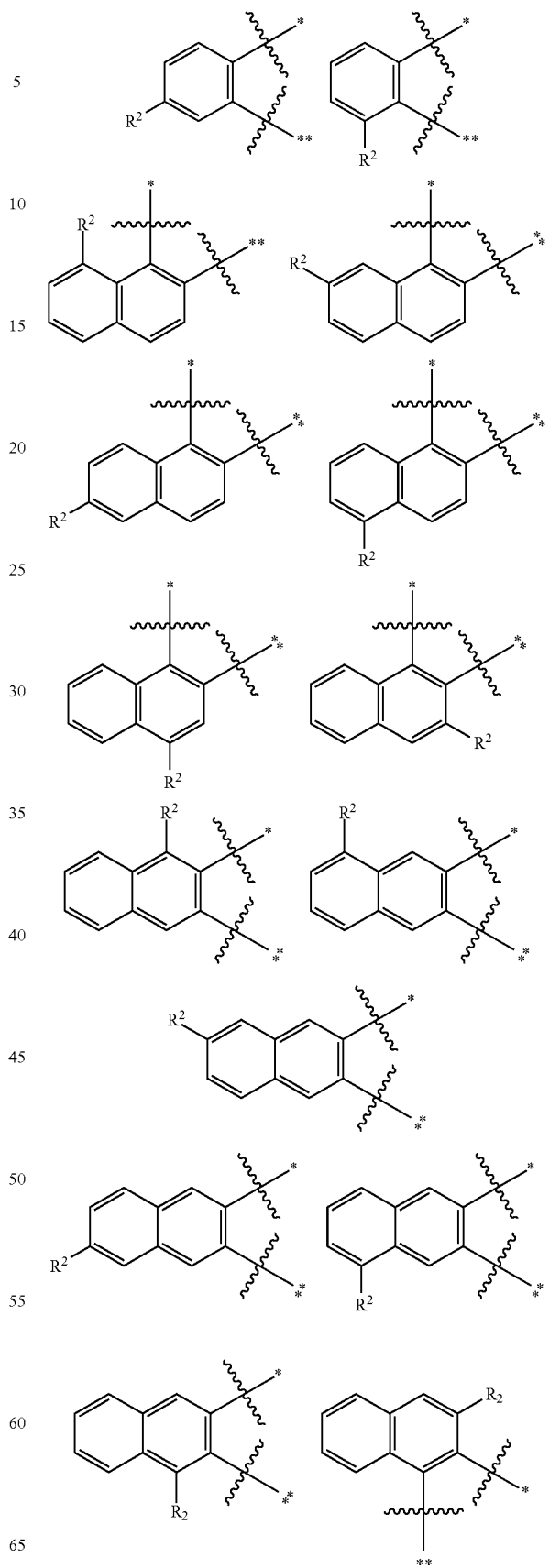

-continued
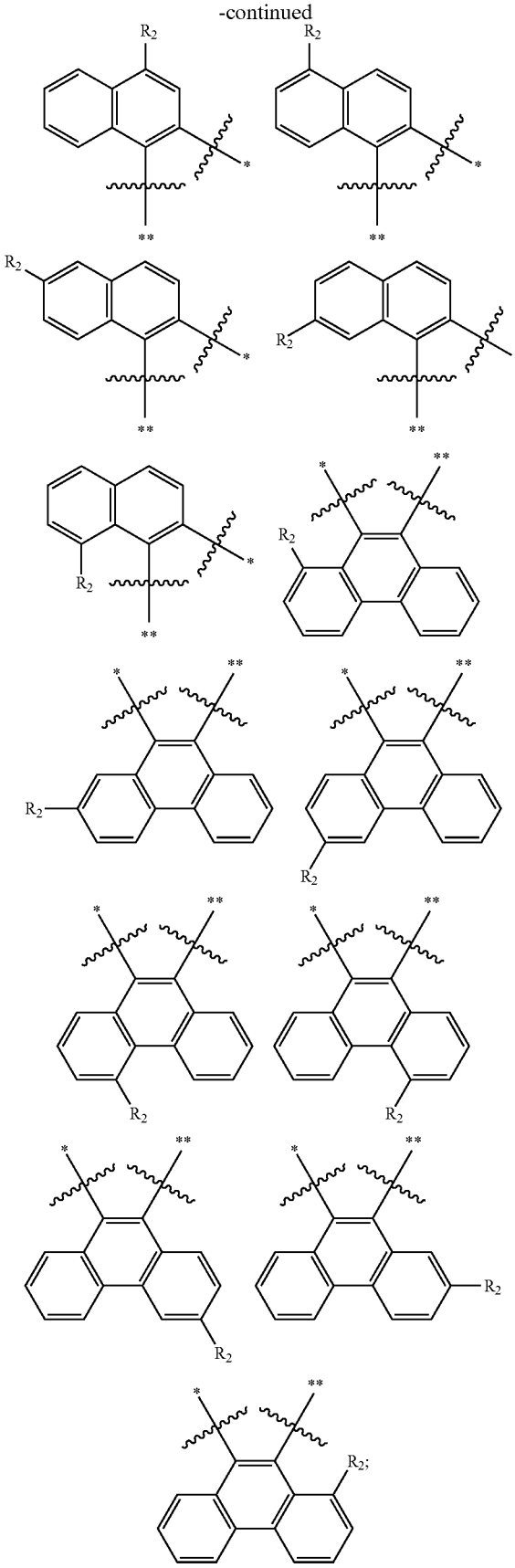
wherein,
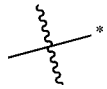
represents a chemical bond for connecting with
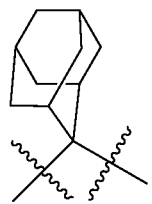 [SMILES: *C1(*)C2CC3CC(C2)CC1C3]
in the above structures, and
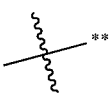
represents a chemical bond for connecting with
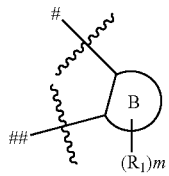
in the above structures.
In some embodiments of the present disclosure, in the Formula 1,
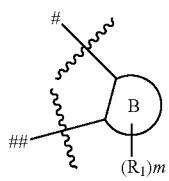
is selected from a group consisting of structures shown as follow:
wherein,
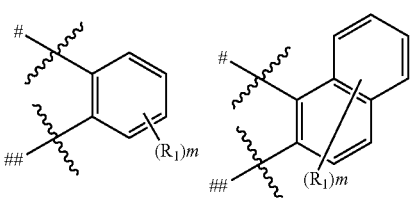

-continued
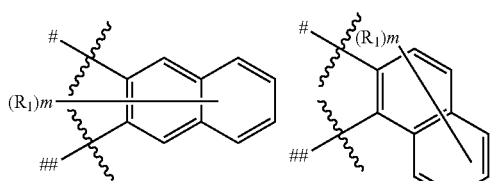
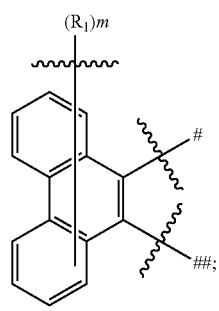
represents a chemical bond for connecting with
in the above structures, and
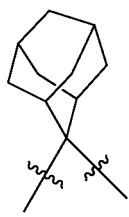 [SMILES: *C1(*)C2CC3CC(C2)CC1C3]
represents a chemical bond for connecting with
in the
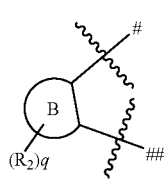
above structures.
In some embodiments of the present disclosure, in
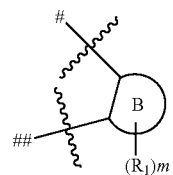
when m is equal to 1,
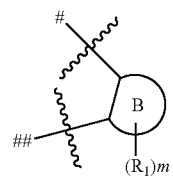
is selected from a group consisting of structures shown as follow:
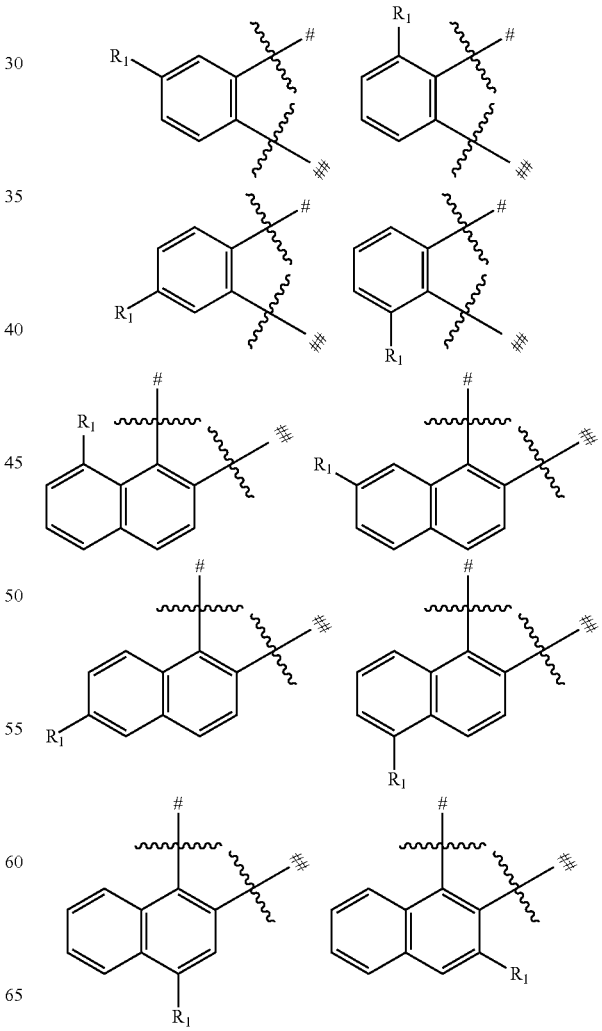

25
-continued
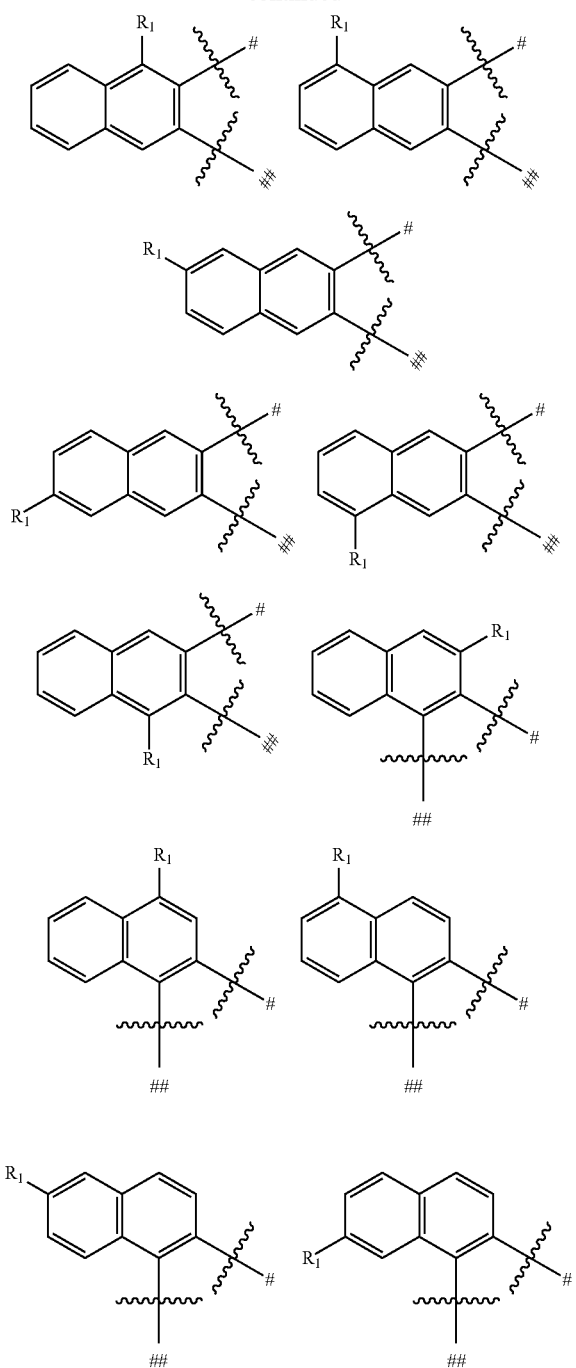
26
-continued
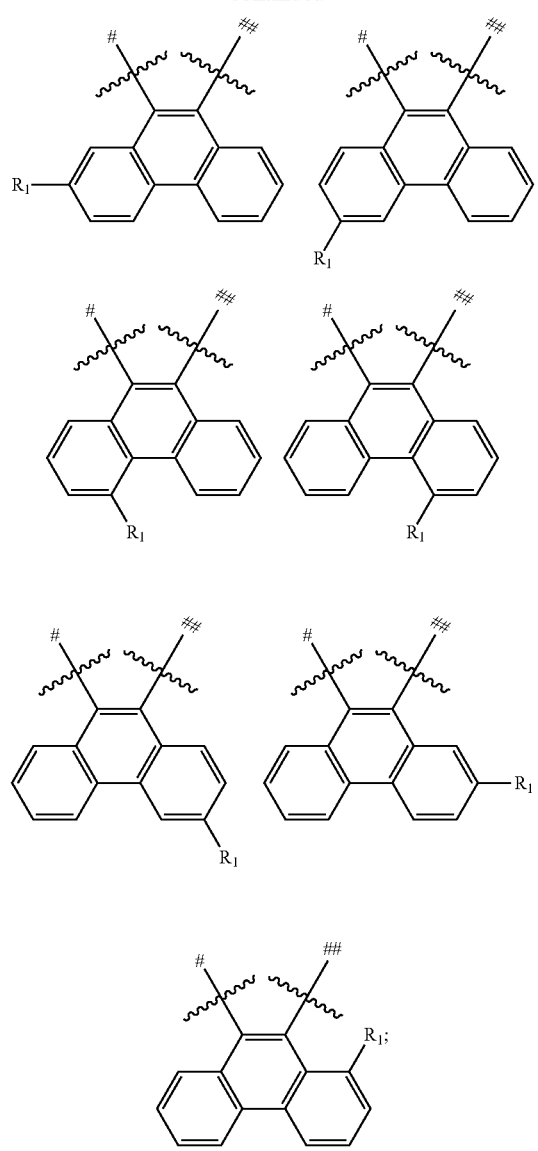
wherein,
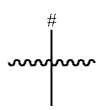
represents a chemical bond for connecting with
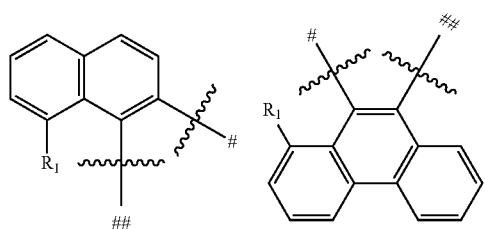
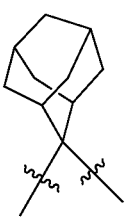 [SMILES: *C1(*)C2CC3CC(C2)CC1C3]

in the above structures, and

represents a chemical bond for connecting with

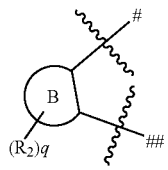

in the above structures.

In some embodiments of the present disclosure, $R_1$ and $R_2$ are respectively and independently selected from hydrogen.

In some embodiments of the present disclosure, the $Ar_1$ is selected from substituted or unsubstituted aryl with 6 to 24 carbon atoms, and substituted or unsubstituted heteroaryl with 3 to 24 carbon atoms.

In some embodiments of the present disclosure, the substituent in the $Ar_1$ is selected from deuterium, a halogen group, cyano, aryl with 6 to 20 carbon atoms, heteroaryl with 3 to 20 carbon atoms, alkyl with 1 to 5 carbon atoms, haloalkyl with 1 to 4 carbon atoms, cycloalkyl with 3 to 10 carbon atoms, trialkylsilyl with 3 to 7 carbon atoms, and triarylsilyl with 18 to 24 carbon atoms.

Preferably, $Ar_1$ is selected from substituted or unsubstituted aryl with 6 to 20 carbon atoms, and substituted or unsubstituted heteroaryl with 3 to 20 carbon atoms.

Preferably, the substituent in $Ar_1$ is selected from deuterium, fluorine, cyano, alkyl with 1 to 5 carbon atoms, aryl with 6 to 15 carbon atoms, and heteroaryl with 12 to 18 carbon atoms.

Specifically, the substituent in the $Ar_1$ includes, but is not limited to, deuterium, fluorine, cyano, methyl, ethyl, n-propyl, isopropyl, tert-butyl, phenyl, naphthyl, biphenyl, anthryl, phenanthryl, dimethylfluorenyl, dibenzofuranyl, dibenzothienyl, carbazolyl, and N-phenylcarbazolyl.

In some embodiments of the present disclosure, the $Ar_1$ is selected from a group consisting of groups represented by i-1 to i-15 shown as follow:

i-1
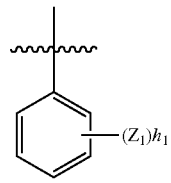

i-2
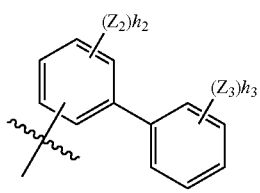

i-3
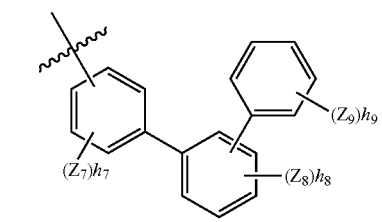

i-4
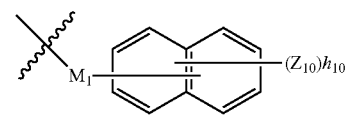

i-5
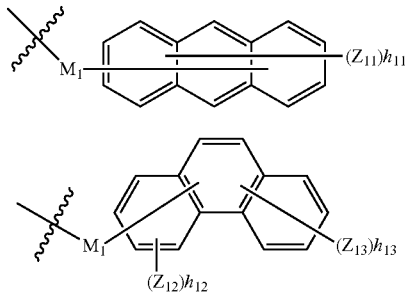

i-6 i-7
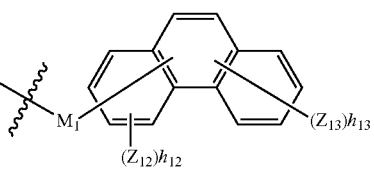

i-8
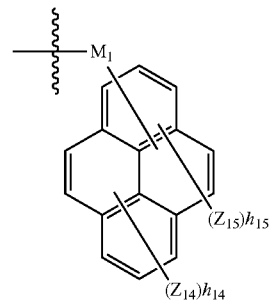

i-9
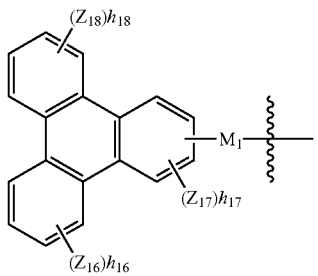

i-10
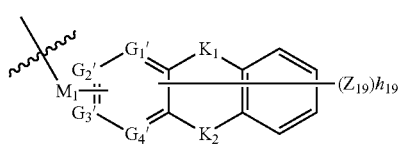

-continued

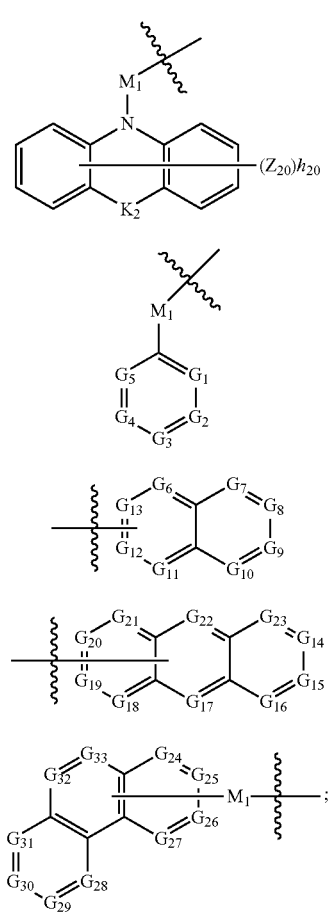

Wherein, $M_1$ is selected from a single bond or

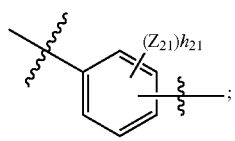

$G_1$ to $G_5$ and $G_1'$ to $G_4'$ are each independently selected from N, C, or $C(J_1)$, and at least one of $G_1$ to $G_5$ is selected from N; when two or more of $G_1$ to $G_5$ are selected from $C(J_1)$, any two $J_1$s are the same or different; and when two or more of $G_1'$ to $G_4'$ are selected from $C(J_1)$, any two $J_1$s are the same or different;

$G_6$ to $G_{13}$ are each independently selected from N, C or $C(J_2)$, and at least one of $G_6$ to $G_{13}$ is selected from N; and when two or more of $G_6$ to $G_{13}$ are selected from $C(J_2)$, any two $J_2$s are the same or different;

$G_{14}$ to $G_{23}$ are each independently selected from N, C or $C(J_3)$, and at least one of $G_{14}$ to $G_{23}$ is selected from N; and when two or more of $G_{14}$ to $G_{23}$ are selected from $C(J_3)$, any two $J_3$s are the same or different;

$G_{24}$ to $G_{33}$ are each independently selected from N, C or $C(J_4)$, and at least one of $G_{24}$ to $G_{33}$ is selected from N; and when two or more of $G_{24}$ to $G_{33}$ are selected from $C(J_4)$, any two $J_4$s are the same or different;

$Z_1$ is selected from hydrogen, deuterium, a halogen group, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, and triarylsilyl with 18 to 24 carbon atoms;

$Z_2$ to $Z_9$, and $Z_{21}$ are each independently selected from: hydrogen, deuterium, a halogen group, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, heteroaryl with 3 to 18 carbon atoms, and triarylsilyl with 18 to 24 carbon atoms;

$Z_{10}$ to $Z_{20}$, and $J_1$ to $J_4$ are each independently selected from: hydrogen, deuterium, a halogen group, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, aryl with 6 to 20 carbon atoms which can be optionally substituted by 0, 1, 2, 3, 4, or 5 substituents independently selected from deuterium, fluorine, cyano, methyl, and tert-butyl, heteroaryl with 3 to 18 carbon atoms, and triarylsilyl with 18 to 24 carbon atoms;

$h_1$ to $h_{21}$ are represented by $h_k$, $Z_1$ to $Z_{21}$ are represented by $Z_k$, k is a variable, and represents any integer from 1 to 21, and $h_k$ represents the number of a substituent $Z_k$; when k is selected from 5 or 17, $h_k$ is selected from 1, 2 or 3; when k is selected from 2, 7, 8, 12, 15, 16, 18 or 21, $h_k$ is selected from 1, 2, 3 or 4; when k is selected from 1, 3, 4, 6, 9 or 14, $h_k$ is selected from 1, 2, 3, 4 or 5; when k is 13, $h_k$ is selected from 1, 2, 3, 4, 5, or 6; when k is selected from 10 or 19, $h_k$ is selected from 1, 2, 3, 4, 5, 6 or 7; when k is 20, $h_k$ is selected from 1, 2, 3, 4, 5, 6, 7, or 8; when k is 11, $h_k$ is selected from 1, 2, 3, 4, 5, 6, 7, 8 or 9; and when $h_k$ is greater than 1, any two $Z_k$s are the same or different;

$K_1$ is selected from O, S, $N(Z_{22})$, $C(Z_{23}Z_{24})$, and $Si(Z_{28}Z_{29})$; where $Z_{22}$, $Z_{23}$, $Z_{24}$, $Z_{28}$, and $Z_{29}$ are each independently selected from aryl with 6 to 18 carbon atoms, heteroaryl with 3 to 18 carbon atoms, alkyl with 1 to 10 carbon atoms, or cycloalkyl with 3 to 10 carbon atoms, or the $Z_{23}$ and the $Z_{24}$ are connected to each other to form a saturated or unsaturated ring with 3 to 15 carbon atoms together with the atoms to which they are commonly connected, or the $Z_{28}$ and the $Z_{29}$ are connected to each other to form a saturated or unsaturated ring with 3 to 15 carbon atoms together with the atoms to which they are commonly connected; and $K_2$ is selected from a single bond, O, S, $N(Z_{25})$, $C(Z_{26}Z_{27})$, and $Si(Z_{30}Z_{31})$; where $Z_{25}$, $Z_{26}$, $Z_{27}$, $Z_{30}$, and $Z_{31}$ are each independently selected from aryl with 6 to 18 carbon atoms, heteroaryl with 3 to 18 carbon atoms, alkyl with 1 to 10 carbon atoms, or cycloalkyl with 3 to 10 carbon atoms, or the $Z_{26}$ and the $Z_{27}$ are connected to each other to form a saturated or unsaturated ring with 3 to 15 carbon atoms together with the atoms to which they are commonly connected, or the $Z_{30}$ and the $Z_{31}$ are connected to each other to form a saturated or unsaturated ring with 3 to 15 carbon atoms together with the atoms to which they are commonly connected.

In some embodiments of the present disclosure, the $Ar_1$ is selected from a substituted or unsubstituted group $V_1$, and the unsubstituted group $V_1$ is selected from a group consisting of the following groups:

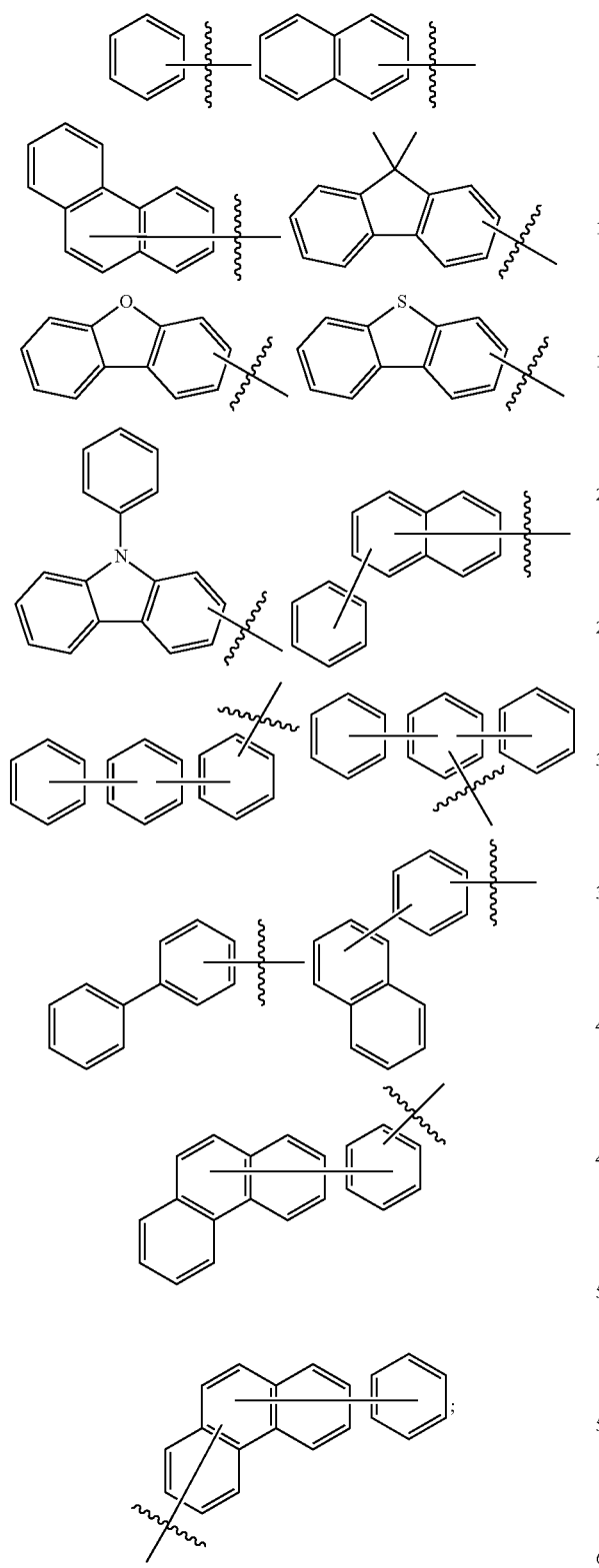
the substituted group $V_1$ has one or two or more substituents, and the substituents in the substituted group $V_1$ are independently selected from deuterium, fluorine, cyano, alkyl with 1 to 5 carbon atoms, cycloalkyl with 3 to 10 carbon atoms, and aryl with 6 to 12 carbon atoms.
Optionally, $Ar_1$ is selected from a group consisting of the following groups:
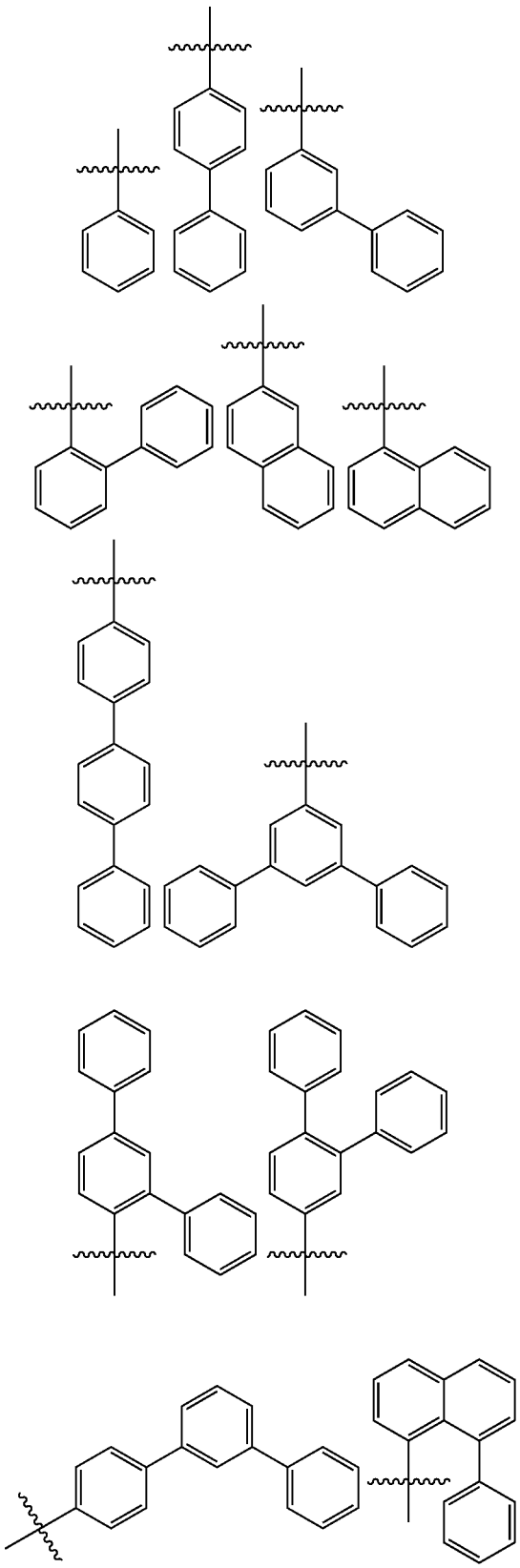

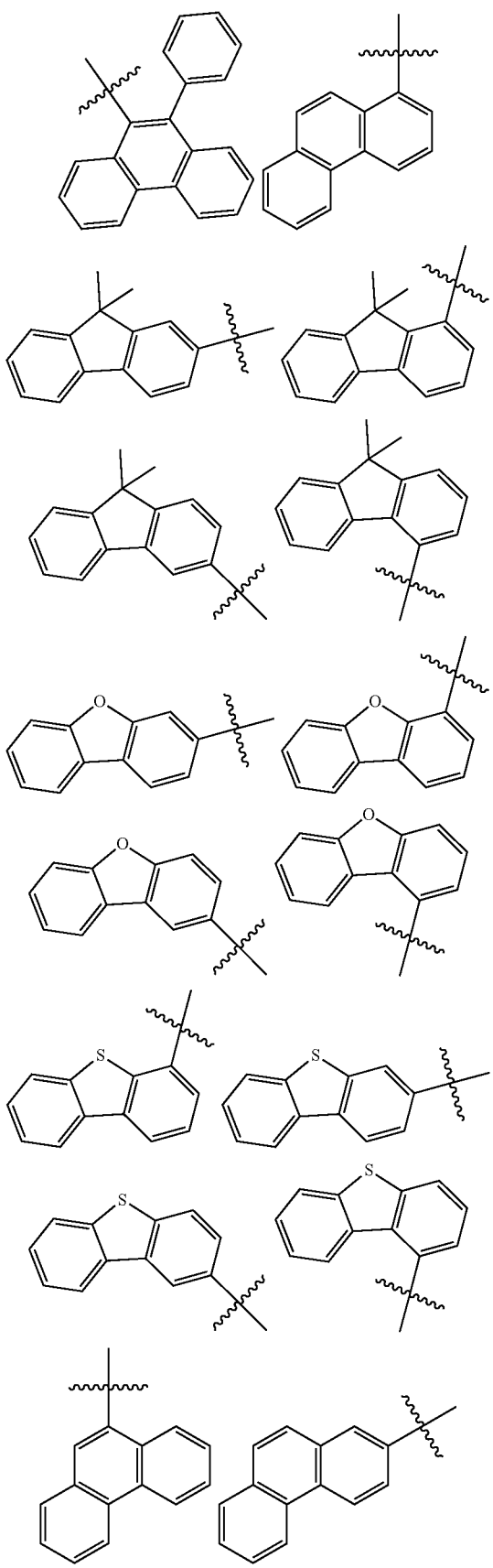

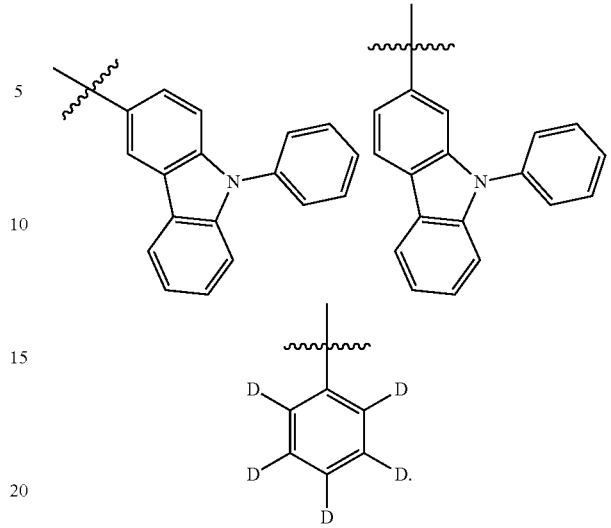

In some embodiments of the present disclosure, $L_1$ and $L_2$ are the same or different, and are each independently selected from a single bond, substituted or unsubstituted arylene with 6 to 20 carbon atoms, and substituted or unsubstituted heteroarylene with 3 to 20 carbon atoms.

In some embodiments of the present disclosure, substituents in $L_1$ and $L_2$ are the same or different, and are each independently selected from deuterium, a halogen group, cyano, alkyl with 1 to 5 carbon atoms, aryl with 6 to 12 carbon atoms, and cycloalkyl with 3 to 10 carbon atoms.

In some embodiments of the present disclosure, $L_1$ and $L_2$ are the same or different, and are each independently selected from a single bond, substituted or unsubstituted phenylene, substituted or unsubstituted naphthylene, substituted or unsubstituted biphenylene, substituted or unsubstituted terphenylene, substituted or unsubstituted fluorenylene, substituted or unsubstituted phenanthrylene, substituted or unsubstituted dibenzothienylene, substituted or unsubstituted dibenzofurylene, substituted or unsubstituted N-phenylcarbazolylene, and substituted or unsubstituted carbazolylene.

In some embodiments of the present disclosure, substituents in $L_1$ and $L_2$ are the same or different, and specific embodiments include, but are not limited to, deuterium, a halogen group, cyano, methyl, ethyl, n-propyl, isopropyl, tert-butyl, phenyl, naphthyl, biphenyl, phenanthryl, and anthryl.

In some embodiments of the present disclosure, $L_1$ and $L_2$ are the same or different, and are each independently selected from a single bond or a group consisting of groups represented by j-1 to j-13 as follow:

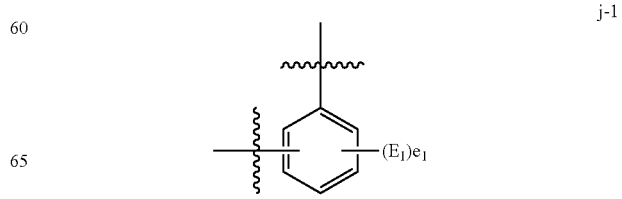

j-1

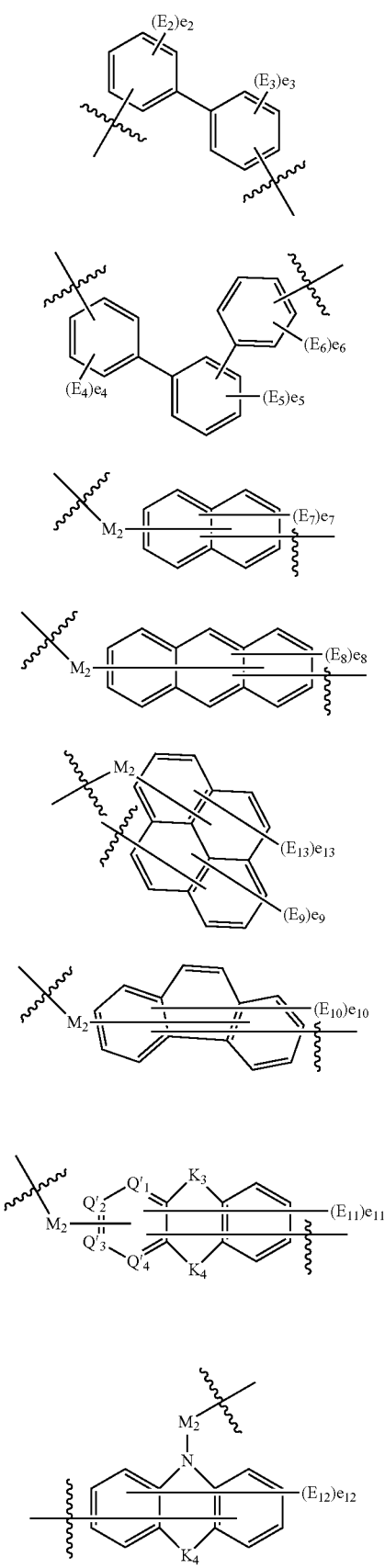

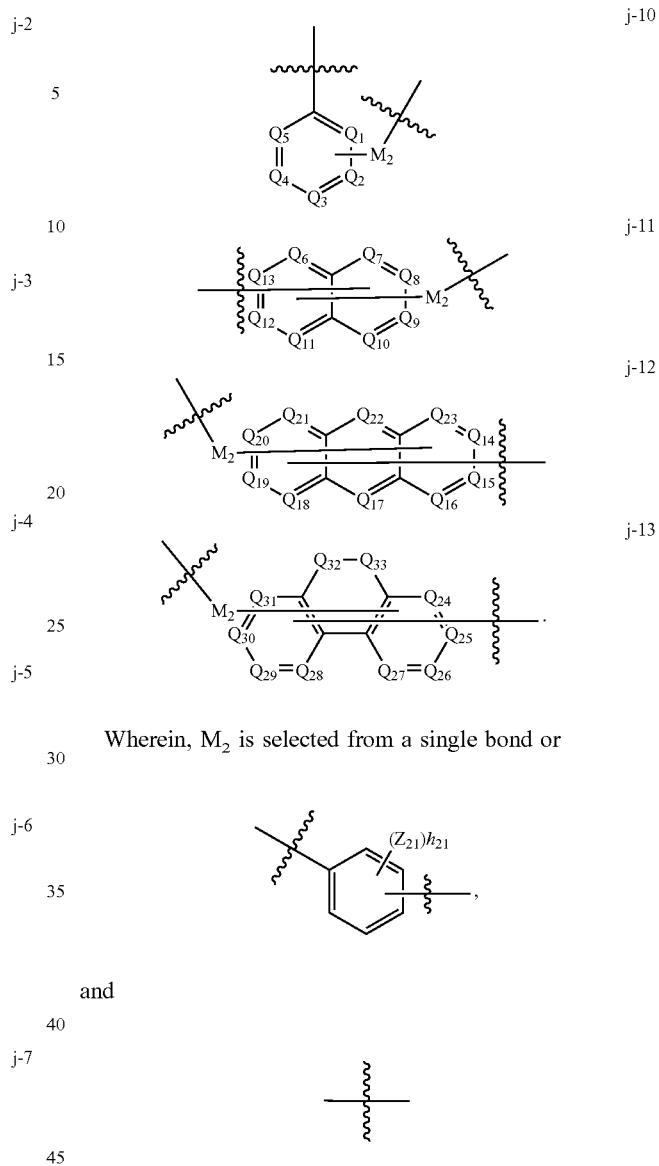

Wherein, $M_2$ is selected from a single bond or represents a chemical bond;

$Q_1$ to $Q_5$ and $Q'_1$ to $Q'_4$ are each independently selected from N or $C(J_5)$, and at least one of $Q_1$-$Q_5$ is selected from N; and when two or more of $Q_1$ to $Q_5$ are selected from $C(J_5)$, any two $J_5$ are the same or different, and when two or more of $Q'_1$ to $Q'_4$ are selected from $C(J_5)$, any two $J_5$s are the same or different;

$Q_6$ to $Q_{13}$ are each independently selected from N, C or $C(J_6)$, and at least one of $Q_6$ to $Q_{13}$ is selected from N; and when two or more of $Q_6$ to $Q_{13}$ are selected from $C(J_6)$, any two $J_6$s are the same or different;

$Q_{14}$ to $Q_{23}$ are each independently selected from N, C or $C(J_7)$, and at least one of $Q_{14}$ to $Q_{23}$ is selected from N; and when two or more of $Q_{14}$ to $Q_{23}$ are selected from $C(J_7)$, any two $J_7$s are the same or different;

$Q_{24}$ to $Q_{33}$ are each independently selected from N, C or $C(J_8)$, and at least one of $Q_{24}$ to $Q_{33}$ is selected from N; and when two or more of $Q_{24}$ to $Q_{33}$ are selected from $C(J_8)$, any two $J_8$s are the same or different;

$E_1$ to $E_{14}$, and $J_5$ to $J_8$ are each independently selected from: hydrogen, deuterium, a halogen group, cyano, heteroaryl with 3 to 20 carbon atoms, aryl with 6 to 20 carbon atoms which can be optionally substituted by 0, 1, 2, 3, 4, or 5 independently selected from deuterium, fluorine, chlorine, cyano, methyl, and tert-butyl, trialkylsilyl with 3 to 12 carbon atoms, alkyl with 1 to 10 carbon atoms, cycloalkyl with 3 to 10 carbon atoms, alkoxy with 1 to 10 carbon atoms, alkylthio with 1 to 10 carbon atoms, phosphinyloxy with 6 to 18 carbon atoms, and triarylsilyl with 18 to 24 carbon atoms;

$e_1$ to $e_{14}$ are represented by $e_r$, $E_1$ to $E_{14}$ are represented by $E_r$, r is a variable, and represents any integer from 1 to 14, and $e_r$ represents the number of a substituent $E_r$; when r is selected from 1, 2, 3, 4, 5, 6, 9, 13 or 14, $e_r$ is selected from 1, 2, 3 or 4; when r is selected from 7 or 11, $e_r$ is selected from 1, 2, 3, 4, 5 or 6; when r is 12, $e_r$ is selected from 1, 2, 3, 4, 5, 6, or 7; when r is selected from 8 or 10, $e_r$ is selected from 1, 2, 3, 4, 5, 6, 7, or 8; and when $e_r$ is greater than 1, any two Ers are the same or different;

$K_3$ is selected from O, S, Se, $N(E_{15})$, $C(E_{16}E_{17})$, and $Si(E_{18}E_{19})$; where $E_{15}$, $E_{16}$, $E_{17}$, $E_{18}$ and $E_{19}$ are each independently selected from: aryl with 6 to 20 carbon atoms, heteroaryl with 3 to 20 carbon atoms, alkyl with 1 to 10 carbon atoms, and cycloalkyl with 3 to 10 carbon atoms, or $E_{16}$ and $E_{17}$ are connected to each other to form a saturated or unsaturated ring with 3 to 15 carbon atoms together with the atoms to which they are commonly connected, or $E_{18}$ and $E_{19}$ are connected to each other to form a saturated or unsaturated ring with 3 to 15 carbon atoms together with the atoms to which they are commonly connected;

$K_4$ is selected from a single bond, O, S, Se, $N(E_{20})$, $C(E_{21}E_{22})$, and $Si(E_{23}E_{24})$; where $E_{20}$ to $E_{24}$ are each independently selected from: aryl with 6 to 20 carbon atoms, heteroaryl with 3 to 20 carbon atoms, alkyl with 1 to 10 carbon atoms, and cycloalkyl with 3 to 10 carbon atoms, or $E_{21}$ and $E_{22}$ are connected to each other to form a saturated or unsaturated ring with 3 to 15 carbon atoms together with the atoms to which they are commonly connected, or $E_{23}$ and $E_{24}$ are connected to each other to form a saturated or unsaturated ring with 3 to 15 carbon atoms together with the atoms to which they are commonly connected.

In some embodiments of the present disclosure, $L_1$ and $L_2$ are each independently selected from a single bond or a substituted or unsubstituted group $V_2$, and the unsubstituted group $V_2$ is selected from a group consisting of the following groups:

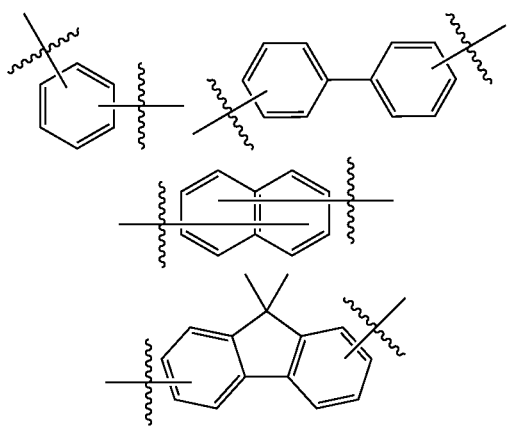

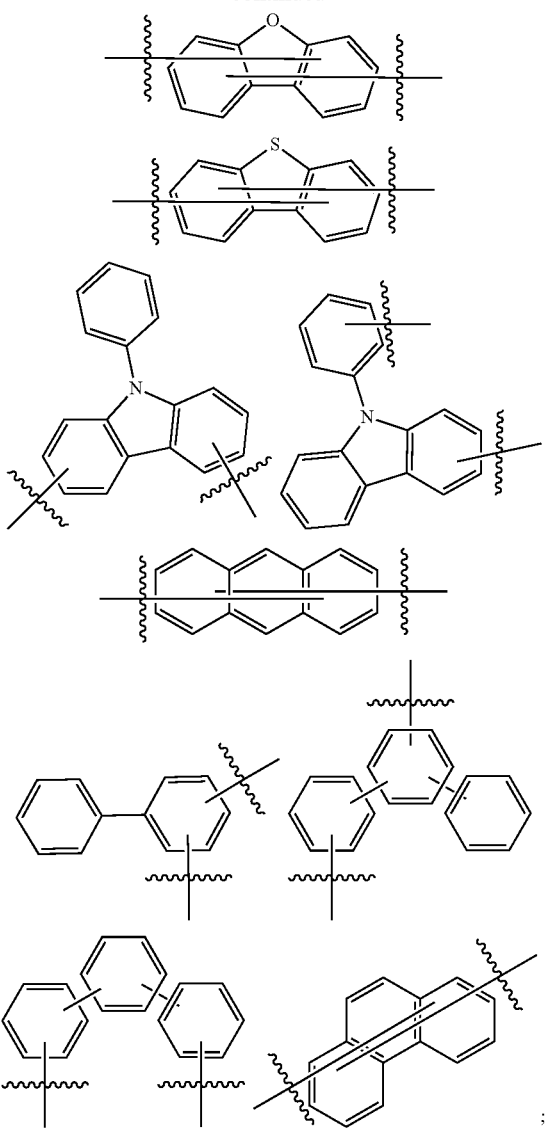

the substituted group $V_2$ has one or two or more substituents, and the substituents in the substituted group $V_2$ are independently selected from deuterium, fluorine, cyano, alkyl with 1 to 5 carbon atoms, and aryl with 6 to 12 carbon atoms.

Optionally, $L_1$ and $L_2$ are each independently selected from a single bond or a group consisting of the following groups:

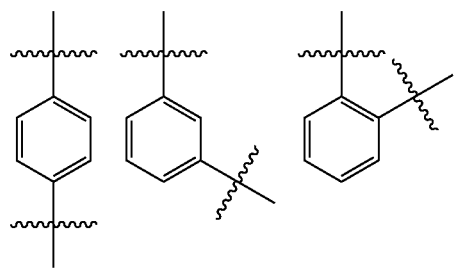

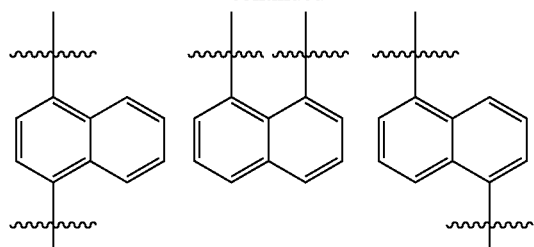
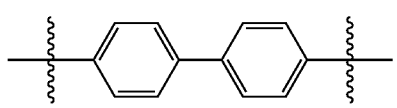
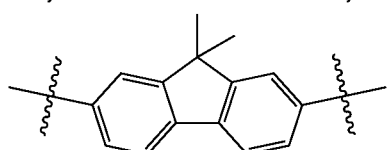
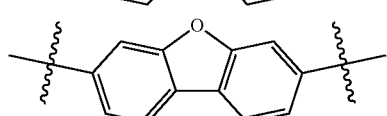
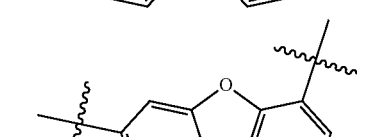
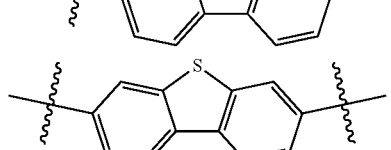
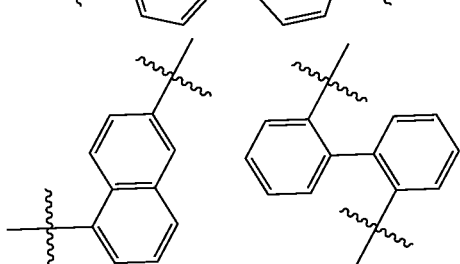
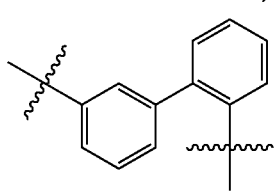
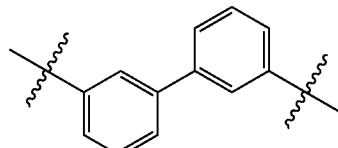
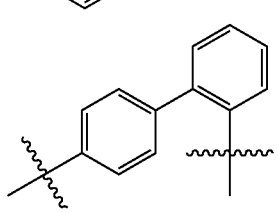
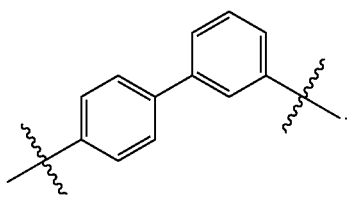
In one specific embodiment of the present disclosure, the organic compound is selected from a group consisting of the following compounds:
1
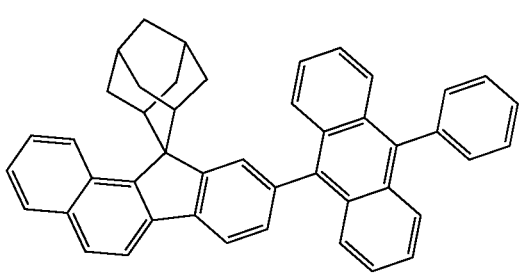
2
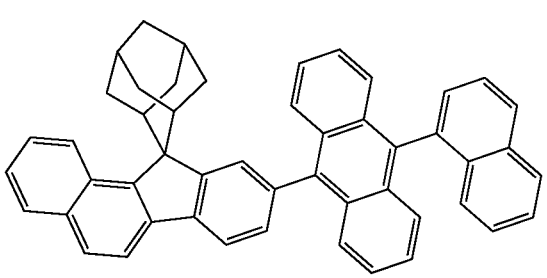
3
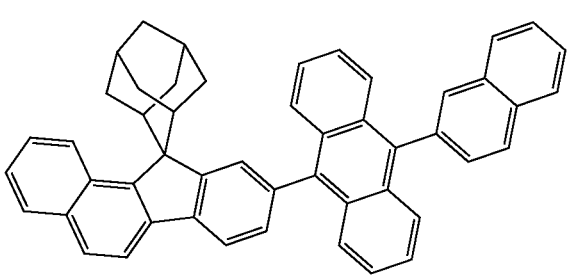
4
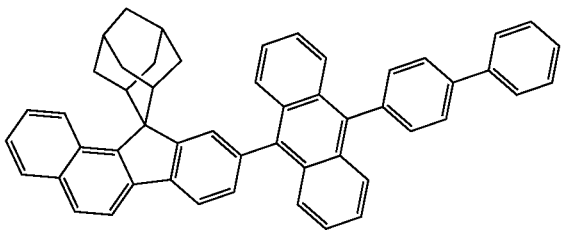

5
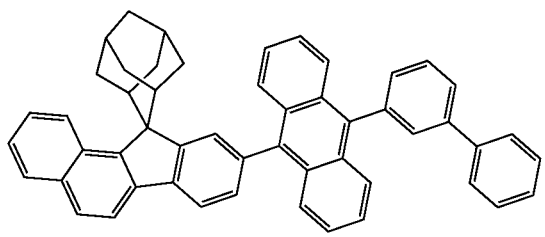
6
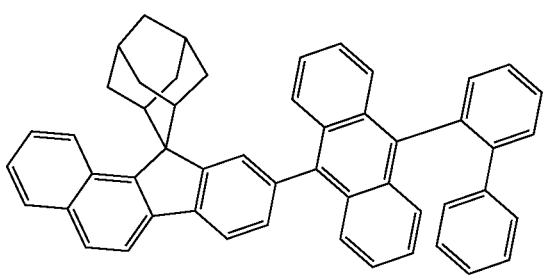
7
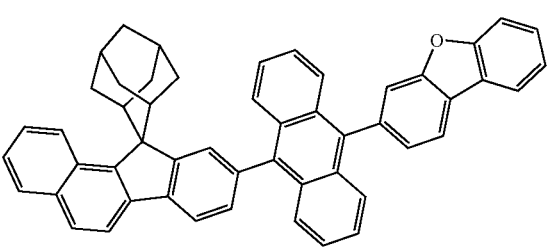
8
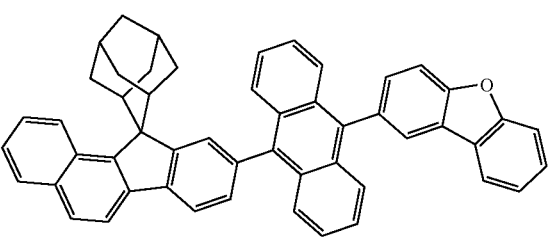
9
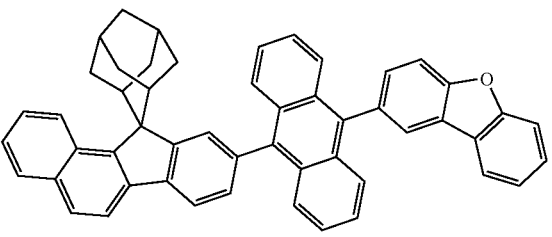
10
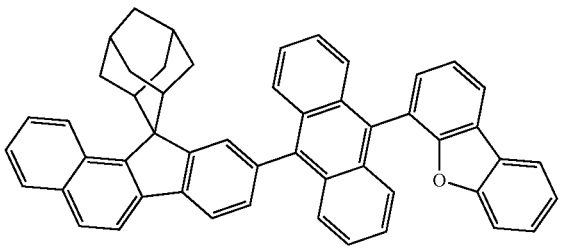
11
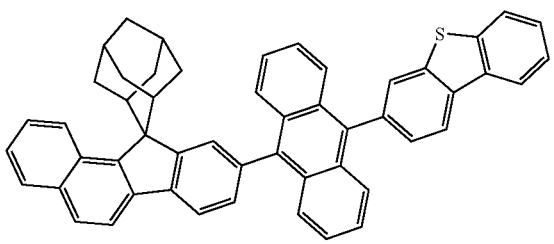
12
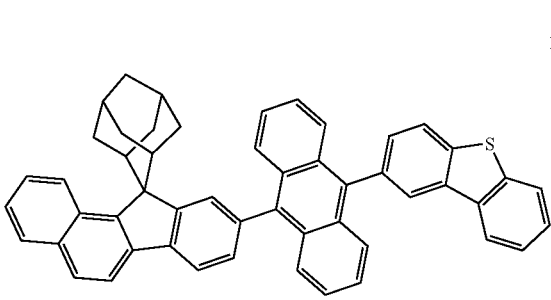
13
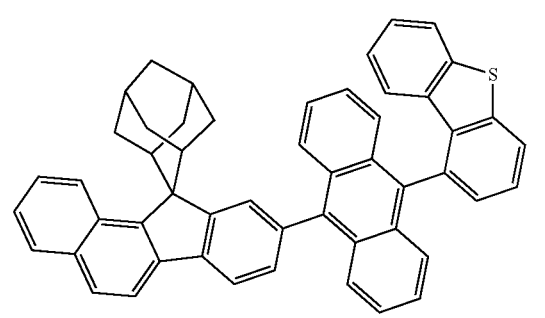
14
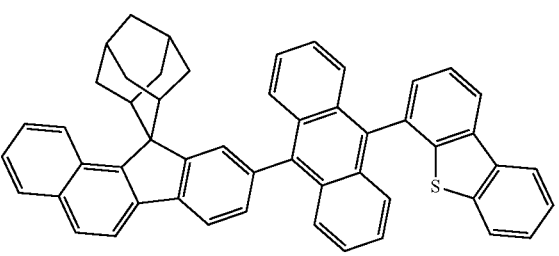
15
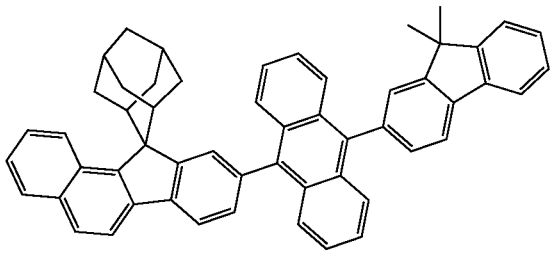

16
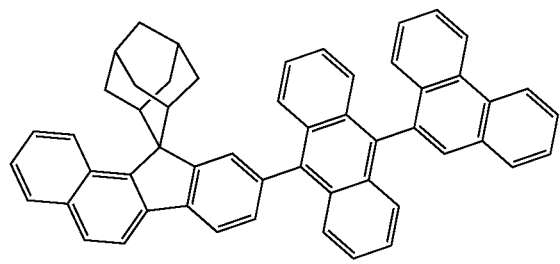
17
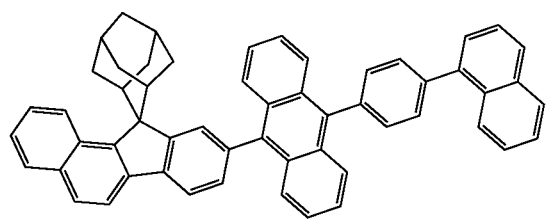
18
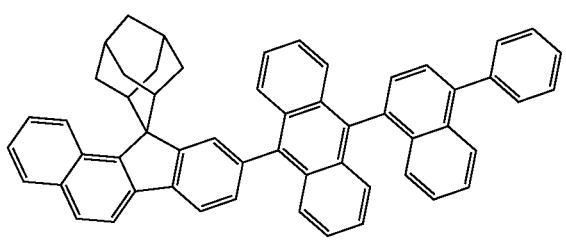
19
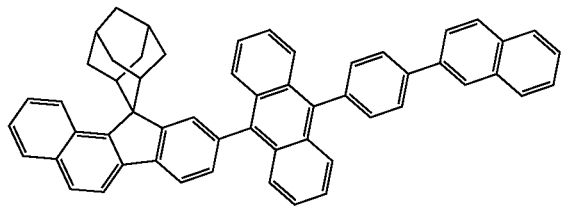
20
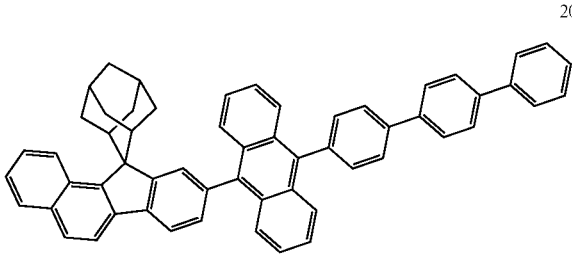
21
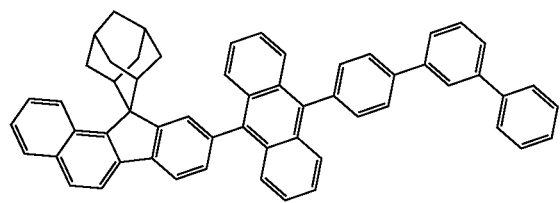
22
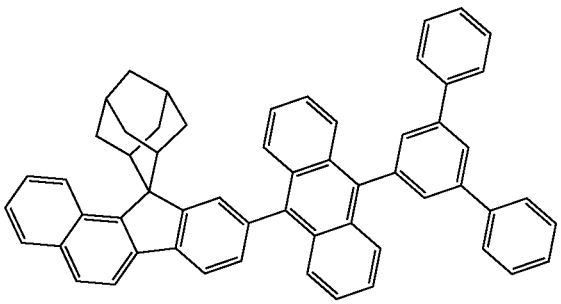
23
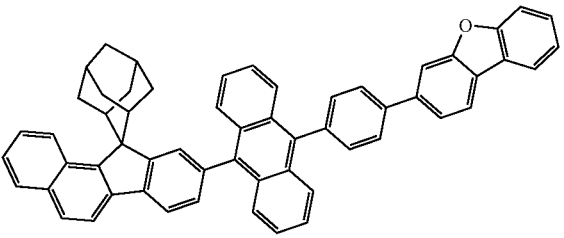
24
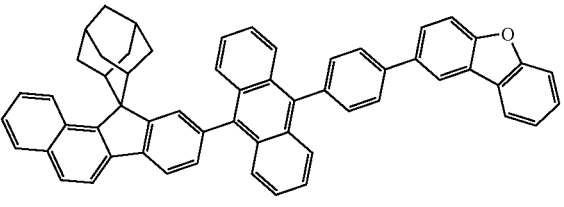
25
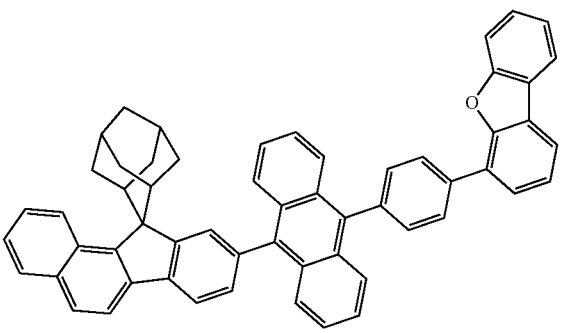
26
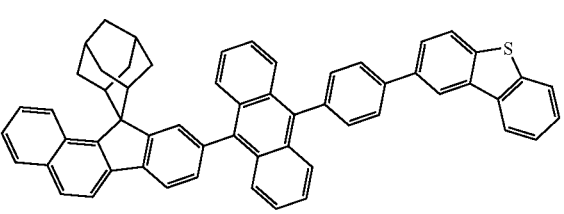

27
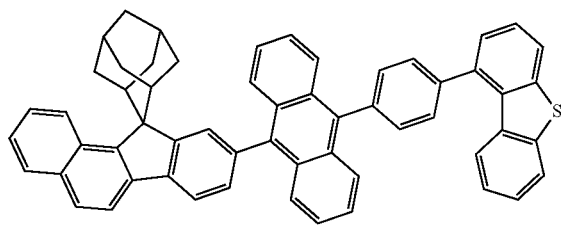
28
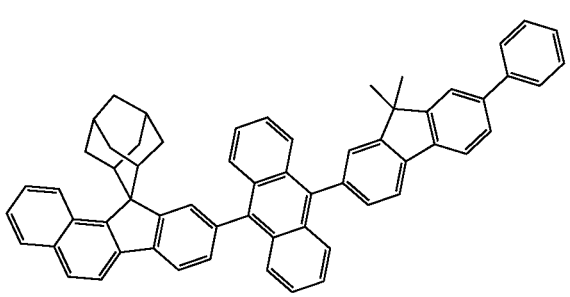
29
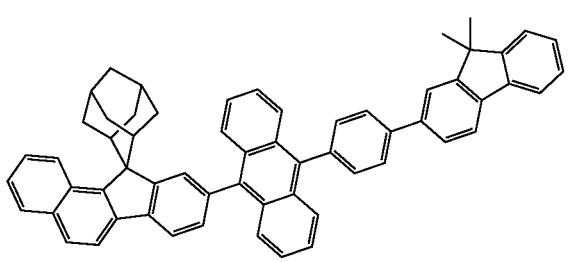
30
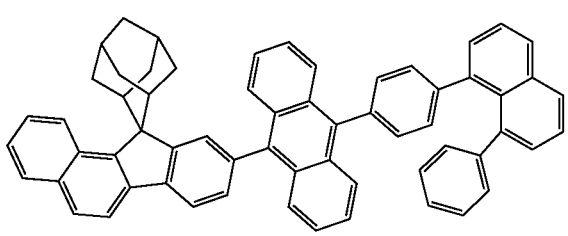
31
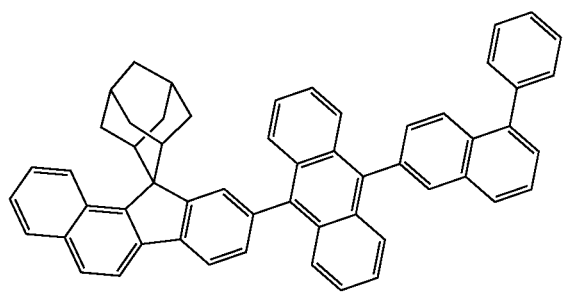
32
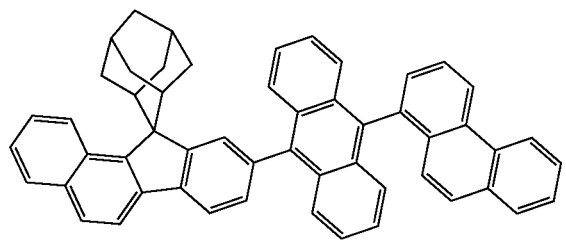
33
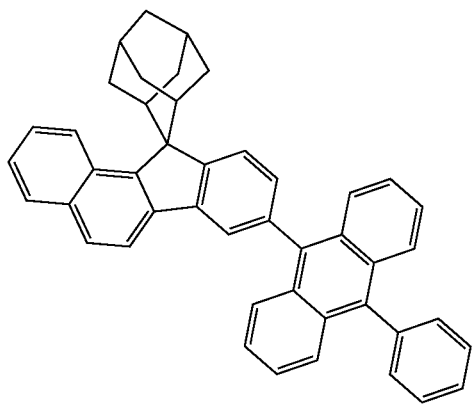
34
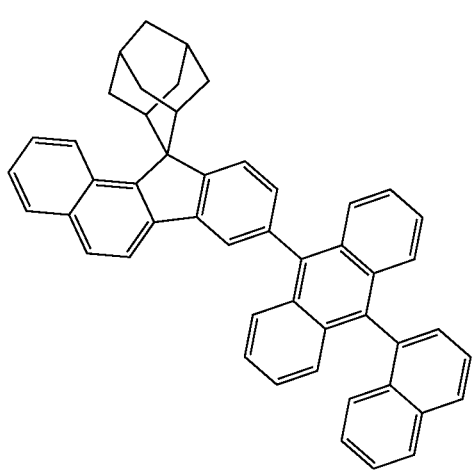
35
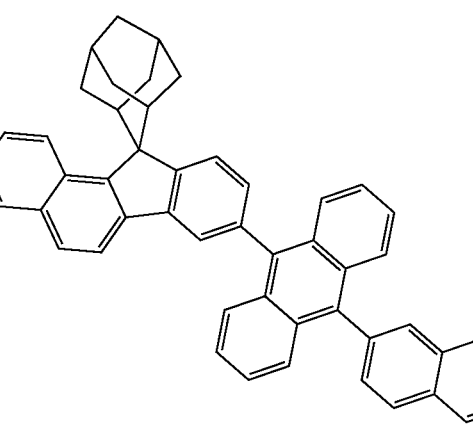

36
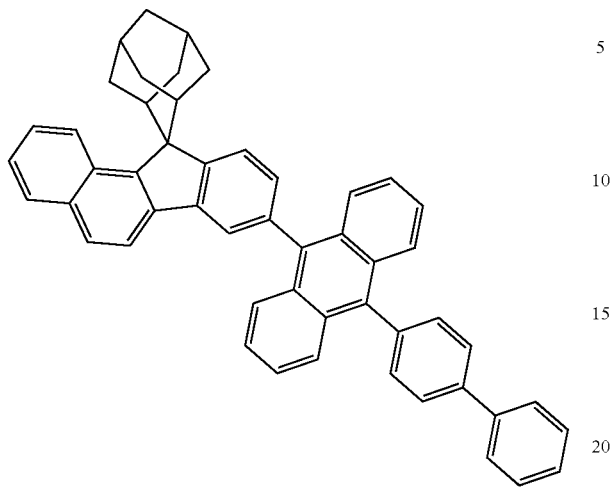
37
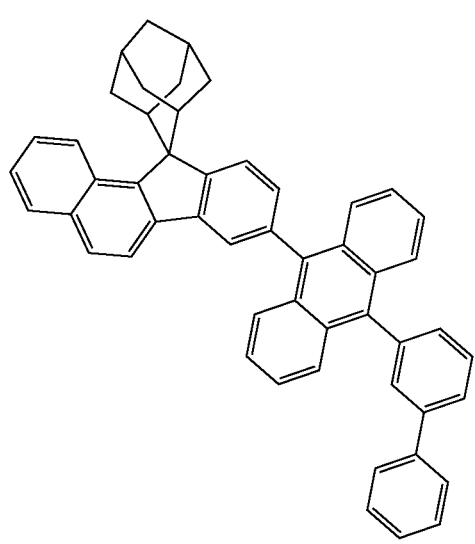
38
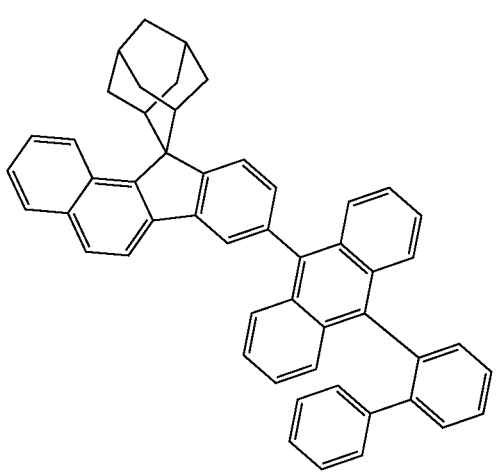
39
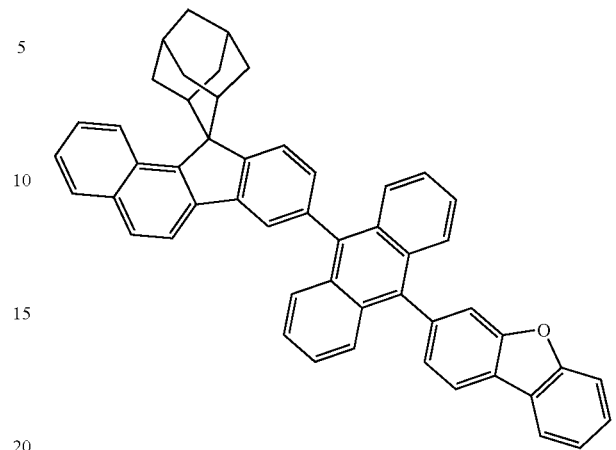
40
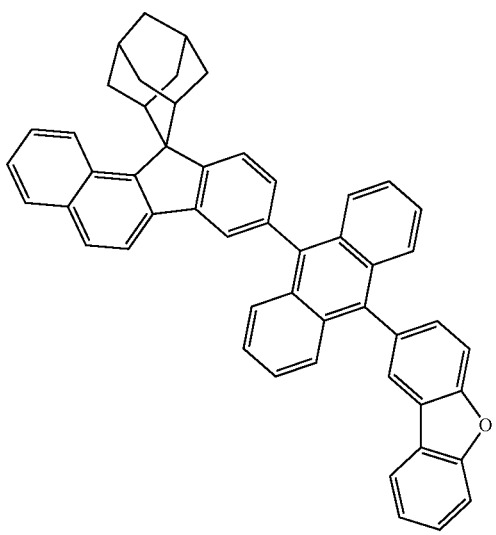
41
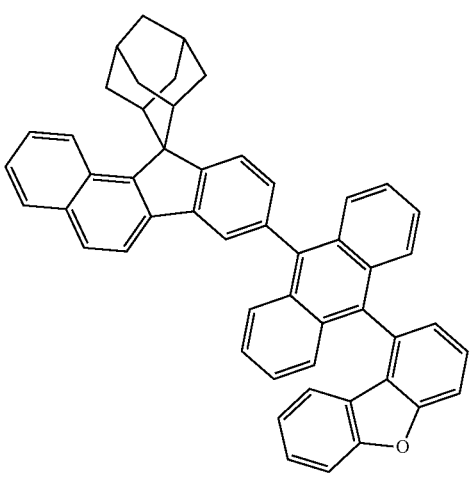

42
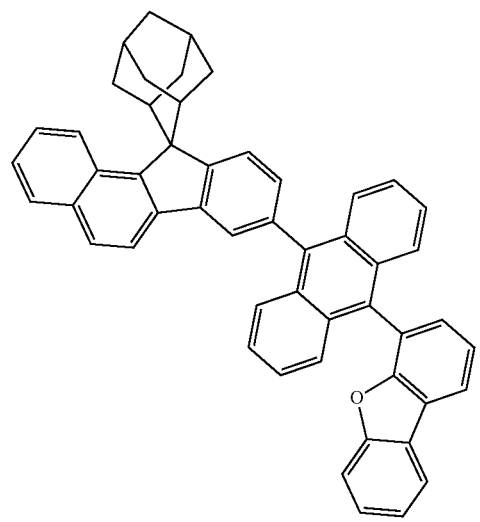
43
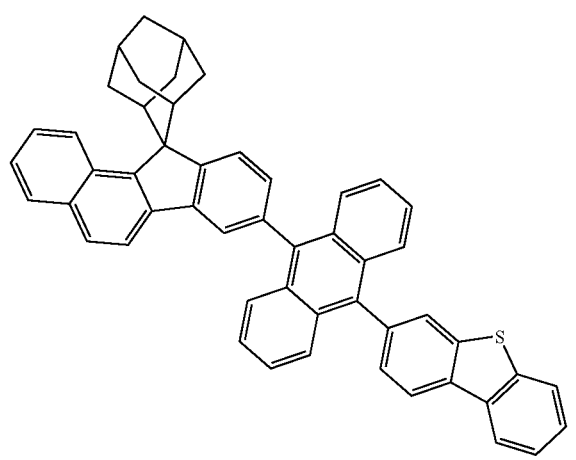
44
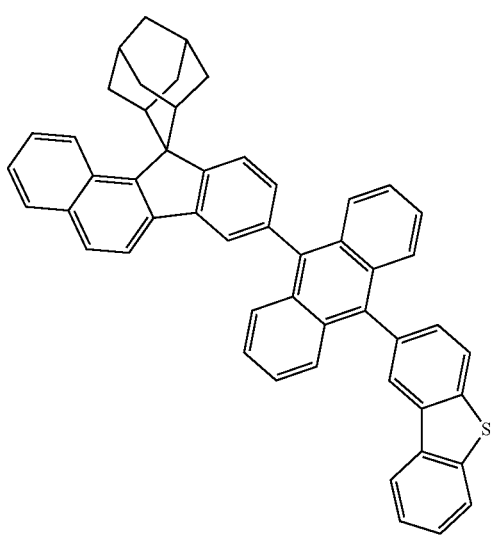
45
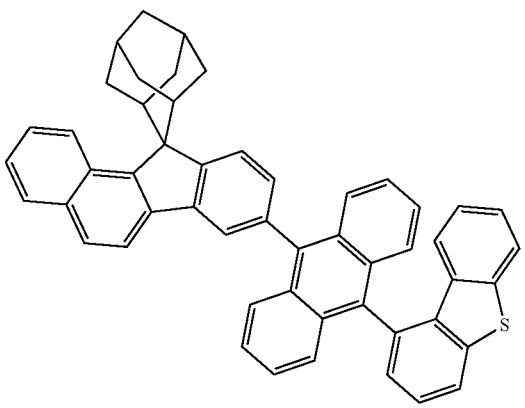
46
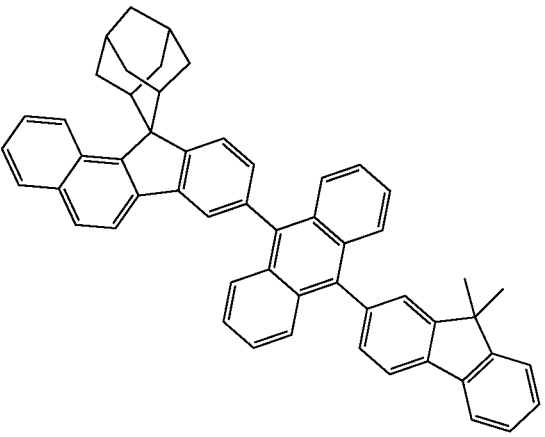
47

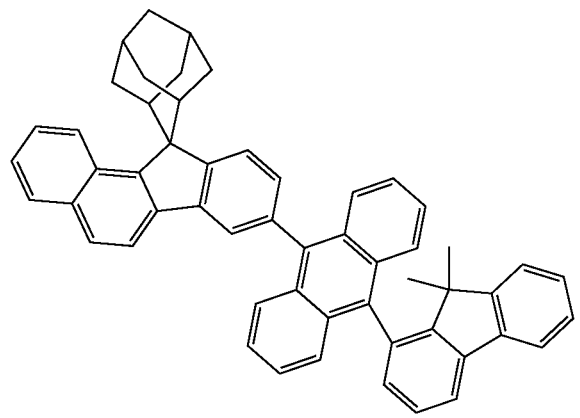
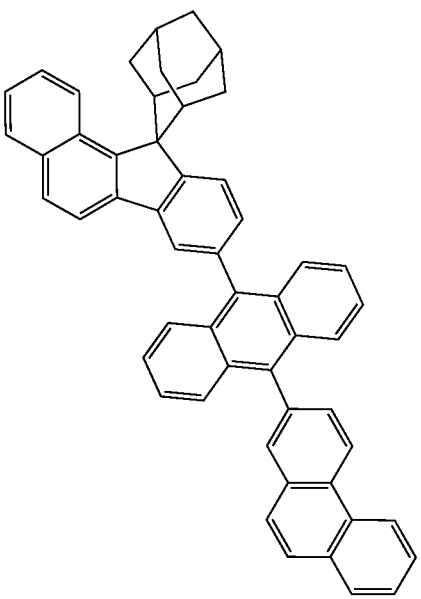
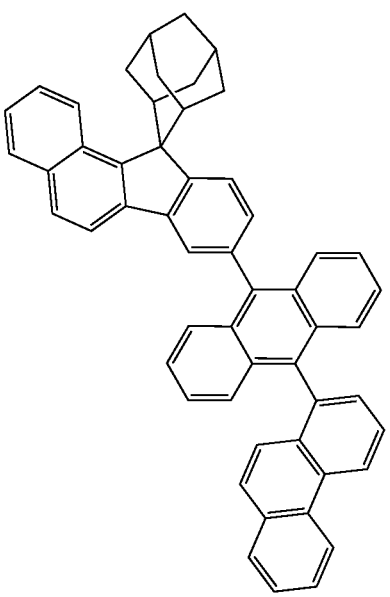

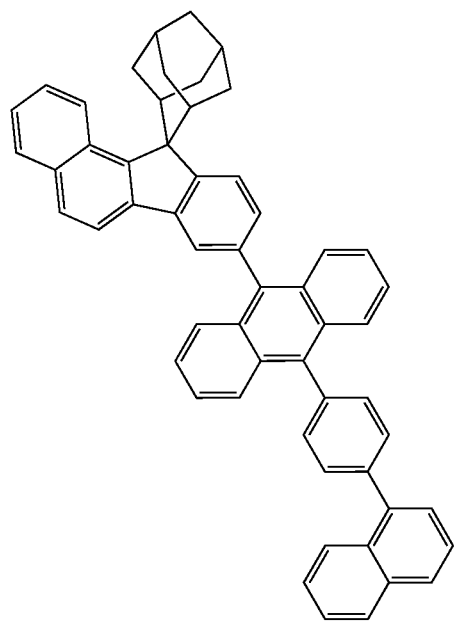
53
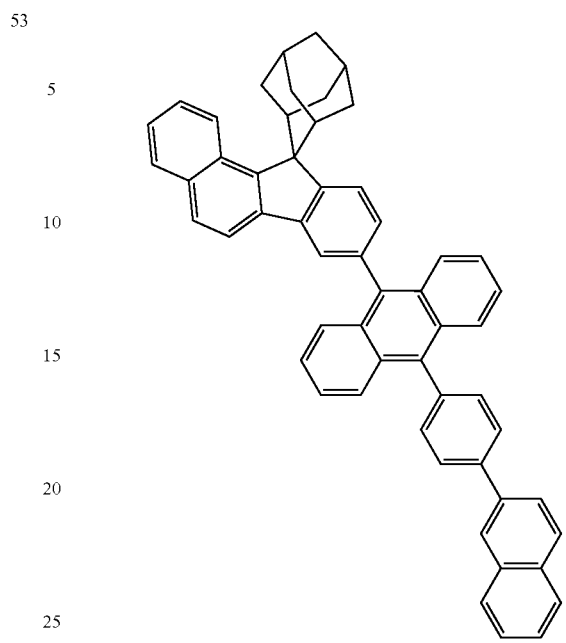
55
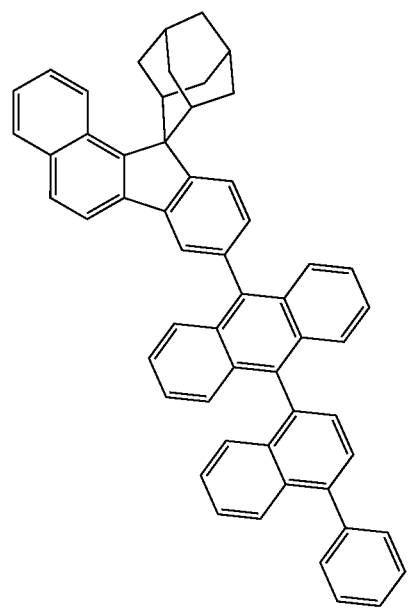
54
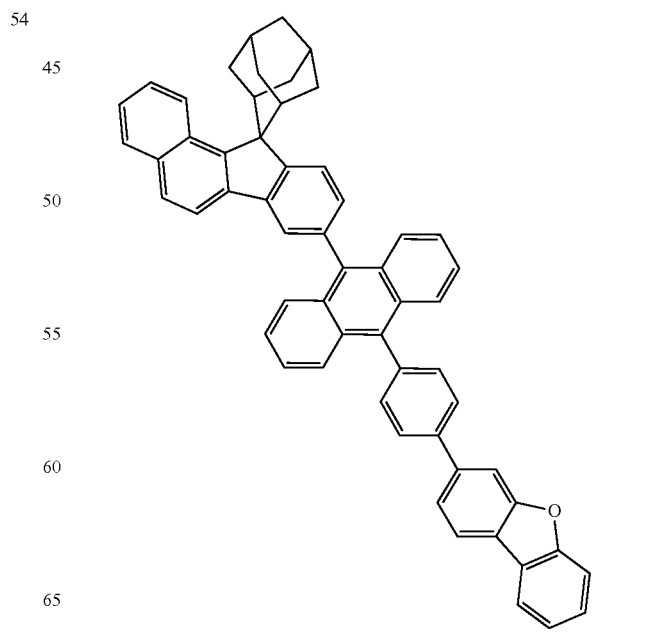
56

57
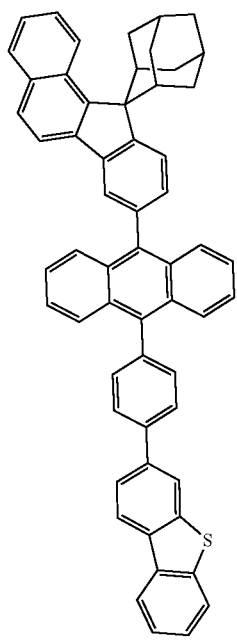
58
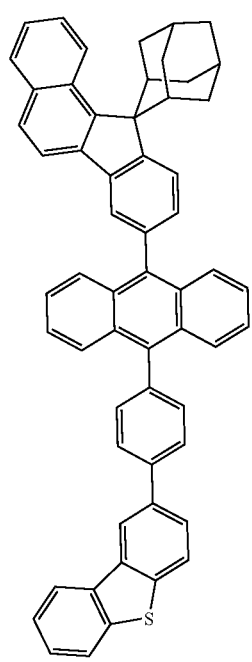
59
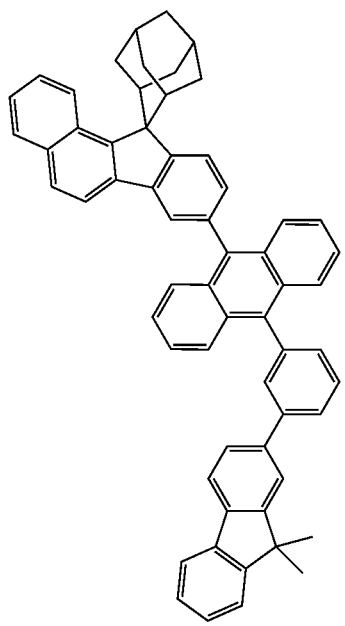
60
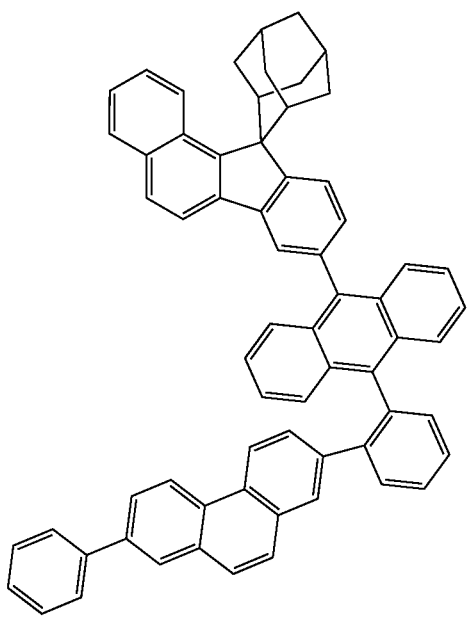

61
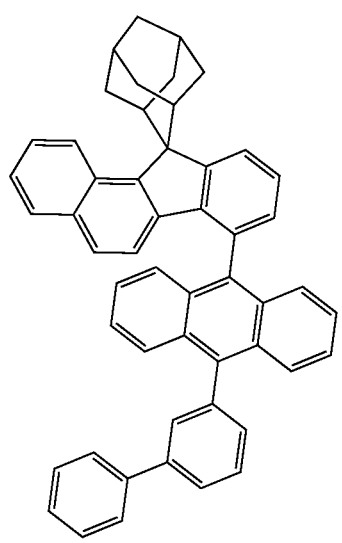
62
63
64
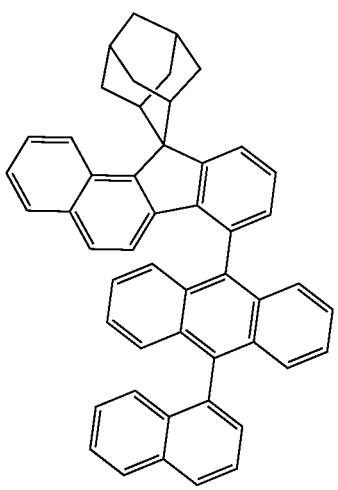
65
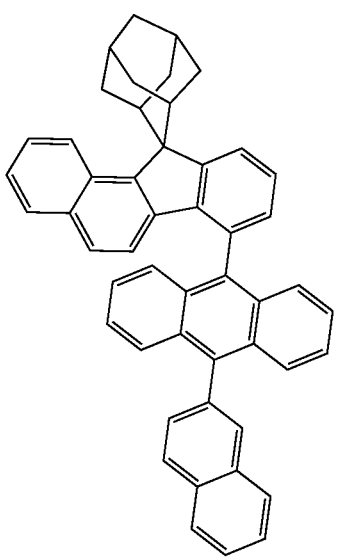
66
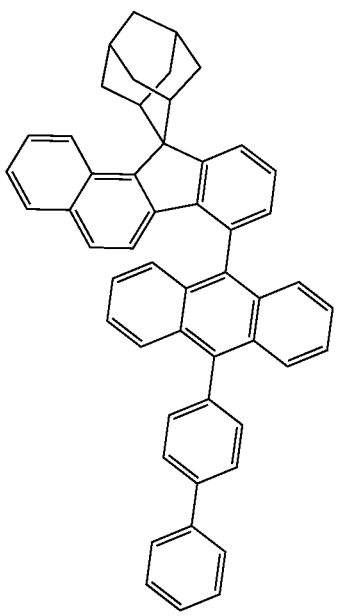

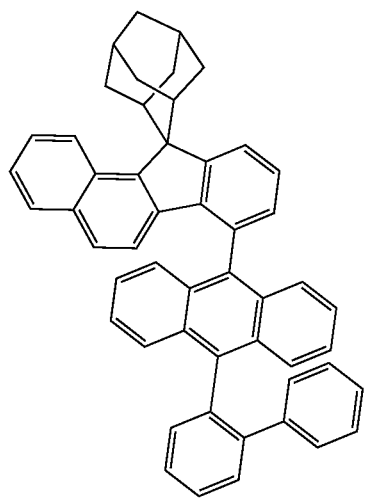
67
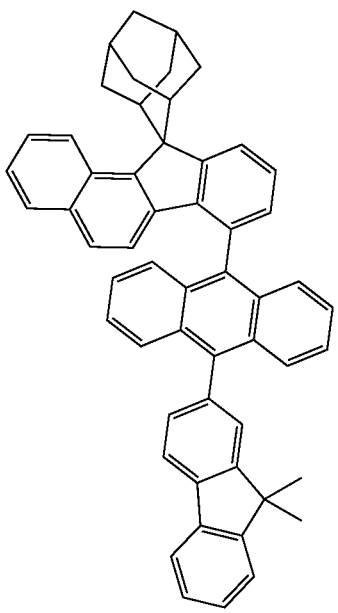
69
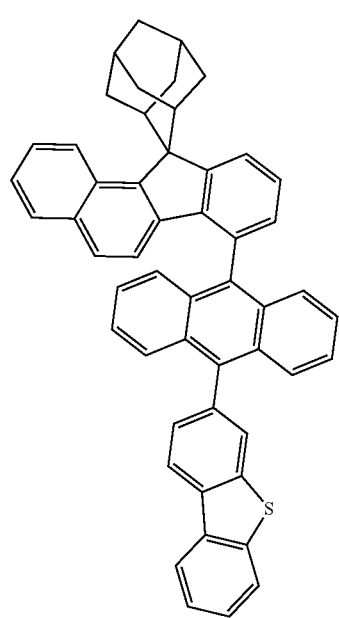
68
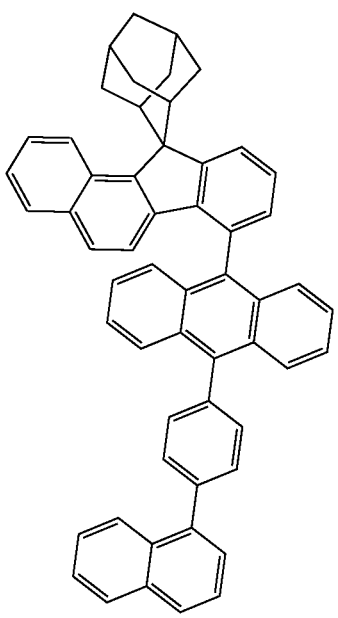
70

-continued
71
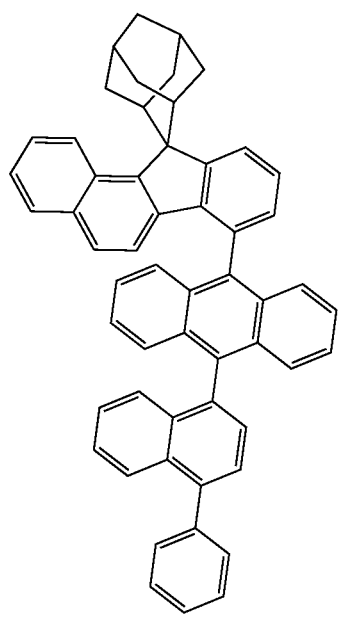
72
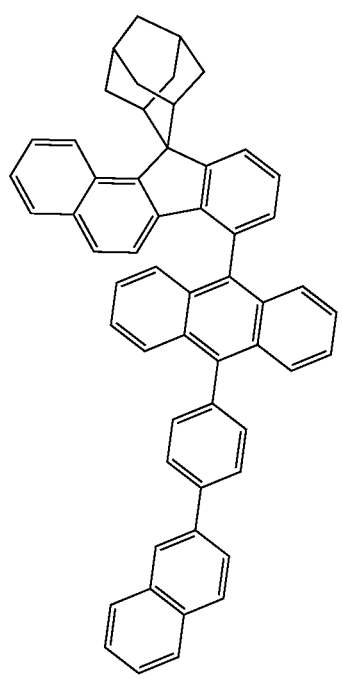
73
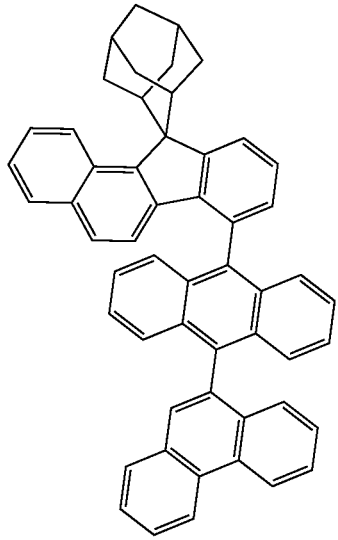
74
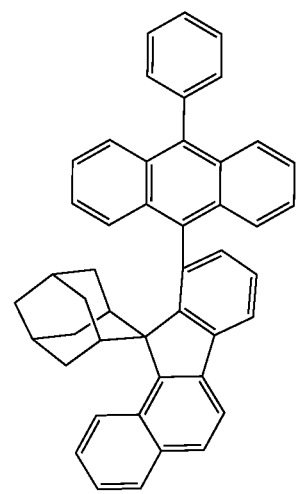
75
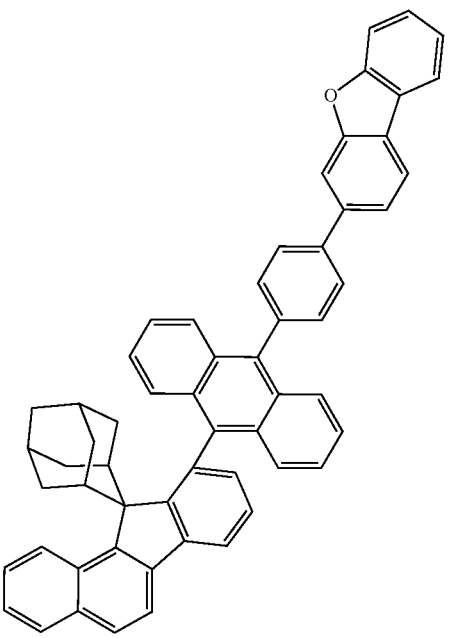

76
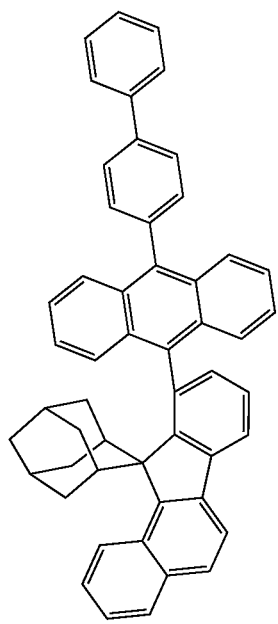
77
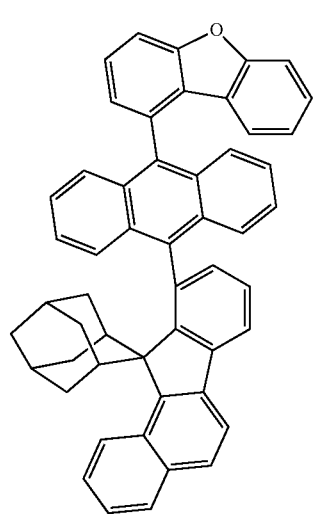
78
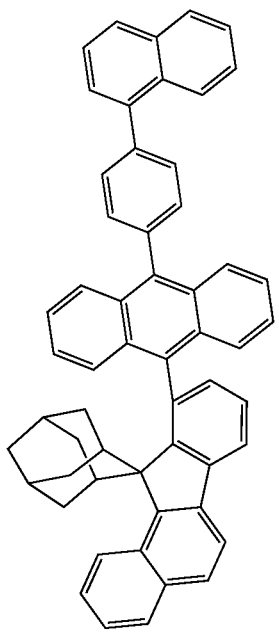
79

80
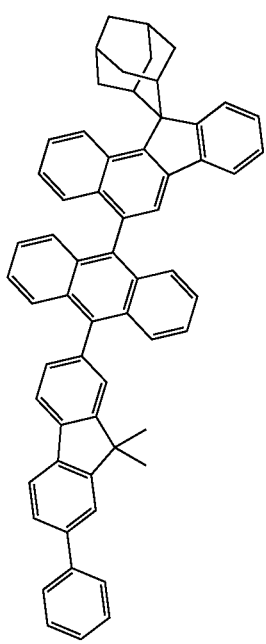
82
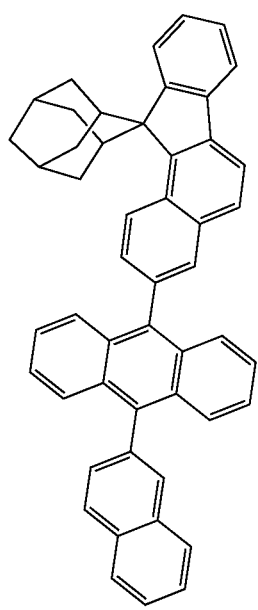
81
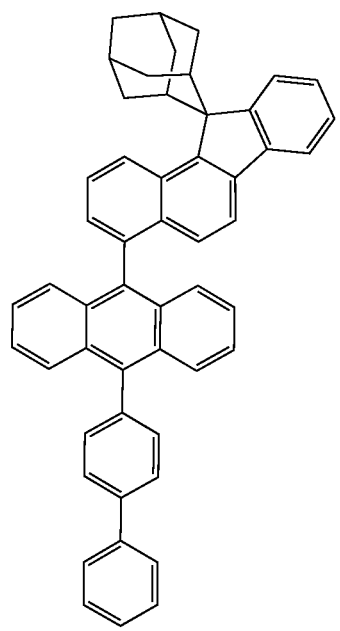
83
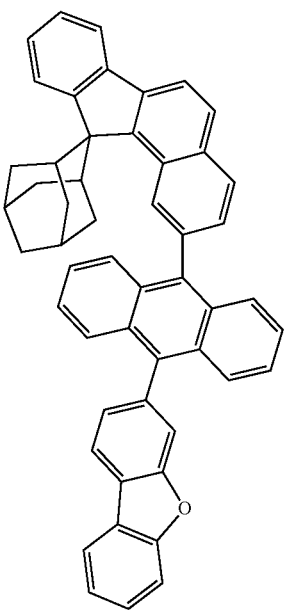

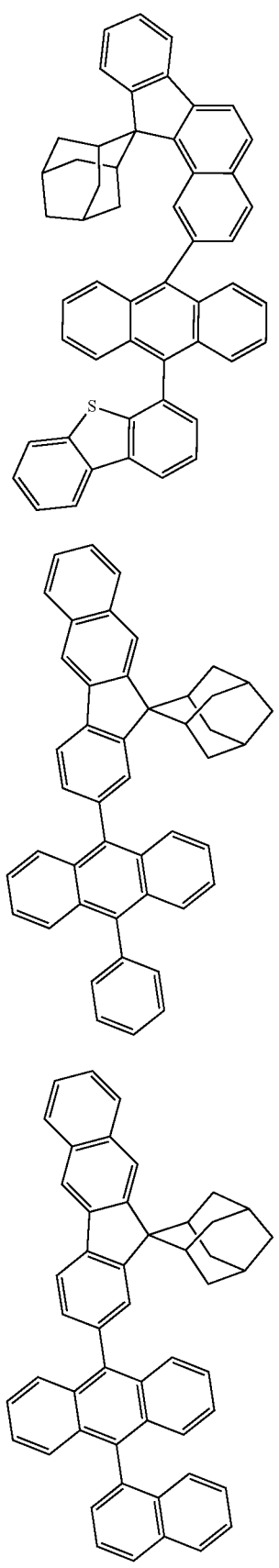

89
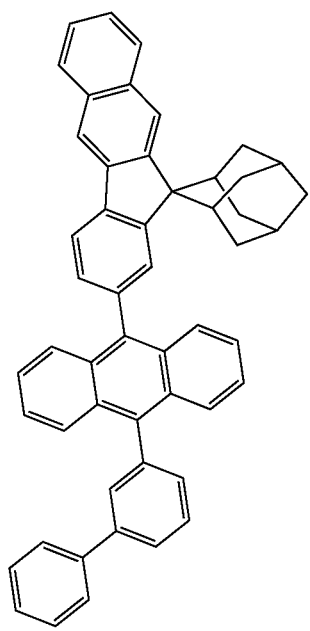
90
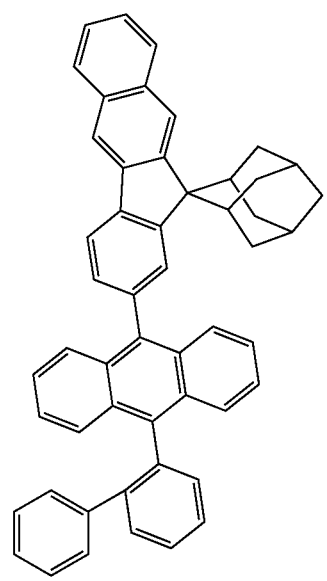
91
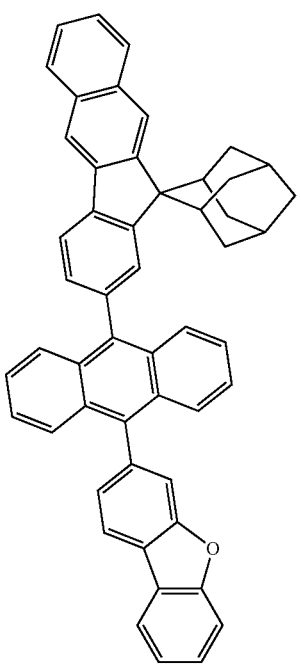
92
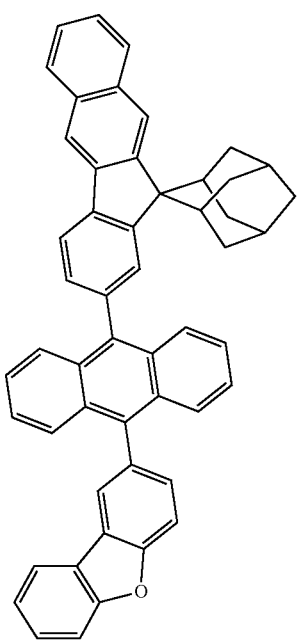

93
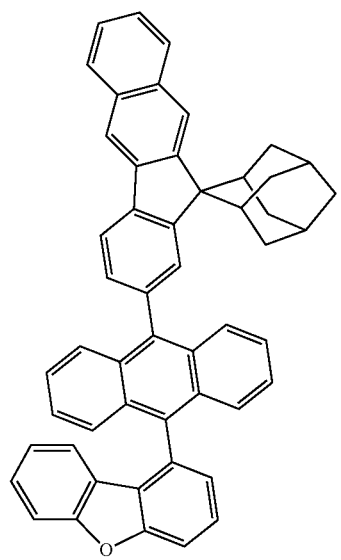
95
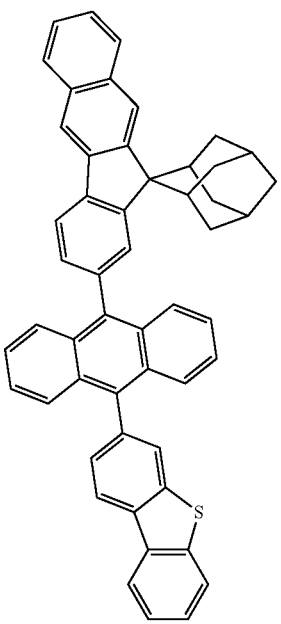
94
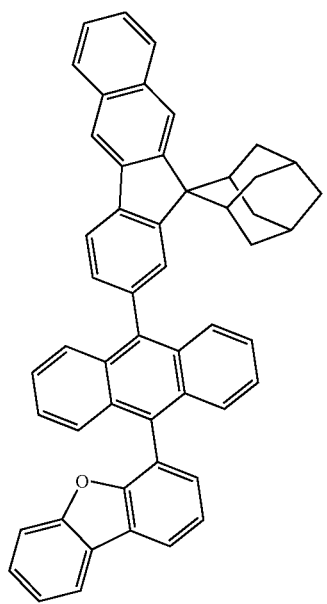
96
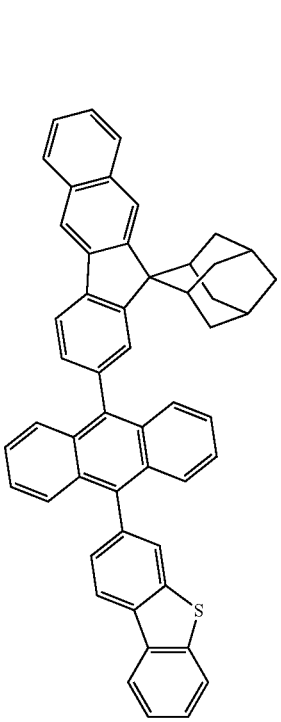

97
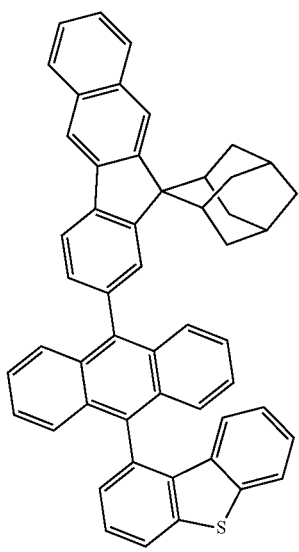
98
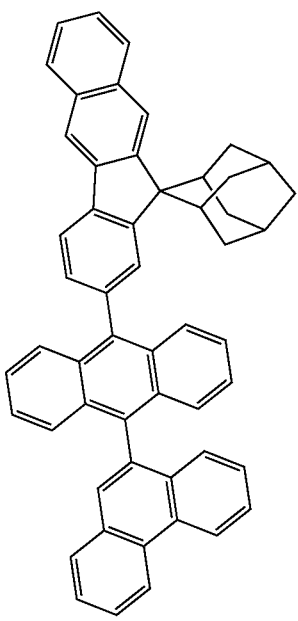
99
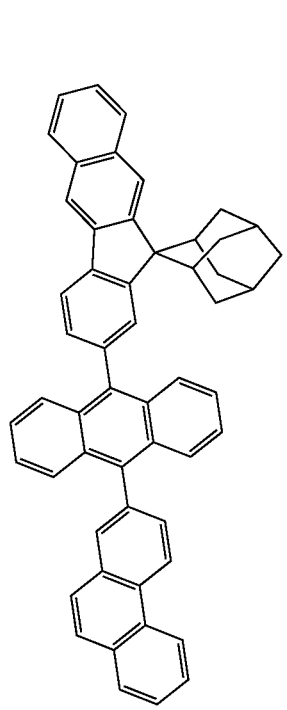
100

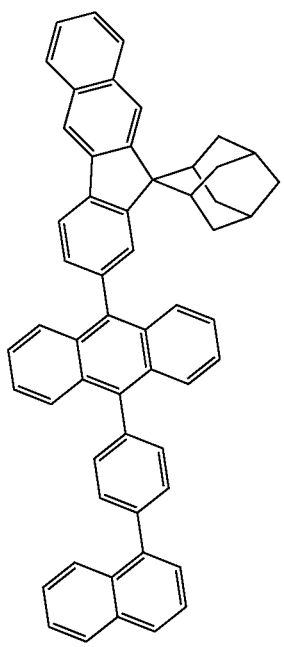
101
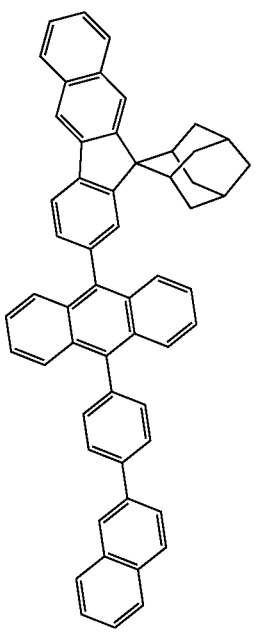
103
102
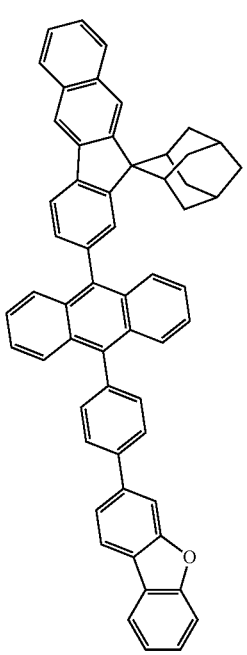
104

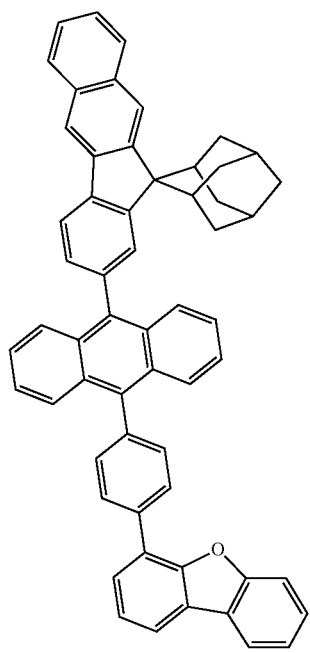
105
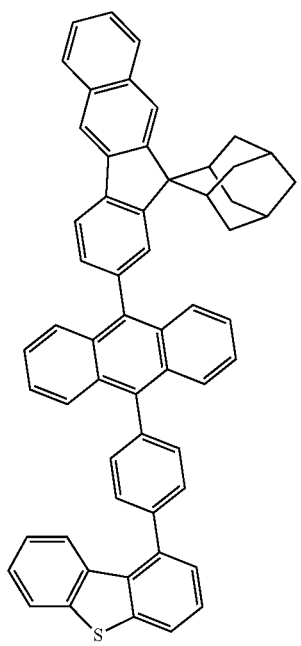
107
106
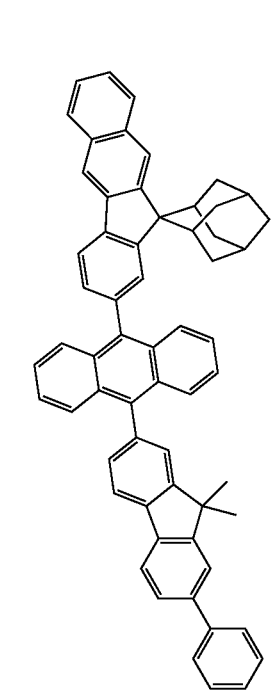
108

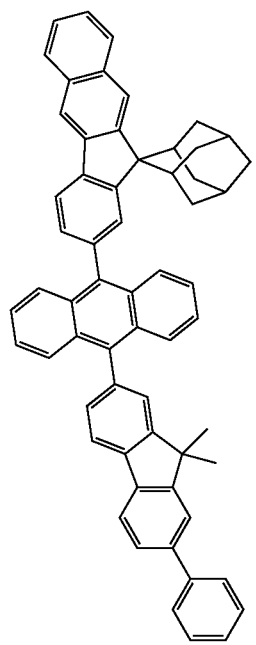
109
110
111
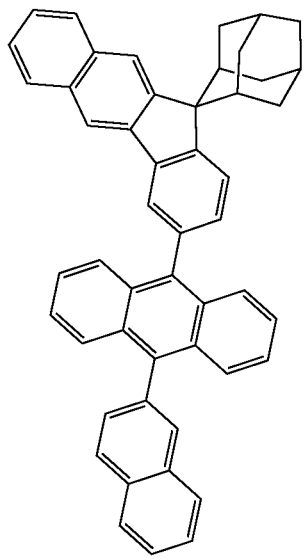
112
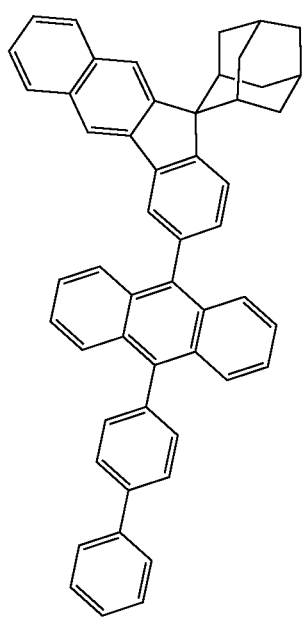
113

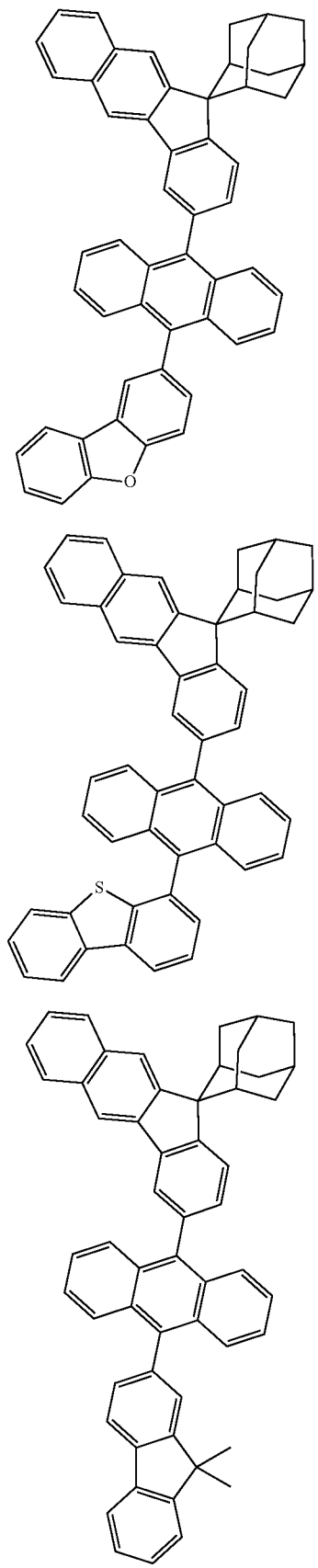
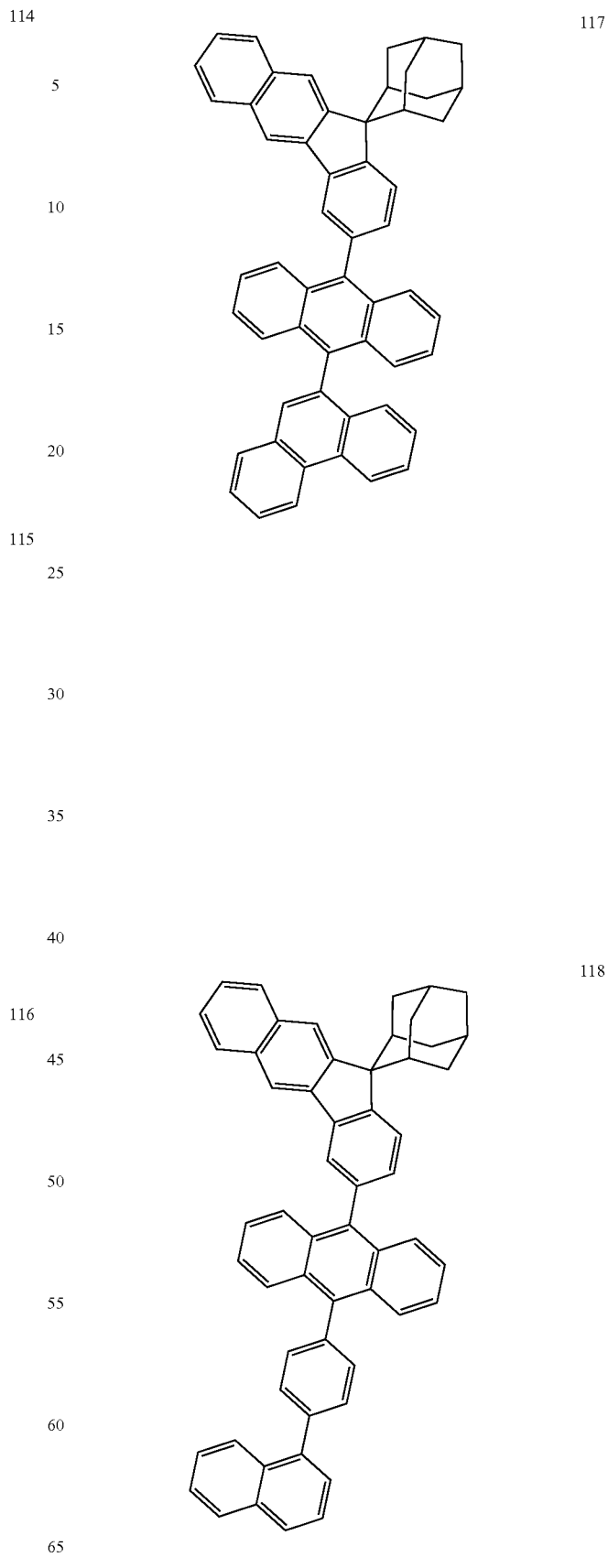

83
-continued
119
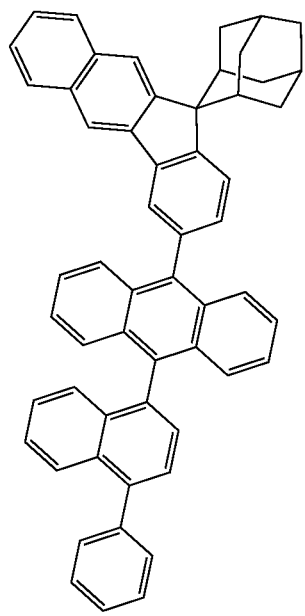
120
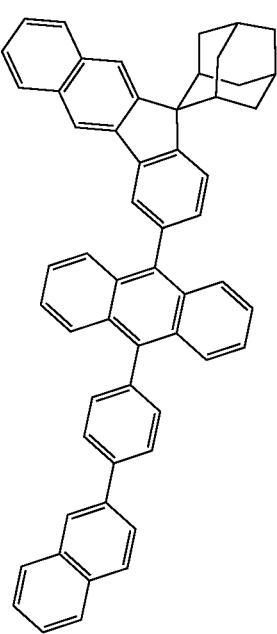
84
-continued
121
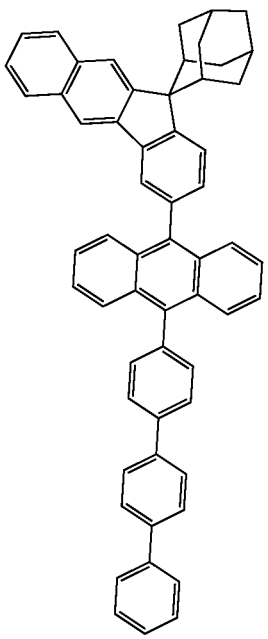
122
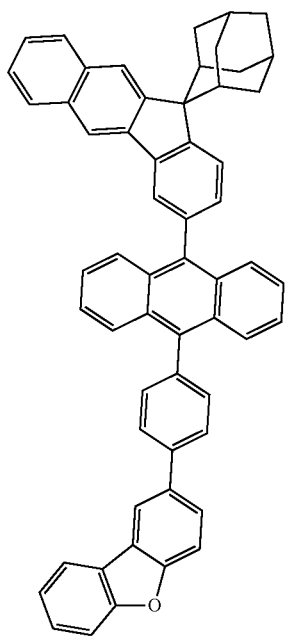

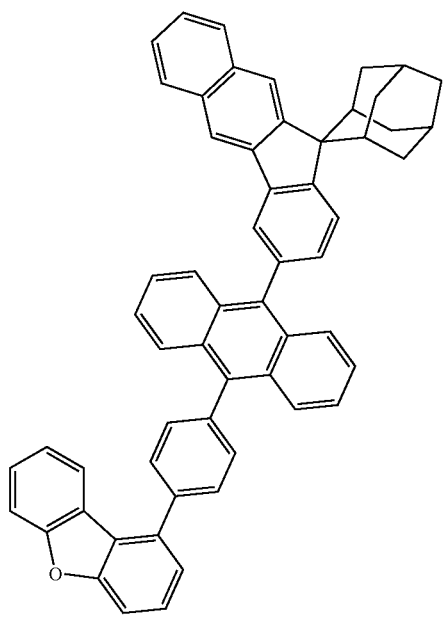
123
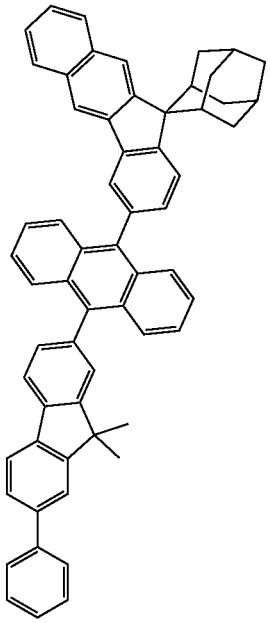
125
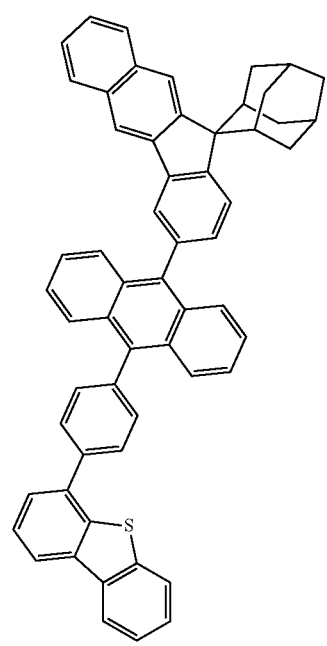
124
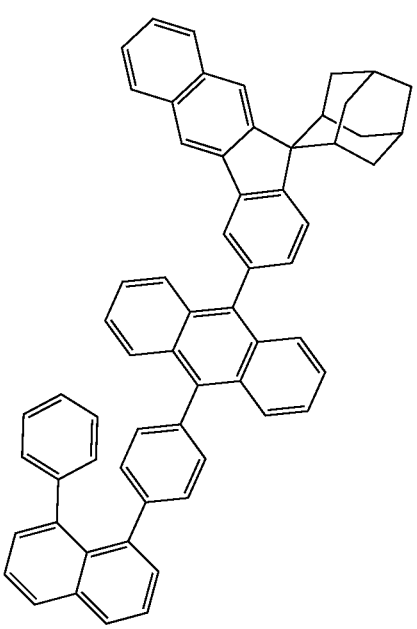
126

127
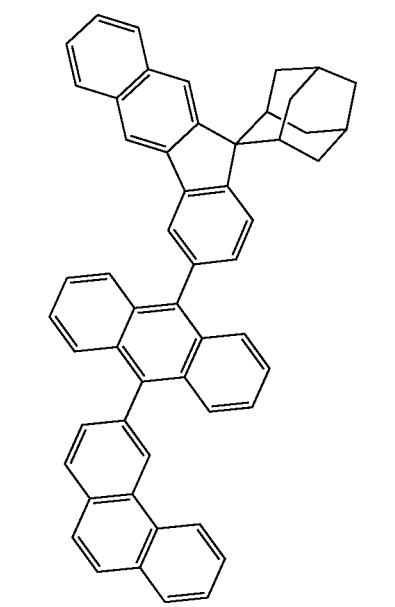
128
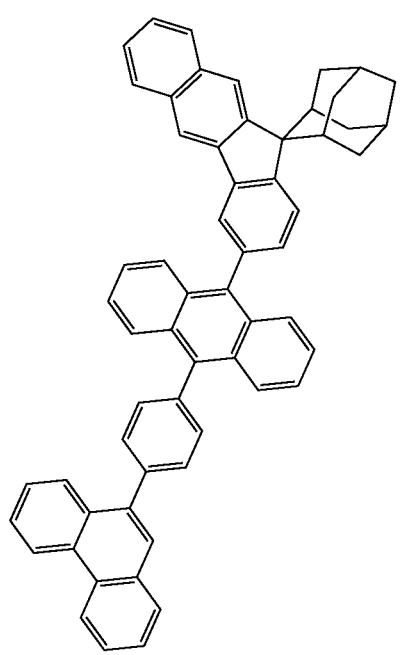
129
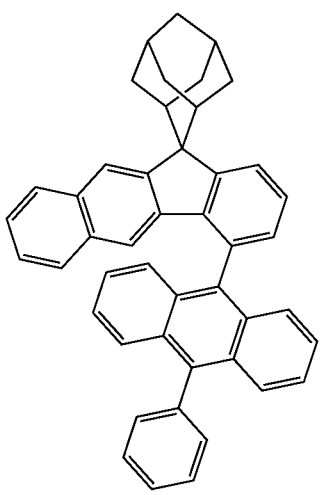
130
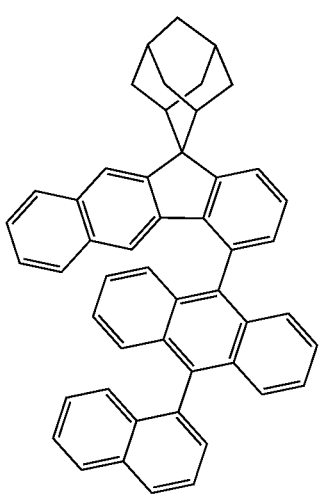
131
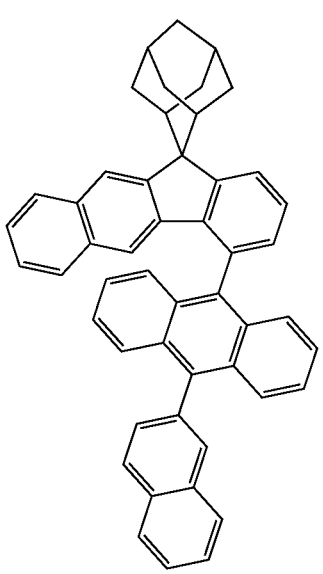

132
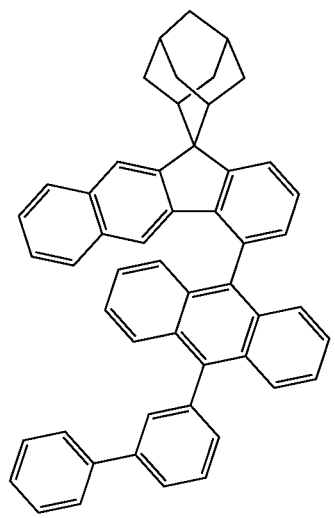
133
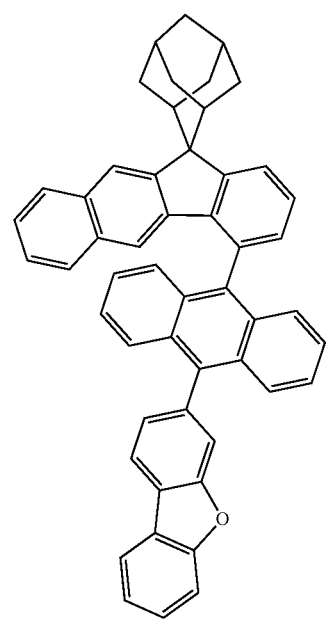
134
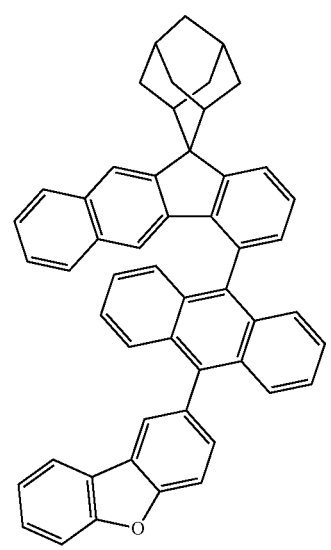
135
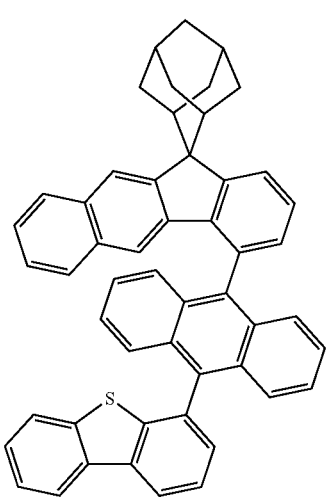
136
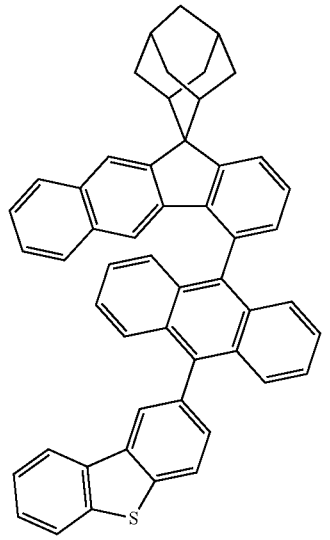
137
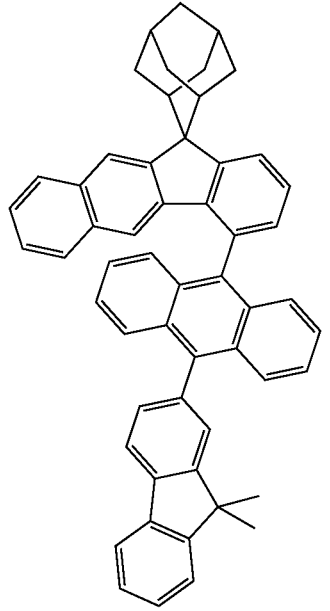

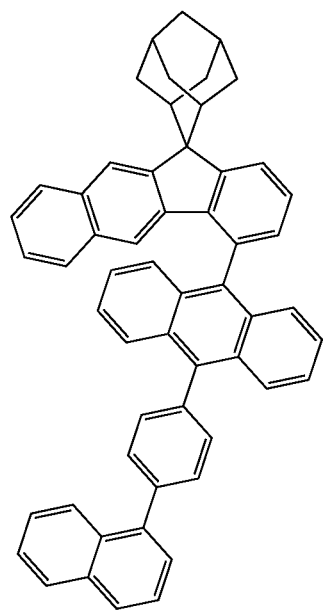
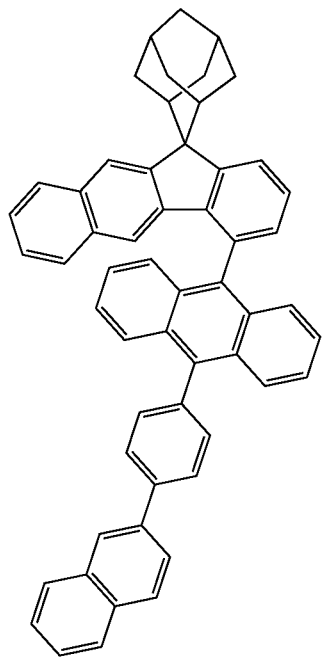

93
-continued
142
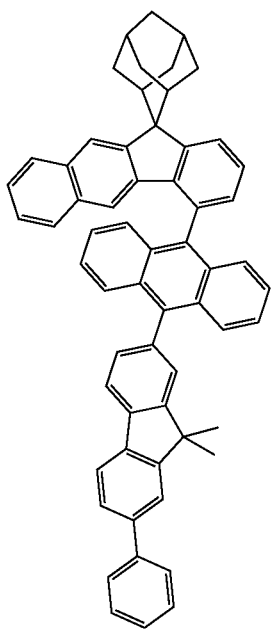
143
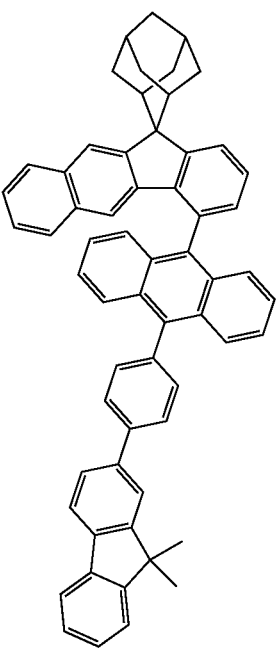
94
-continued
144
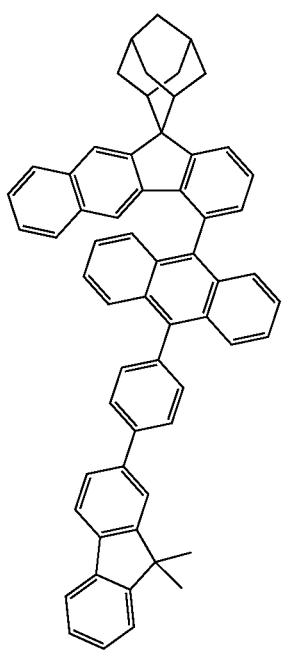
145
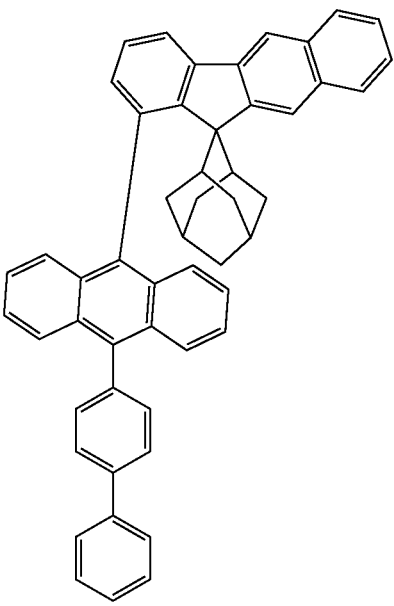

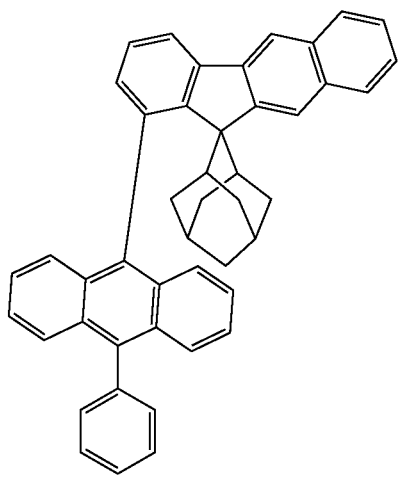
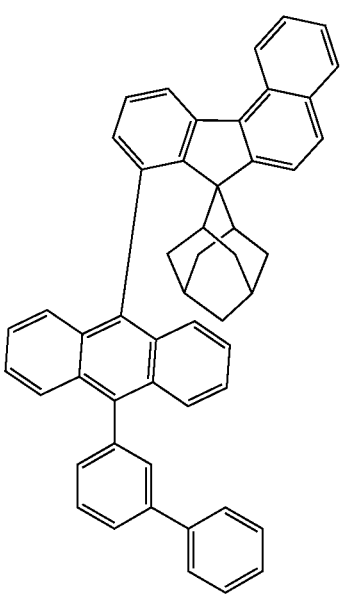
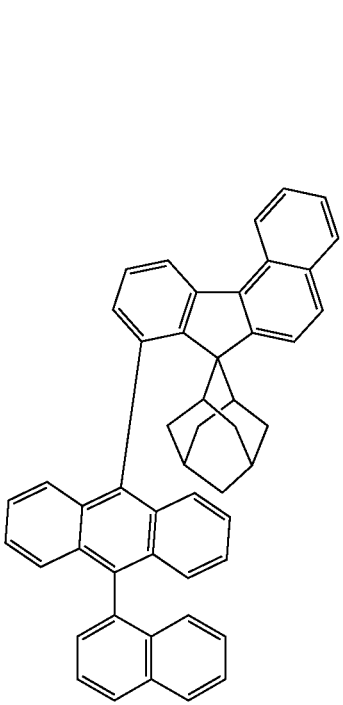

151
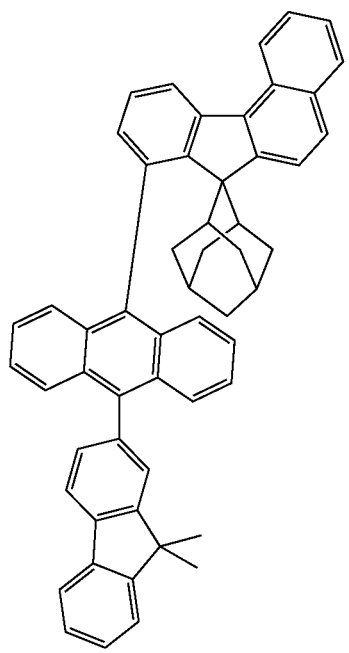
152
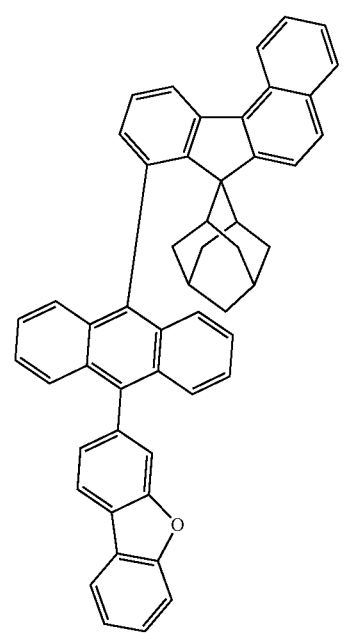
153
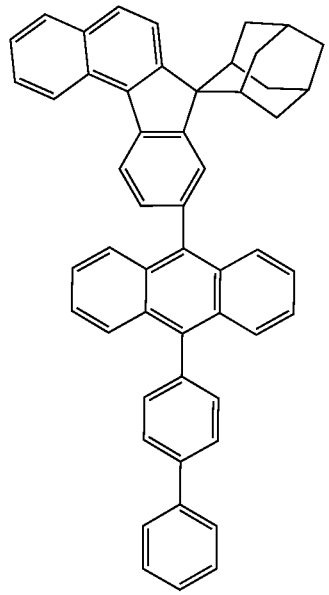
154
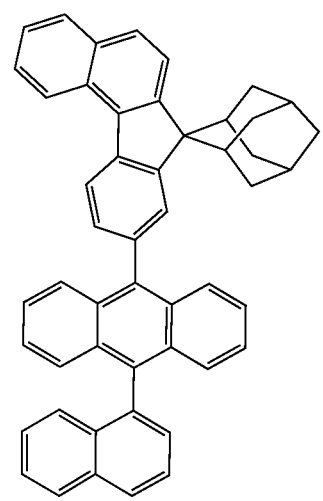
155
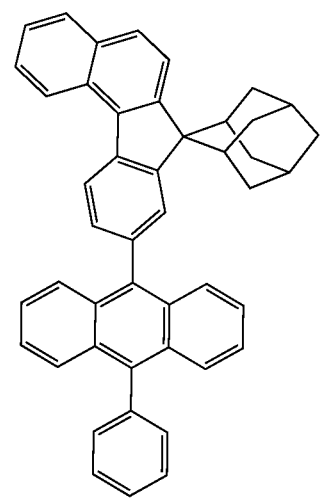

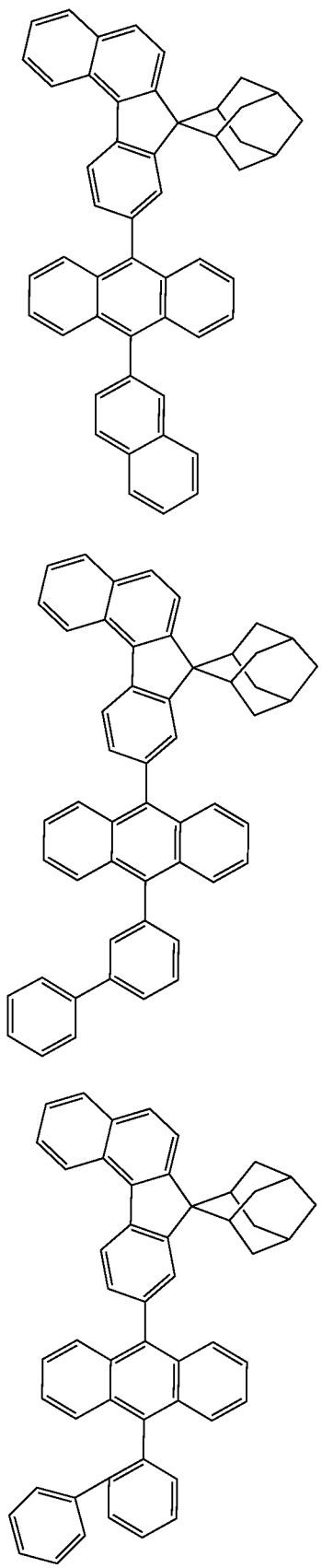

101
-continued
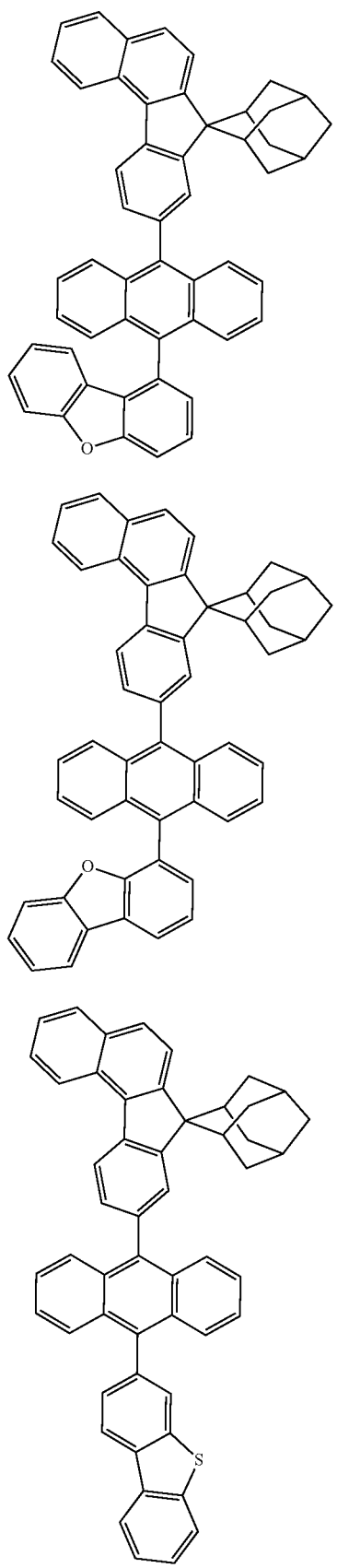
102
-continued
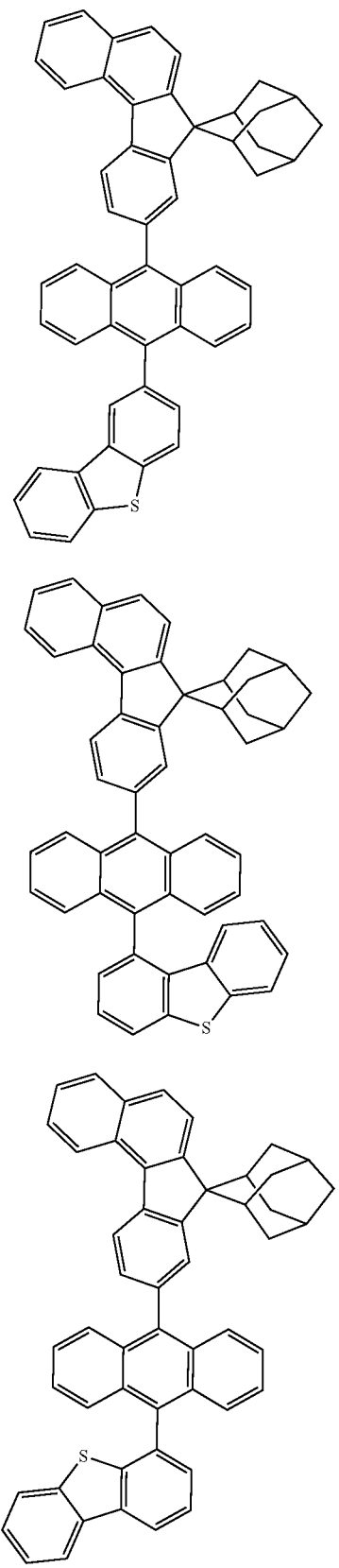

103
-continued
167
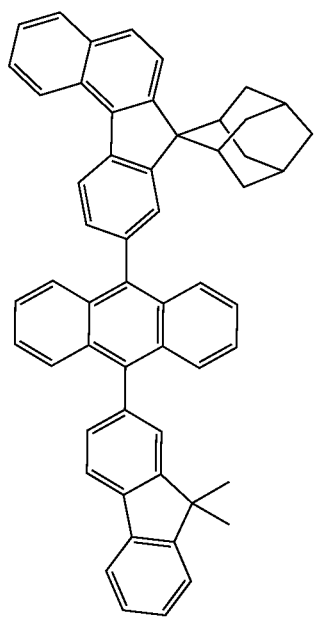
168
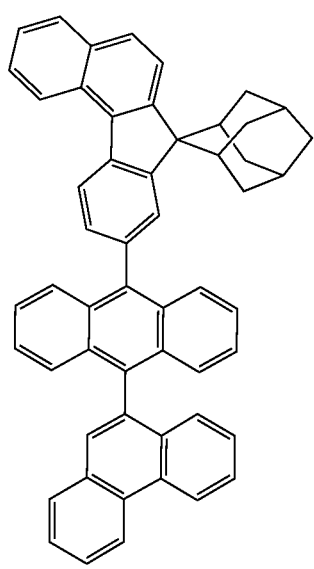
104
-continued
169
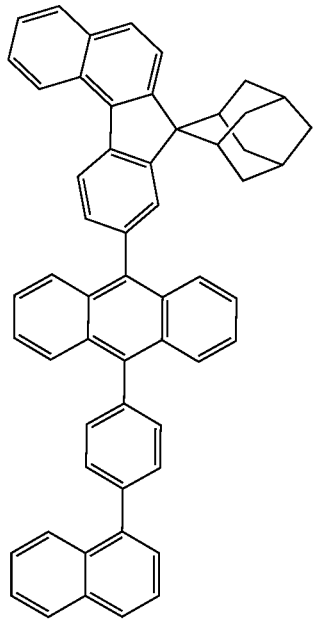
170
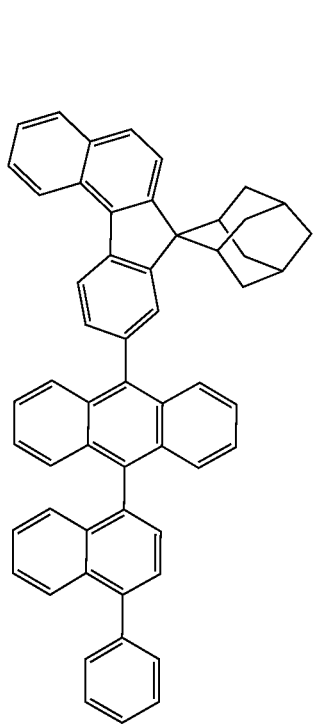

105
-continued
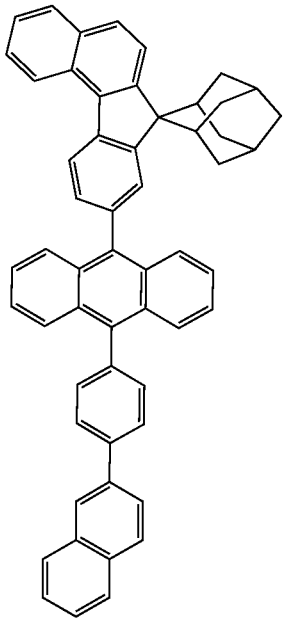
171
106
-continued
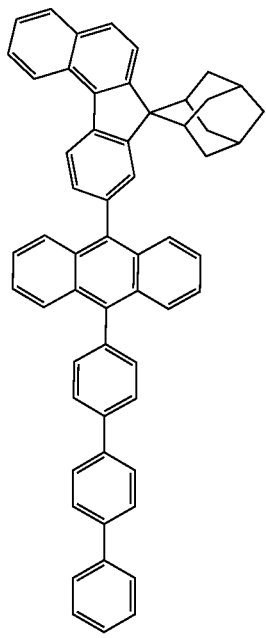
173
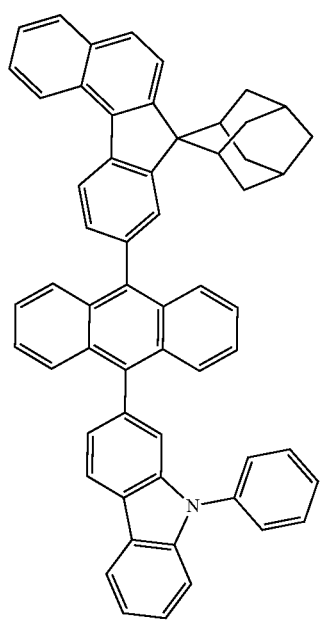
172
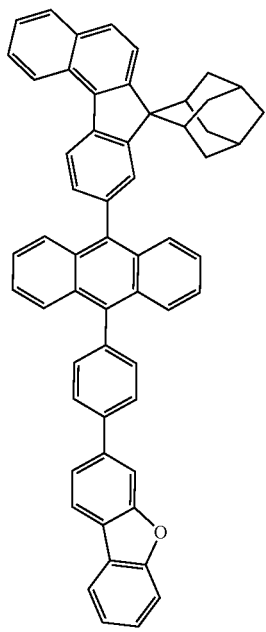
174

107
-continued
175
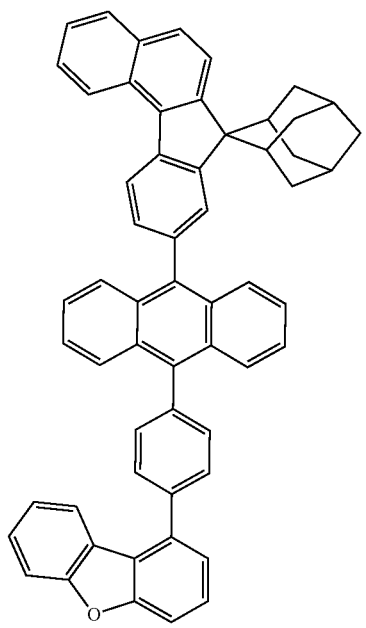
176
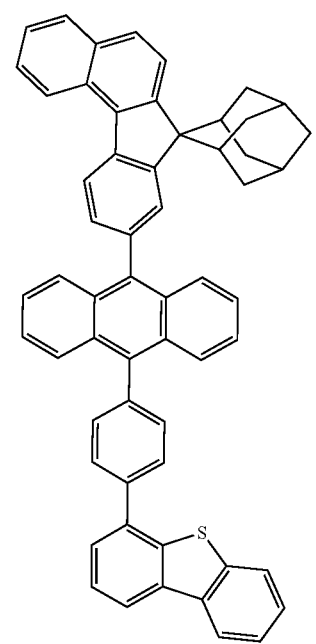
108
-continued
177
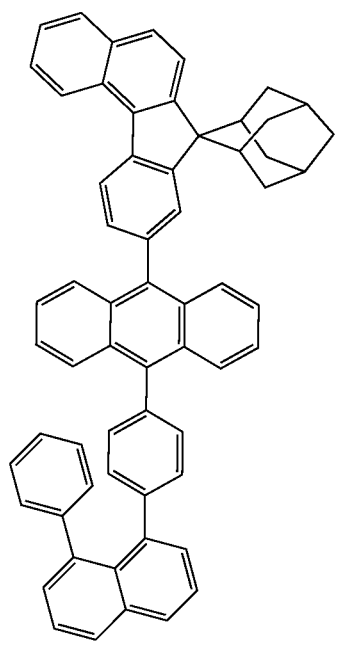
178
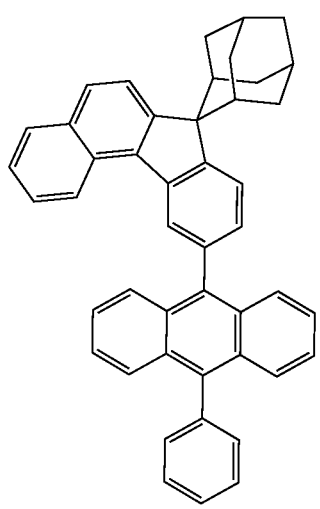
179
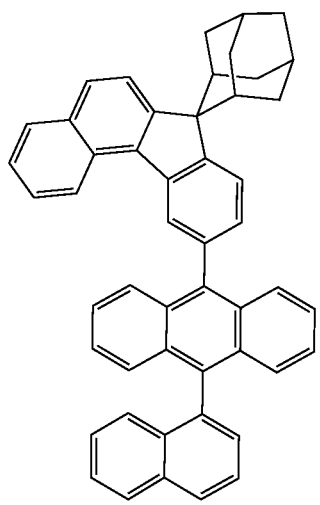

109
-continued
180
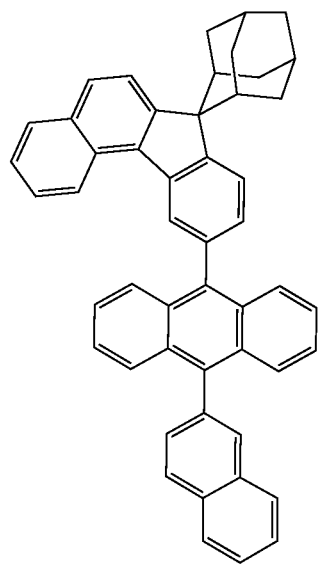
181
110
-continued
182
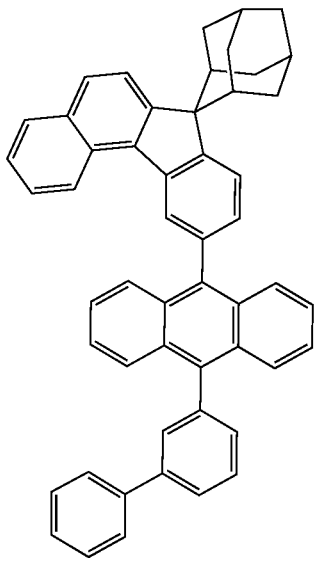
183

184
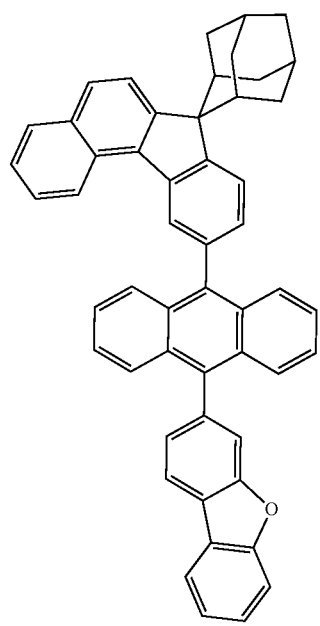
185
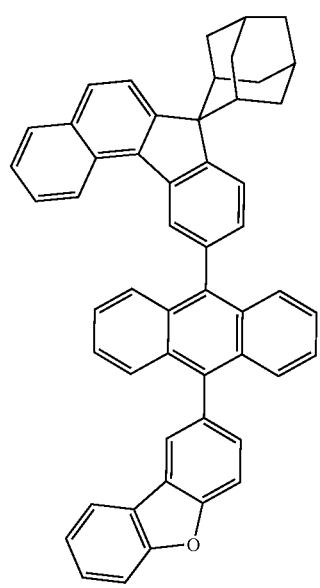
186
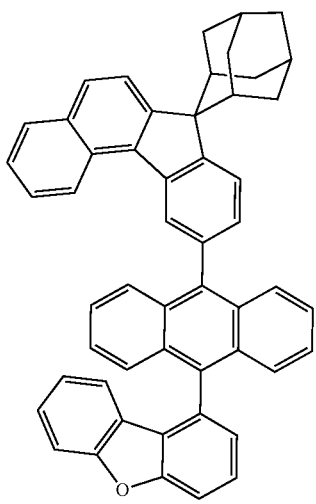
187
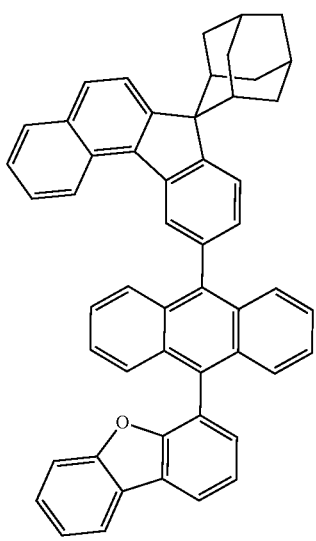
188
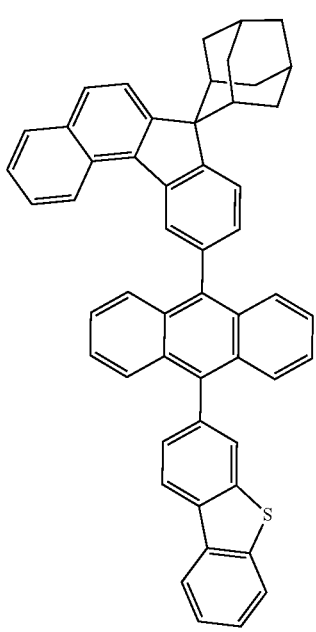

189
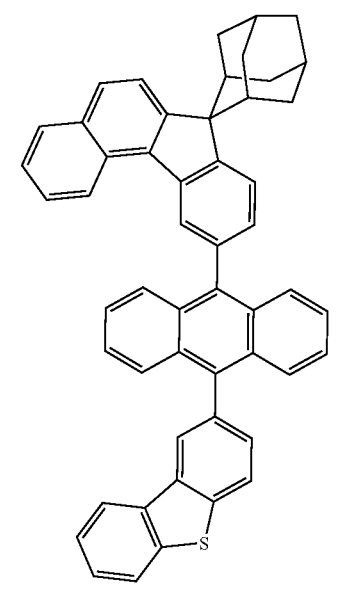
190
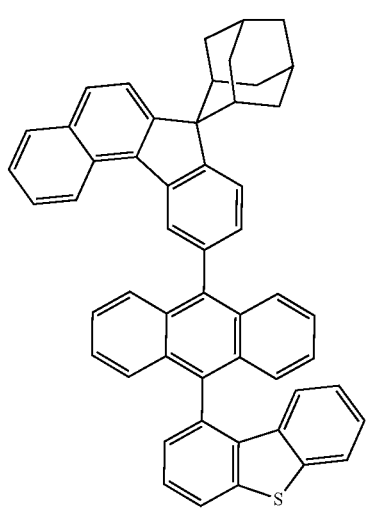
191
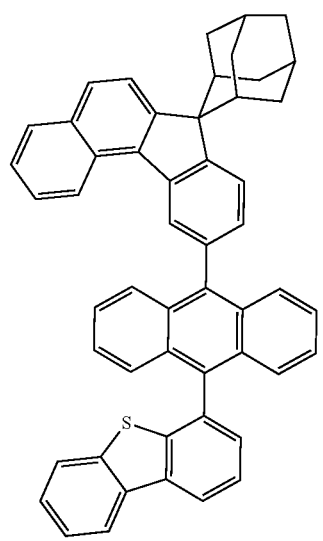
192
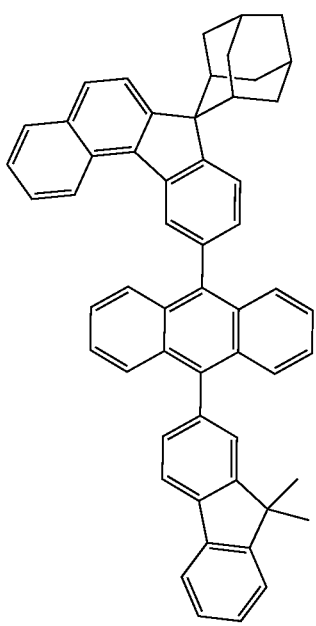
193
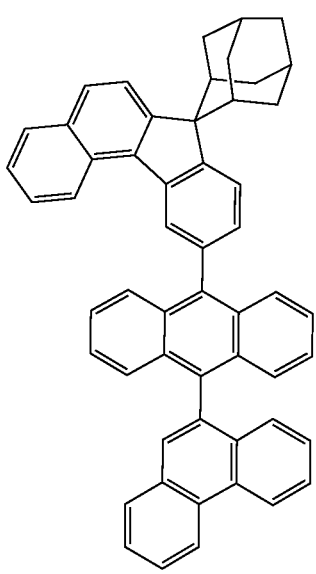

194
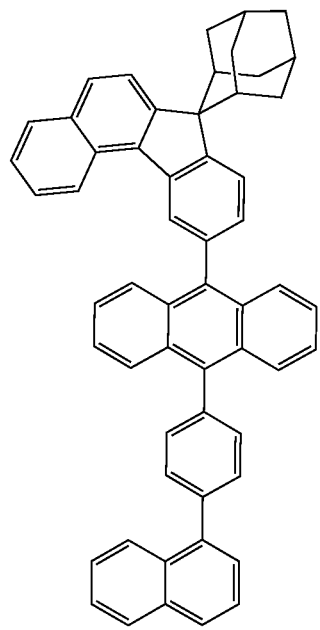
196
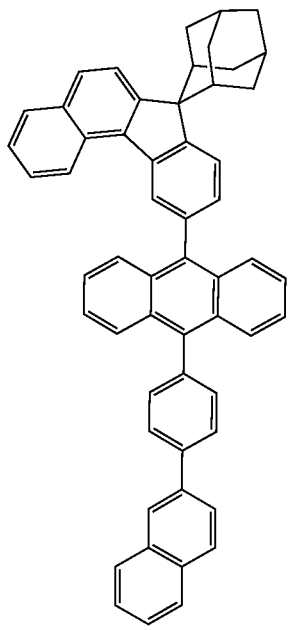
195
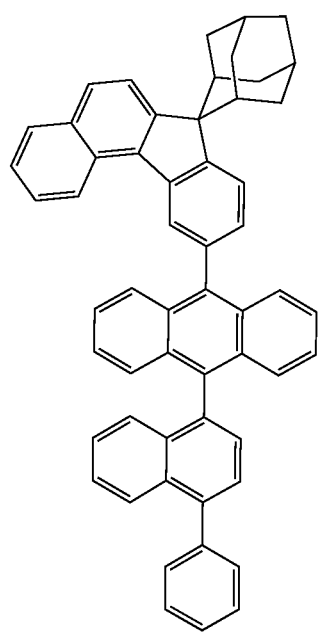
197
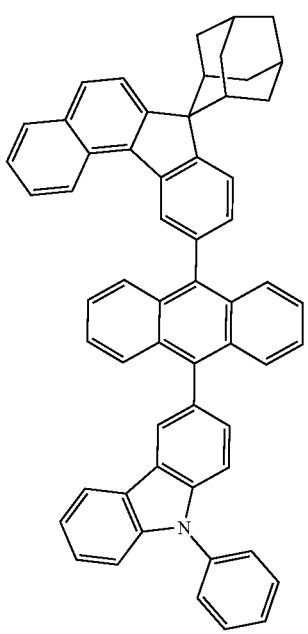

198
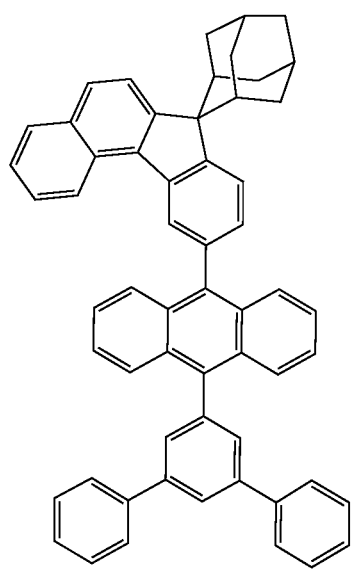
199
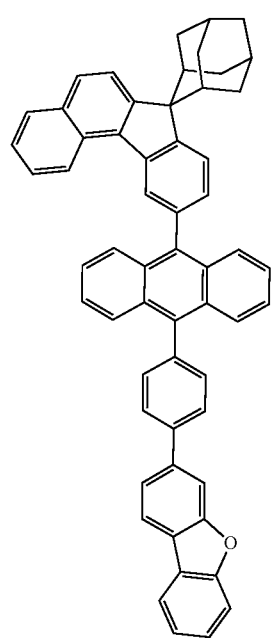
200
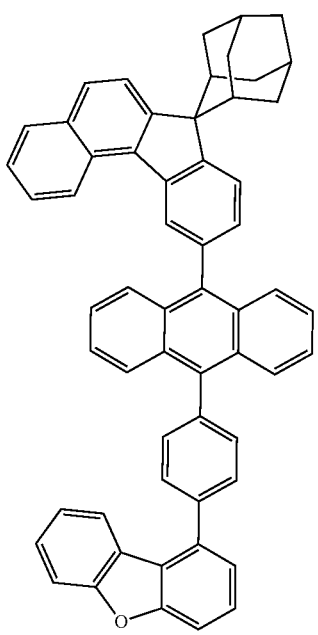
201

119
-continued
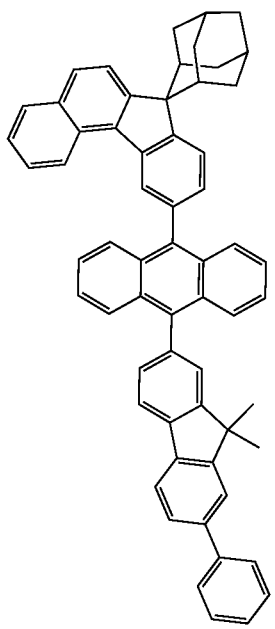
202
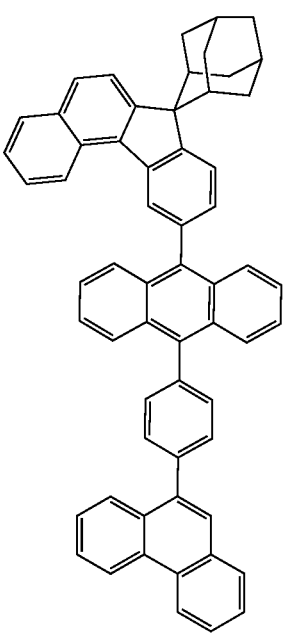
203
120
-continued
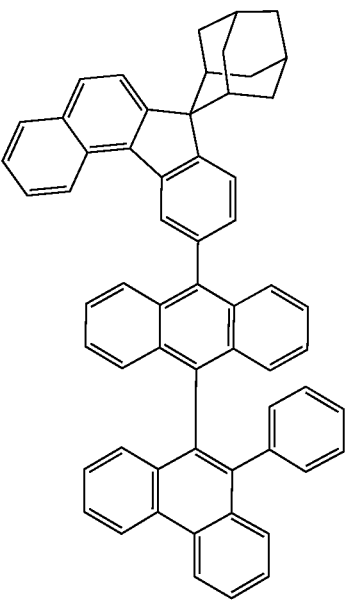
204
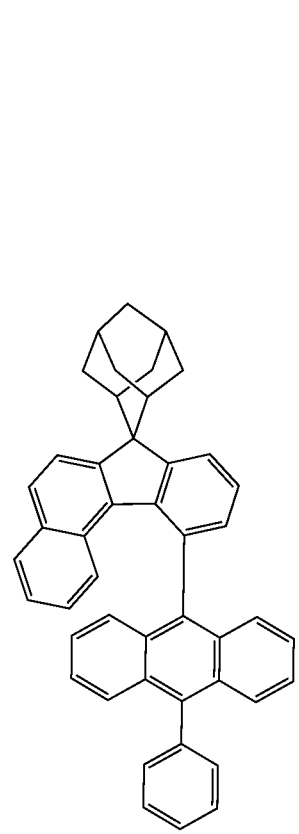
205

121
-continued
206
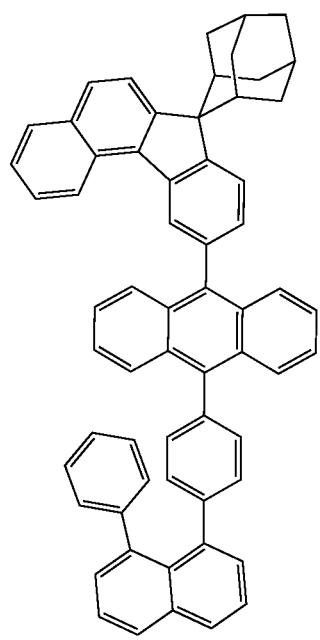
207
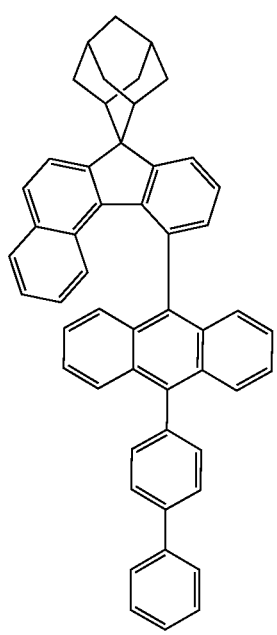
122
208
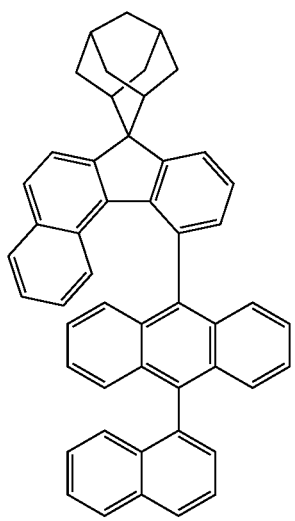
209
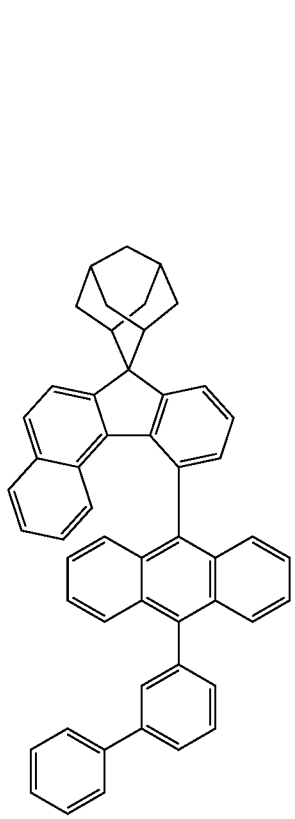

123
-continued
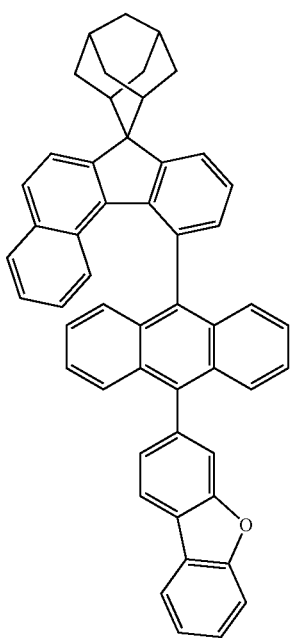
210
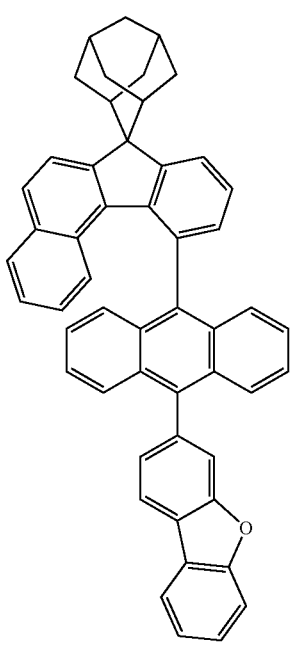
211
124
-continued
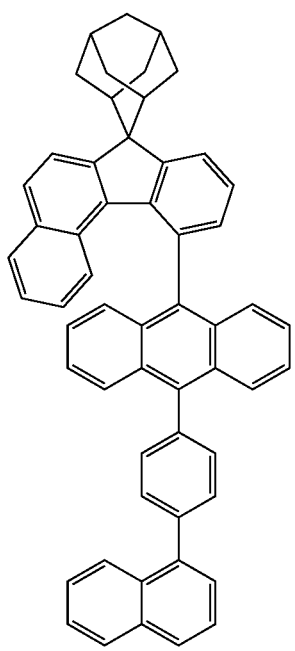
212
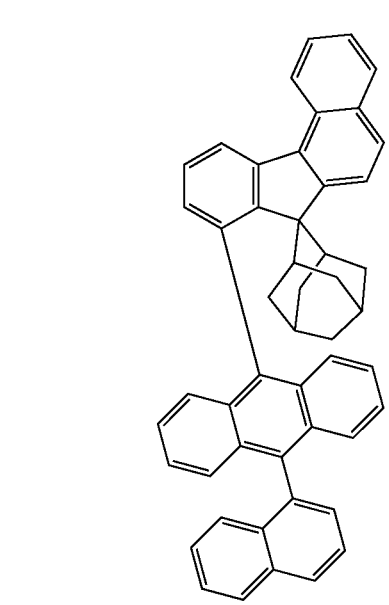
213

214
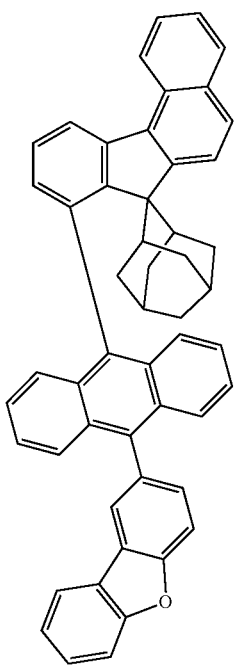
216
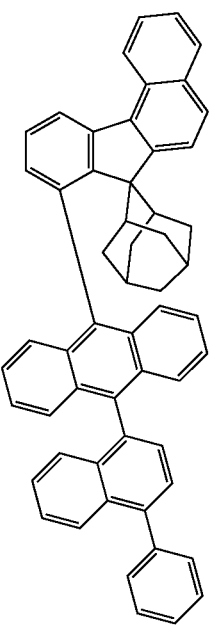
215
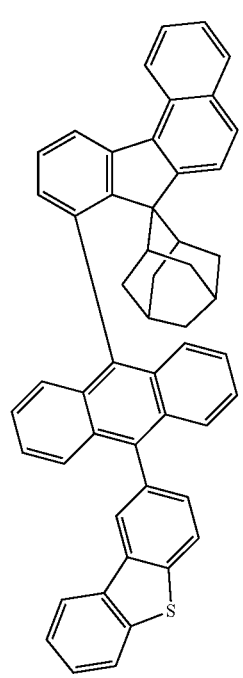
217
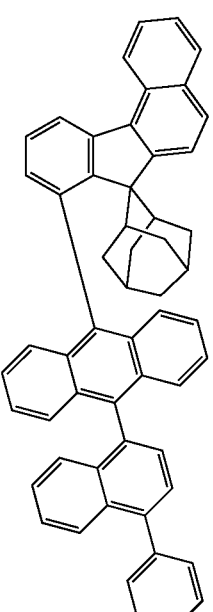

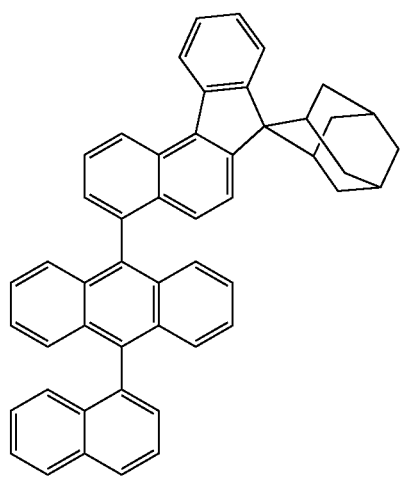
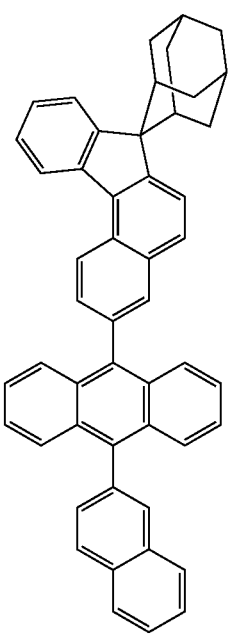

129
-continued
223
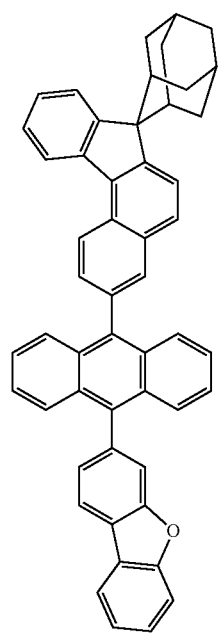
224
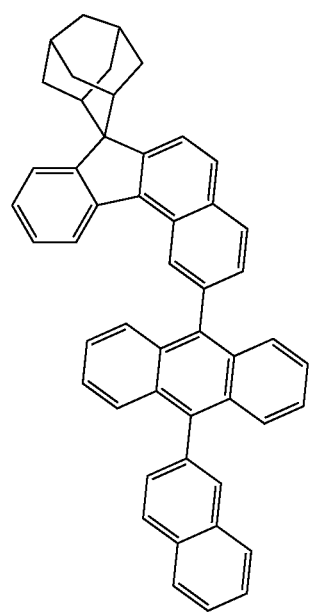
130
-continued
225
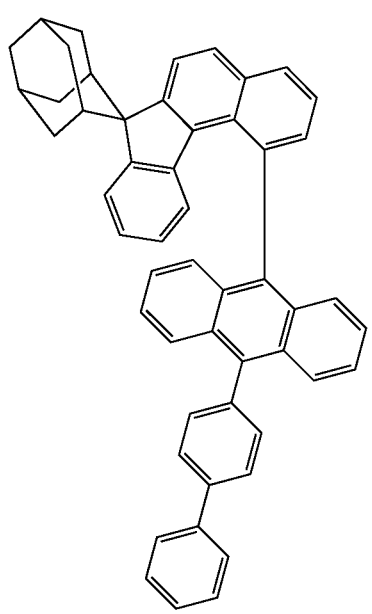
226

131
-continued
227
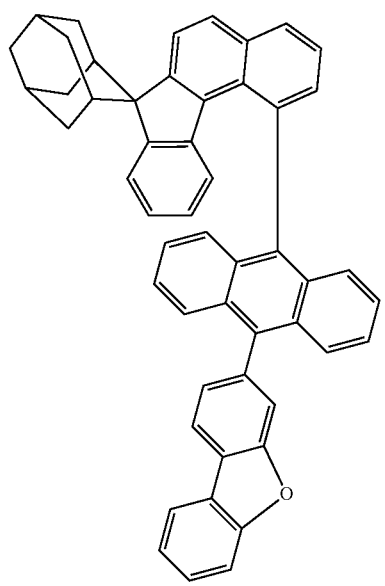
228
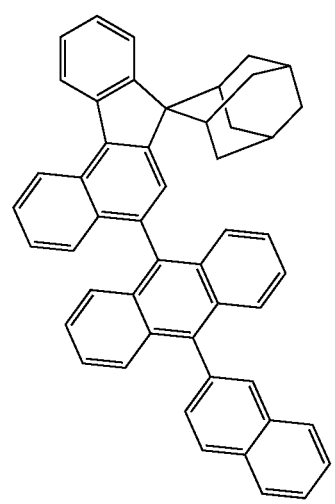
132
-continued
230
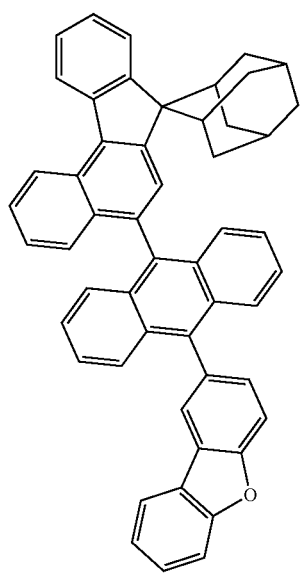
231
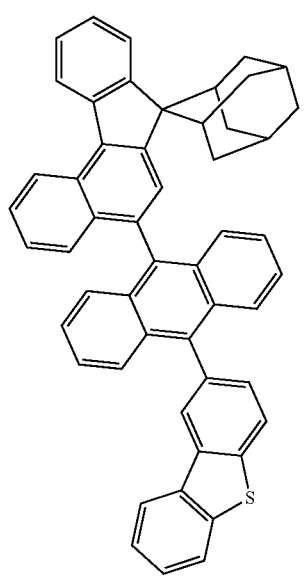

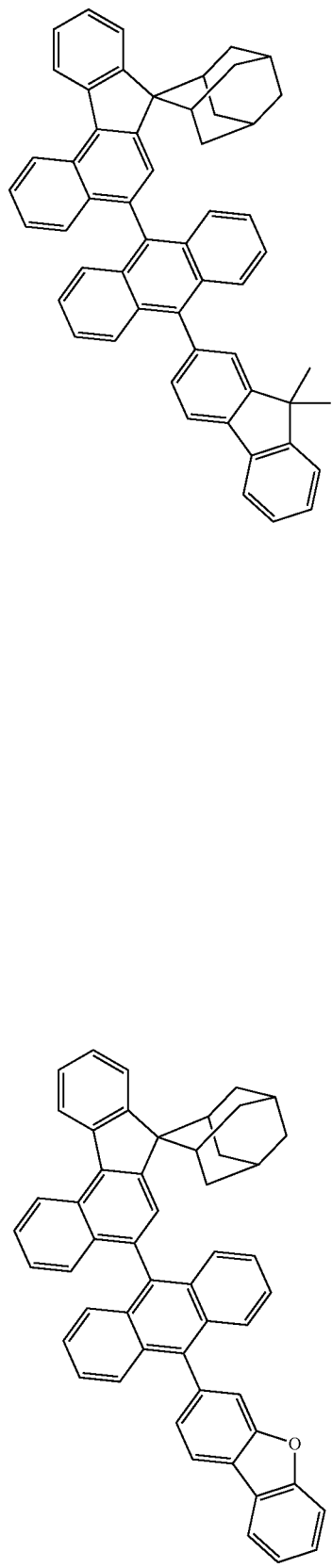
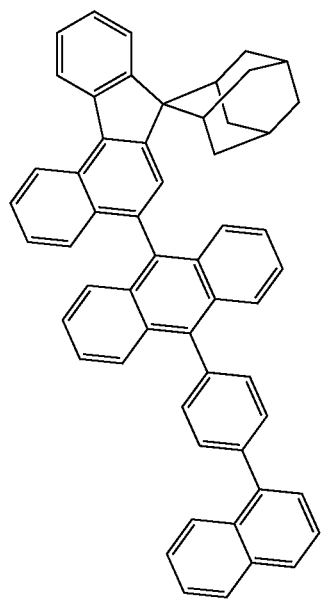
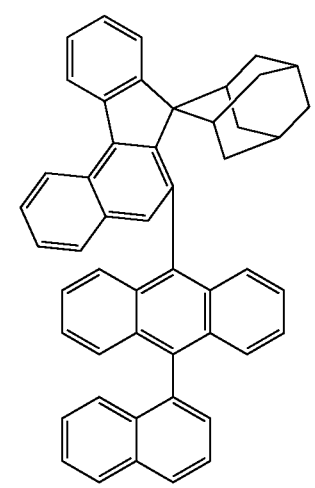
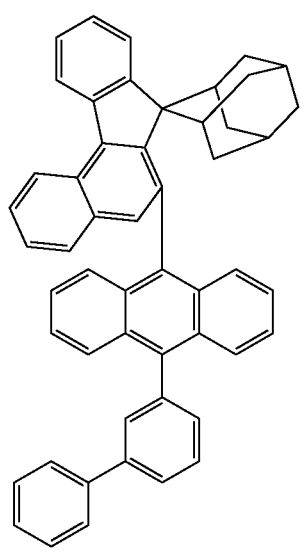

238
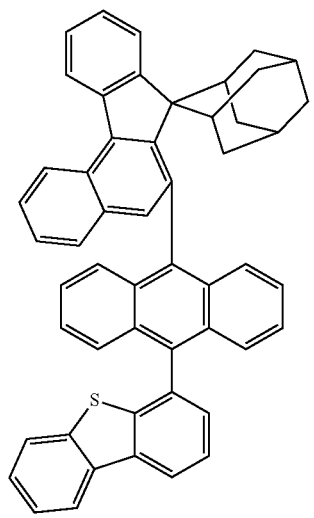
241
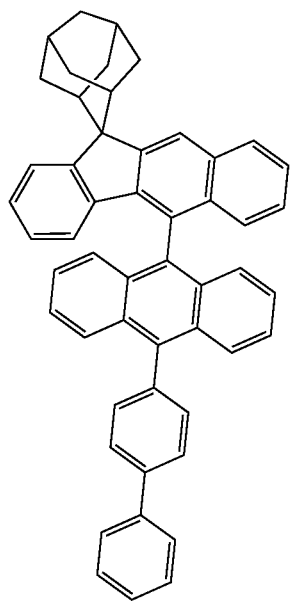
239
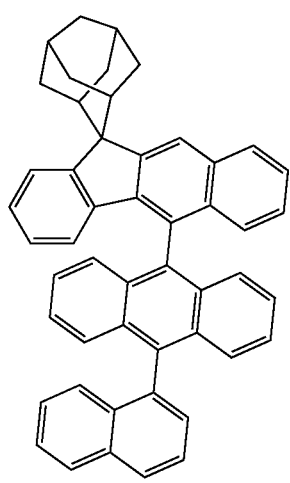
242
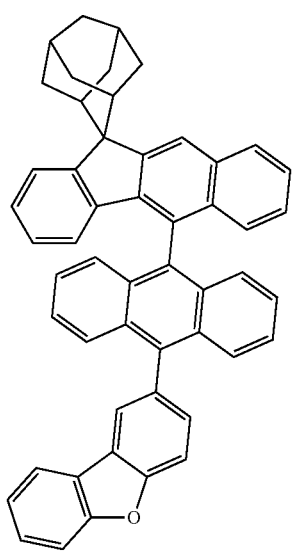
240
243
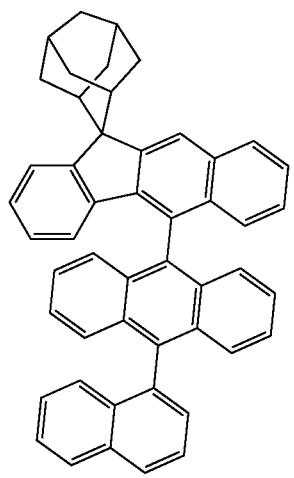

244
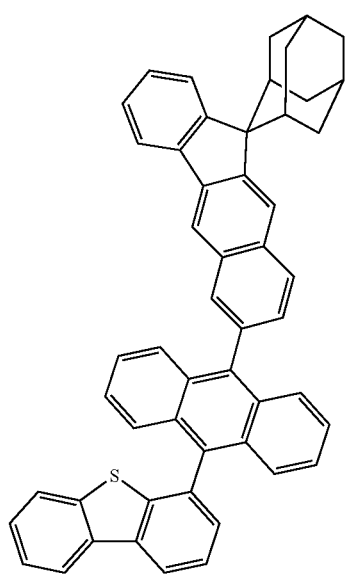
245
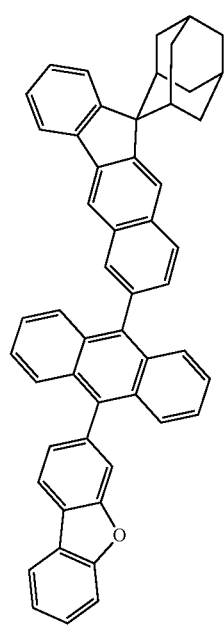
246
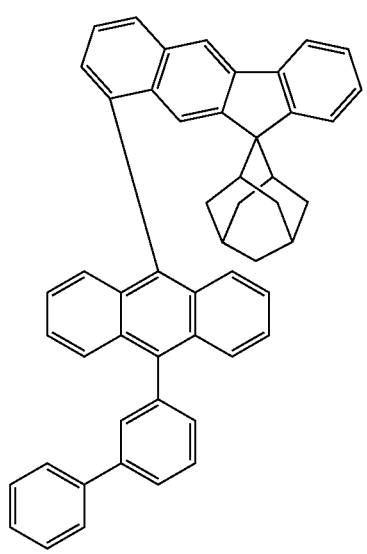
247
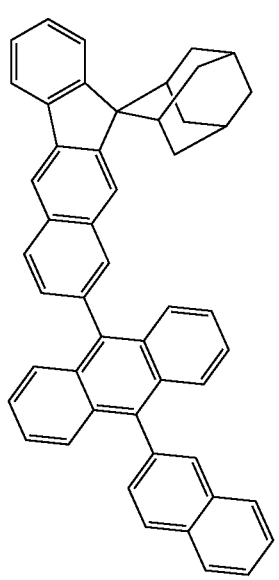

248
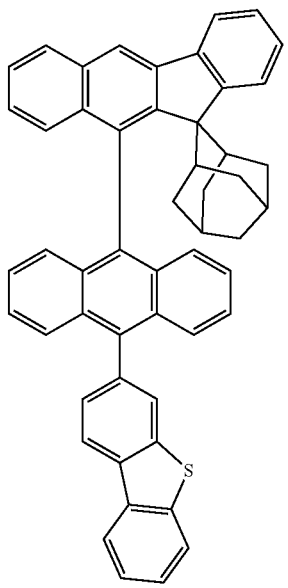
249
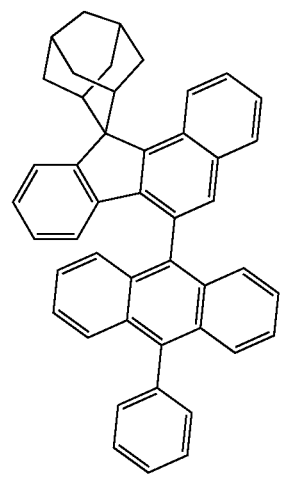
250
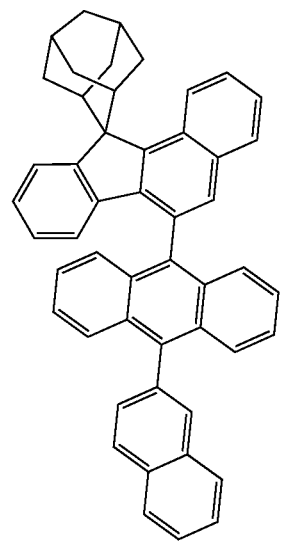
251
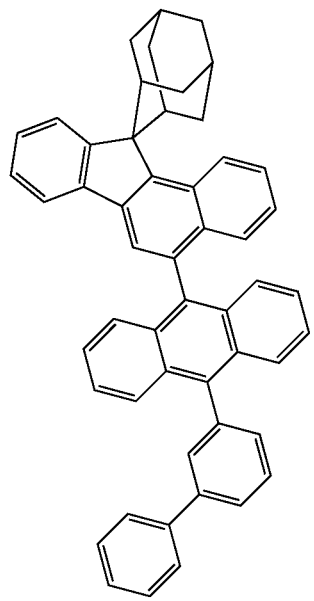
252
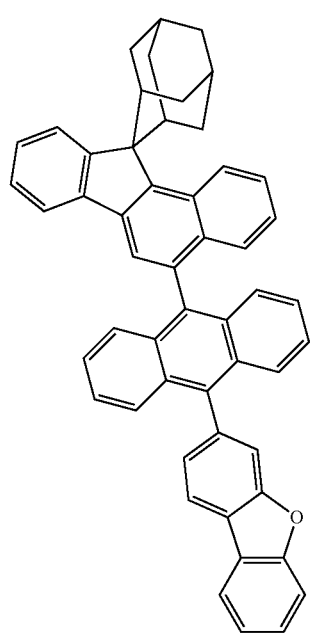

253
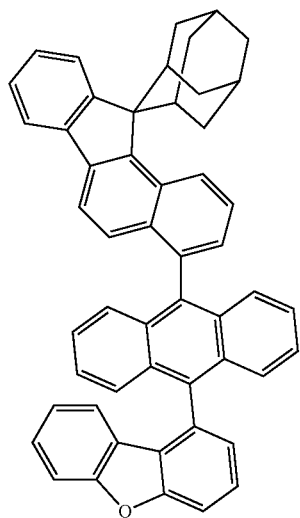
254
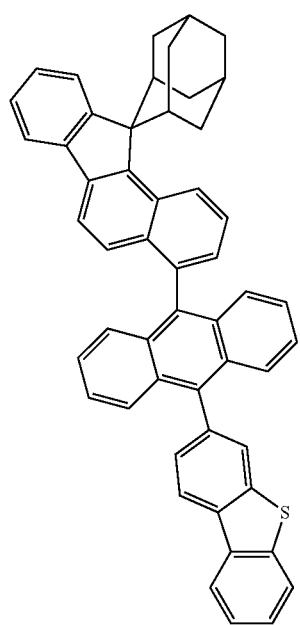
255
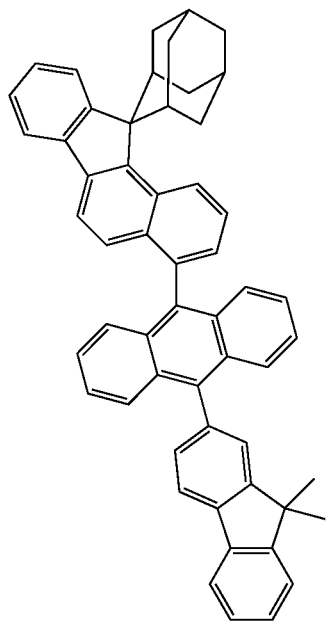
256
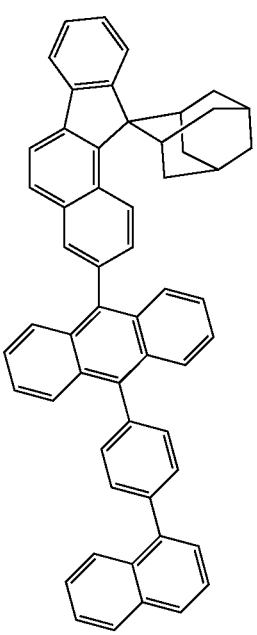

257
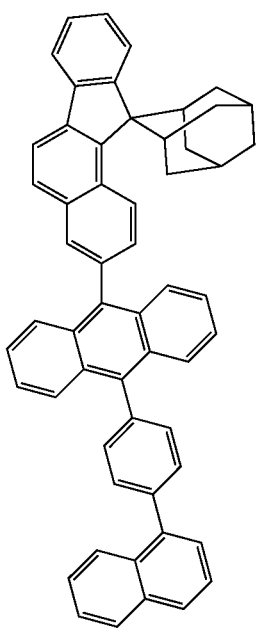
258
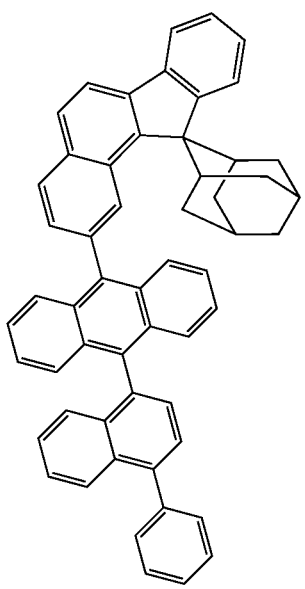
259
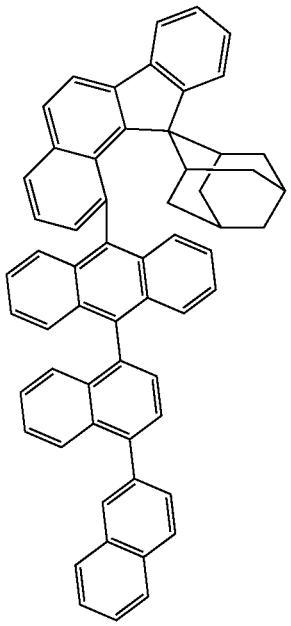
260
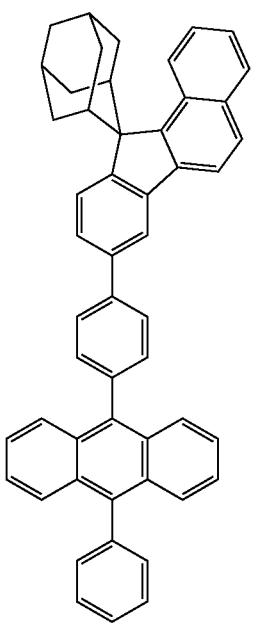

145
-continued
261
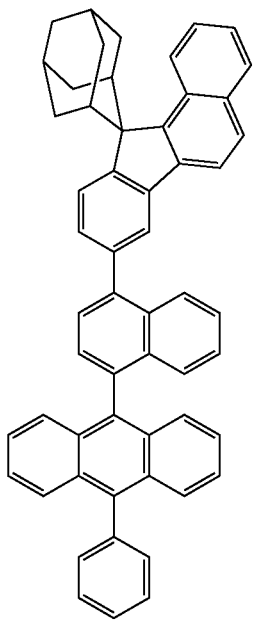
262
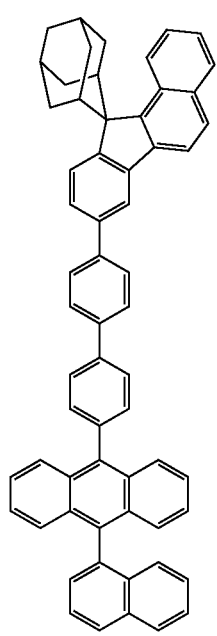
146
-continued
263
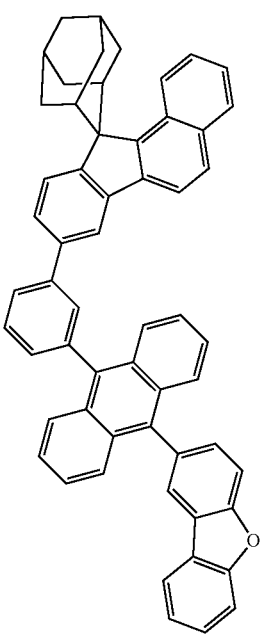
264
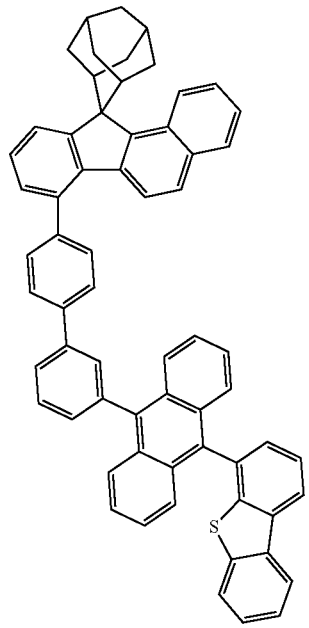

147
-continued
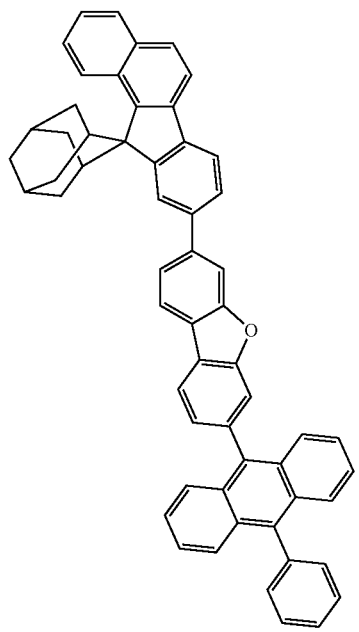
265
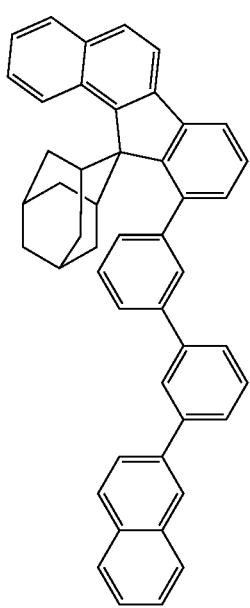
266
148
-continued
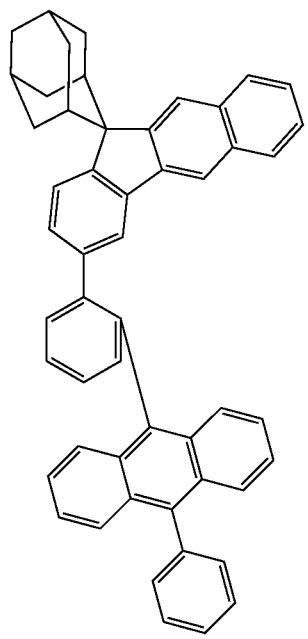
267
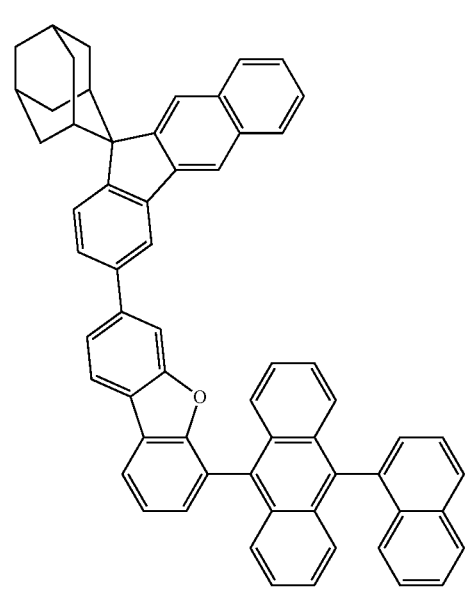
268

149
-continued
269
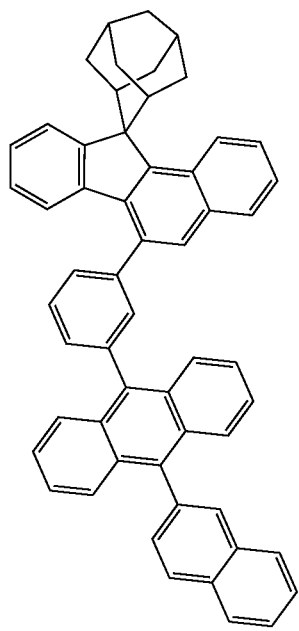
270
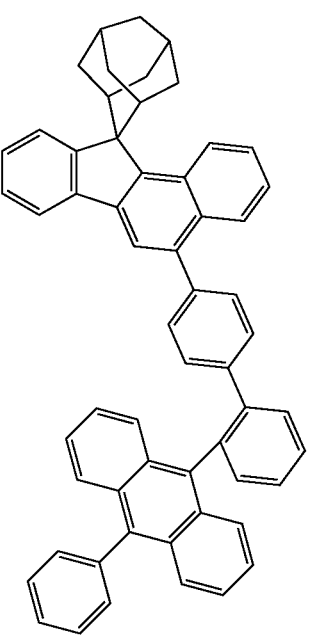
150
-continued
271
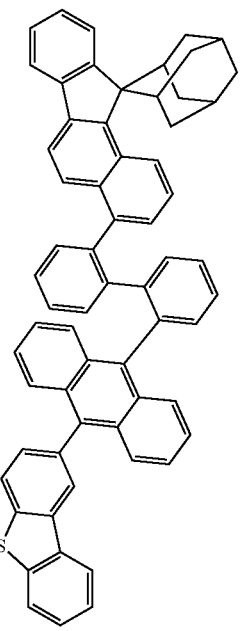
272
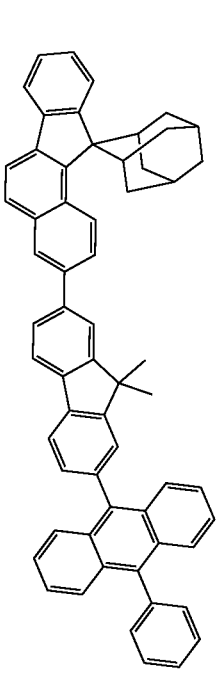

151
-continued
273
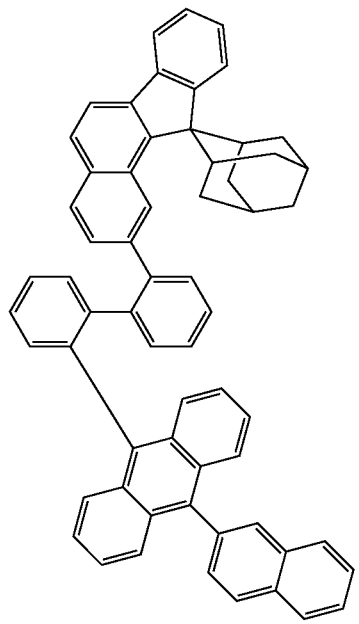
274
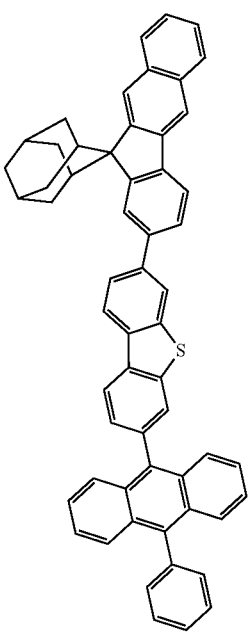
152
-continued
275
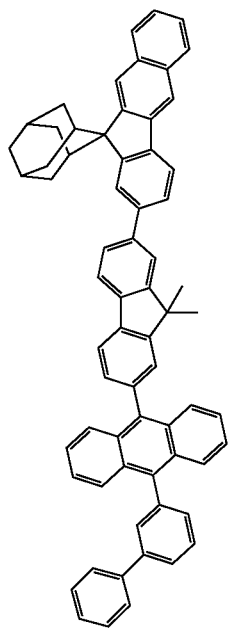
276
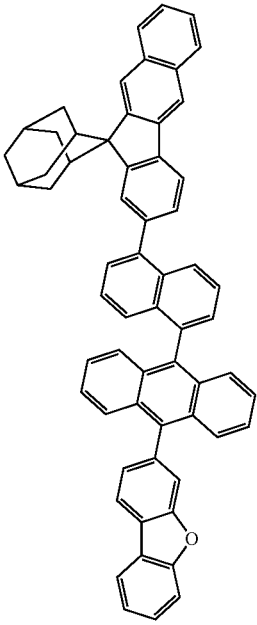

153
-continued
277
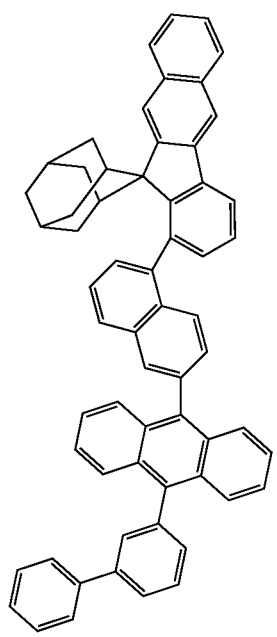
278
154
-continued
279
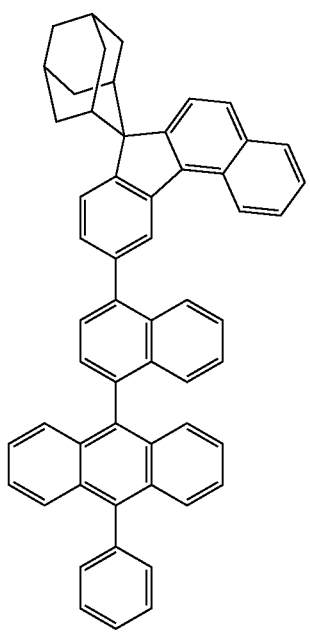
280
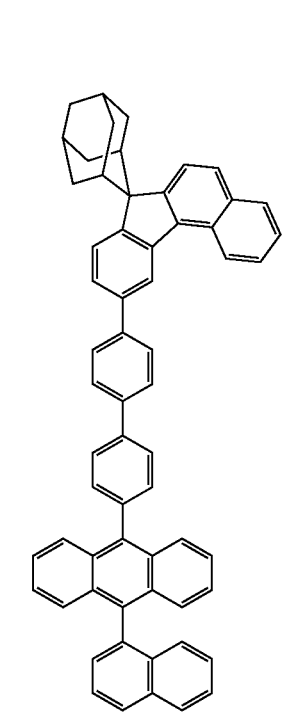

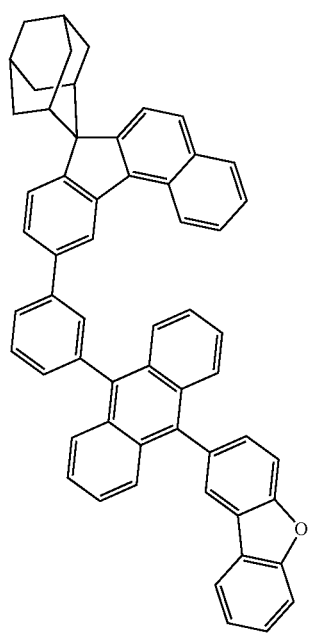
281
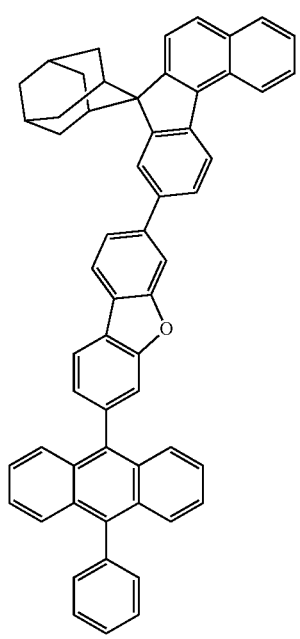
283
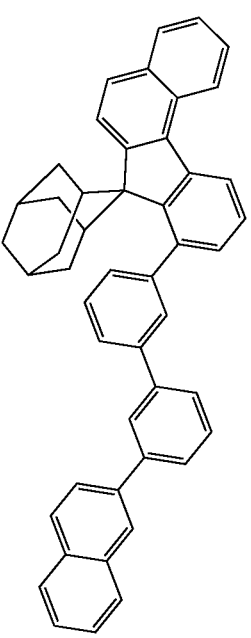
284

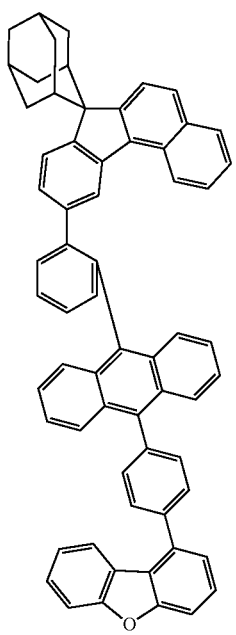
285
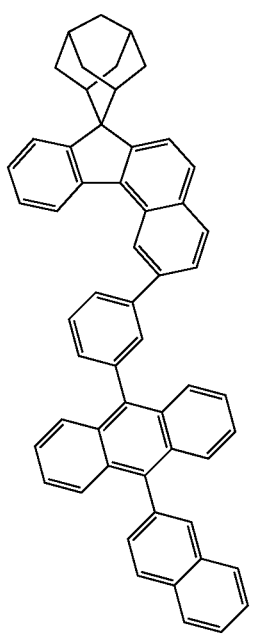
287
286
288
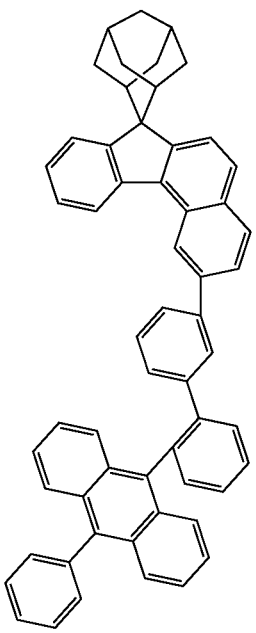

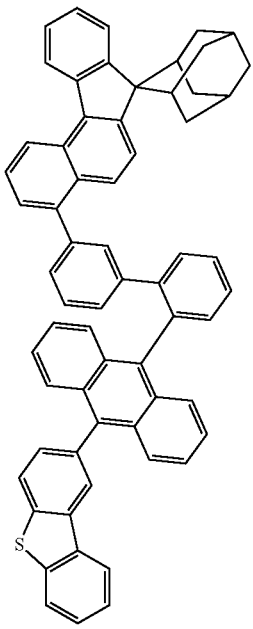
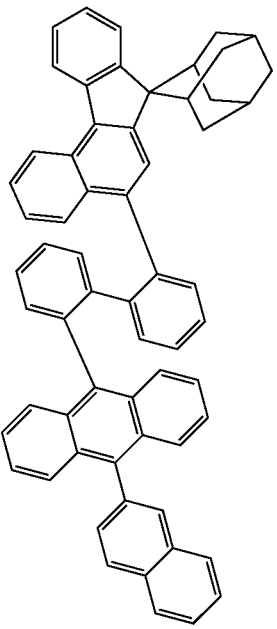
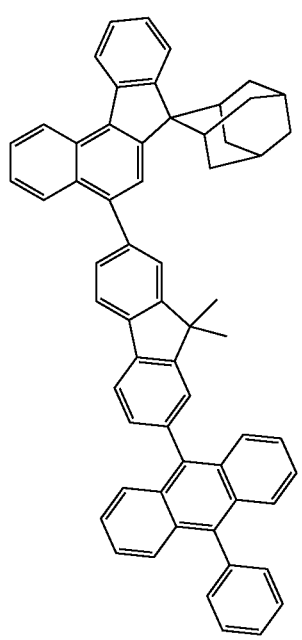
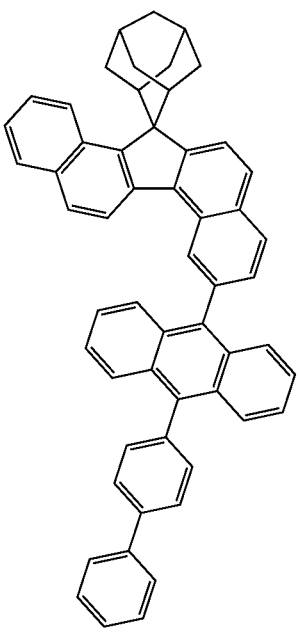

293
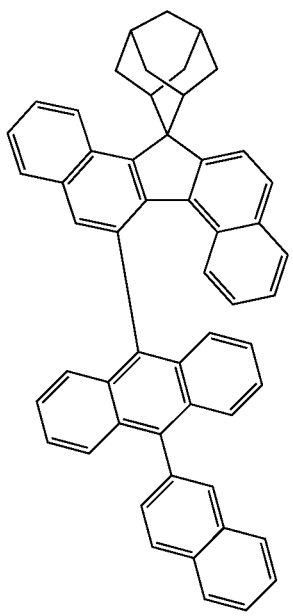
294
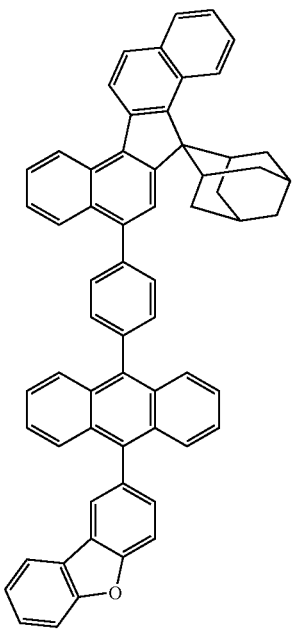
295
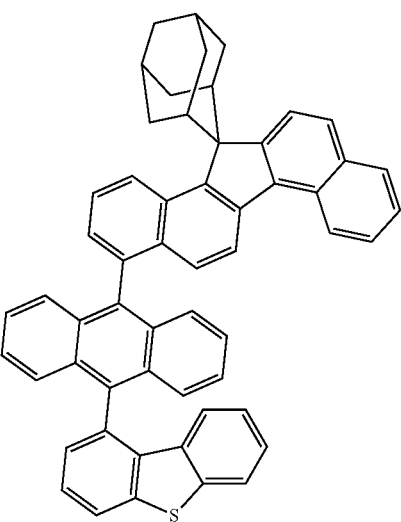
296
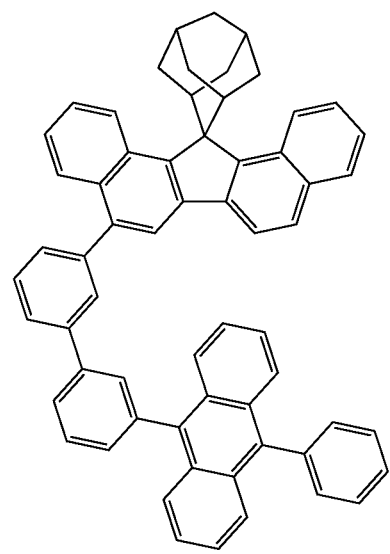
297
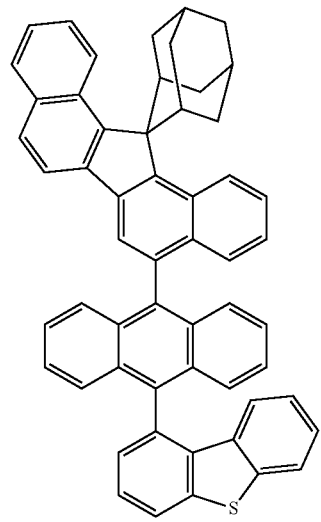

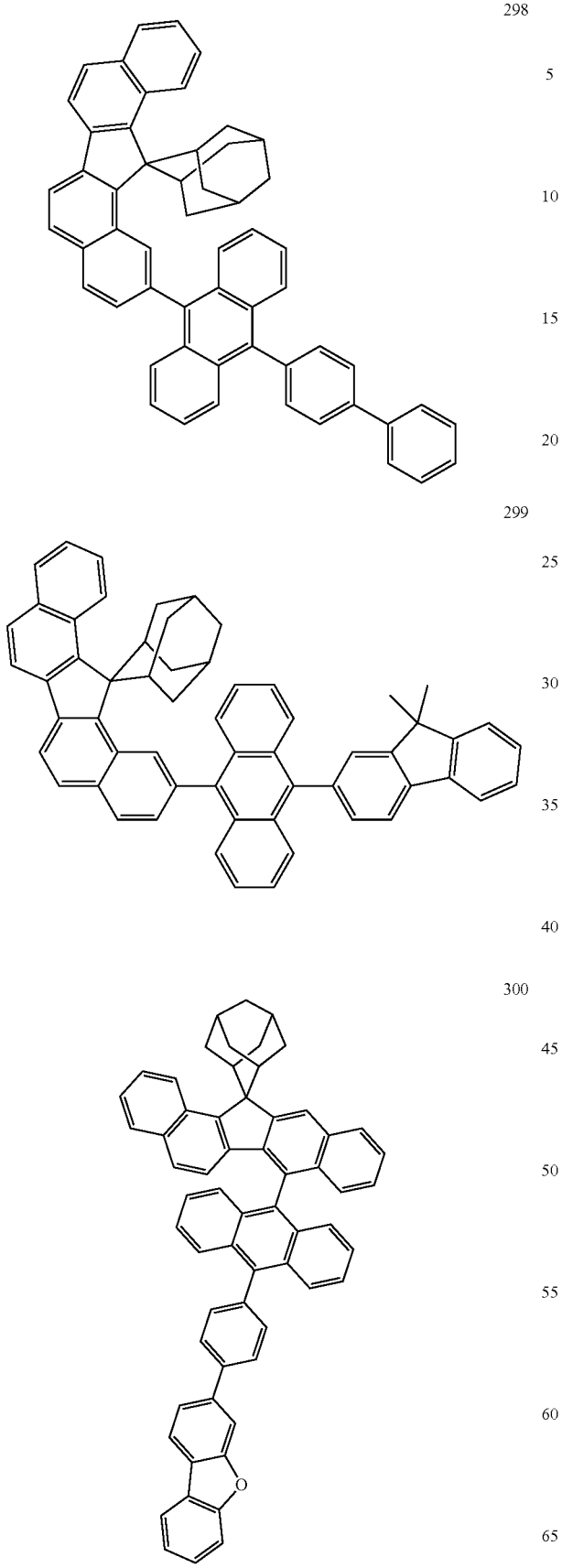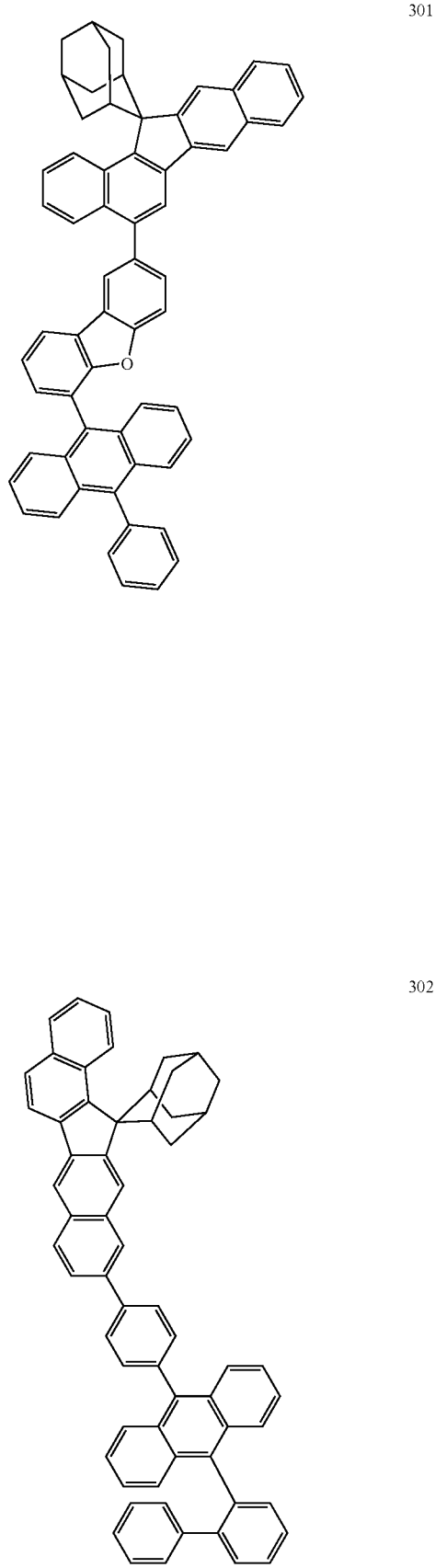

303
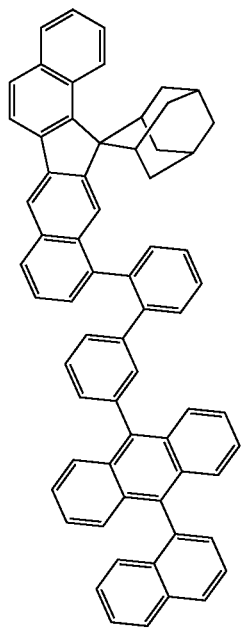
304
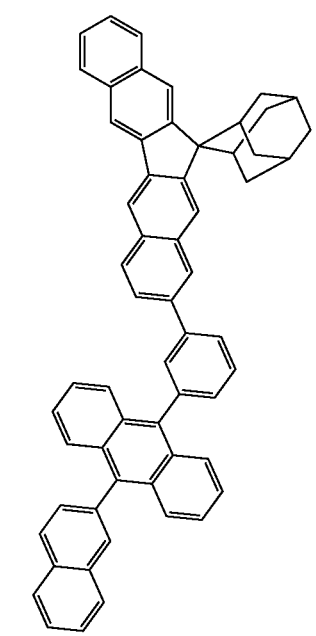
305
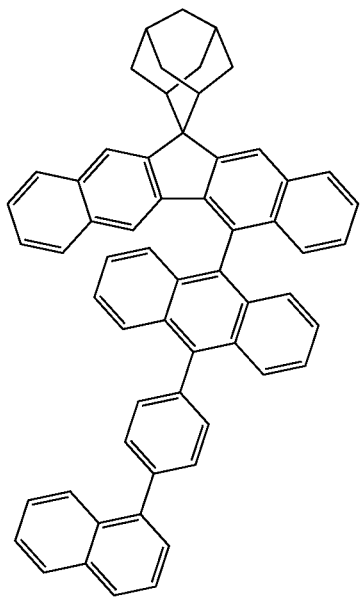
306

167
-continued
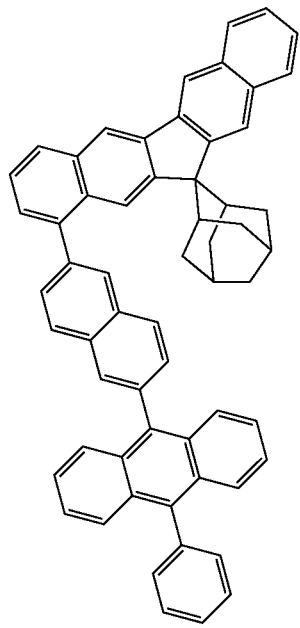
307
168
-continued
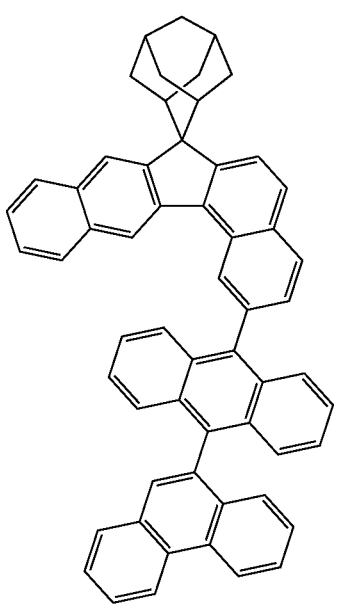
309
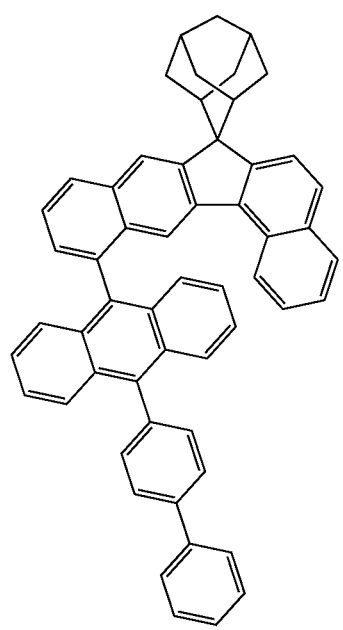
308
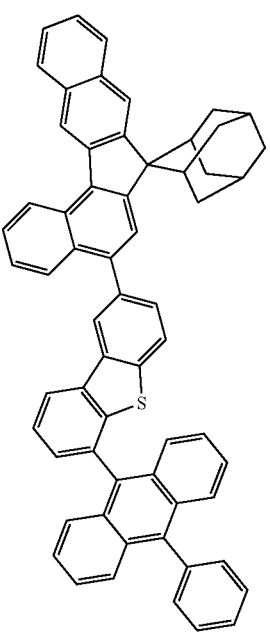
310

169
-continued
311
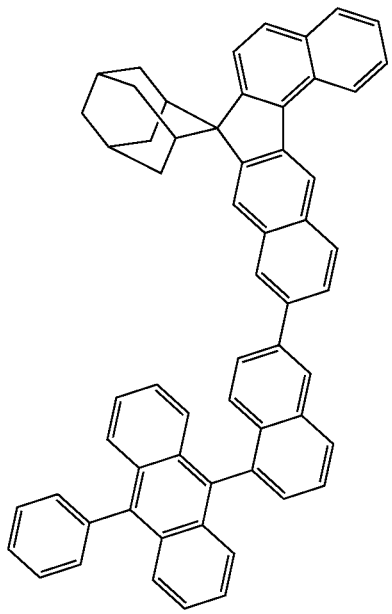
312
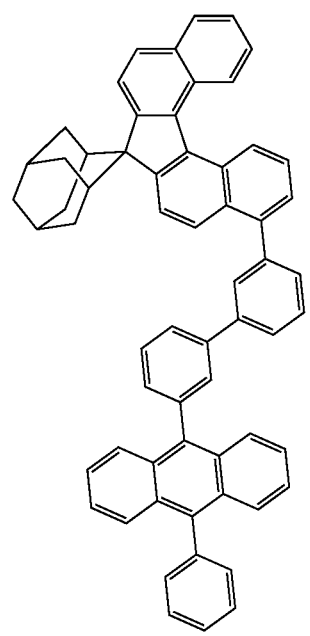
170
-continued
313
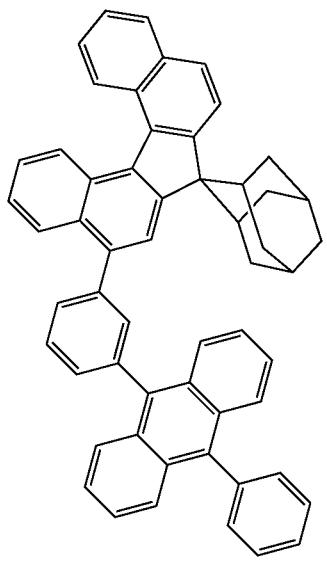
314
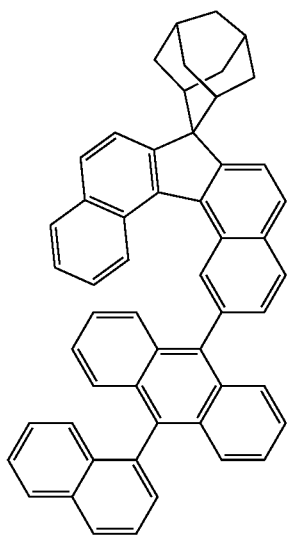

315
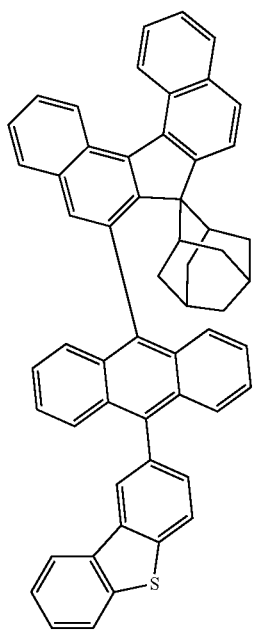
317
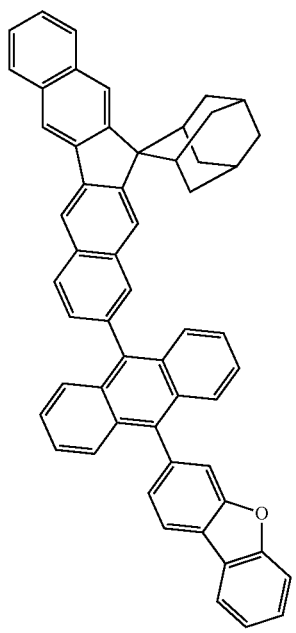
316
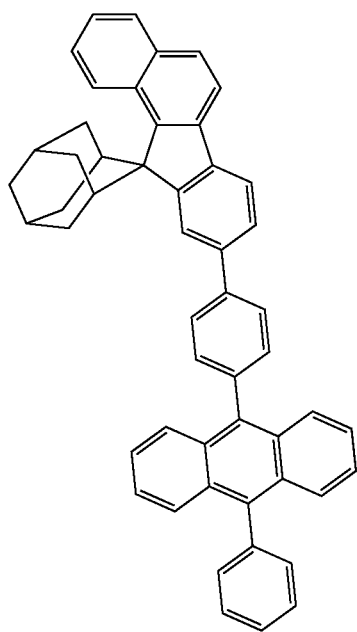
318
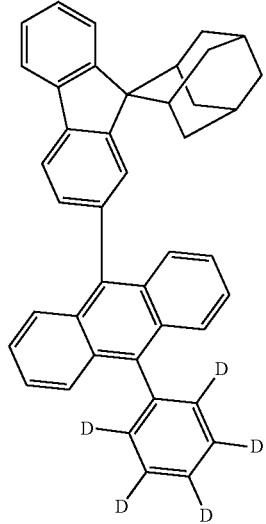

173
-continued
319
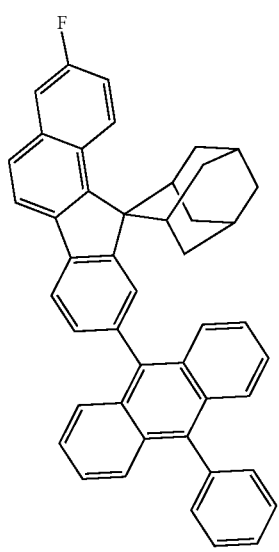
320
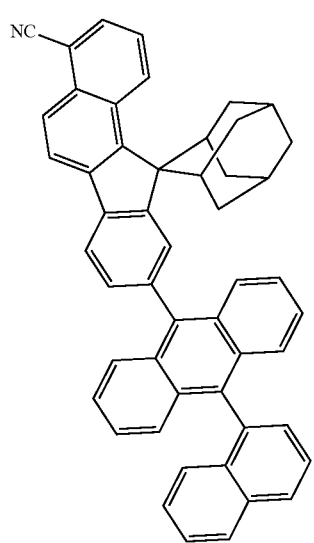
174
-continued
321
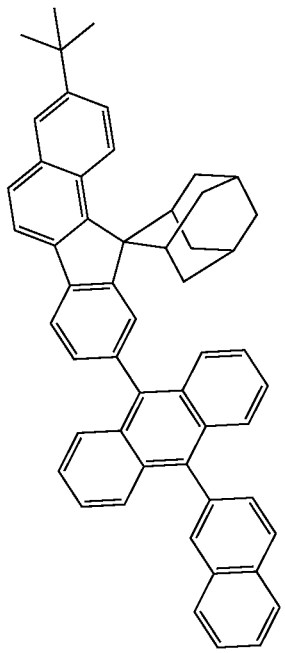
322
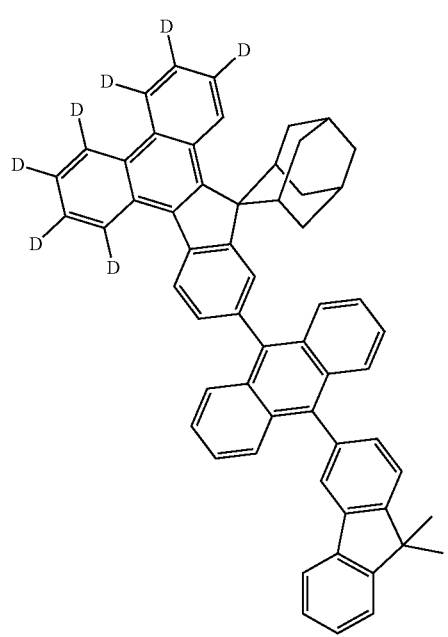

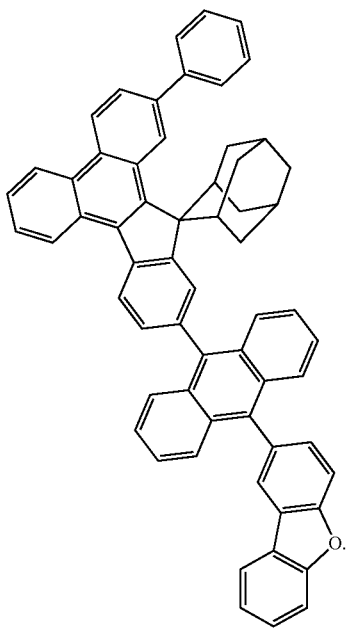

323

In a second aspect, the present disclosure provides an electronic element, comprising an anode and a cathode which is arranged oppositely to the anode, and a functional layer disposed between the anode and the cathode; and the functional layer comprises the organic compound of the first aspect of the present disclosure.

The organic compound provided by the present disclosure can be used to form at least one organic film layer in the functional layer to improve the efficiency and service life characteristics of electronic elements.

In one specific embodiment, the functional layer comprises an organic light-emitting layer, and the organic light-emitting layer comprising the organic compound. In general, the organic light-emitting layer may comprise a host material and a guest material, where the host material comprises the organic compound of the present disclosure.

According to one embodiment of the present disclosure, the electronic element is an organic electroluminescent device, for example a blue light device. As shown in FIG. 1, the organic electroluminescent device may comprise an anode 100, a hole transport layer 321, an electron blocking layer 322, an organic light-emitting layer 330 as an energy conversion layer, an electron transport layer 340, and a cathode 200 which are sequentially stacked.

Optionally, the anode 100 comprises an anode material, which is preferably a material with a large work function that facilitates hole injection into the functional layer.

Specific embodiments of the anode material include: metals such as nickel, platinum, vanadium, chromium, copper, zinc, and gold, or their alloy; metal oxides such as zinc oxide, indium oxide, indium tin oxide (ITO) and indium zinc oxide (IZO); combined metals and oxides, such as ZnO:Al or $SnO_2$:Sb; or a conductive polymer such as poly(3-methylthiophene), poly[3,4-(ethylene-1,2-dioxy)thiophene] (PEDT), polypyrrole, and polyaniline, but are not limited to this. A transparent electrode comprising indium tin oxide (ITO) as the anode is preferably included.

Optionally, the hole transport layer 321 and the electron blocking layer 322 each comprise one or more hole transport materials, and the hole transport materials may be selected from a carbazole polymer, carbazole-linked triarylamine compounds, or other types of compounds.

Optionally, the organic light-emitting layer 330 may be composed of a single light-emitting material and may also comprise a host material and a guest material. The host material of the organic light-emitting layer may comprise the organic compound of the present disclosure. In some embodiments of the present disclosure, the organic light-emitting layer 330 is composed of the host material and the guest material, and holes injected into the organic light-emitting layer 330 and electrons injected into the organic light-emitting layer 330 can be recombined in the organic light-emitting layer 330 to form excitons, the excitons transfer energy to the host material, and the host material transfers energy to the guest material, thus enabling the guest material to emit light.

The host material of the organic light-emitting layer 330 may be a metal chelate compound, a bis-styryl derivative, an aromatic amine derivative, a dibenzofuran derivative, or other types of materials, which is not specially limited in the present disclosure. In one embodiment of the present disclosure, the host material of the organic light-emitting layer 330 can be the organic compound of the present disclosure.

The guest material of the organic light-emitting layer 330 may be a compound having a condensed aryl ring or its derivative, a compound having a heteroaryl ring or its derivative, an aromatic amine derivative, or other materials, which is not specially limited in the present disclosure. In some embodiments of the present disclosure, the organic electroluminescent device is a blue light device and the guest material of the organic light-emitting layer 330 is BD-1.

The electron transport layer 340 may be of a single-layer structure or a multi-layer structure and may comprise one or more electron transport materials, and the electron transport materials can be selected from, but are not limited to, a benzimidazole derivative, an oxadiazole derivative, a quinoxaline derivative, or other electron transport materials. In one embodiment of the present disclosure, the electron transport layer 340 may be composed of ET-06 and LiQ.

In the present disclosure, the cathode 200 may comprise a cathode material, which is a material having a small work function that facilitates electron injection into the functional layer. Specific embodiments of the cathode material include, but are not limited to, metals such as magnesium, calcium, sodium, potassium, titanium, indium, yttrium, lithium, gadolinium, aluminum, silver, tin, and lead or their alloy; or multilayer materials such as LiF/Al, Liq/Al, $LiO_2$/Al, LiF/Ca, LiF/Al, and $BaF_2$/Ca. A metal electrode comprising silver and magnesium as the cathode is preferably included.

Optionally, as shown in FIG. 1, a hole injection layer 310 may also be arranged between the anode 100 and the hole transport layer 321 to enhance the ability to inject holes into the hole transport layer 321. The hole injection layer 310 can be made of a benzidine derivative, a starburst arylamine compound, a phthalocyanine derivative or other materials, which is not specially limited in the present disclosure. For example, the hole injection layer 310 may be composed of F4-TCNQ.

Optionally, as shown in FIG. 1, an electron injection layer 350 may also be arranged between the cathode 200 and the electron transport layer 340 to enhance the ability to inject electrons into the electron transport layer 340. The electron injection layer 350 may comprise an inorganic material such as an alkali metal sulfide and an alkali metal halide, or may comprise a complex of an alkali metal and an organic substance. In one embodiment of the present disclosure, the electron injection layer 350 may be composed of a metal Yb.

Optionally, the organic electroluminescent device of the present disclosure is a blue light device.

Optionally, a hole blocking layer 341 may also be arranged between the organic light-emitting layer 330 and the electron transport layer 340.

In a third aspect, the present disclosure provides an electronic device, comprising the electronic element of the second aspect of the present disclosure.

Figure 2:
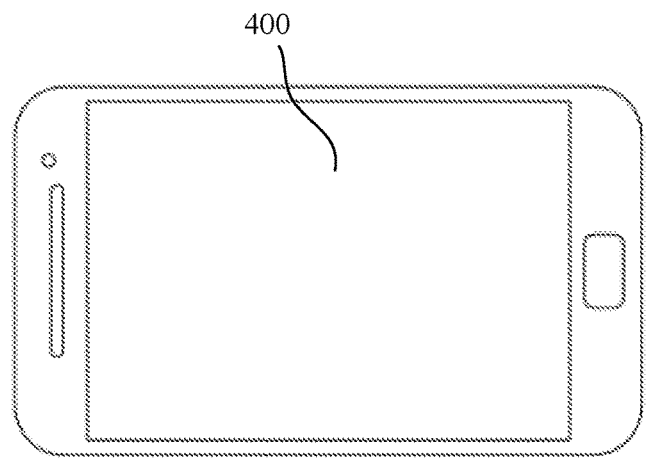
FIG. 2 is a structural schematic diagram of a first electronic device according to one embodiment of the present disclosure.

According to one embodiment, as shown in FIG. 2, the electronic device is a first electronic device 400 including the organic electroluminescent device described above. The first electronic device 400 may, for example, be a display device, a lighting device, an optical communication device, or other types of electronic devices, and may include, for example, but is not limited to, a computer screen, a mobile phone screen, a television, electronic paper, an emergency lighting lamp, an optical module, and the like.

Figure 3:
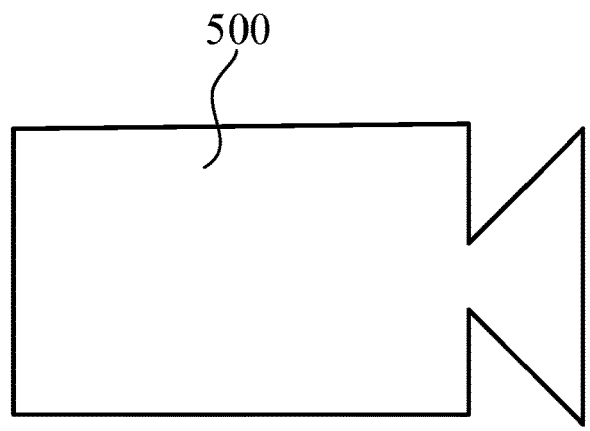
FIG. 3 is a structural schematic diagram of a second electronic device according to another embodiment of the present disclosure.

According to another embodiment, as shown in FIG. 3, the electronic device is a second electronic device 500 including a photoelectric conversion device. The second electronic device 500 may, for example, be a solar power plant, a light detector, a fingerprint recognition device, an optical module, a CCD camera, or other types of electronic devices.

Compounds of which the synthesis methods were not mentioned in the present disclosure are all commercially obtained raw material products.

Intermediates and compounds in the present disclosure are analyzed and detected by an ICP-7700 mass spectrometer.

A synthesis method of the organic compound of the present disclosure is specifically described below in conjunction with synthesis examples.

The synthesis method of the organic compound provided is not particularly limited in the present disclosure, and those skilled in the art can determine a suitable synthesis method according to the organic compound of the present disclosure in combination with preparation methods provided in synthesis examples. In other words, the synthesis examples of the present disclosure exemplarily provide preparation methods for the organic compounds, and raw materials used may be commercially obtained or obtained by a method well known in the art. Those skilled in the art can obtain all organic compounds provided by the present disclosure according to these exemplary preparation methods, and all specific preparation methods for the organic compounds are not described in detail herein, and those skilled in the art should not understand as limiting the present disclosure.

The compounds of the present disclosure were synthesized by using the following method

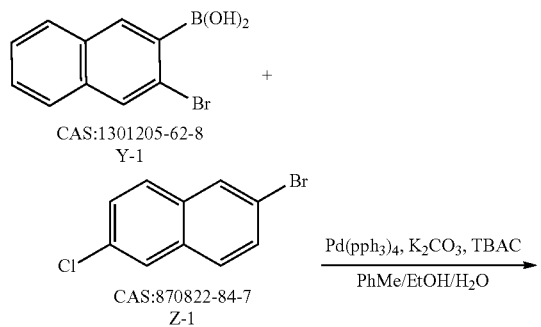

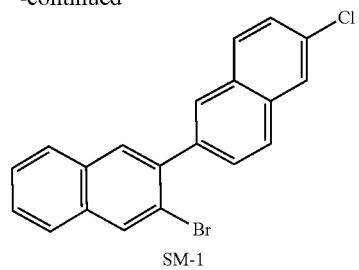

Y-1 (100 g, 398.5 mmol), Z-1 (96.3 g, 398.5 mmol), tetrakis(triphenylphosphine)palladium (2.3 g, 1.9 mmol), potassium carbonate (110.2 g, 797.1 mmol), tetrabutylammonium chloride (0.55 g, 1.9 mmol), toluene (800 mL), ethanol (400 mL) and deionized water (200 mL) were added into a three-necked flask, heated to 78° C. under nitrogen protection, and the reaction solution was stirred for 6 h; the resulting reaction solution was cooled to room temperature, toluene (300 mL) was added into the reaction solution for extraction, the organic phases were combined, dried over anhydrous magnesium sulfate, and filtered to obtain a filtrate, and the filtrate was concentrated under reduced pressure to obtain a crude product; and the obtained crude product was purified by silica gel column chromatography using n-heptane as a mobile phase, and then purified by recrystallization with a dichloromethane/n-heptane system (a ratio volume of 1:3) to obtain SM-1 (112.8 g, yield: 77%).

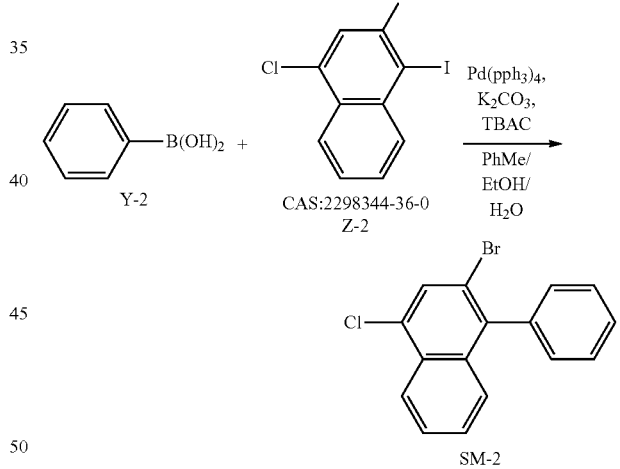

Y-2 (33.2 g, 272.2 mmol), Z-2 (100 g, 272.2 mmol), tetrakis(triphenylphosphine)palladium (9.4 g, 8.2 mmol), potassium carbonate (112.8 g, 816.5 mmol), tetrabutylammonium chloride (0.75 g, 2.72 mmol), toluene (800 mL), ethanol (400 mL) and deionized water (200 mL) were added into a three-necked flask, heated to 78° C. under nitrogen protection, and stirred for 8 h; the resulting reaction solution was cooled to room temperature, toluene (300 mL) was added into the reaction solution for extraction, the organic phases were combined, dried over anhydrous magnesium sulfate, and filtered to obtain a filtrate, and the filtrate was concentrated under reduced pressure to obtain a crude product; and the obtained crude product was purified by recrystallization using a dichloromethane/n-heptane system (a ratio volume of 1:3) to obtain SM-2 (64.8 g, yield: 75%).

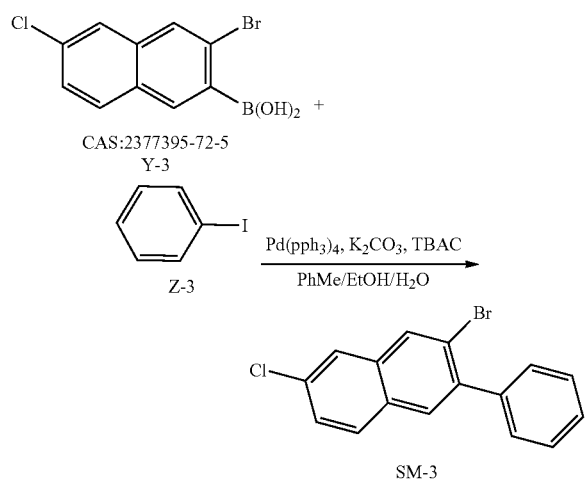

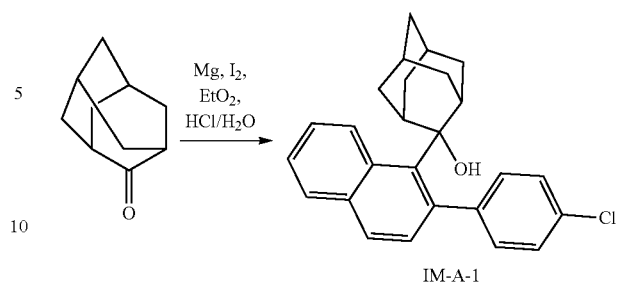

IM-A-1

Y-3 (100 g, 350.5 mmol), Z-3 (71.5 g, 350.5 mmol), tetrakis(triphenylphosphine)palladium (12.1 g, 10.5 mmol), potassium carbonate (145.3 g, 1051.5 mmol), tetrabutylammonium chloride (0.97 g, 3.5 mmol), toluene (800 mL), ethanol (400 mL) and deionized water (200 mL) were added into a three-necked flask, heated to 78° C. under nitrogen protection, and stirred for 6 h; the resulting reaction solution was cooled to room temperature, toluene (300 mL) was added into the reaction solution for extraction, the organic phases were combined, dried over anhydrous magnesium sulfate, and filtered to obtain a filtrate, and the filtrate was concentrated under reduced pressure to obtain a crude product; and the obtained crude product was purified by silica gel column chromatography using n-heptane as a mobile phase, and then purified by recrystallization with a dichloromethane/n-heptane system (a ratio volume of 1:3) to obtain SM-3 (82.4 g, yield: 74%).

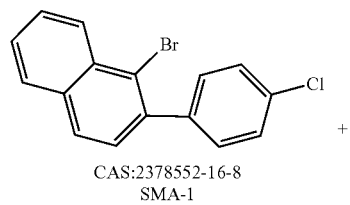

Magnesium ribbons (22.9, 944.5 mmol) and diethyl ether (250 mL) were placed in a dry round bottom flask under nitrogen protection, and iodine (250 mg) was added. Then a solution of SMA-1 (100 g, 314.4 mmol) dissolved into diethyl ether (500 mL) was slowly added dropwise into the flask, and after dropwise addition was complete, the mixture was heated to 35° C., and the reaction solution was stirred for 3 h; the resulting reaction solution was cooled to 0° C., and a solution of adamantanone (37.8 g, 252 mmol) dissoved into diethyl ether (500 mL) was slowly added dropwise into the reaction solution, and after dropwise addition was complete, the mixed solution was heated to 35° C., and continued to be stirred for 6 h; the resulting reaction solution was cooled to room temperature, 5% hydrochloric acid was added into the reaction solution until pH<7, stirring was performed for 1 h, diethyl ether (500 mL) was added into the reaction solution for extraction, the organic phases were combined, dried over anhydrous magnesium sulfate, and filtered, and a solvent was removed under reduced pressure; and the obtained crude product was purified by silica gel column chromatography using n-heptane as a mobile phase to obtain an intermediate IM-A-1 (78.5 g, yield: 80%) as a solid.

Intermediates IM-A-X were synthesized with reference to the method for the intermediate IM-A-1, except that the intermediates IM-A-X were prepared by using SMA-X/SM-X shown in Table 1 instead of SMA-1, where the prepared intermediates IM-A-X are as shown in Table 1.

TABLE 1

| SMA-X/SM-X | Intermediate IM-A-X | Yield (%) |
|---|---|---|
| CAS: 2378552-17-9<br>SMA-2 | IM-A-2 | 79 |

TABLE 1-continued
| SMA-X/SM-X | Intermediate IM-A-X | Yield (%) |
|---|---|---|
| 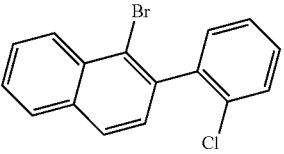 [SMILES: Clc1ccccc1-c1ccc2ccccc2c1Br]<br>CAS: 2378552-18-0<br>SMA-3 | 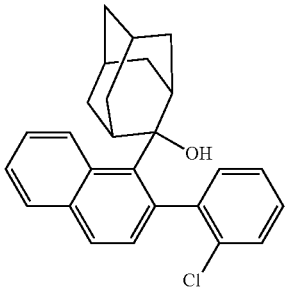 [SMILES: OC1(c2c(-c3ccccc3Cl)ccc3ccccc23)C2CC3CC(C2)CC1C3]<br>IM-A-3 | 77 |
| 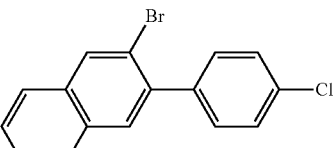<br>CAS: 1421694-50-9<br>SMA-4 | 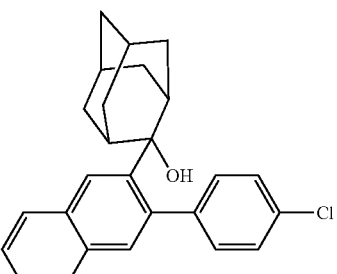<br>IM-A-4 | 76 |
| 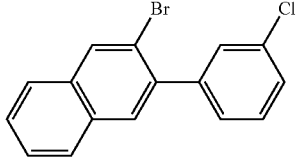 [SMILES: Clc1cccc(-c2cc3ccccc3cc2Br)c1]<br>CAS: 2378552-14-6<br>SMA-5 | 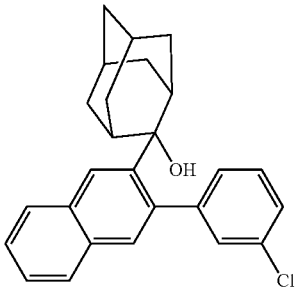 [SMILES: OC1(c2cc3ccccc3cc2-c2cccc(Cl)c2)C2CC3CC(C2)CC1C3]<br>IM-A-5 | 77 |
| 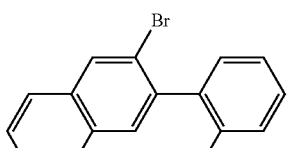<br>CAS: 2378552-15-7<br>SMA-6 | 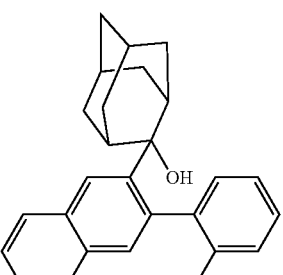<br>IM-A-6 | 75 |

TABLE 1-continued
| SMA-X/SM-X | Intermediate IM-A-X | Yield (%) |
|---|---|---|
| 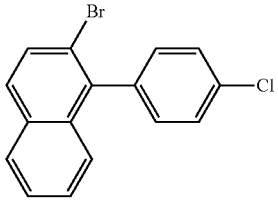 [SMILES: Clc1ccc(-c2c(Br)ccc3ccccc23)cc1]<br>CAS: 2378552-11-3<br>SMA-7 | 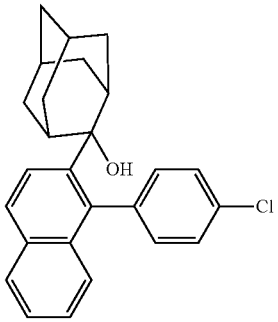 [SMILES: OC1(c2ccc3ccccc3c2-c2ccc(Cl)cc2)C2CC3CC(C2)CC1C3]<br>IM-A-7 | 74 |
| 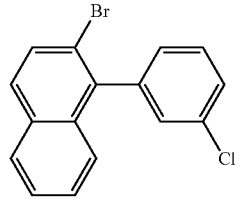 [SMILES: Clc1cccc(-c2c(Br)ccc3ccccc23)c1]<br>CAS: 2378552-12-4<br>SMA-8 | 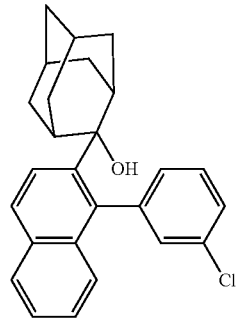 [SMILES: OC1(c2ccc3ccccc3c2-c2cccc(Cl)c2)C2CC3CC(C2)CC1C3]<br>IM-A-8 | 78 |
| 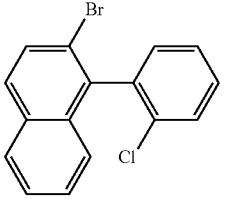 [SMILES: Clc1ccccc1-c1c(Br)ccc2ccccc12]<br>CAS: 2378552-13-5<br>SMA-9 | 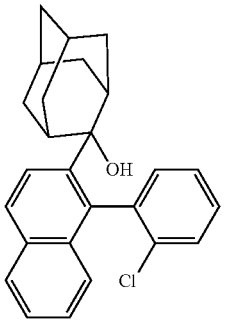 [SMILES: OC1(c2ccc3ccccc3c2-c2ccccc2Cl)C2CC3CC(C2)CC1C3]<br>IM-A-9 | 77 |
| 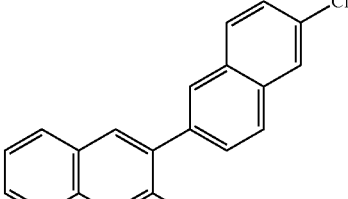<br>SM-1 | 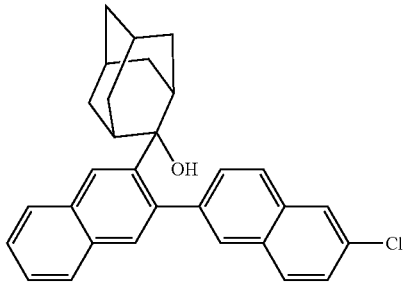 [SMILES: OC1(c2cc3ccccc3cc2-c2ccc3cc(Cl)ccc3c2)C2CC3CC(C2)CC1C3]<br>IM-A-10 | 78 |

TABLE 1-continued

| SMA-X/SM-X | Intermediate IM-A-X | Yield (%) |
|---|---|---|
| 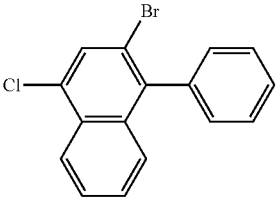 [SMILES: Clc1cc(Br)c(-c2ccccc2)c2ccccc12]<br>SM-2 | 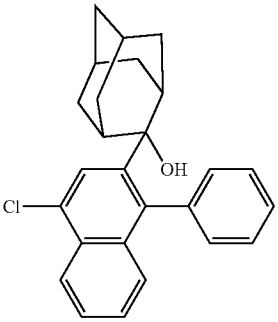 [SMILES: OC1(c2cc(Cl)c3ccccc3c2-c2ccccc2)C2CC3CC(C2)CC1C3]<br>IM-A-11 | 78 |
| 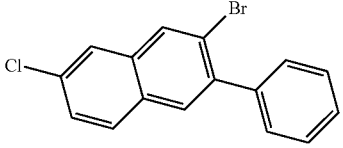 [SMILES: Clc1ccc2cc(-c3ccccc3)c(Br)cc2c1]<br>SM-3 | 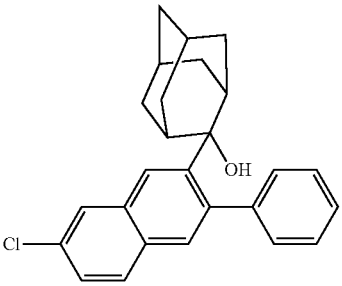 [SMILES: OC1(c2cc3cc(Cl)ccc3cc2-c2ccccc2)C2CC3CC(C2)CC1C3]<br>IM-A-12 | 77 |

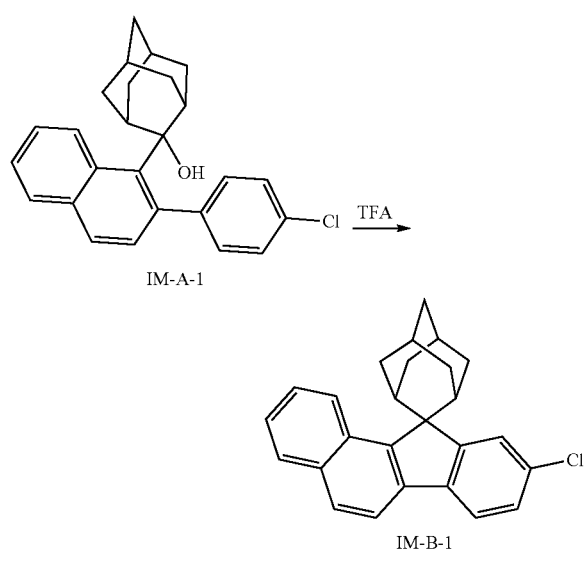

The intermediate IM-A-1 (40 g, 102.8 mmol), and trifluoroacetic acid (400 mL) were added into a reaction flask, stirring was started, then the system was gradually heated to 80° C., a reaction was carried out under reflux for 12 h, after the reaction was completed, the resulting reaction solution was poured into water (600 mL), after stirring for 30 min, filtering was performed, rinsing was performed with water, rinsing was performed with ethanol, and the obtained crude product was recrystallized with dichloromethane:n-heptane=(a volume ratio 1:2) to obtain an intermediate IM-1B-1 (30.5 g, yield: 800%).

Intermediates IM-B-X/intermediates M-B-X-0 were synthesized with reference to the synthesis method for the intermediate IM-B-1, except that the intermediates IM-B-X/intermediates IM-B-X-0 were prepared by using intermediates IM-A-X shown in Table 2 instead of the intermediate IM-A-1, where the prepared intermediates IM-B-X/intermediates IM-B-X-0 are as shown in Table 2.

TABLE 2
| Intermediate IM-A-X | Intermediate IM-B-X/ intermediate IM-B-X-O | Yield (%) |
|---|---|---|
| 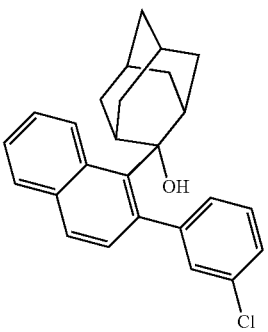 [SMILES: OC1(c2c(-c3cccc(Cl)c3)ccc3ccccc23)C2CC3CC(C2)CC1C3]<br>IM-A-2 | 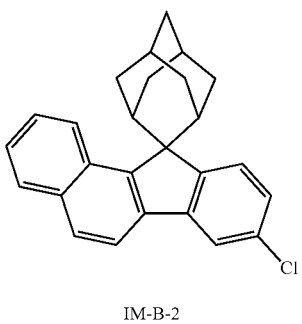<br>IM-B-2 | 41 |
|  | 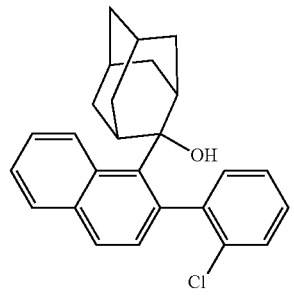 [SMILES: OC1(c2c(-c3ccccc3Cl)ccc3ccccc23)C2CC3CC(C2)CC1C3]<br>IM-B-2-0 | 39 |
| 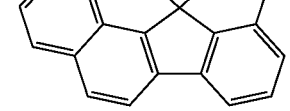<br>IM-A-3 | 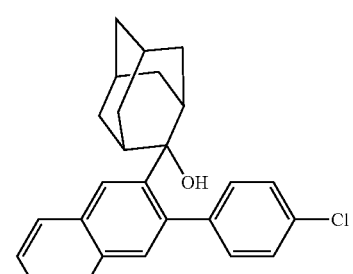<br>IM-B-3 | 81 |
| 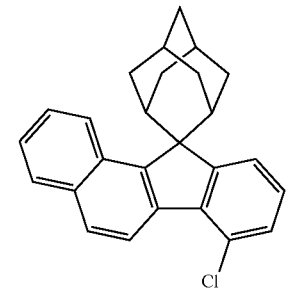 [SMILES: Clc1cccc2c1-c1ccc3ccccc3c1C21C2CC3CC(C2)CC1C3]<br>IM-A-4 | 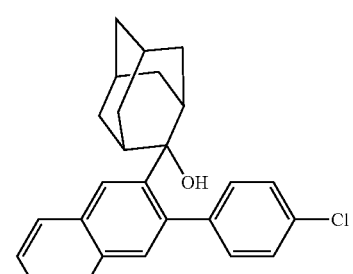<br>IM-B-4 | 83 |

TABLE 2-continued
| Intermediate IM-A-X | Intermediate IM-B-X/ intermediate IM-B-X-O | Yield (%) |
|---|---|---|
| 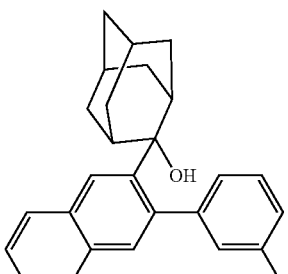<br>IM-A-5 | 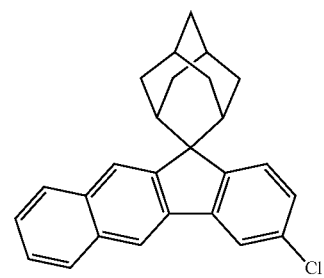 [SMILES: Clc1ccc2c(c1)-c1cc3ccccc3cc1C21C2CC3CC(C2)CC1C3]<br>IM-B-5 | 38 |
|  | 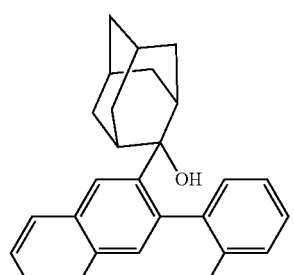<br>IM-B-5-0 | 39 |
| 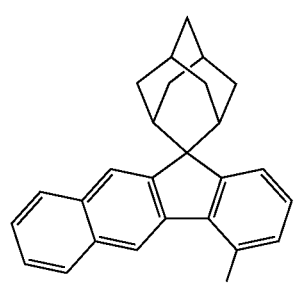<br>IM-A-6 | 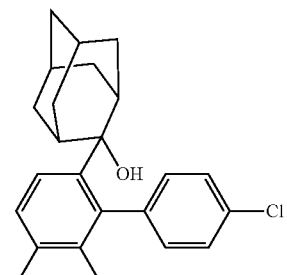<br>IM-B-6 | 84 |
| 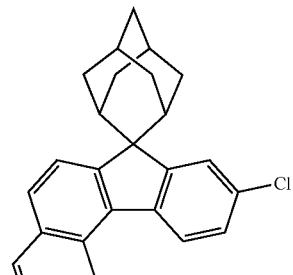<br>IM-A-7 | <br>IM-B-7 | 83 |

TABLE 2-continued
| Intermediate IM-A-X | Intermediate IM-B-X/ intermediate IM-B-X-O | Yield (%) |
|---|---|---|
| 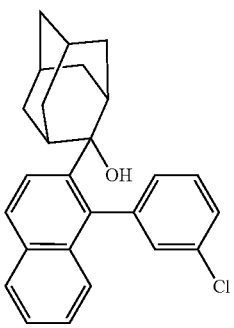 [SMILES: OC1(c2ccc3ccccc3c2-c2cccc(Cl)c2)C2CC3CC(C2)CC1C3] IM-A-8 | 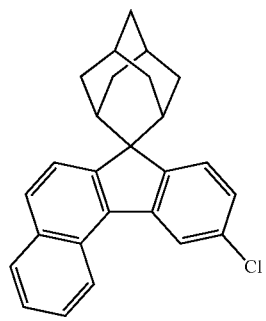 [SMILES: Clc1ccc2c(c1)-c1c(ccc3ccccc13)C21C2CC3CC(C2)CC1C3] IM-B-8 | 38 |
| | 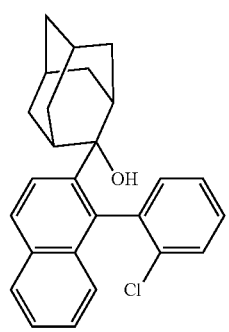 [SMILES: OC1(c2ccc3ccccc3c2-c2ccccc2Cl)C2CC3CC(C2)CC1C3] IM-B-8-0 | 37 |
| 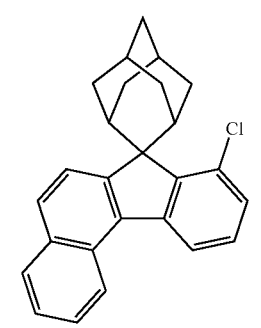 [SMILES: Clc1cccc2c1C1(c3ccc4ccccc4c3-2)C2CC3CC(C2)CC1C3] IM-A-9 | 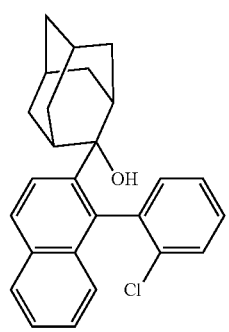 [SMILES: OC1(c2ccc3ccccc3c2-c2ccccc2Cl)C2CC3CC(C2)CC1C3] IM-B-9 | 82 |
| 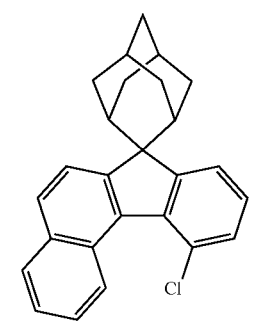 [SMILES: Clc1cccc2c1-c1c(ccc3ccccc13)C21C2CC3CC(C2)CC1C3] IM-A-10 | 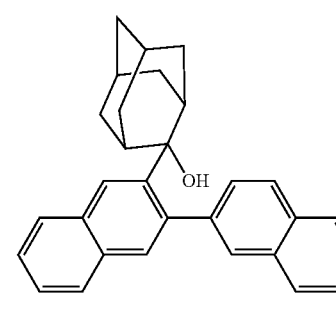 IM-B-10 | 82 |

TABLE 2-continued

| Intermediate IM-A-X | Intermediate IM-B-X/ intermediate IM-B-X-O | Yield (%) |
|---|---|---|
| IM-A-11 | IM-B-11 | 84 |
| IM-A-12 | IM-B-12 | 83 |

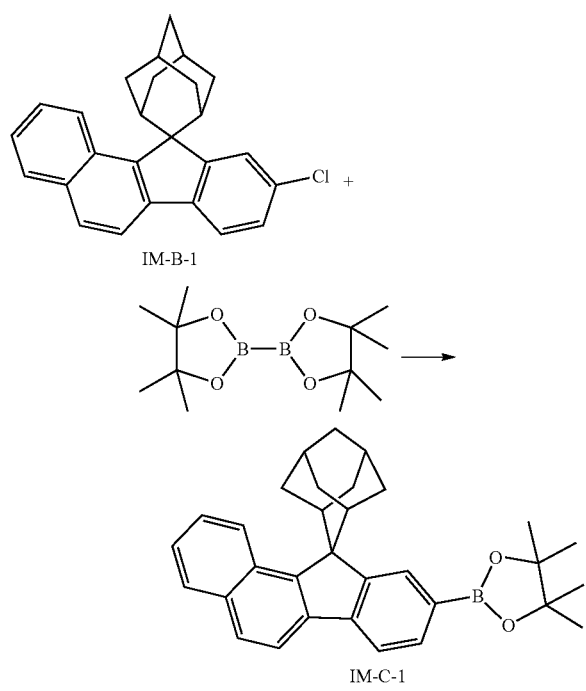

IM-B-1

IM-C-1

The intermediate IM-B-1 (15 g, 40.4 mmol), bis(pinacolato)diboron (10.3 g, 40.4 mmol), tris(dibenzylideneacetone)dipalladium (0.74 g, 0.81 mmol), 2-dicyclohexylphosphino-2,4,6-triisopropylbiphenyl (0.19 g, 0.40 mmol), potassium acetate (7.9 g, 80.8 mmol) and 1,4-dioxane (150 mL) were added into a reaction flask, heated to 110° C. under nitrogen protection, and stirred under heating and refluxing for 5 h. After cooling to room temperature, the resulting reaction solution was extracted with dichloromethane and water, an organic layer was dried over anhydrous magnesium sulfate, and filtered, the filtrate was allowed to pass through a short silica gel column, a solvent was removed under reduced pressure, and a crude product was purified by recrystallization using a dichloromethane/n-heptane (a volume ratio of 1:3) system to obtain an intermediate IM-C-1 (14.0 g, yield: 75%).

Intermediates IM-C-X/intermediates IM-C-X-0 were synthesized with reference to the method for the intermediate IM-C-1, except that the intermediates IM-C-X/intermediates IM-C-X-0 were prepared by using intermediates IM-B-X/intermediates IM-B-X-0 shown in Table 3 instead of the intermediate IM-B-1, where the prepared intermediates IM-C-X/intermediates IM-C-X-0 are as shown in Table 3.

TABLE 3
| Intermediate IM-B-X/ intermediate IM-B-X-0 | Intermediate IM-C-X/ intermediate IM-C-X-0 | Yield (%) |
|---|---|---|
| 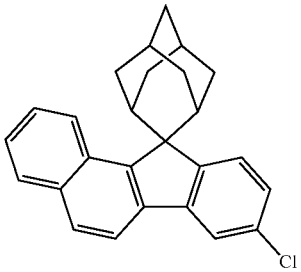 [SMILES: Clc1ccc2c(c1)-c1ccc3ccccc3c1C21C2CC3CC(C2)CC1C3] IM-B-2 | 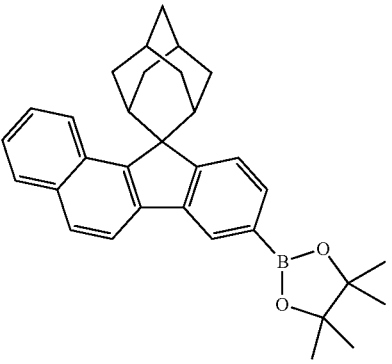 [SMILES: CC1(C)OB(c2ccc3c(c2)-c2ccc4ccccc4c2C32C3CC4CC(C3)CC2C4)OC1(C)C] IM-C-2 | 75 |
| 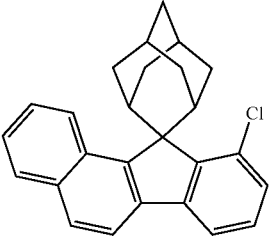 [SMILES: Clc1cccc2c1C1(c3c-2ccc2ccccc32)C2CC3CC(C2)CC1C3] IM-B-2-0 | 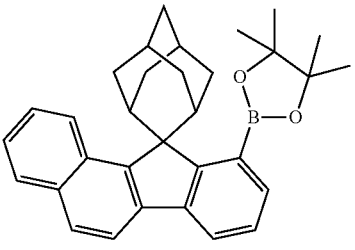 [SMILES: CC1(C)OB(c2cccc3c2C2(c4c-3ccc3ccccc43)C3CC4CC(C3)CC2C4)OC1(C)C] IM-C-2-0 | 73 |
| 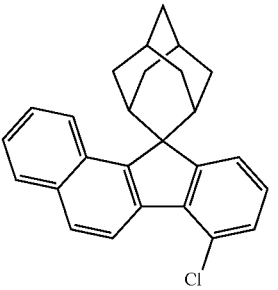 [SMILES: Clc1cccc2c1-c1ccc3ccccc3c1C21C2CC3CC(C2)CC1C3] IM-B-3 | 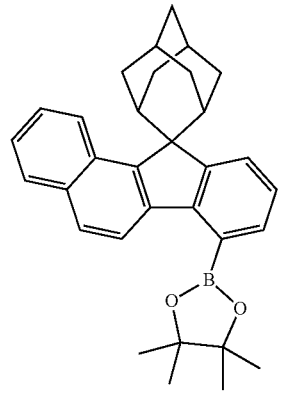 [SMILES: CC1(C)OB(c2cccc3c2-c2ccc4ccccc4c2C32C3CC4CC(C3)CC2C4)OC1(C)C] IM-C-3 | 71 |
| 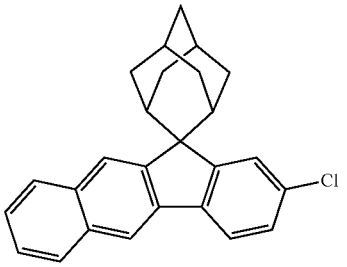 [SMILES: Clc1ccc2c(c1)C1(c3cc4ccccc4cc3-2)C2CC3CC(C2)CC1C3] IM-B-4 | 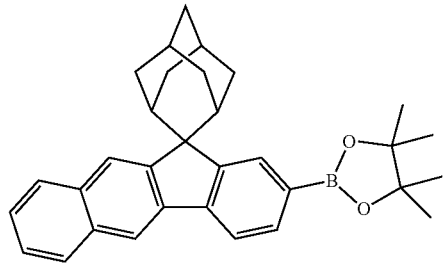 [SMILES: CC1(C)OB(c2ccc3c(c2)C2(c4cc5ccccc5cc4-3)C3CC4CC(C3)CC2C4)OC1(C)C] IM-C-4 | 74 |

TABLE 3-continued

| Intermediate IM-B-X/ intermediate IM-B-X-0 | Intermediate IM-C-X/ intermediate IM-C-X-0 | Yield (%) |
|---|---|---|
| IM-B-5 | IM-C-5 | 73 |
| IM-B-5-0 | IM-C-5-0 | 76 |
| IM-B-6 | IM-C-6 | 73 |
| IM-B-7 | IM-C-7 | 74 |

TABLE 3-continued
| Intermediate IM-B-X/ intermediate IM-B-X-0 | Intermediate IM-C-X/ intermediate IM-C-X-0 | Yield (%) |
|---|---|---|
| 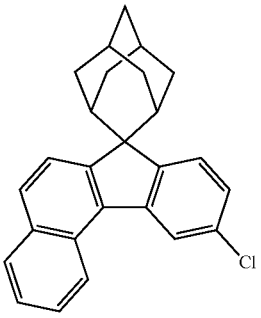 [SMILES: Clc1ccc2c(c1)-c1c(ccc3ccccc13)C21C2CC3CC(C2)CC1C3]<br>IM-B-8 | 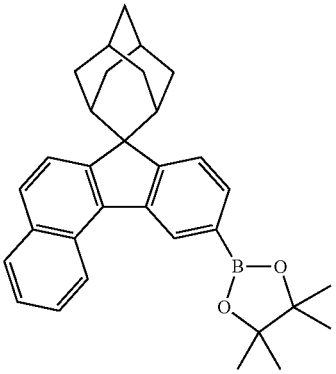 [SMILES: CC1(C)OB(c2ccc3c(c2)-c2c(ccc4ccccc24)C32C3CC4CC(C3)CC2C4)OC1(C)C]<br>IM-C-8 | 75 |
| 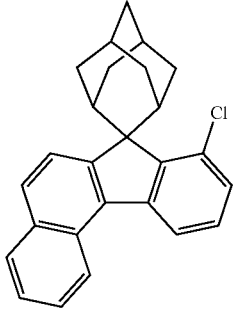 [SMILES: Clc1cccc2c1C1(c3ccc4ccccc4c3-2)C2CC3CC(C2)CC1C3]<br>IM-B-8-0 | 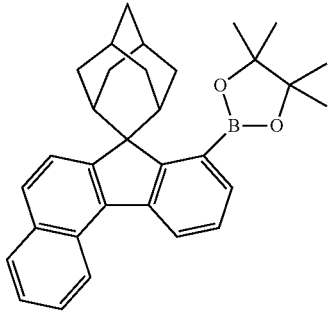 [SMILES: CC1(C)OB(c2cccc3c2C2(c4ccc5ccccc5c4-3)C3CC4CC(C3)CC2C4)OC1(C)C]<br>IM-C-8-0 | 74 |
| 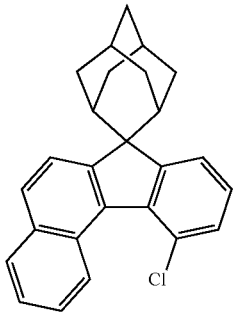 [SMILES: Clc1cccc2c1-c1c(ccc3ccccc13)C21C2CC3CC(C2)CC1C3]<br>IM-B-9 | 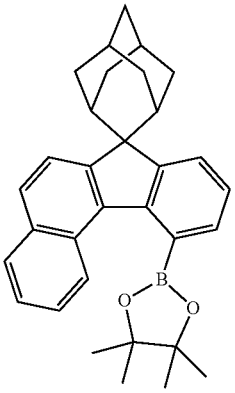 [SMILES: CC1(C)OB(c2cccc3c2-c2c(ccc4ccccc24)C32C3CC4CC(C3)CC2C4)OC1(C)C]<br>IM-C-9 | 76 |
| 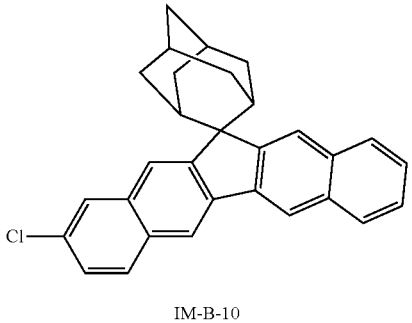<br>IM-B-10 | 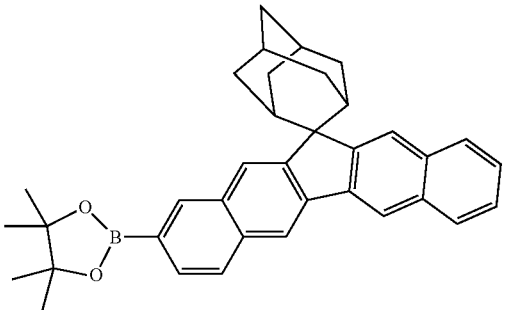 [SMILES: CC1(C)OB(c2ccc3cc4c(cc3c2)C2(c3cc5ccccc5cc3-4)C3CC4CC(C3)CC2C4)OC1(C)C]<br>IM-C-10 | 75 |

TABLE 3-continued

| Intermediate IM-B-X/ intermediate IM-B-X-0 | Intermediate IM-C-X/ intermediate IM-C-X-0 | Yield (%) |
|---|---|---|
| IM-B-11 | IM-C-11 | 73 |
| IM-B-12 | IM-C-12 | 74 |

IM-C-1 + 4-bromophenylboronic acid →[Pd(OAc)$_2$ K$_2$CO$_3$ x-Phos / PhMe EtOH H$_2$O] IM-M-1

The intermediate IM-C-1 (10 g, 21.6 mmol), p-bromophenylboronic acid (4.34 g, 21.6 mmol), palladium acetate (0.05 g, 0.22 mmol), 2-dicyclohexylphosphino-2',4',6'-triisopropylbiphenyl (0.21 g, 0.43 mmol) and potassium carbonate (5.98 g, 43.2 mmol) were added into toluene (80 mL), absolute ethanol (40 mL) and deionized water (20 mL), the mixture was heated to 80° C. under nitrogen protection, stirred for 2 h and then cooled to room temperature, the resulting reaction solution was washed with water, dried over magnesium sulfate, and filtered, and a solvent was removed from the filtrate under reduced pressure; and a crude product was purified by recrystallization using a dichloromethane/n-heptane system (a volume ratio of 1:3) to obtain IM-M-1 (7.4 g, yield: 75%).

Intermediates IM-M-X were synthesized with reference to the method for the intermediate IM-M-1, except that the intermediates IM-M-X were prepared by using intermediates IM-C-X/intermediates IM-C-X-0 shown in Table 4 instead of the intermediate IM-C-1, and SM A was used instead of p-bromophenylboronic acid, and the prepared intermediates IM-M-X are as shown in Table 4.

TABLE 4

| Intermediate IM-C-X/ intermediate IM-C-X-0 | SM A | Intermediate IM-M-X | Yield (%) |
|---|---|---|---|
| 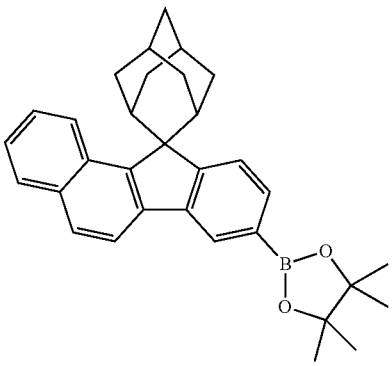 [SMILES: CC1(C)OB(c2ccc3c(c2)-c2ccc4ccccc4c2C32C3CC4CC(C3)CC2C4)OC1(C)C]<br>IM-C-2 | 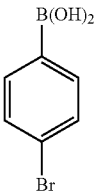 | 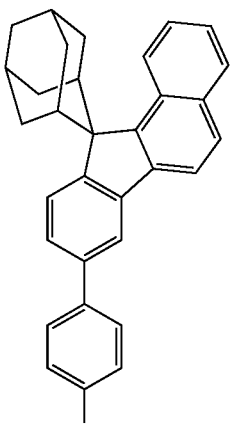<br>IM-M-2 | 73 |
| 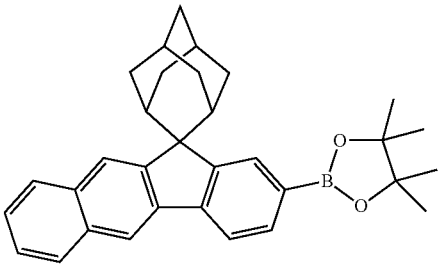 [SMILES: CC1(C)OB(c2ccc3c(c2)C2(c4cc5ccccc5cc4-3)C3CC4CC(C3)CC2C4)OC1(C)C]<br>IM-C-4 | 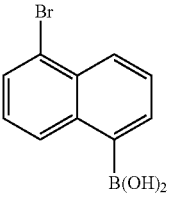 | 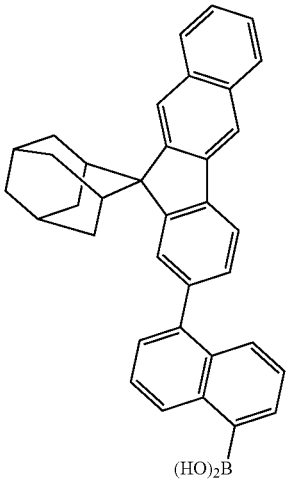 [SMILES: OB(O)c1cccc2c(-c3ccc4c(c3)C3(c5cc6ccccc6cc5-4)C4CC5CC(C4)CC3C5)cccc12]<br>IM-M-3 | 72 |

TABLE 4-continued

| Intermediate IM-C-X/ intermediate IM-C-X-0 | SM A | Intermediate IM-M-X | Yield (%) |
|---|---|---|---|
| 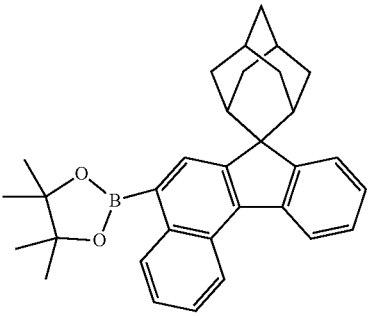 [SMILES: CC1(C)OB(c2cc3c(c4ccccc24)-c2ccccc2C32C3CC4CC(C3)CC2C4)OC1(C)C]<br>IM-C-11 | 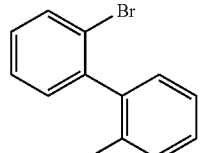 | 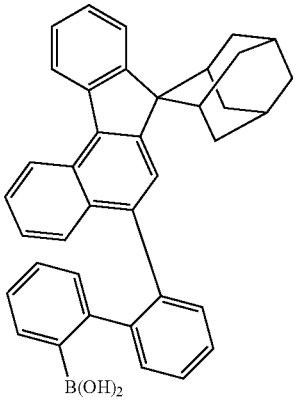 [SMILES: OB(O)c1ccccc1-c1ccccc1-c1cc2c(c3ccccc13)-c1ccccc1C21C2CC3CC(C2)CC1C3]<br>IM-M-4 | 73 |

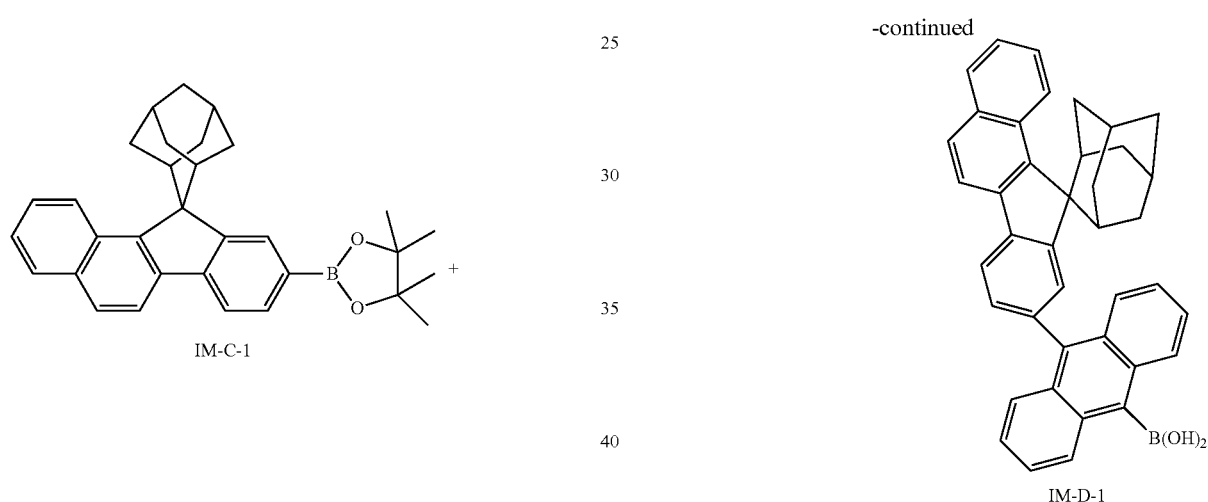

The intermediate IM-C-1 (10 g, 21.6 mmol), 10-bromoanthracene-9-boronic acid (6.51 g, 21.6 mmol), palladium acetate (0.05 g, 0.22 mmol), 2-dicyclohexylphosphino-2',4',6'-triisopropylbiphenyl (0.21 g, 0.43 mmol) and potassium carbonate (5.98 g, 43.2 mmol) were added into toluene (80 mL), absolute ethanol (40 mL) and deionized water (20 mL), the mixture was heated to 80° C. under nitrogen protection, stirred for 2 h and then cooled to room temperature, the resulting reaction solution was washed with water, dried over magnesium sulfate, and filtered, and a solvent was removed from the filtrate under reduced pressure; and a crude product was purified by recrystallization using a dichloromethane/n-heptane system (a volume ratio of 1:3) to obtain an intermediate IM-D-1 (8.42 g, yield: 70%).

Intermediates IM-D-X/intermediates IM-D-X-0 were synthesized with reference to the method for the intermediate IM-D-1, except that the intermediates IM-D-X/intermediates IM-D-X-0 were prepared by using intermediates IM-C-X/intermediates IM-C-X-0/intermediates IM-M-X instead of the intermediate IM-C-1, where the prepared intermediates IM-D-X/intermediates IM-D-X-0 are as shown in Table 5.

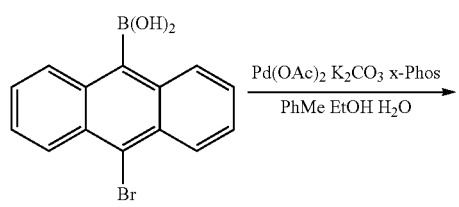

TABLE 5
| Intermediate IM-C-X/ intermediate IM-C-X-0/ intermediate IM-M-X | Intermediate IM-D-X/ intermediate IM-D-X-0 | Yield (%) |
|---|---|---|
| 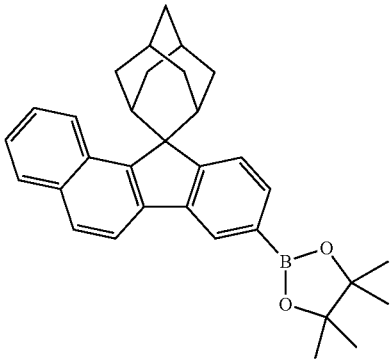 [SMILES: CC1(C)OB(c2ccc3c(c2)-c2ccc4ccccc4c2C32C3CC4CC(C3)CC2C4)OC1(C)C]<br>IM-C-2 | 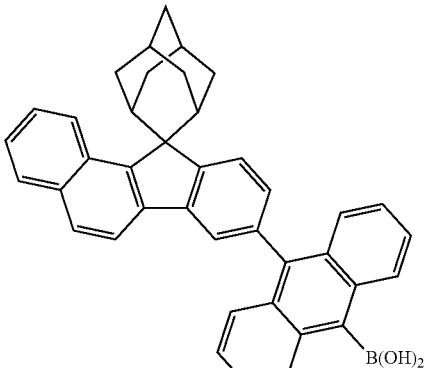<br>IM-D-2 | 71 |
| 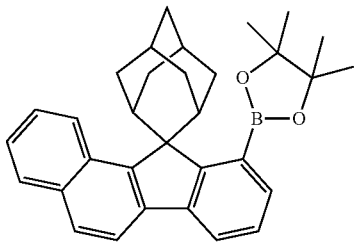 [SMILES: CC1(C)OB(c2cccc3c2C2(c4c-3ccc3ccccc43)C3CC4CC(C3)CC2C4)OC1(C)C]<br>IM-C-2-0 | 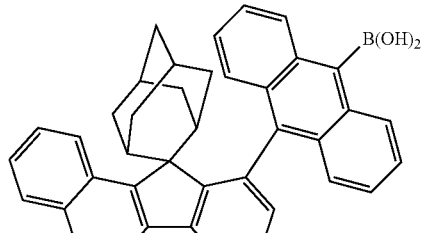<br>IM-D-2-0 | 70 |
| 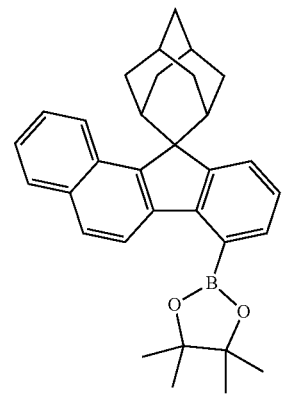 [SMILES: CC1(C)OB(c2cccc3c2-c2ccc4ccccc4c2C32C3CC4CC(C3)CC2C4)OC1(C)C]<br>IM-C-3 | 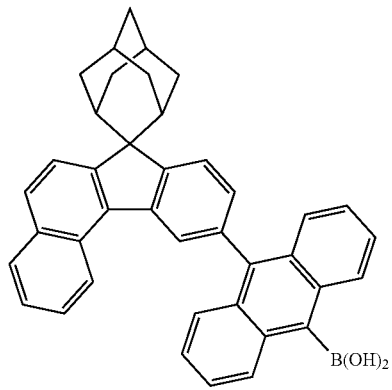 [SMILES: OB(O)c1c2ccccc2c(-c2ccc3c(c2)-c2c(ccc4ccccc24)C32C3CC4CC(C3)CC2C4)c2ccccc12]<br>IM-D-3 | 71 |
| 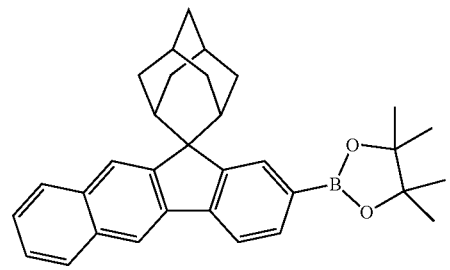 [SMILES: CC1(C)OB(c2ccc3c(c2)C2(c4cc5ccccc5cc4-3)C3CC4CC(C3)CC2C4)OC1(C)C]<br>IM-C-4 | 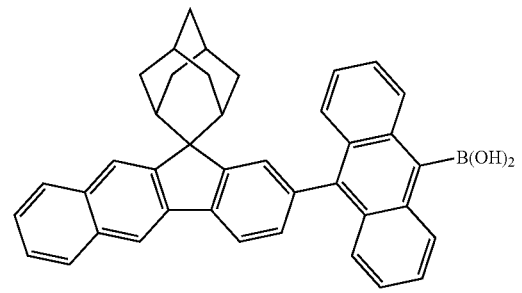 [SMILES: OB(O)c1c2ccccc2c(-c2ccc3c(c2)C2(c4cc5ccccc5cc4-3)C3CC4CC(C3)CC2C4)c2ccccc12]<br>IM-D-4 | 72 |

TABLE 5-continued
| Intermediate IM-C-X/ intermediate IM-C-X-0/ intermediate IM-M-X | Intermediate IM-D-X/ intermediate IM-D-X-0 | Yield (%) |
|---|---|---|
| 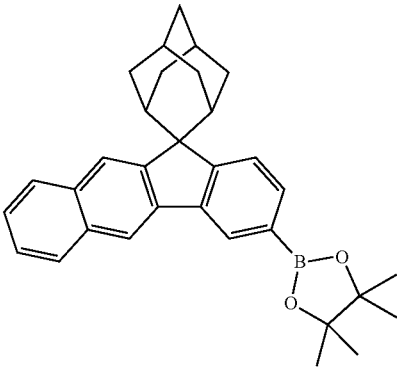 [SMILES: CC1(C)OB(c2ccc3c(c2)-c2cc4ccccc4cc2C32C3CC4CC(C3)CC2C4)OC1(C)C]<br>IM-C-5 | 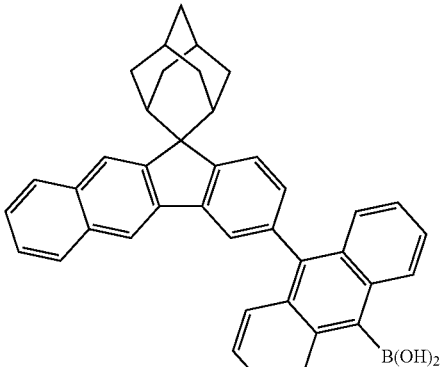<br>IM-D-5 | 73 |
| 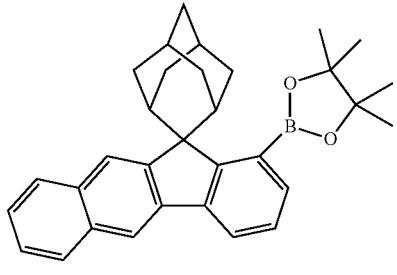 [SMILES: CC1(C)OB(c2cccc3c2C2(c4cc5ccccc5cc4-3)C3CC4CC(C3)CC2C4)OC1(C)C]<br>IM-C-5-0 | 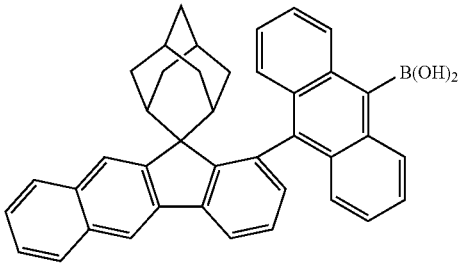 [SMILES: OB(O)c1c2ccccc2c(-c2cccc3c2C2(c4cc5ccccc5cc4-3)C3CC4CC(C3)CC2C4)c2ccccc12]<br>IM-D-5-0 | 74 |
| 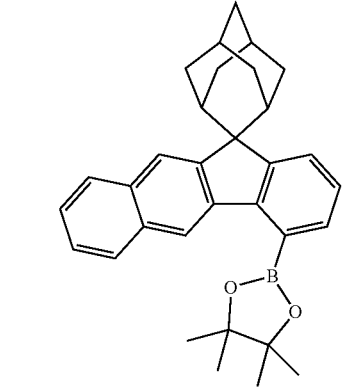 [SMILES: CC1(C)OB(c2cccc3c2-c2cc4ccccc4cc2C32C3CC4CC(C3)CC2C4)OC1(C)C]<br>IM-C-6 | 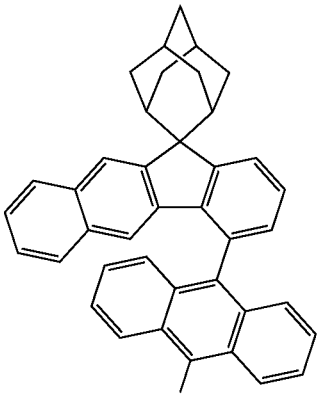<br>IM-D-6 | 70 |
| 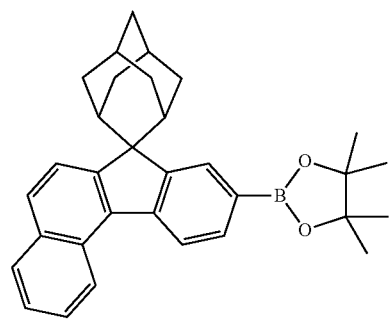 [SMILES: CC1(C)OB(c2ccc3c(c2)C2(c4ccc5ccccc5c4-3)C3CC4CC(C3)CC2C4)OC1(C)C]<br>IM-C-7 | 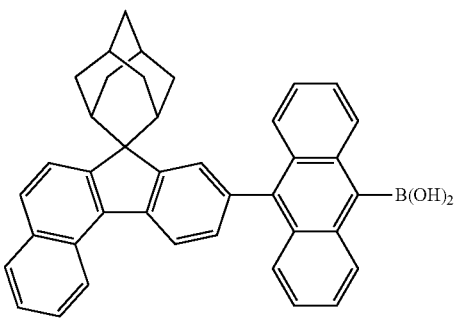 [SMILES: OB(O)c1c2ccccc2c(-c2ccc3c(c2)C2(c4ccc5ccccc5c4-3)C3CC4CC(C3)CC2C4)c2ccccc12]<br>IM-D-7 | 71 |

TABLE 5-continued
| Intermediate IM-C-X/ intermediate IM-C-X-0/ intermediate IM-M-X | Intermediate IM-D-X/ intermediate IM-D-X-0 | Yield (%) |
|---|---|---|
| 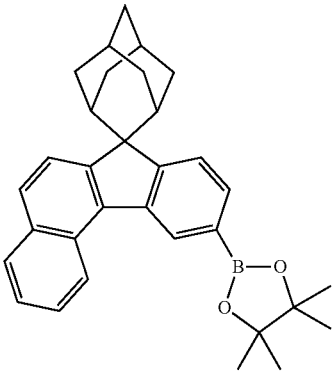 [SMILES: CC1(C)OB(c2ccc3c(c2)-c2c(ccc4ccccc24)C32C3CC4CC(C3)CC2C4)OC1(C)C]<br>IM-C-8 | 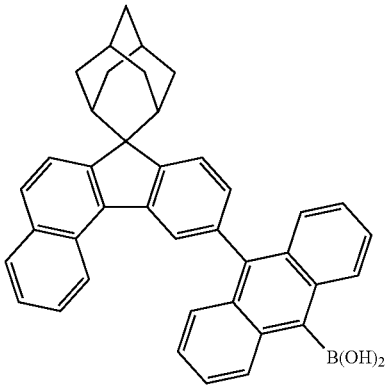 [SMILES: OB(O)c1c2ccccc2c(-c2ccc3c(c2)-c2c(ccc4ccccc24)C32C3CC4CC(C3)CC2C4)c2ccccc12]<br>IM-D-8 | 70 |
| 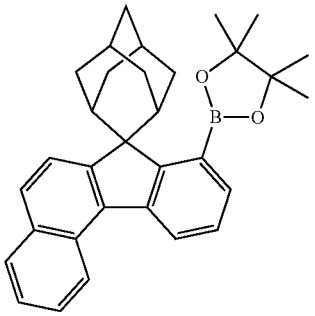 [SMILES: CC1(C)OB(c2cccc3c2C2(c4ccc5ccccc5c4-3)C3CC4CC(C3)CC2C4)OC1(C)C]<br>IM-C-8-0 | 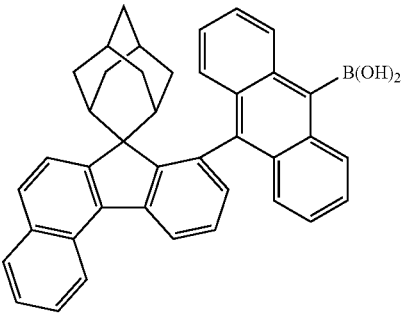 [SMILES: OB(O)c1c2ccccc2c(-c2cccc3c2C2(c4ccc5ccccc5c4-3)C3CC4CC(C3)CC2C4)c2ccccc12]<br>IM-D-8-0 | 71 |
| 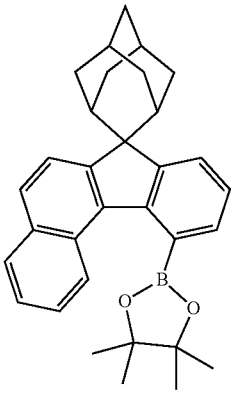 [SMILES: CC1(C)OB(c2cccc3c2-c2c(ccc4ccccc24)C32C3CC4CC(C3)CC2C4)OC1(C)C]<br>IM-C-9 | 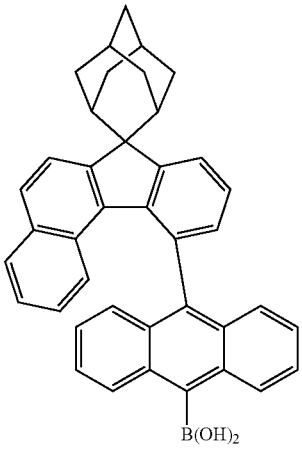 [SMILES: OB(O)c1c2ccccc2c(-c2cccc3c2-c2c(ccc4ccccc24)C32C3CC4CC(C3)CC2C4)c2ccccc12]<br>IM-D-9 | 70 |

TABLE 5-continued
| Intermediate IM-C-X/ intermediate IM-C-X-0/ intermediate IM-M-X | Intermediate IM-D-X/ intermediate IM-D-X-0 | Yield (%) |
|---|---|---|
| 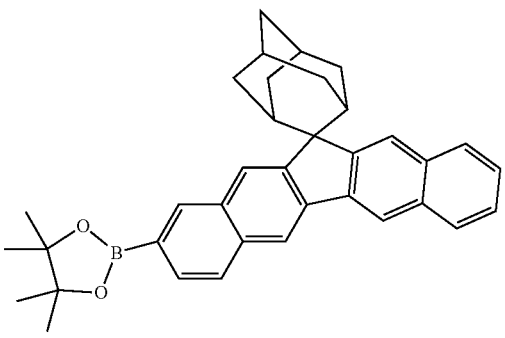 [SMILES: CC1(C)OB(c2ccc3cc4c(cc3c2)C2(c3cc5ccccc5cc3-4)C3CC4CC(C3)CC2C4)OC1(C)C]<br>IM-C-10 | 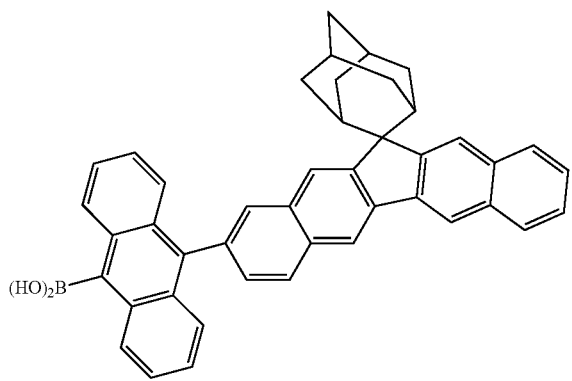 [SMILES: OB(O)c1c2ccccc2c(-c2ccc3cc4c(cc3c2)C2(c3cc5ccccc5cc3-4)C3CC4CC(C3)CC2C4)c2ccccc12]<br>IM-D-10 | 72 |
| 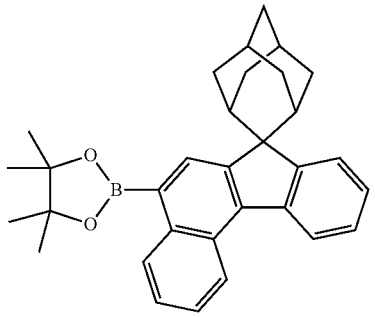 [SMILES: CC1(C)OB(c2cc3c(c4ccccc24)-c2ccccc2C32C3CC4CC(C3)CC2C4)OC1(C)C]<br>IM-C-11 | 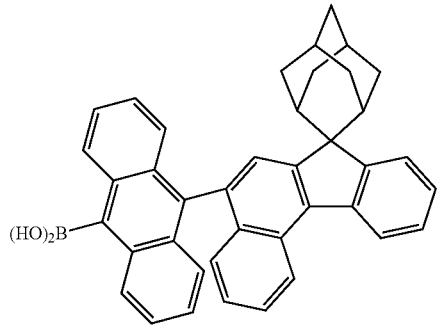 [SMILES: OB(O)c1c2ccccc2c(-c2cc3c(c4ccccc24)-c2ccccc2C32C3CC4CC(C3)CC2C4)c2ccccc12]<br>IM-D-11 | 72 |
| 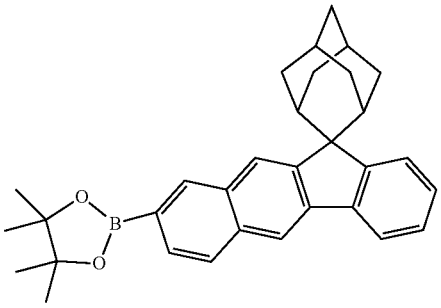 [SMILES: CC1(C)OB(c2ccc3cc4c(cc3c2)C2(c3ccccc3-4)C3CC4CC(C3)CC2C4)OC1(C)C]<br>IM-C-12 | 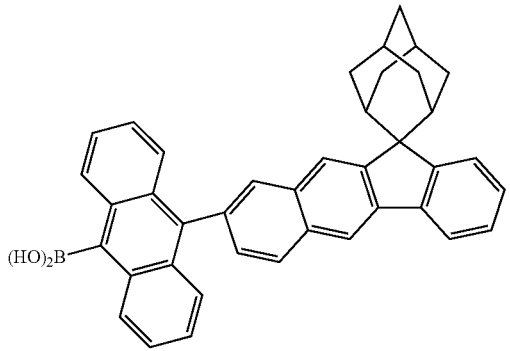 [SMILES: OB(O)c1c2ccccc2c(-c2ccc3cc4c(cc3c2)C2(c3ccccc3-4)C3CC4CC(C3)CC2C4)c2ccccc12]<br>IM-D-12 | 73 |

TABLE 5-continued
| Intermediate IM-C-X/ intermediate IM-C-X-0/ intermediate IM-M-X | Intermediate IM-D-X/ intermediate IM-D-X-0 | Yield (%) |
|---|---|---|
| 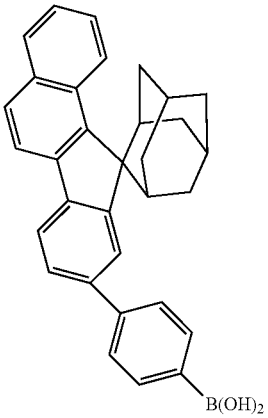 [SMILES: OB(O)c1ccc(-c2ccc3c(c2)C2(c4c-3ccc3ccccc43)C3CC4CC(C3)CC2C4)cc1]<br>IM-M-1 | 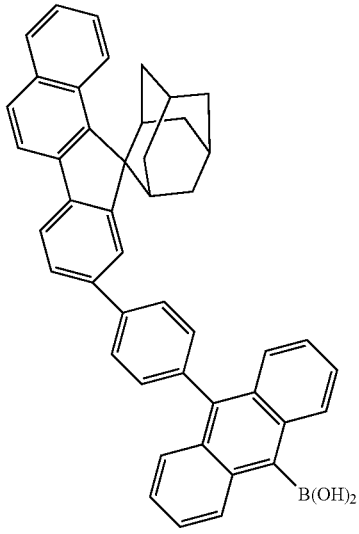 [SMILES: OB(O)c1c2ccccc2c(-c2ccc(-c3ccc4c(c3)C3(c5c-4ccc4ccccc54)C4CC5CC(C4)CC3C5)cc2)c2ccccc12]<br>IM-D-13 | 74 |
| 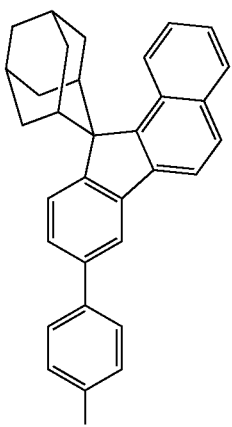<br>IM-M-2 | 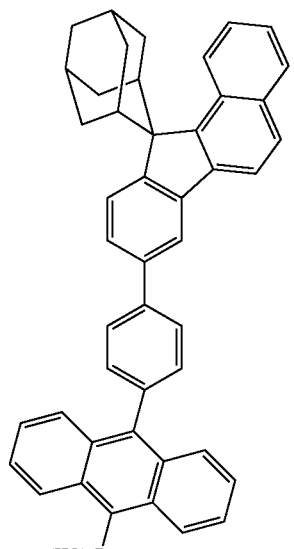<br>IM-D-13-0 | 75 |

TABLE 5-continued
| Intermediate IM-C-X/ intermediate IM-C-X-0/ intermediate IM-M-X | Intermediate IM-D-X/ intermediate IM-D-X-0 | Yield (%) |
|---|---|---|
| 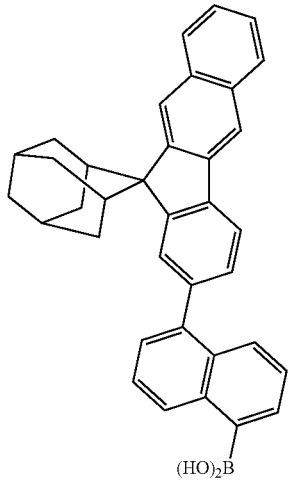 [SMILES: OB(O)c1cccc2c(-c3ccc4c(c3)C3(c5cc6ccccc6cc5-4)C4CC5CC(C4)CC3C5)cccc12]<br>IM-M-3 | 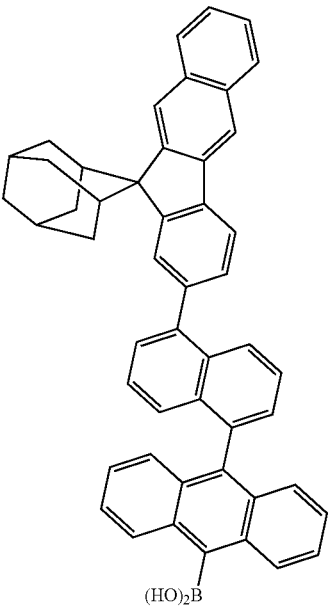 [SMILES: OB(O)c1c2ccccc2c(-c2cccc3c(-c4ccc5c(c4)C4(c6cc7ccccc7cc6-5)C5CC6CC(C5)CC4C6)cccc23)c2ccccc12]<br>IM-D-14 | 76 |
| 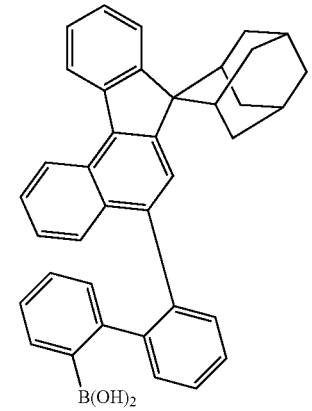 [SMILES: OB(O)c1ccccc1-c1ccccc1-c1cc2c(c3ccccc13)-c1ccccc1C21C2CC3CC(C2)CC1C3]<br>IM-M-4 | 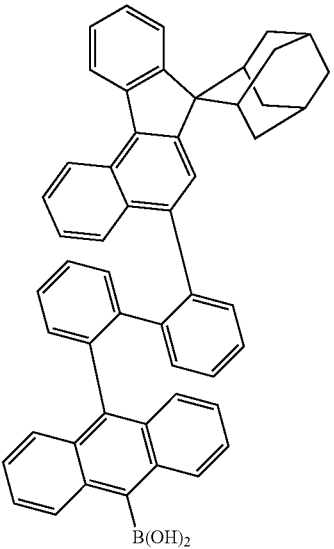 [SMILES: OB(O)c1c2ccccc2c(-c2ccccc2-c2ccccc2-c2cc3c(c4ccccc24)-c2ccccc2C32C3CC4CC(C3)CC2C4)c2ccccc12]<br>IM-D-15 | 72 |

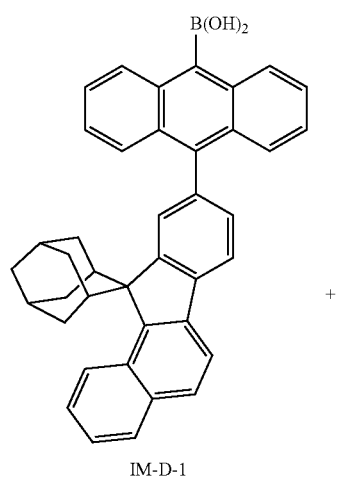

IM-D-1

+

Br —[phenyl]
Pd(PPh₃)₄ K₂CO₃ TBAC
―――――――――――――→
PhMe EtOH H₂O

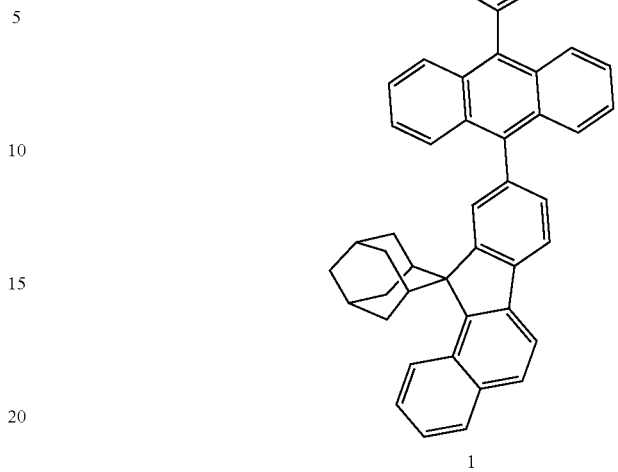

1

The intermediate IM-D-1 (5 g, 8.98 mmol), bromobenzene (1.41 g, 8.98 mmol), tetrakis(triphenylphosphine)palladium (0.52 g, 0.44 mmol), potassium carbonate (3.71 g, 26.9 mmol), and tetrabutylammonium chloride (0.12 g, 0.45 mmol) were respectively added into a three-necked flask, toluene (40 mL), ethanol (20 mL), and water (10 mL) were measured and added into the reactor, the mixture was refluxed at 80° C. for 12 h, when the reaction was finished, extraction was performed with dichloromethane and water, an organic phase was taken and dried over anhydrous MgSO₄, suction filtration was performed, an organic layer was concentrated, and a crude product was purified by passing through a silica gel column to obtain a compound 1 (4.23 g, yield: 80%).

Compounds X were synthesized with reference to the method for the compound 1 except that the compounds X were prepared by using intermediates IM-D-X/intermediates IM-D-X-0 instead of the intermediate IM-D-1, and SM B was used instead of bromobenzene, and the prepared compounds X are as shown in Table 6.

TABLE 6

| Intermediate IM-D-X/ intermediate IM-D-X-0 | Raw material SM B | Compound X | Yield (%) |
|---|---|---|---|
| IM-D-1 | naphthyl-Br | 2 | 76 |
| IM-D-1 | biphenyl-Br | 5 | 77 |

TABLE 6-continued
| Intermediate IM-D-X/ intermediate IM-D-X-0 | Raw material SM B | Compound X | Yield (%) |
|---|---|---|---|
| | 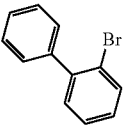 [SMILES: Brc1ccccc1-c1ccccc1] | 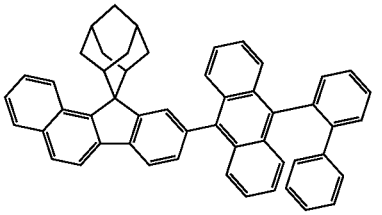 [SMILES: c1ccc(-c2ccccc2-c2c3ccccc3c(-c3ccc4c(c3)C3(c5c-4ccc4ccccc54)C4CC5CC(C4)CC3C5)c3ccccc23)cc1]<br>6 | 75 |
| | 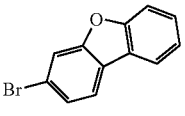 [SMILES: Brc1ccc2c(c1)oc1ccccc12] | 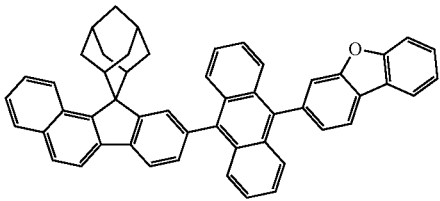 [SMILES: c1ccc2c3c(ccc2c1)-c1ccc(-c2c4ccccc4c(-c4ccc5c(c4)oc4ccccc45)c4ccccc24)cc1C31C2CC3CC(C2)CC1C3]<br>7 | 74 |
| 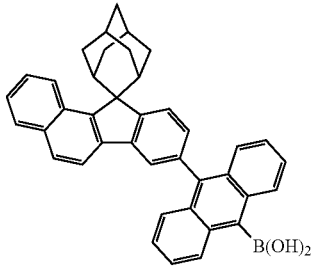 [SMILES: OB(O)c1c2ccccc2c(-c2ccc3c(c2)-c2ccc4ccccc4c2C32C3CC4CC(C3)CC2C4)c2ccccc12]<br>IM-D-2 | 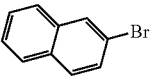 [SMILES: Brc1ccc2ccccc2c1] | 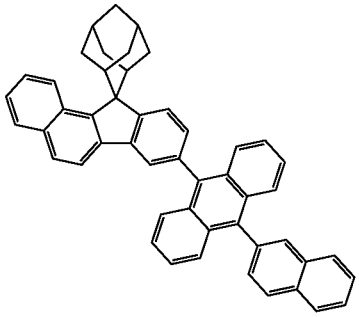 [SMILES: c1ccc2cc(-c3c4ccccc4c(-c4ccc5c(c4)-c4ccc6ccccc6c4C54C5CC6CC(C5)CC4C6)c4ccccc34)ccc2c1]<br>35 | 76 |
| |  | 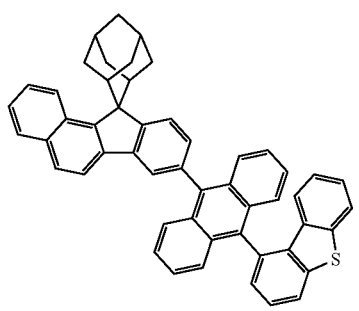 [SMILES: c1ccc2c3c(ccc2c1)-c1cc(-c2c4ccccc4c(-c4cccc5sc6ccccc6c45)c4ccccc24)ccc1C31C2CC3CC(C2)CC1C3]<br>45 | 75 |

TABLE 6-continued

| Intermediate IM-D-X/ intermediate IM-D-X-0 | Raw material SM B | Compound X | Yield (%) |
|---|---|---|---|
| | (Br-fluorene with dimethyl) | Structure 49 | 74 |
| IM-D-2-0 | (Br-dibenzofuran-phenyl) | Structure 75 | 76 |
| IM-D-3 | (Br-phenanthrene) | Structure 73 | 73 |

TABLE 6-continued
| Intermediate IM-D-X/ intermediate IM-D-X-0 | Raw material SM B | Compound X | Yield (%) |
|---|---|---|---|
|  | 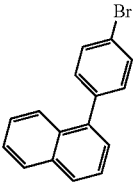 [SMILES: Brc1ccc(-c2cccc3ccccc23)cc1] | 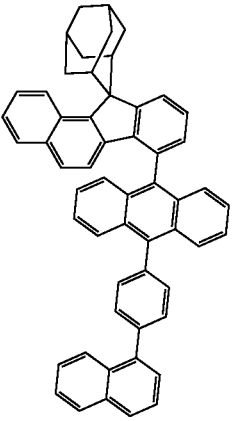 [SMILES: c1cc(-c2c3ccccc3c(-c3ccc(-c4cccc5ccccc45)cc3)c3ccccc23)c2c(c1)C1(c3c-2ccc2ccccc32)C2CC3CC(C2)CC1C3] 70 | 72 |
| 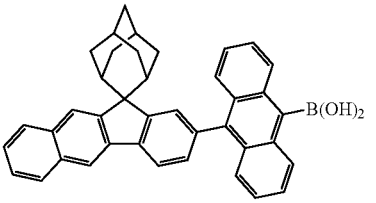 [SMILES: OB(O)c1c2ccccc2c(-c2ccc3c(c2)C2(c4cc5ccccc5cc4-3)C3CC4CC(C3)CC2C4)c2ccccc12] IM-D-4 | 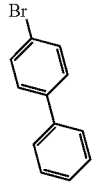 | 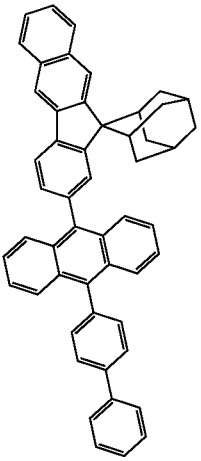 [SMILES: c1ccc(-c2ccc(-c3c4ccccc4c(-c4ccc5c(c4)C4(c6cc7ccccc7cc6-5)C5CC6CC(C5)CC4C6)c4ccccc34)cc2)cc1] 88 | 73 |
|  | 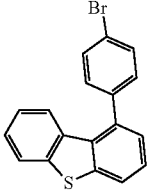 [SMILES: Brc1ccc(-c2cccc3sc4ccccc4c23)cc1] | 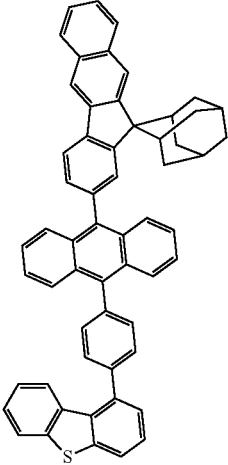 [SMILES: c1ccc2cc3c(cc2c1)-c1ccc(-c2c4ccccc4c(-c4ccc(-c5cccc6sc7ccccc7c56)cc4)c4ccccc24)cc1C31C2CC3CC(C2)CC1C3] 107 | 75 |

TABLE 6-continued
| Intermediate IM-D-X/ intermediate IM-D-X-0 | Raw material SM B | Compound X | Yield (%) |
|---|---|---|---|
| 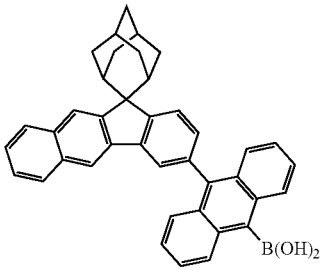 [SMILES: OB(O)c1c2ccccc2c(-c2ccc3c(c2)-c2cc4ccccc4cc2C32C3CC4CC(C3)CC2C4)c2ccccc12] IM-D-5 | 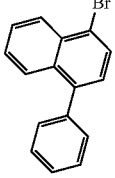 | 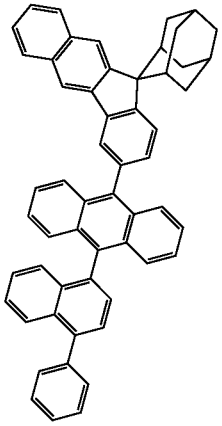 [SMILES: c1ccc(-c2ccc(-c3c4ccccc4c(-c4ccc5c(c4)-c4cc6ccccc6cc4C54C5CC6CC(C5)CC4C6)c4ccccc34)c3ccccc23)cc1] 119 | 74 |
| 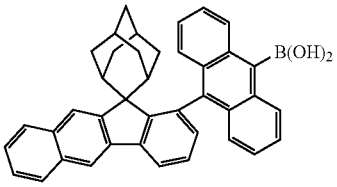 [SMILES: OB(O)c1c2ccccc2c(-c2cccc3c2C2(c4cc5ccccc5cc4-3)C3CC4CC(C3)CC2C4)c2ccccc12] IM-D-5-0 | 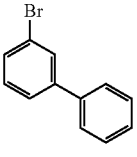 | 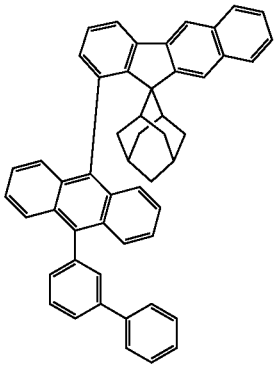 [SMILES: c1ccc(-c2cccc(-c3c4ccccc4c(-c4cccc5c4C4(c6cc7ccccc7cc6-5)C5CC6CC(C5)CC4C6)c4ccccc34)c2)cc1] 148 | 75 |
| 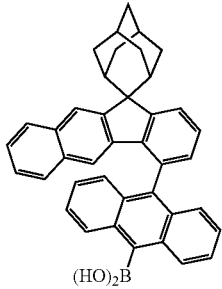 [SMILES: OB(O)c1c2ccccc2c(-c2cccc3c2-c2cc4ccccc4cc2C32C3CC4CC(C3)CC2C4)c2ccccc12] IM-D-6 | 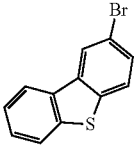 [SMILES: Brc1ccc2sc3ccccc3c2c1] | 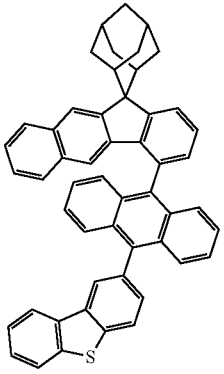 [SMILES: c1cc(-c2c3ccccc3c(-c3ccc4sc5ccccc5c4c3)c3ccccc23)c2c(c1)C1(c3cc4ccccc4cc3-2)C2CC3CC(C2)CC1C3] 136 | 73 |

TABLE 6-continued

| Intermediate IM-D-X/ intermediate IM-D-X-0 | Raw material SM B | Compound X | Yield (%) |
|---|---|---|---|
| IM-D-7 | (3-bromodibenzofuran) | 162 | 72 |
|  | (1-(4-bromophenyl)dibenzofuran) | 175 | 71 |
| IM-D-8 | (3-bromobiphenyl) | 186 | 70 |

TABLE 6-continued
| Intermediate IM-D-X/ intermediate IM-D-X-0 | Raw material SM B | Compound X | Yield (%) |
|---|---|---|---|
| | 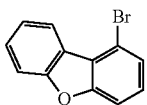 [SMILES: Brc1cccc2oc3ccccc3c12] | 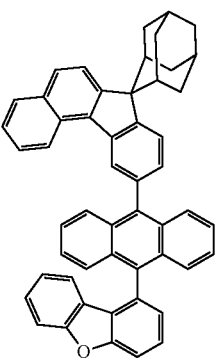 [SMILES: c1ccc2c3c(ccc2c1)C1(c2ccc(-c4c5ccccc5c(-c5cccc6oc7ccccc7c56)c5ccccc45)cc2-3)C2CC3CC(C2)CC1C3] 186 | 71 |
| 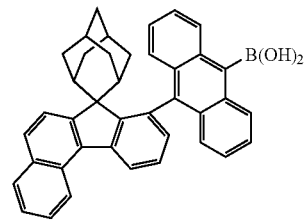 [SMILES: OB(O)c1c2ccccc2c(-c2cccc3c2C2(c4ccc5ccccc5c4-3)C3CC4CC(C3)CC2C4)c2ccccc12] IM-D-8-0 | 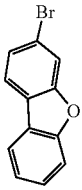 | 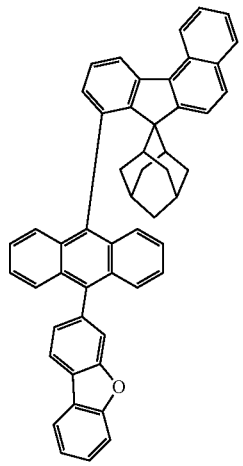 [SMILES: c1cc2c(c(-c3c4ccccc4c(-c4ccc5c(c4)oc4ccccc45)c4ccccc34)c1)C1(c3ccc4ccccc4c3-2)C2CC3CC(C2)CC1C3] 152 | 73 |
| 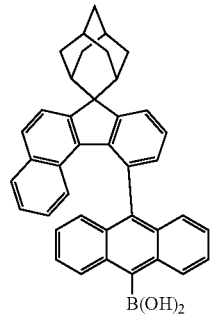 [SMILES: OB(O)c1c2ccccc2c(-c2cccc3c2-c2c(ccc4ccccc24)C32C3CC4CC(C3)CC2C4)c2ccccc12] IM-D-9 | 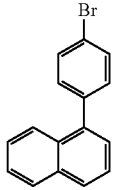 | 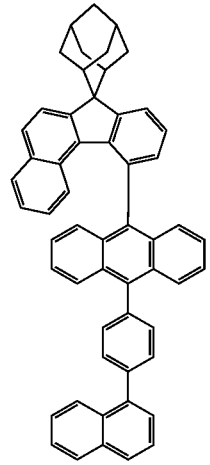 [SMILES: c1cc(-c2c3ccccc3c(-c3ccc(-c4cccc5ccccc45)cc3)c3ccccc23)c2c(c1)C1(c3ccc4ccccc4c3-2)C2CC3CC(C2)CC1C3] 212 | 72 |

TABLE 6-continued
| Intermediate IM-D-X/ intermediate IM-D-X-0 | Raw material SM B | Compound X | Yield (%) |
|---|---|---|---|
| 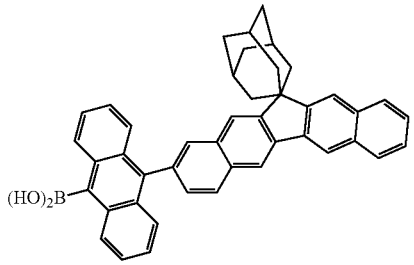 IM-D-10 | 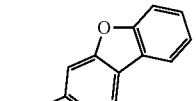 | 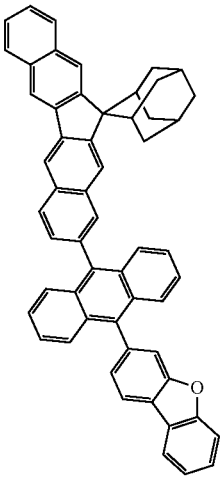 [SMILES: c1ccc2cc3c(cc2c1)-c1cc2ccc(-c4c5ccccc5c(-c5ccc6c(c5)oc5ccccc56)c5ccccc45)cc2cc1C31C2CC3CC(C2)CC1C3] 317 | 71 |
| 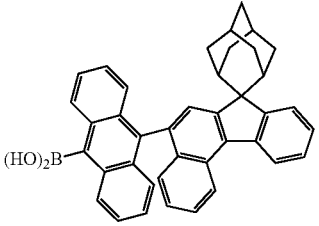 [SMILES: OB(O)c1c2ccccc2c(-c2cc3c(c4ccccc24)-c2ccccc2C32C3CC4CC(C3)CC2C4)c2ccccc12] IM-D-11 | 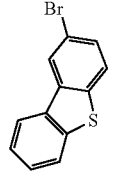 | 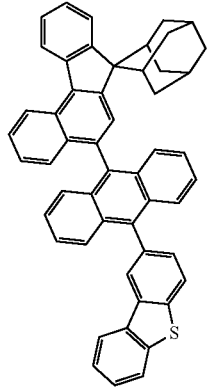 [SMILES: c1ccc2c(c1)-c1c(cc(-c3c4ccccc4c(-c4ccc5sc6ccccc6c5c4)c4ccccc34)c3ccccc13)C21C2CC3CC(C2)CC1C3] 231 | 70 |
| 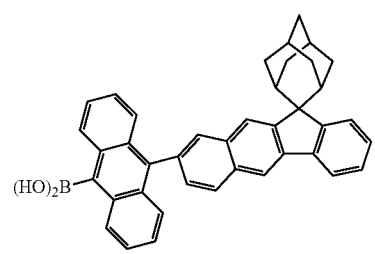 [SMILES: OB(O)c1c2ccccc2c(-c2ccc3cc4c(cc3c2)C2(c3ccccc3-4)C3CC4CC(C3)CC2C4)c2ccccc12] IM-D-12 | 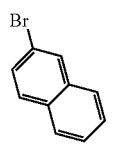 | 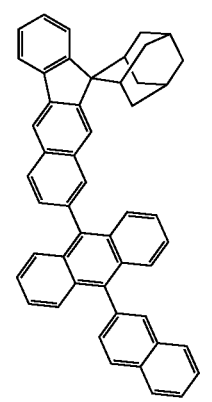 [SMILES: c1ccc2c(c1)-c1cc3ccc(-c4c5ccccc5c(-c5ccc6ccccc6c5)c5ccccc45)cc3cc1C21C2CC3CC(C2)CC1C3] 247 | 73 |

TABLE 6-continued
| Intermediate IM-D-X/ intermediate IM-D-X-0 | Raw material SM B | Compound X | Yield (%) |
|---|---|---|---|
| 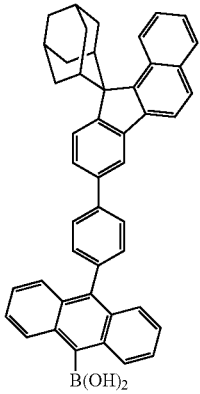 [SMILES: OB(O)c1c2ccccc2c(-c2ccc(-c3ccc4c(c3)-c3ccc5ccccc5c3C43C4CC5CC(C4)CC3C5)cc2)c2ccccc12]<br>IM-D-13-0 |  | 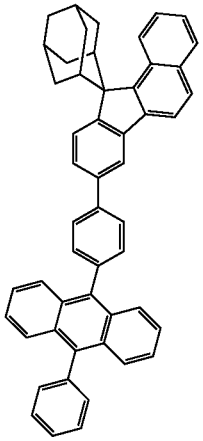 [SMILES: c1ccc(-c2c3ccccc3c(-c3ccc(-c4ccc5c(c4)-c4ccc6ccccc6c4C54C5CC6CC(C5)CC4C6)cc3)c3ccccc23)cc1]<br>260 | 72 |
| 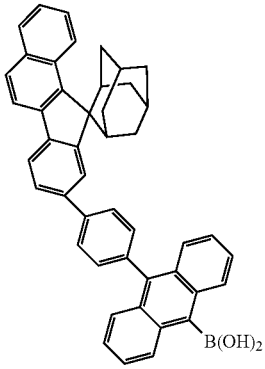 [SMILES: OB(O)c1c2ccccc2c(-c2ccc(-c3ccc4c(c3)C3(c5c-4ccc4ccccc54)C4CC5CC(C4)CC3C5)cc2)c2ccccc12]<br>IM-D-13 |  | 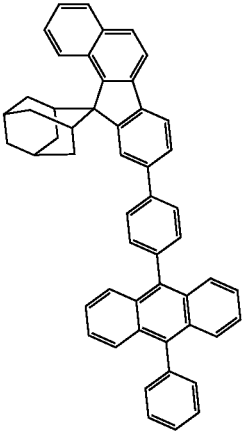 [SMILES: c1ccc(-c2c3ccccc3c(-c3ccc(-c4ccc5c(c4)C4(c6c-5ccc5ccccc65)C5CC6CC(C5)CC4C6)cc3)c3ccccc23)cc1]<br>316 | 73 |
| 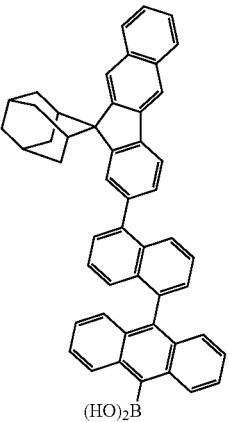 [SMILES: OB(O)c1c2ccccc2c(-c2cccc3c(-c4ccc5c(c4)C4(c6cc7ccccc7cc6-5)C5CC6CC(C5)CC4C6)cccc23)c2ccccc12]<br>IM-D-14 | 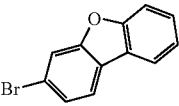 [SMILES: Brc1ccc2c(c1)oc1ccccc12] | 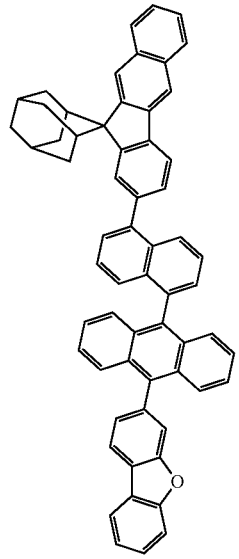 [SMILES: c1ccc2cc3c(cc2c1)-c1ccc(-c2cccc4c(-c5c6ccccc6c(-c6ccc7c(c6)oc6ccccc67)c6ccccc56)cccc24)cc1C31C2CC3CC(C2)CC1C3]<br>276 | 71 |

TABLE 6-continued

| Intermediate IM-D-X/ intermediate IM-D-X-0 | Raw material SM B | Compound X | Yield (%) |
|---|---|---|---|
| 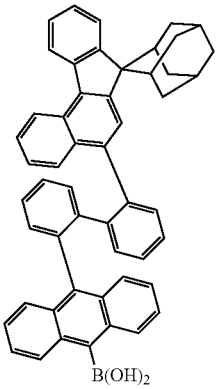 [SMILES: OB(O)c1c2ccccc2c(-c2ccccc2-c2ccccc2-c2cc3c(c4ccccc24)-c2ccccc2C32C3CC4CC(C3)CC2C4)c2ccccc12]<br>IM-D-15 | 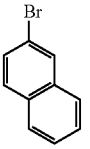 [SMILES: Brc1ccc2ccccc2c1] | 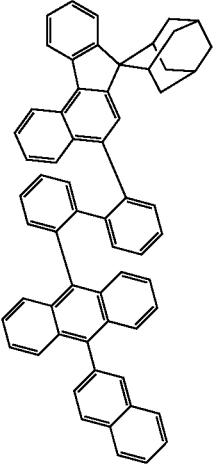 [SMILES: c1ccc(-c2cc3c(c4ccccc24)-c2ccccc2C32C3CC4CC(C3)CC2C4)c(-c2ccccc2-c2c3ccccc3c(-c3ccc4ccccc4c3)c3ccccc23)c1]  291 | 73 |

Mass spectrum data for the compounds in Table 6 are as shown in Table 7.

TABLE 7

| Compound | Mass spectrum [M + H]+ | Compound | Mass spectrum [M + H]+ |
|---|---|---|---|
| 1 | 589.3 | 136 | 695.3 |
| 2 | 639.3 | 162 | 679.3 |
| 5 | 665.3 | 175 | 755.3 |
| 6 | 665.3 | 182 | 665.3 |
| 7 | 679.3 | 186 | 679.3 |
| 35 | 639.3 | 152 | 679.3 |
| 45 | 695.3 | 212 | 715.3 |
| 49 | 705.3 | 317 | 729.3 |
| 75 | 755.3 | 231 | 711.3 |
| 73 | 689.3 | 247 | 639.3 |
| 70 | 715.3 | 260 | 681.3 |
| 88 | 665.3 | 316 | 681.3 |
| 107 | 771.3 | 276 | 805.3 |
| 119 | 715.3 | 291 | 791.3 |
| 148 | 665.3 | | |

NMR data for some of the compounds in Table 6 are shown in Table 8.

TABLE 8

| Compound | NMR data |
|---|---|
| Compound 2 | $^1$HNMR (400 MHz, CD$_2$Cl$_2$): 8.67 (d, 2H), 8.55 (d, 2H), 8.51 (d, 1H), 7.95-7.90 (m, 3H), 7.85-7.74 (m, 5H), 7.70 (s, 1H), 7.61-7.57 (m, 2H), 7.54-7.45 (m, 6H), 7.42-7.36 (m, 2H), 2.82-2.77 (m, 2H), 2.45 (d, 1H), 2.03 (s, 2H), 1.92-1.80 (m, 3H), 1.44-1.34 (m, 2H), 1.27-1.14 (m, 3H), 1.04 (d, 1H). |
| Compound 107 | $^1$HNMR (400 MHz, CD$_2$Cl$_2$): 8.60 (d, 1H), 8.54-8.50 (m, 4H), 8.55 (s, 1H), 7.98 (d, 1H), 7.93-7.87 (m, 5H), 7.83-7.77 (m, 3H), 7.76 (s, 1H), 7.68 (s, 1H), 7.65 (d, 1H), 7.58-7.53 (m, 6H), 7.49-7.35 (m, 4H), 2.83-2.78 (m, 2H), 2.46 (d, 1H), 2.04 (s, 2H), 1.93-1.81 (m, 3H), 1.45-1.36 (m, 2H), 1.28-1.15 (m, 3H), 1.06 (d, 1H). |
| Compound 212 | $^1$HNMR (400 MHz, CD$_2$Cl$_2$): 8.15-8.12 (m, 4H), 7.99 (d, 1H), 7.89-7.73 (m, 9H), 7.64-7.60 (m, 1H), 7.55 (d, 2H), 7.54-7.38 (m, 10H), 7.05 (d,1H), 2.85-2.79 (m, 2H), 2.45 (d, 1H), 2.03 (s, 2H), 1.94-1.82 (m, 3H), 1.46-1.37 (m, 2H), 1.27-1.15 (m, 3H), 1.05 (d, 1H). |

DEVICE EXAMPLES

Example 1

An anode was prepared by the following process: an ITO substrate (manufactured by Corning) with a thickness of 1500 Å was cut into a dimension of 40 mm×40 mm×0.7 mm to be prepared into an experimental substrate with a cathode pattern, an anode pattern and an insulating layer pattern by adopting a photoetching process, and surface treatment was performed by utilizing ultraviolet ozone and O$_2$:N$_2$ plasma so as to increase the work function of the anode (the experimental substrate) and remove scum.

F4-TCNQ was vacuum-evaporated on the experimental substrate (the anode) to form a hole injection layer (HIL) with a thickness of 100 Å, and a compound NPB was vacuum-evaporated on the hole injection layer to form a hole transport layer (HTL) with a thickness of 1100 Å.

A compound EB-01 was evaporated on the HTL to be used as an electron blocking layer (EBL) with a thickness of 100 Å.

A compound 1 as a host was doped simultaneously with BD-1 at a film thickness ratio of 100:3 on the EBL to form an organic light-emitting layer (EML) with a thickness of 200 Å.

ET-06 and LiQ were evaporated on the EML at a film thickness ratio of 1:1 to form an electron transport layer (ETL) with a thickness of 300 Å, Yb was evaporated on the electron transport layer to form an electron injection layer (EIL) with a thickness of 15 Å, and then magnesium (Mg) and silver (Ag) were vacuum-evaporated on the electron injection layer at a film thickness ratio of 1:9 to form a cathode with a thickness of 110 Å.

In addition, CP-5 with a thickness of 650 Å was evaporated on the cathode to form an organic capping layer (CPL), thus completing the manufacture of an organic light-emitting device.

Examples 2 to 29

An organic electroluminescent device was manufactured by the same method as that in Example 1 except that compounds shown in the following Table 10 were used instead of the compound 1 when the organic light-emitting layer was formed.

Comparative Example 1

An organic electroluminescent device was manufactured by the same method as that in Example 1 except that a compound A shown in the following Table 9 was used instead of the compound 1 when the organic light-emitting layer was formed.

Comparative Example 2

An organic electroluminescent device was manufactured by the same method as that in Example 1 except that a compound B shown in the following Table 9 was used instead of the compound 1 when the organic light-emitting layer was formed.

Comparative Example 3

An organic electroluminescent device was manufactured by the same method as that in Example 1 except that a compound C shown in the following Table 9 was used instead of the compound 1 when the organic light-emitting layer was formed.

Comparative Example 4

An organic electroluminescent device was manufactured by the same method as that in Example 1 except that a compound D shown in the following Table 9 was used instead of the compound 1 when the organic light-emitting layer was formed.

The structures of compounds used in Examples 1 to 29 and Comparative Examples 1 to 4 are as shown in Table 9 below:

TABLE 9

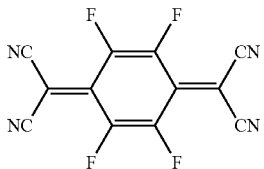 [SMILES: N#CC(C#N)=c1c(F)c(F)c(=C(C#N)C#N)c(F)c1F]

F4-TCNQ

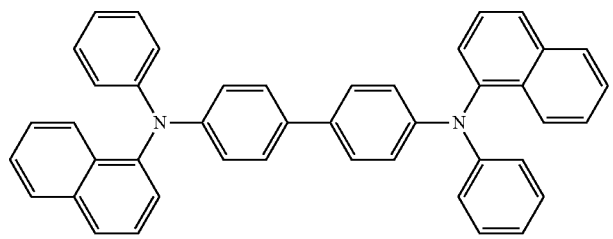 [SMILES: c1ccc(N(c2ccc(-c3ccc(N(c4ccccc4)c4cccc5ccccc45)cc3)cc2)c2cccc3ccccc23)cc1]

NPB

TABLE 9-continued
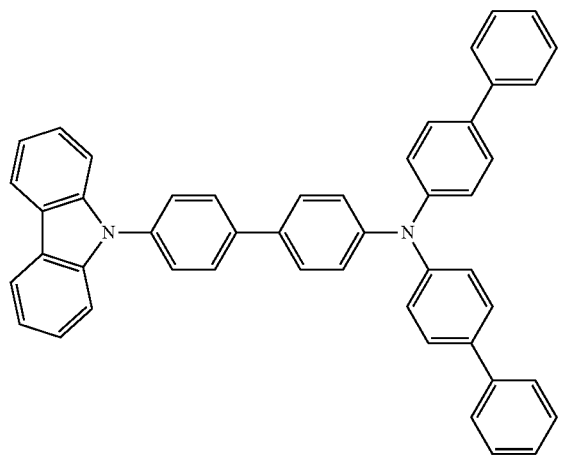 [SMILES: c1ccc(-c2ccc(N(c3ccc(-c4ccccc4)cc3)c3ccc(-c4ccc(-n5c6ccccc6c6ccccc65)cc4)cc3)cc2)cc1]
EB-01
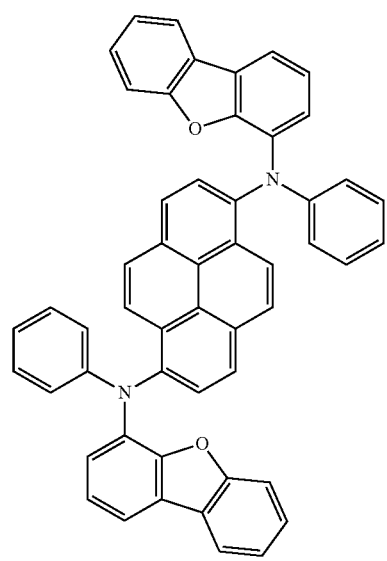 [SMILES: c1ccc(N(c2ccc3ccc4c(N(c5ccccc5)c5cccc6c5oc5ccccc56)ccc5ccc2c3c54)c2cccc3c2oc2ccccc23)cc1]
BD-1
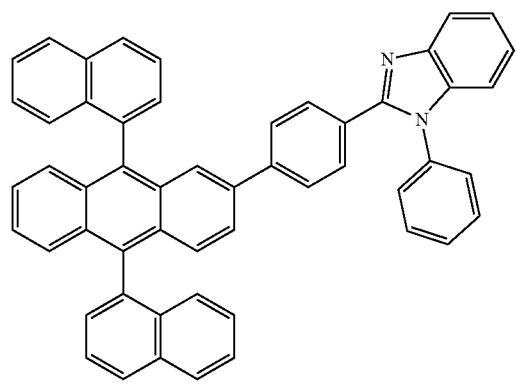 [SMILES: c1ccc(-n2c(-c3ccc(-c4ccc5c(-c6cccc7ccccc67)c6ccccc6c(-c6cccc7ccccc67)c5c4)cc3)nc3ccccc32)cc1]
ET-06

TABLE 9-continued
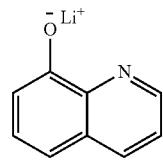
LiQ
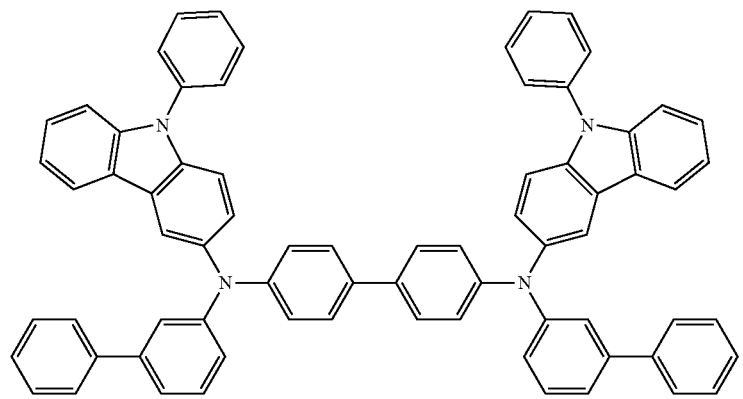 [SMILES: c1ccc(-c2cccc(N(c3ccc(-c4ccc(N(c5cccc(-c6ccccc6)c5)c5ccc6c(c5)c5ccccc5n6-c5ccccc5)cc4)cc3)c3ccc4c(c3)c3ccccc3n4-c3ccccc3)c2)cc1]
CP-5
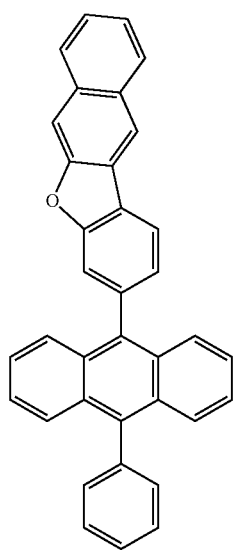 [SMILES: c1ccc(-c2c3ccccc3c(-c3ccc4c(c3)oc3cc5ccccc5cc34)c3ccccc23)cc1]
Compound A

TABLE 9-continued
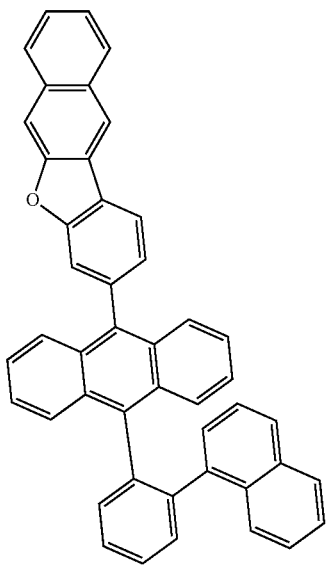 [SMILES: c1ccc(-c2c3ccccc3c(-c3ccc4c(c3)oc3cc5ccccc5cc34)c3ccccc23)c(-c2cccc3ccccc23)c1]
Compound B
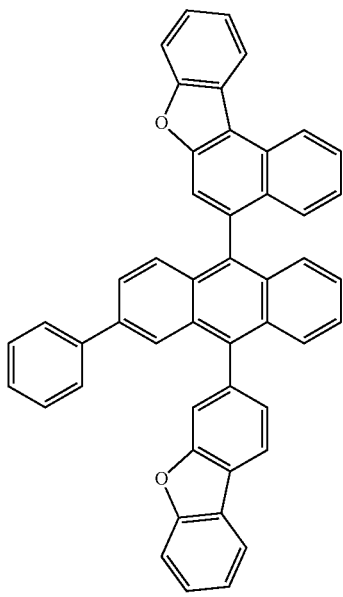 [SMILES: c1ccc(-c2ccc3c(-c4cc5oc6ccccc6c5c5ccccc45)c4ccccc4c(-c4ccc5c(c4)oc4ccccc45)c3c2)cc1]
Compound C
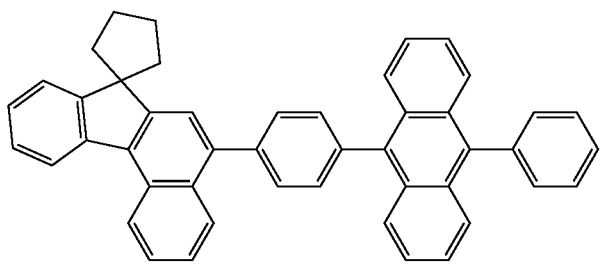 [SMILES: c1ccc(-c2c3ccccc3c(-c3ccc(-c4cc5c(c6ccccc46)-c4ccccc4C54CCCC4)cc3)c3ccccc23)cc1]
Compound D For the organic electroluminescent devices manufactured in Examples 1 to 29 and Comparative Examples 1 to 4, the IVL performance of the devices was analyzed under a condition of 20 mA/cm$^2$, and the T95 service life was tested at 15 mA/cm$^2$, and the results are as shown in Table 10.

TABLE 10

|  | Compound | Volt (V) | Cd/A | lm/W | CIE-x | CIE-y | EQE % | T95 (hrs)@15 mA/cm$^2$ |
|---|---|---|---|---|---|---|---|---|
| Example 1 | Compound 1 | 3.93 | 6.78 | 5.42 | 0.14 | 0.05 | 13.95 | 293 |
| Example 2 | Compound 2 | 3.91 | 6.73 | 5.41 | 0.14 | 0.05 | 13.84 | 295 |
| Example 3 | Compound 5 | 3.87 | 6.65 | 5.40 | 0.14 | 0.05 | 13.68 | 290 |
| Example 4 | Compound 6 | 3.95 | 6.71 | 5.34 | 0.14 | 0.05 | 13.80 | 304 |
| Example 5 | Compound 7 | 3.87 | 6.55 | 5.32 | 0.14 | 0.05 | 13.47 | 311 |
| Example 6 | Compound 35 | 3.96 | 6.55 | 5.20 | 0.14 | 0.05 | 13.47 | 325 |
| Example 7 | Compound 45 | 3.89 | 6.62 | 5.35 | 0.14 | 0.05 | 13.62 | 303 |
| Example 8 | Compound 49 | 3.83 | 6.74 | 5.53 | 0.14 | 0.05 | 13.86 | 297 |
| Example 9 | Compound 75 | 3.94 | 6.59 | 5.25 | 0.14 | 0.05 | 13.56 | 196 |
| Example 10 | Compound 73 | 3.94 | 6.66 | 5.31 | 0.14 | 0.05 | 13.70 | 329 |
| Example 11 | Compound 70 | 3.87 | 6.71 | 5.45 | 0.14 | 0.05 | 13.80 | 297 |
| Example 12 | Compound 88 | 3.87 | 6.74 | 5.47 | 0.14 | 0.05 | 13.86 | 291 |
| Example 13 | Compound 107 | 3.86 | 6.55 | 5.33 | 0.14 | 0.05 | 13.47 | 317 |
| Example 14 | Compound 119 | 3.91 | 6.53 | 5.25 | 0.14 | 0.05 | 13.43 | 314 |
| Example 15 | Compound 148 | 3.96 | 6.58 | 5.22 | 0.14 | 0.05 | 13.54 | 215 |
| Example 16 | Compound 136 | 3.86 | 6.58 | 5.36 | 0.14 | 0.05 | 13.54 | 305 |
| Example 17 | Compound 162 | 3.97 | 6.77 | 5.36 | 0.14 | 0.05 | 13.93 | 314 |
| Example 18 | Compound 175 | 3.87 | 6.80 | 5.52 | 0.14 | 0.05 | 13.99 | 303 |
| Example 19 | Compound 182 | 3.85 | 6.48 | 5.29 | 0.14 | 0.05 | 13.33 | 311 |
| Example 20 | Compound 186 | 3.88 | 6.77 | 5.48 | 0.14 | 0.05 | 13.93 | 309 |
| Example 21 | Compound 152 | 3.90 | 6.52 | 5.25 | 0.14 | 0.05 | 13.41 | 190 |
| Example 22 | Compound 212 | 3.95 | 6.55 | 5.21 | 0.14 | 0.05 | 13.47 | 314 |
| Example 23 | Compound 317 | 3.96 | 6.56 | 5.20 | 0.14 | 0.05 | 13.49 | 230 |
| Example 24 | Compound 231 | 3.92 | 6.54 | 5.24 | 0.14 | 0.05 | 13.45 | 305 |
| Example 25 | Compound 247 | 3.97 | 6.56 | 5.19 | 0.14 | 0.05 | 13.49 | 254 |
| Example 26 | Compound 260 | 3.93 | 6.42 | 5.13 | 0.14 | 0.05 | 13.21 | 316 |
| Example 27 | Compound 316 | 3.90 | 6.50 | 5.24 | 0.14 | 0.05 | 13.37 | 308 |
| Example 28 | Compound 276 | 3.95 | 6.46 | 5.14 | 0.14 | 0.05 | 13.29 | 296 |
| Example 29 | Compound 291 | 3.92 | 6.52 | 5.23 | 0.14 | 0.05 | 13.41 | 243 |
| Comparative Example 1 | Compound A | 4.05 | 5.96 | 4.69 | 0.14 | 0.05 | 12.26 | 155 |
| Comparative Example 2 | Compound B | 4.04 | 6.02 | 4.74 | 0.14 | 0.05 | 12.38 | 158 |
| Comparative Example 3 | Compound C | 4.11 | 5.85 | 4.50 | 0.14 | 0.05 | 12.03 | 162 |
| Comparative Example 4 | Compound D | 4.09 | 5.91 | 4.66 | 0.14 | 0.05 | 12.16 | 170 |

From the results of Table 10, it can be seen that according to Examples 1 to 29 of the compounds as light-emitting host materials and device comparative Examples 1 to 4 corresponding to known compounds, for the above organic electroluminescent device manufactured by using the compounds used in the present disclosure as organic light-emitting layers, the luminous efficiency (Cd/A) is improved by at least 6.64%, the external quantum efficiency (EQE %) is improved by at least 6.70%, the service life is improved by at least 11.76%, and the service life can be increased by 174 h at most.

314
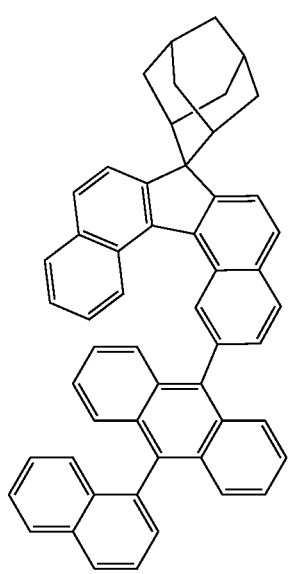
316
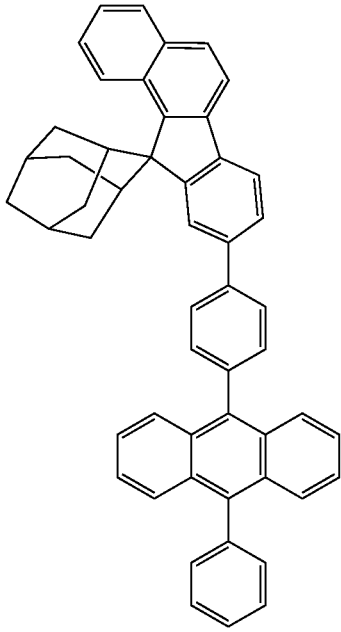
315
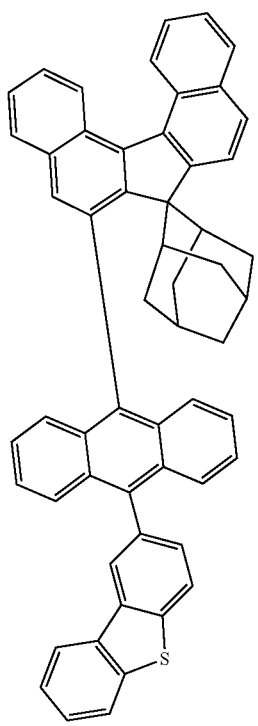
317
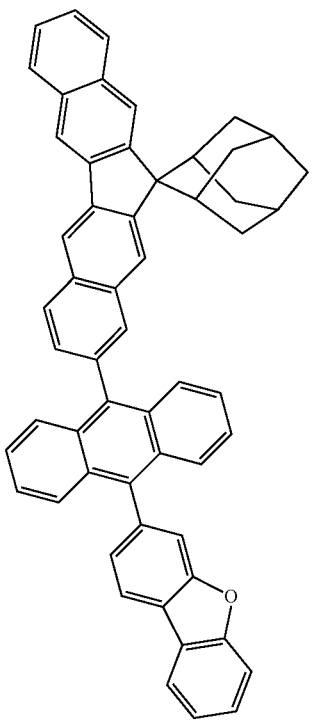

397
-continued
319
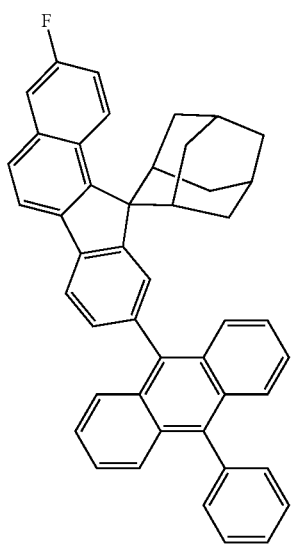
320
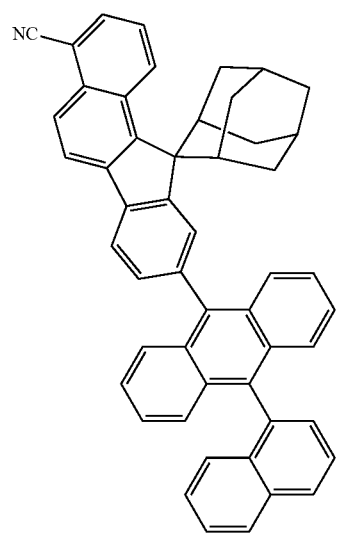
398
-continued
321
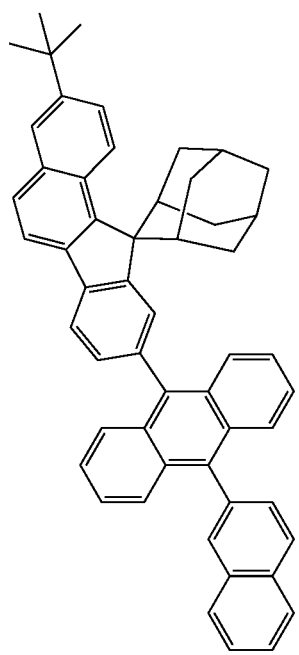
322
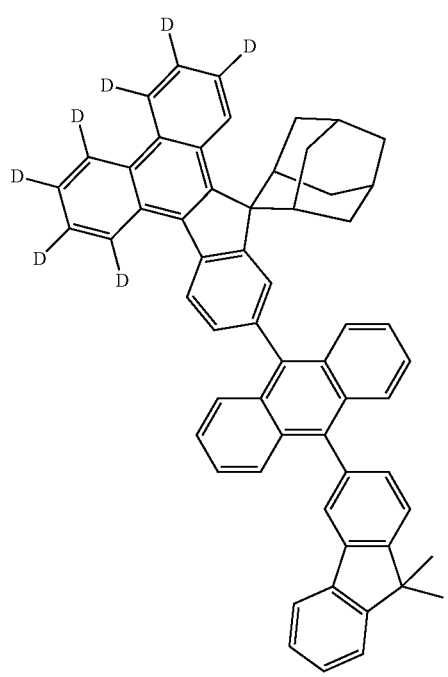

323
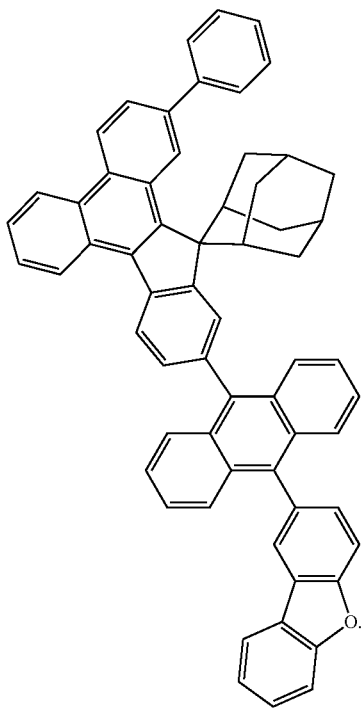

What is claimed is:

1. An organic compound, having a structural formula represented by Formula 1:

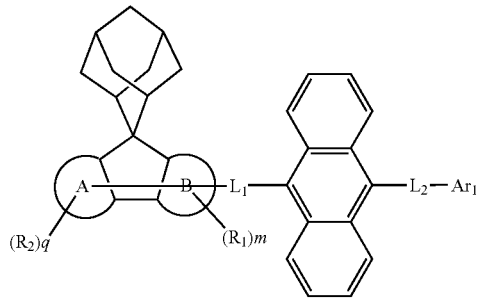

Formula 1 wherein ring A and ring B are the same or different, and are each independently selected from a benzene ring or a fused aromatic ring with 10 to 14 ring-forming carbon atoms, and at least one of ring A and ring B is selected from the fused aromatic ring with 10 to 14 ring-forming carbon atoms;

$R_1$ and $R_2$ are the same or different, and are respectively and independently selected from: hydrogen, deuterium, a halogen group, cyano, alkyl with 1 to 10 carbon atoms, cycloalkyl with 3 to 15 carbon atoms, and aryl with 6 to 12 carbon atoms, and heteroaryl with 11 to 12 carbon atoms;

m represents the number of $R_1$, q represents the number of $R_2$, and m and q are respectively and independently selected from 1, 2, 3, 4, 5, 6, 7 or 8;

$Ar_1$ is selected from a substituted or unsubstituted $V_1$, wherein the unsubstituted $V_1$ is selected from a group consisting of the following groups:

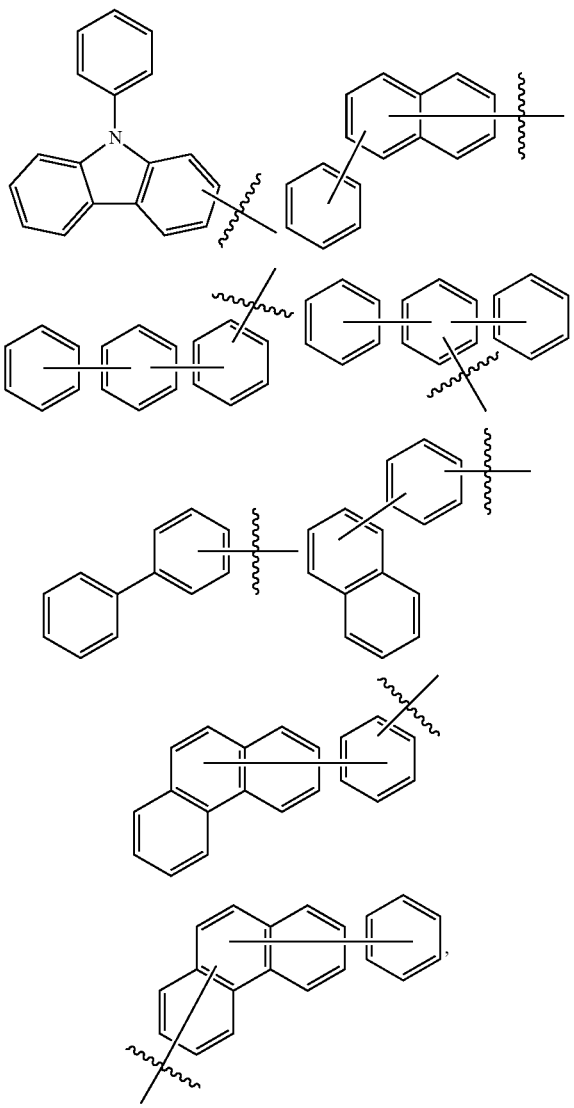

and wherein the substituted $V_1$ has one or more substituents, and the substituents in the substituted $V_1$ are independently selected from deuterium, fluorine, cyano, alkyl with 1 to 5 carbon atoms, and aryl with 6 to 12 carbon atoms;

$L_1$ and $L_2$ are each independently selected from a single bond or a substituted or unsubstituted $V_2$, wherein the unsubstituted $V_2$ is selected from a group consisting of the following groups:

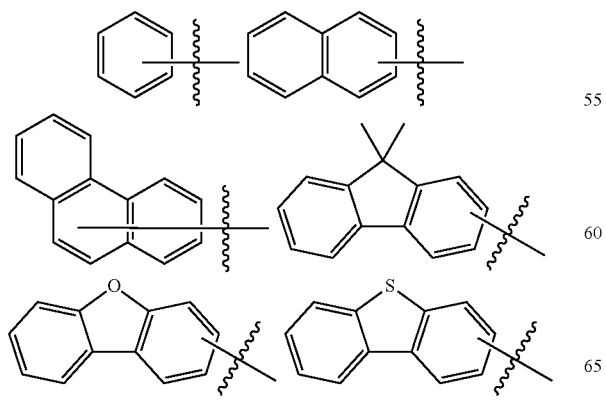

-continued

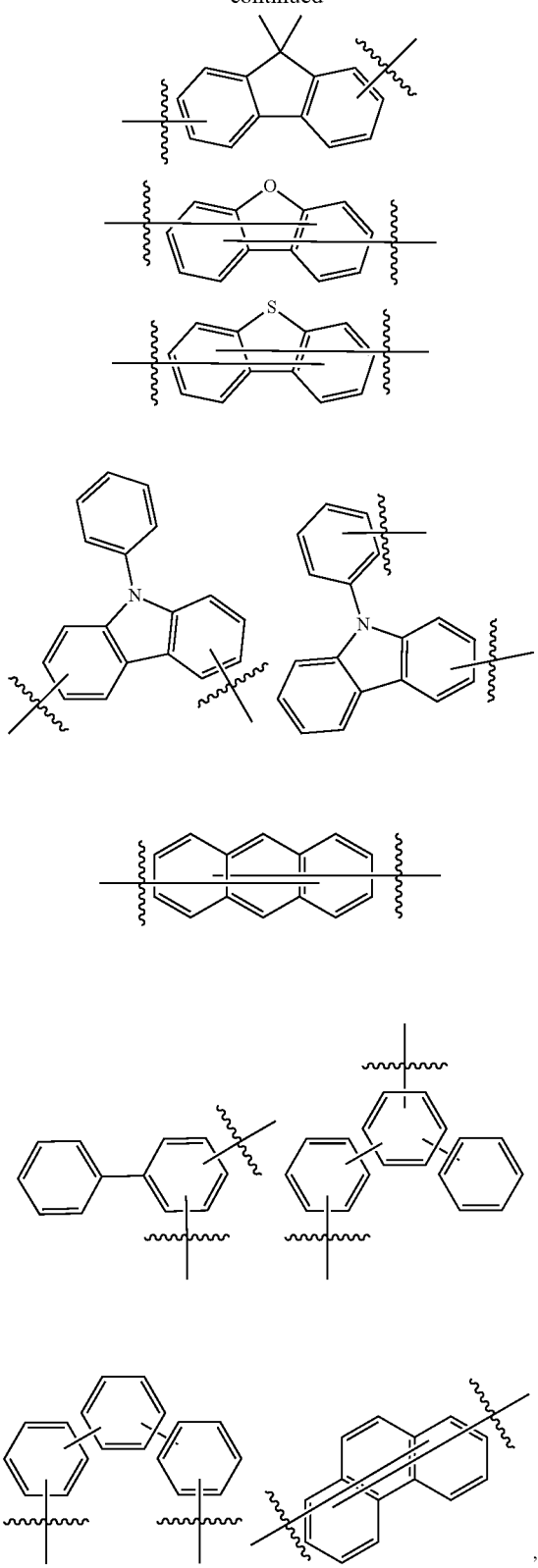

and wherein the substituted $V_2$ has one or more substituents, and the substituents in the substituted $V_2$ are independently selected from deuterium, fluorine, cyano, alkyl with 1 to 5 carbon atoms, and aryl with 6 to 12 carbon atoms; and the organic compound is not

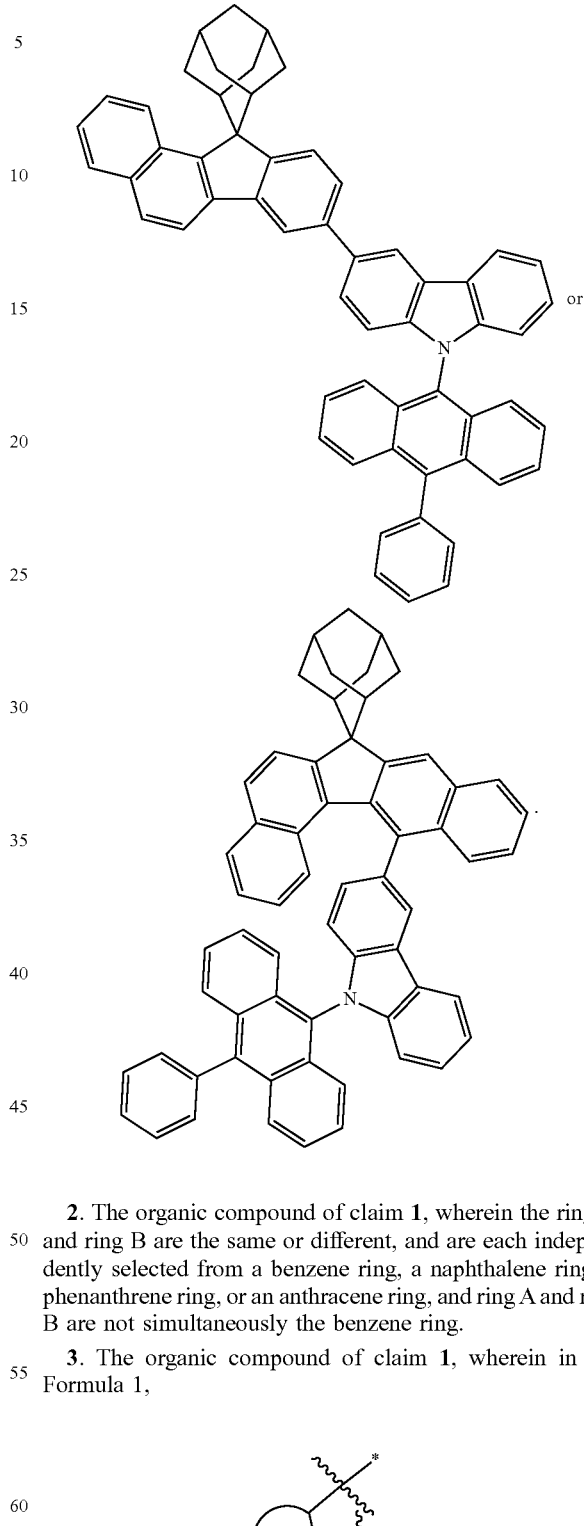

2. The organic compound of claim 1, wherein the ring A and ring B are the same or different, and are each independently selected from a benzene ring, a naphthalene ring, a phenanthrene ring, or an anthracene ring, and ring A and ring B are not simultaneously the benzene ring.

3. The organic compound of claim 1, wherein in the Formula 1,

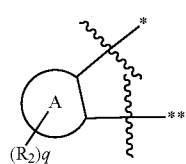

is selected from a group consisting of structures shown as follow:

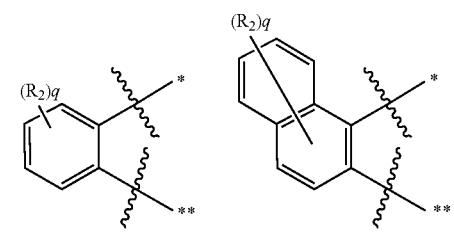
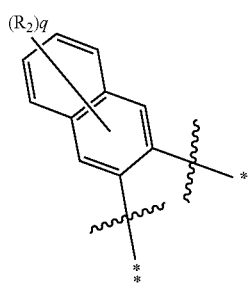
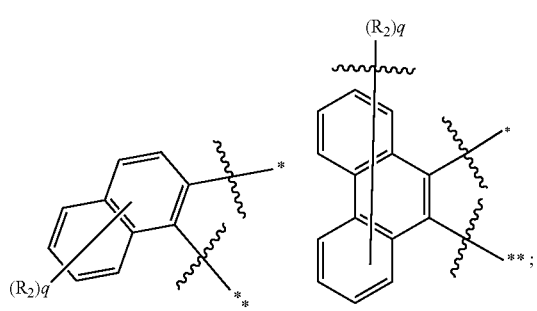
wherein,
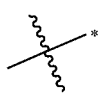
represents a chemical bond for connecting with
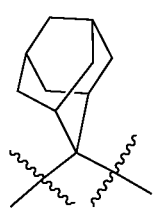 [SMILES: *C1(*)C2CC3CC(C2)CC1C3]
in the above structures, and
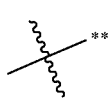
represents a chemical bond for connecting with
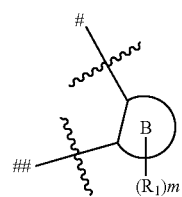
in the above structures.
4. The organic compound of claim 1, wherein in the formula 1,
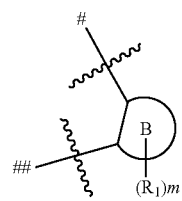
is selected from a group consisting of structures shown as follow:
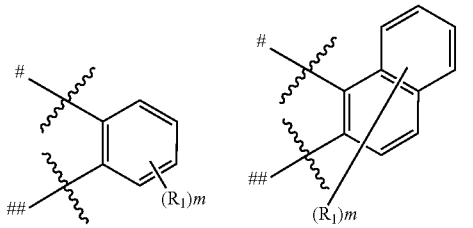
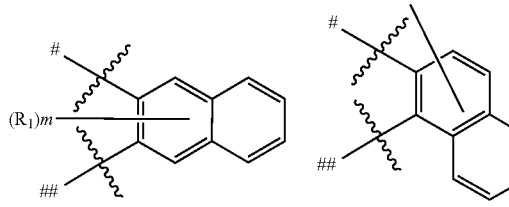
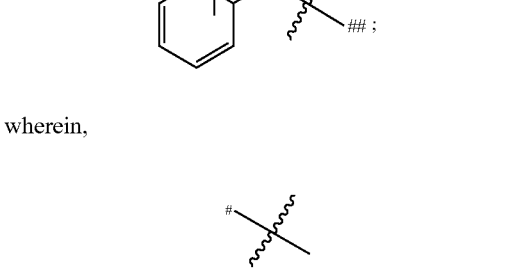
wherein,

represents a chemical bond for connecting with

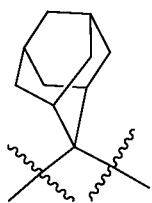 [SMILES: *C1(*)C2CC3CC(C2)CC1C3]

in the above structures, and

represents a chemical bond for connecting with

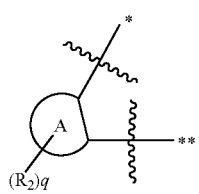

in the above structures.

5. The organic compound of claim 1, wherein $L_1$ and $L_2$ are the same or different, and are each independently selected from a single bond, substituted or unsubstituted phenylene, substituted or unsubstituted naphthylene, substituted or unsubstituted biphenylene, substituted or unsubstituted terphenylene, substituted or unsubstituted phenanthrylene, substituted or unsubstituted dibenzothienylene, substituted or unsubstituted dibenzofurylene, and substituted or unsubstituted N-phenylcarbazolylene.

6. An electronic element, comprising:
an anode;
a cathode which is arranged oppositely to the anode; and
a functional layer disposed between the anode and the cathode, wherein the functional layer comprises the organic compound of claim 1.

7. The electronic element of claim 6, wherein the electronic element is an organic electroluminescent device.

8. An electronic device, comprising the electronic element of claim 6.

9. The organic compound of claim 5, wherein substituents in $L_1$ and $L_2$ are the same or different, and are each independently selected from deuterium, fluorine, cyano, methyl, ethyl, n-propyl, isopropyl, tert-butyl, phenyl, naphthyl, and biphenyl.

10. The electronic element of claim 6, wherein the functional layer comprises an organic light-emitting layer, the organic light-emitting layer comprises the organic compound.

11. The electronic element of claim 10, wherein the organic light-emitting layer comprises a host material and a guest material, the host material comprises the organic compound.

12. The electronic element of claim 7, wherein the organic electroluminescent device is a blue light device.

13. An organic compound, wherein the organic compound is selected from a group consisting of the following compounds:

1

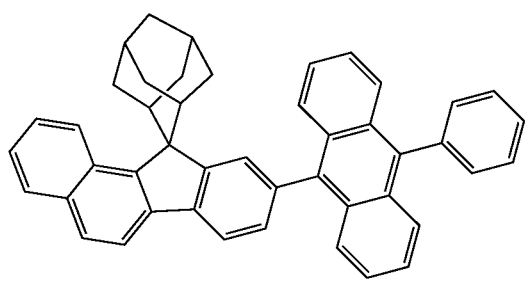

2

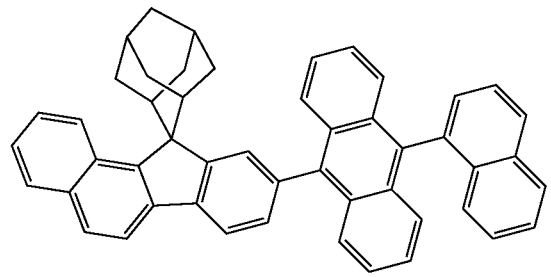

3

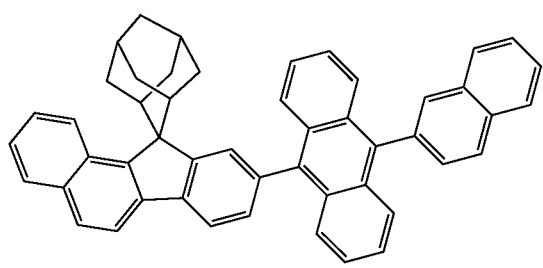

4

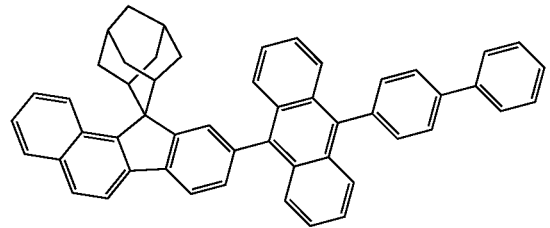

5
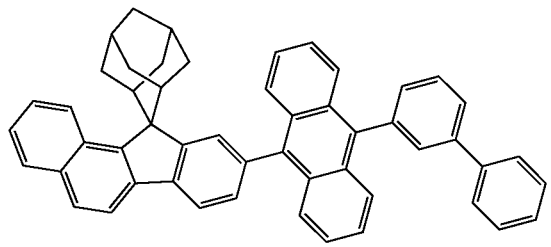
6
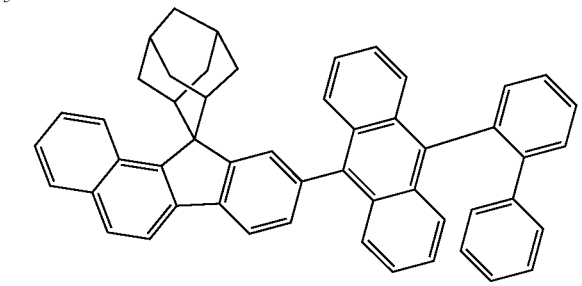
7
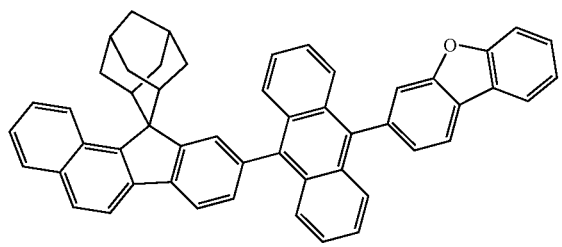
8
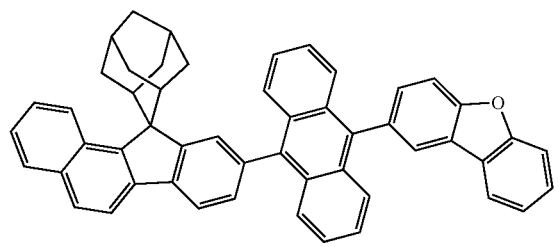
9
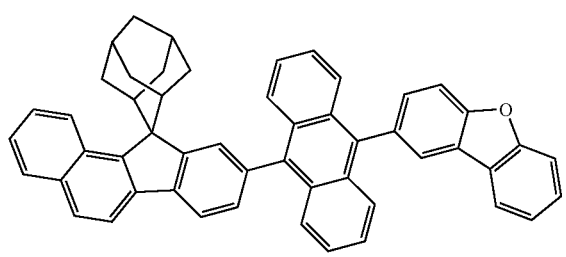
10
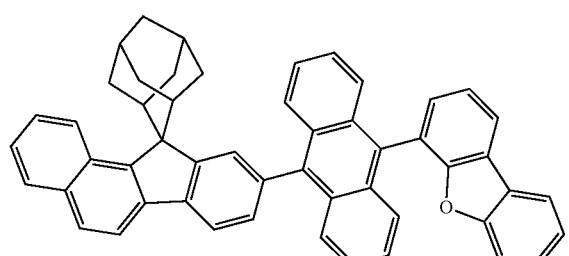
11
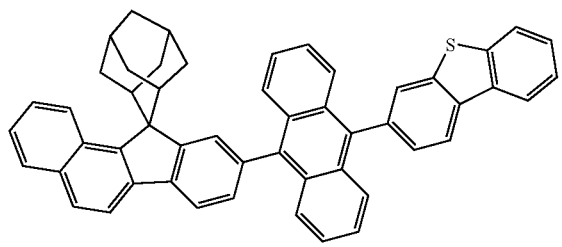
12
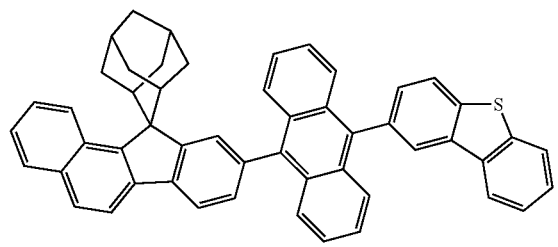
13
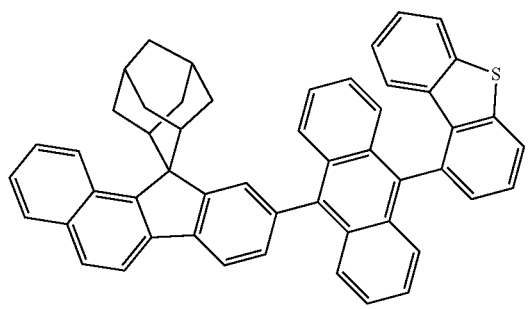
14
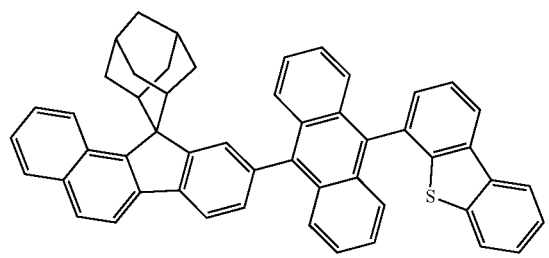
15
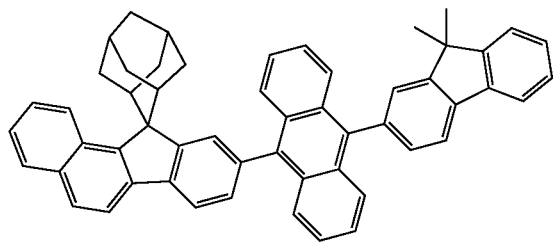
16
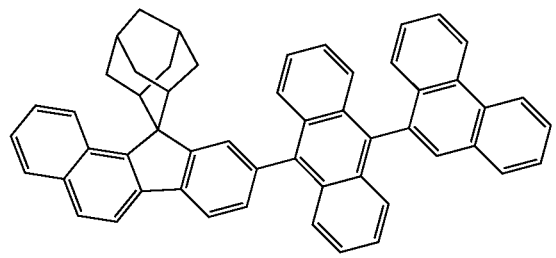

-continued
17
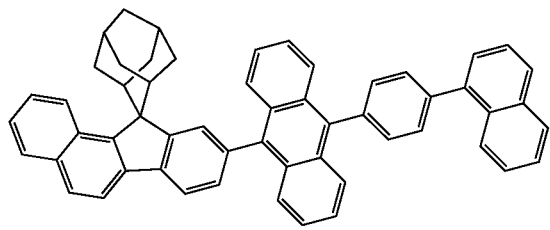
18
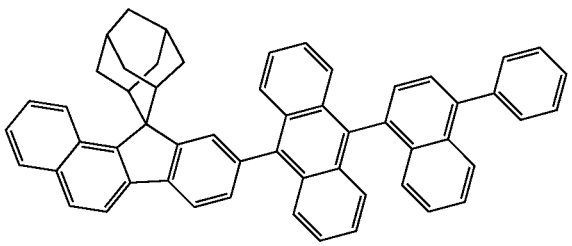
19
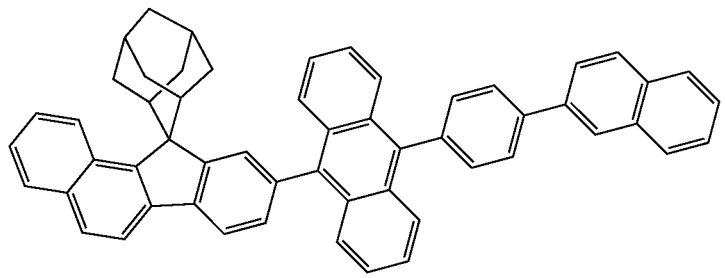
20
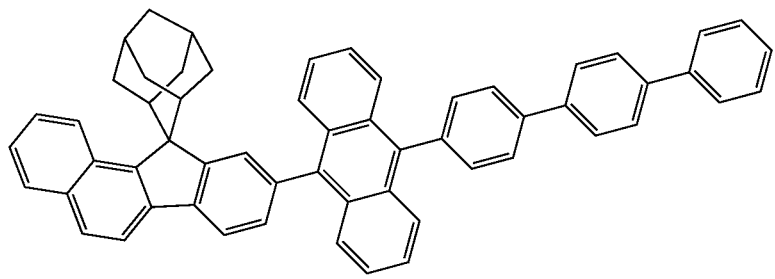
21
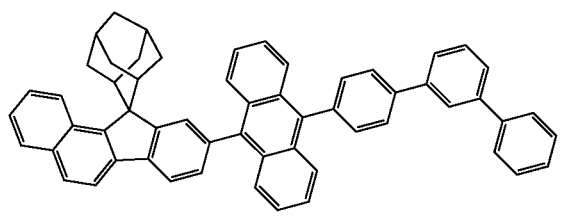
22
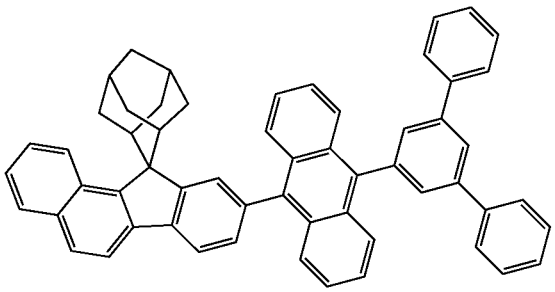
23
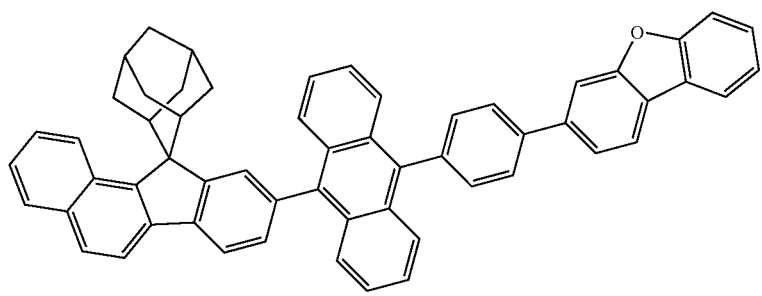

-continued
24
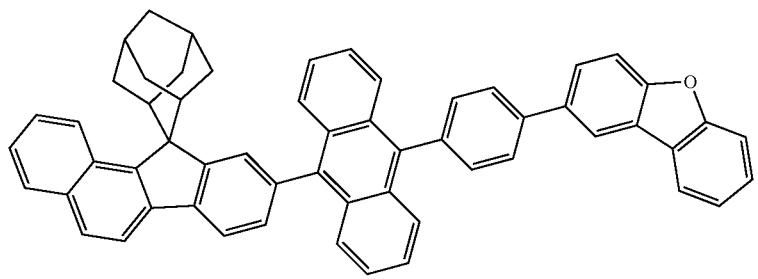
25
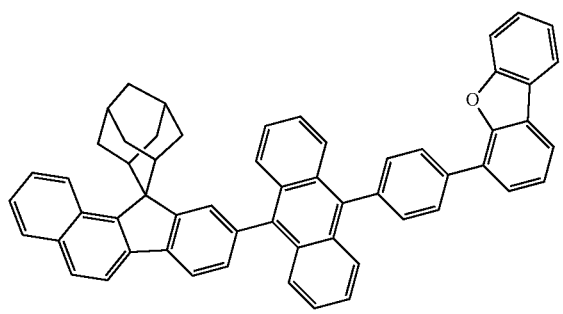
26
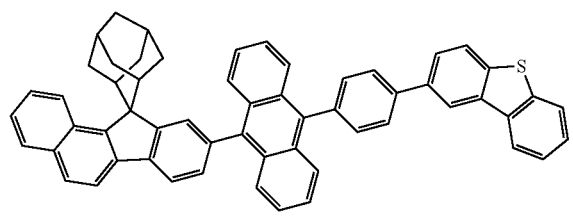
27
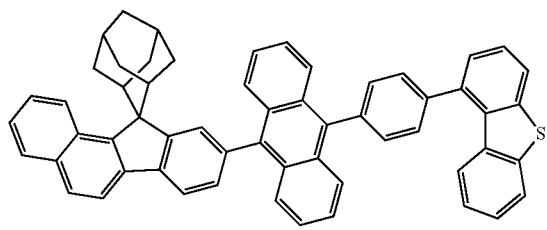
28
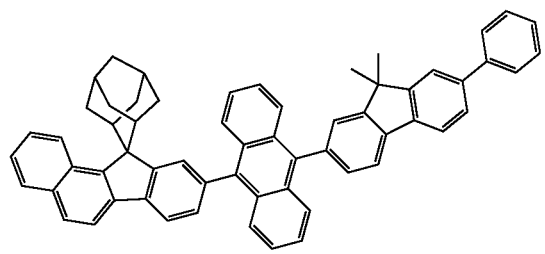
29
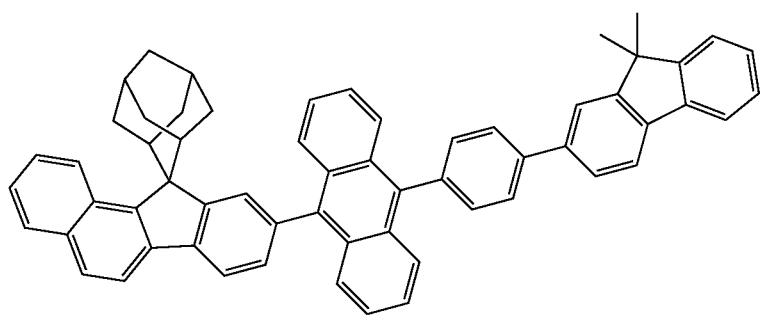
30
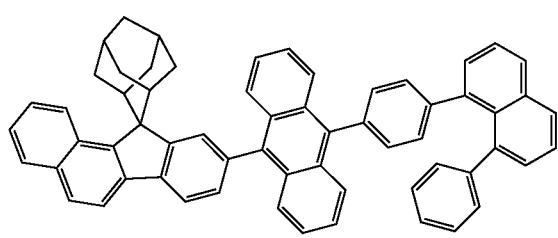
31
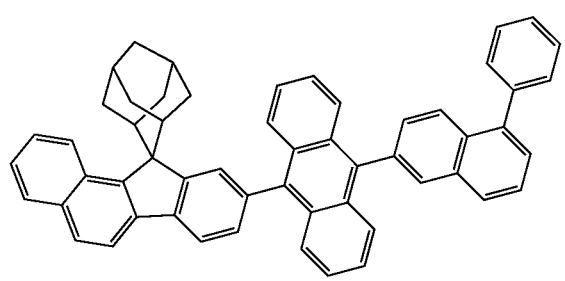

32
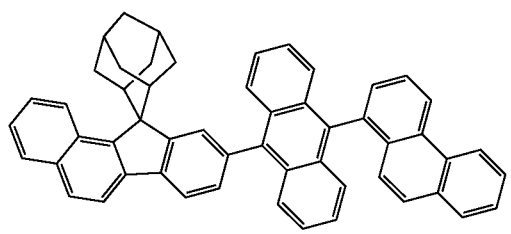
33
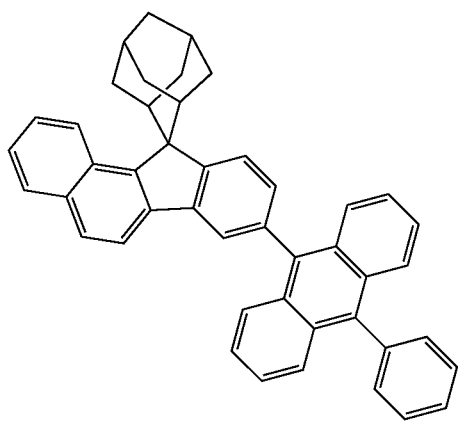
34
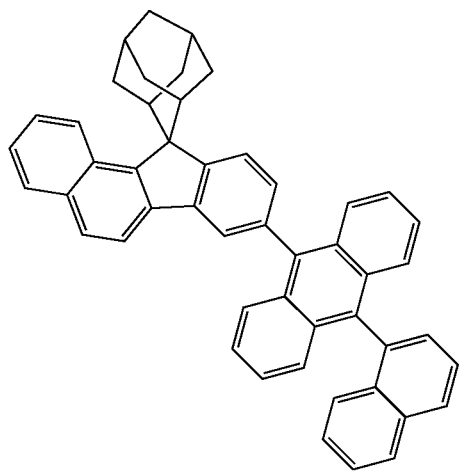
35
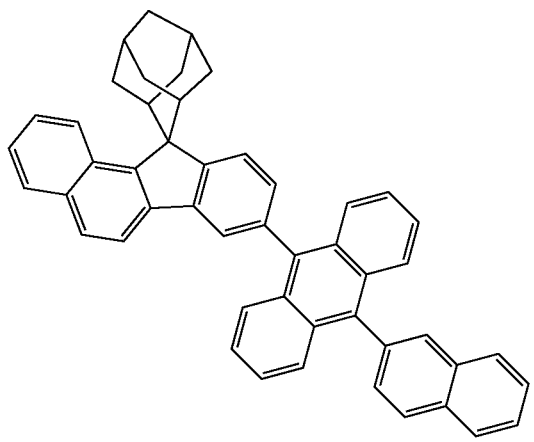
36
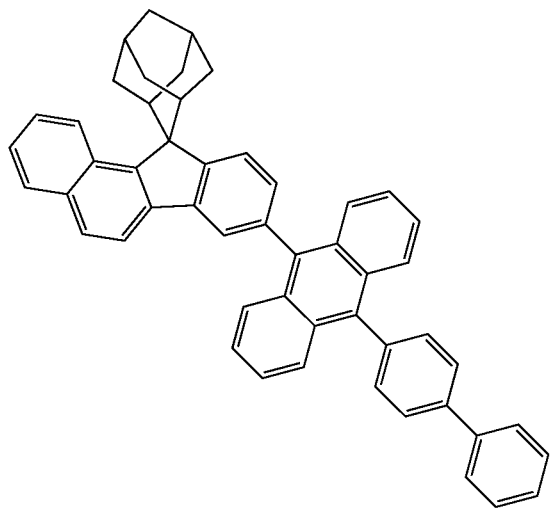
37
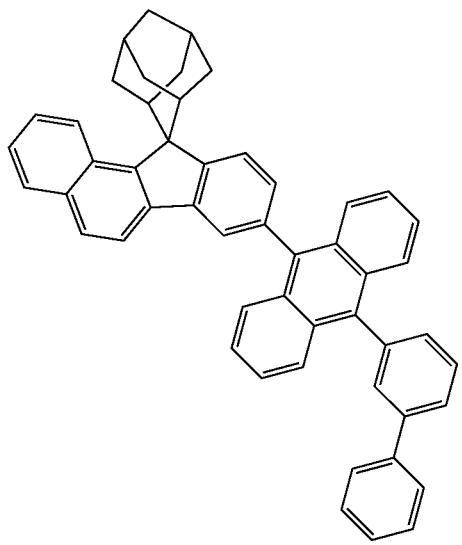

-continued
38
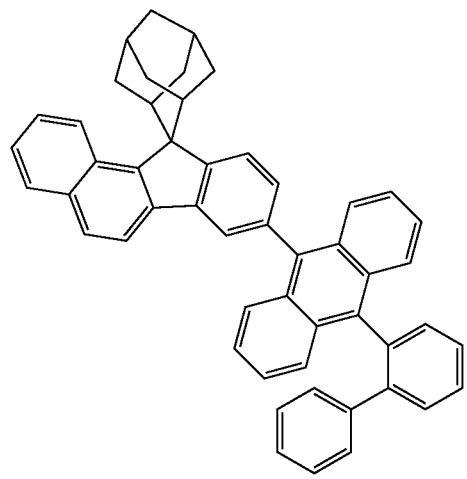
39
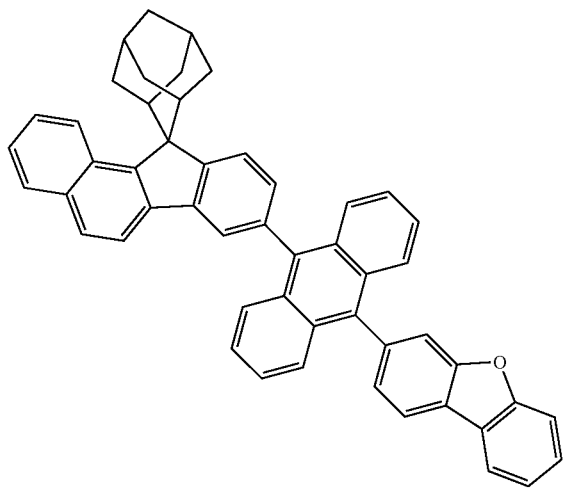
40
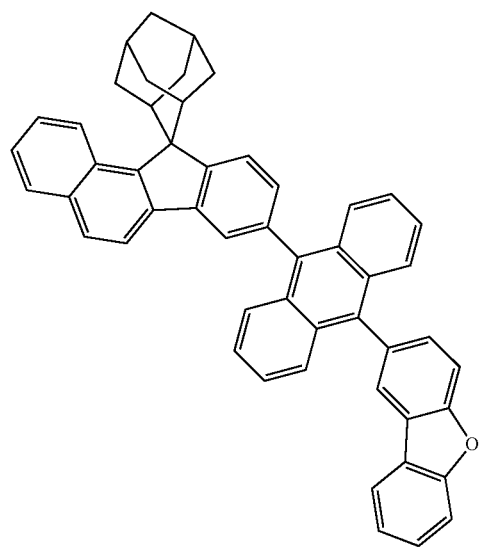
41
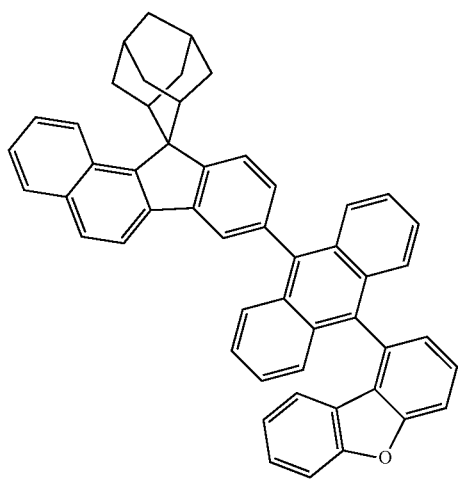
42
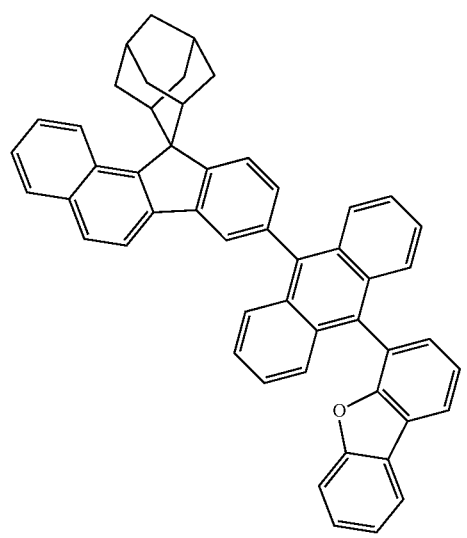
43
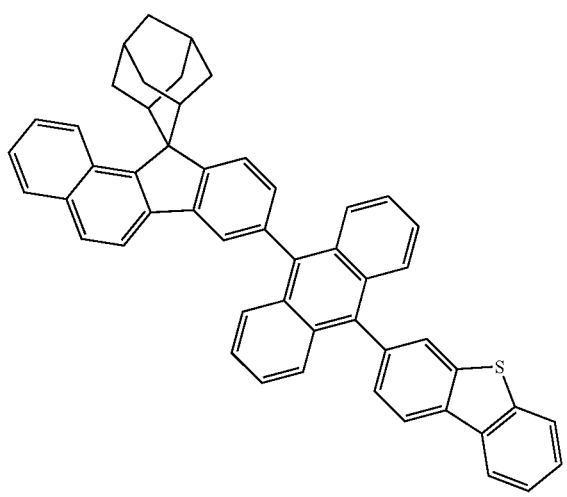

-continued
44
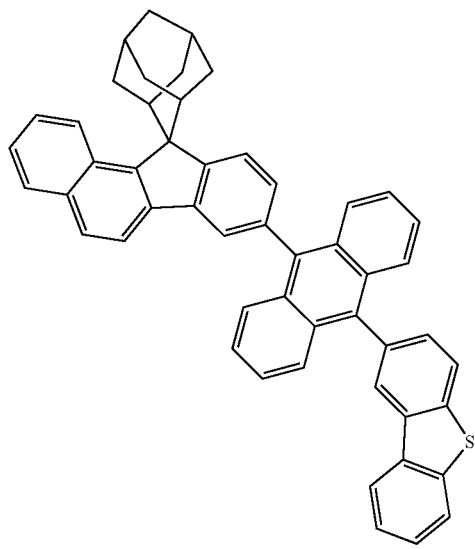
45
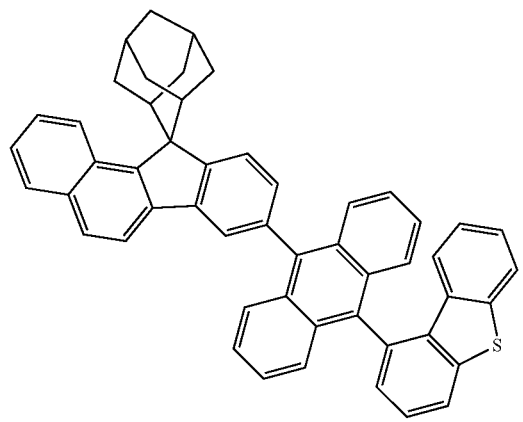
46
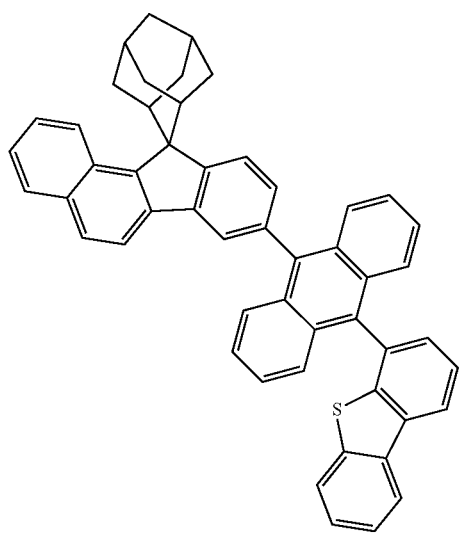
47
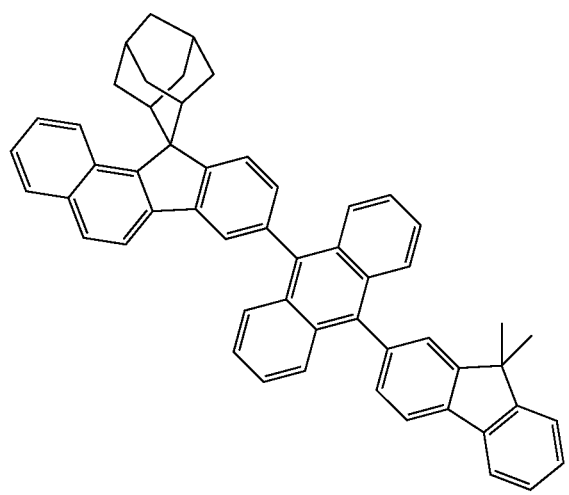
48
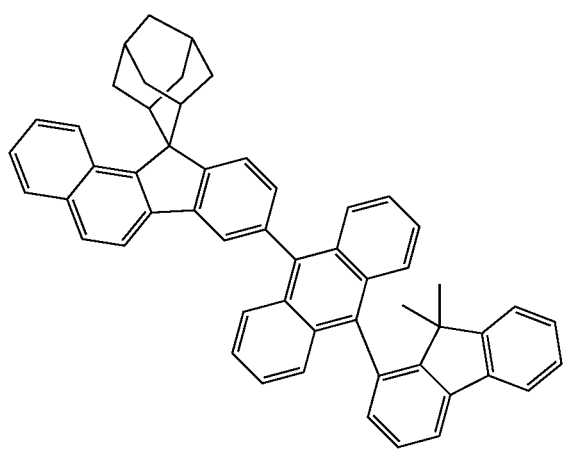
49
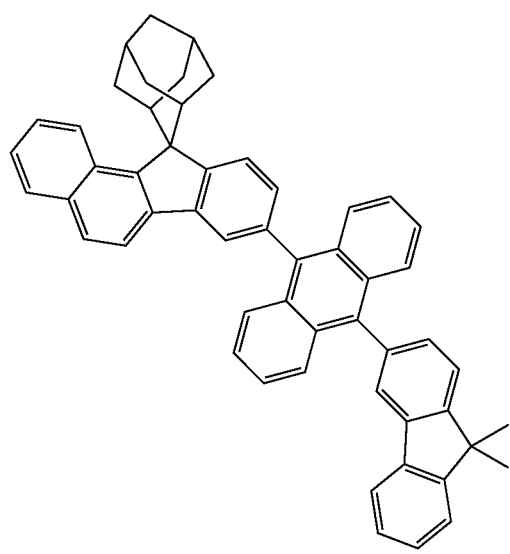

-continued
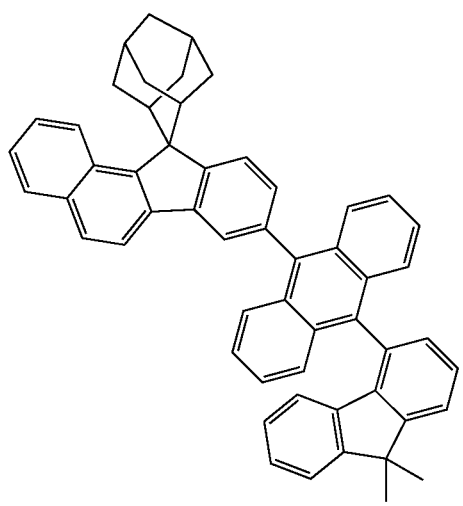
50
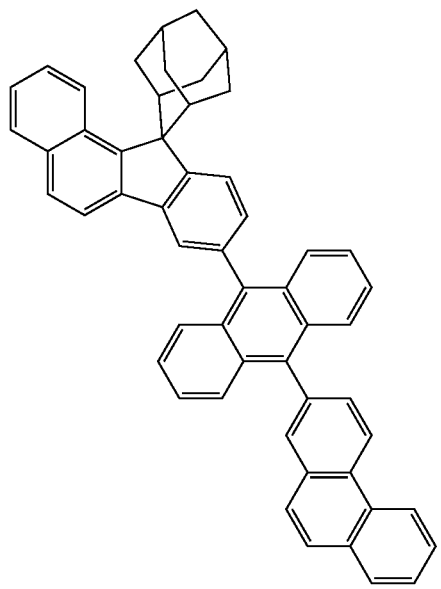
51
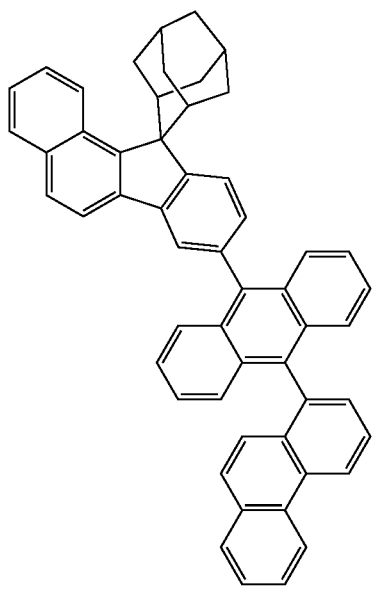
52
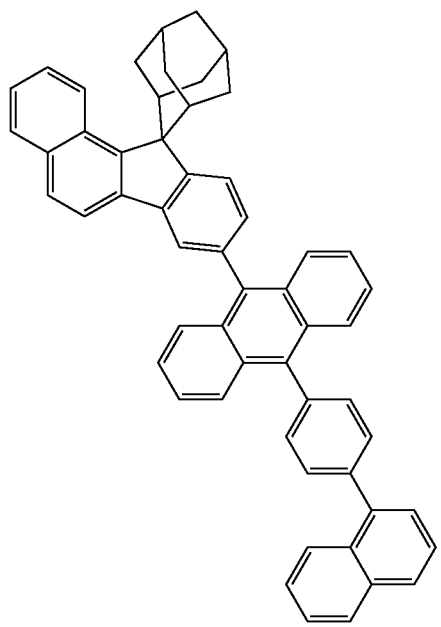
53

-continued
54
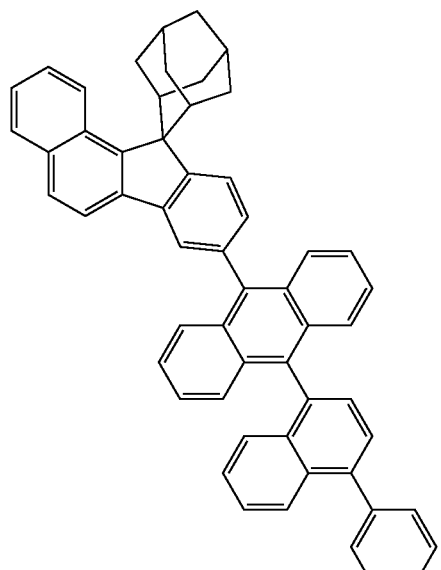
55
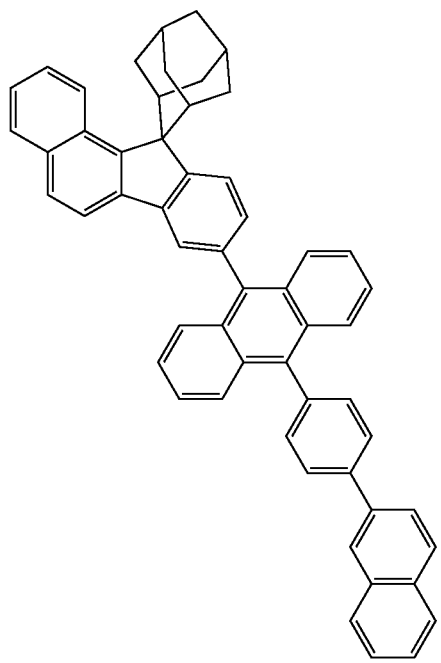
56
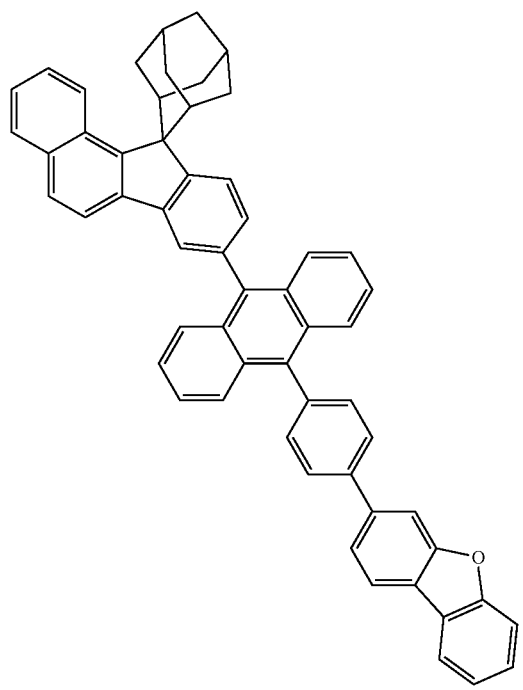
57
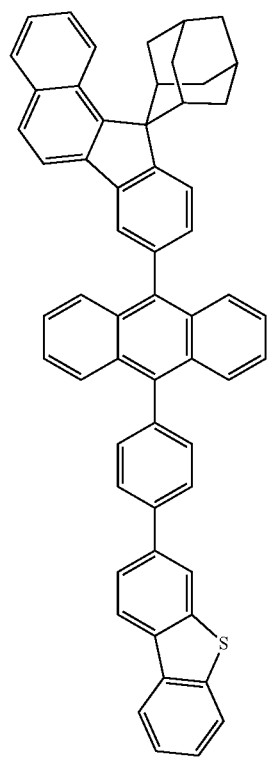

58
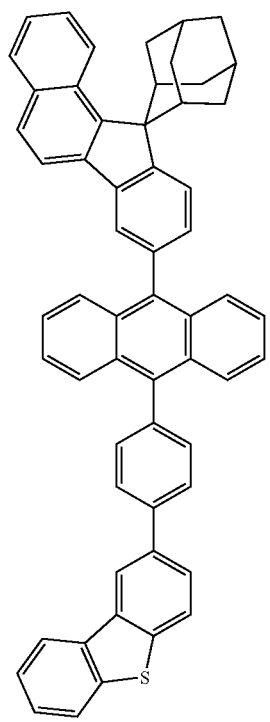
59
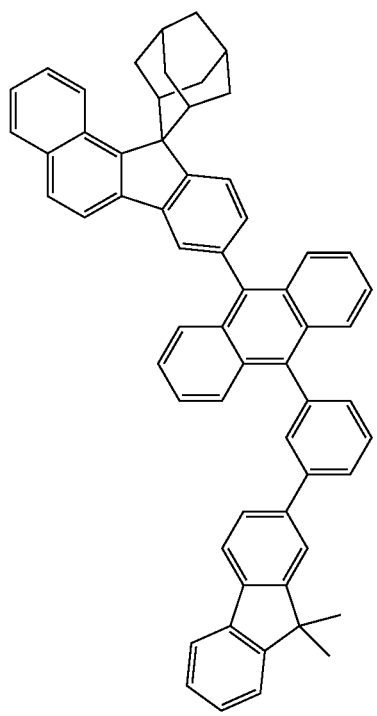
60
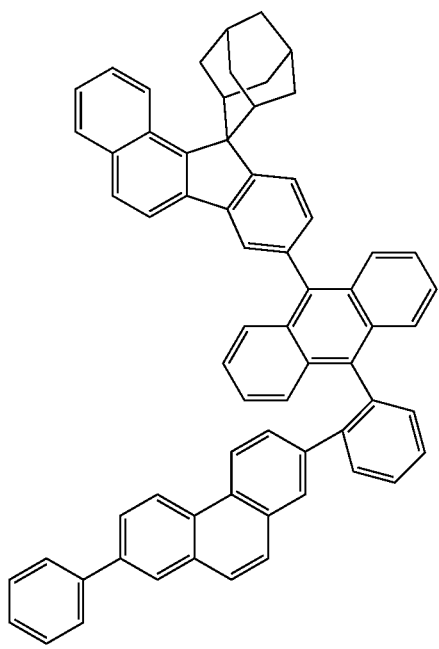
61
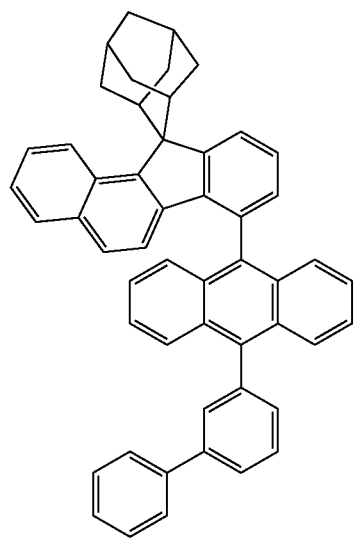

-continued
62
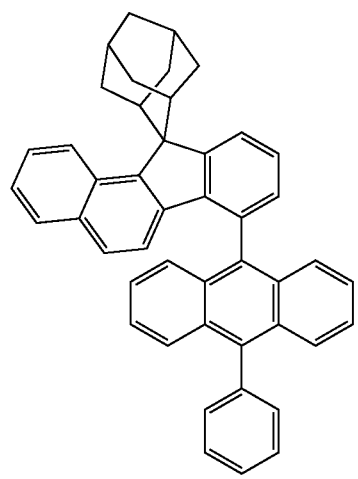
63
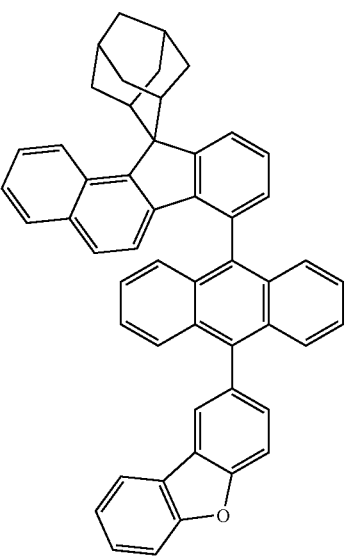
64
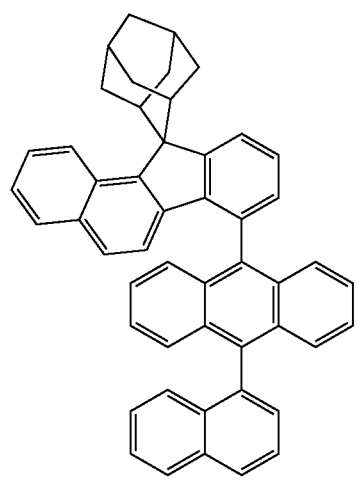
65
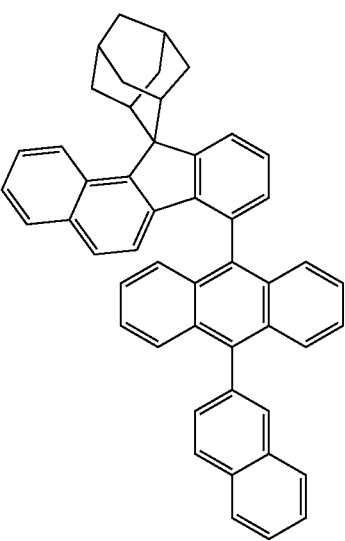

-continued
66
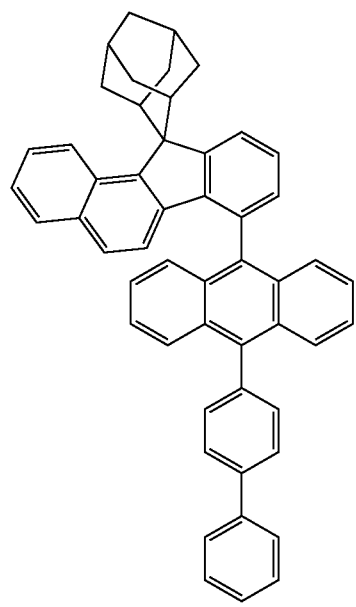
67
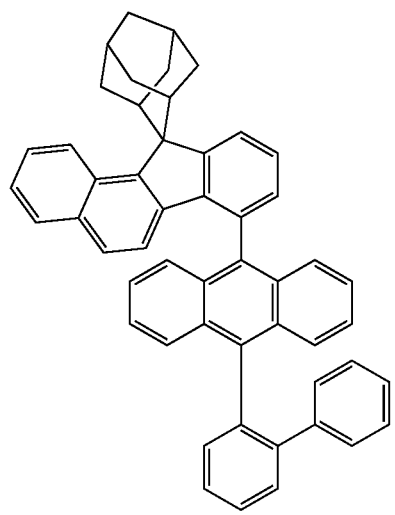
68
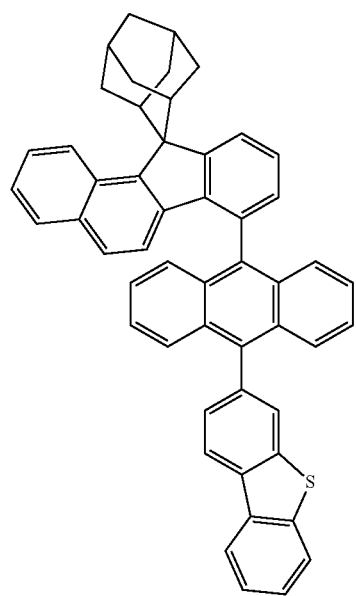
69
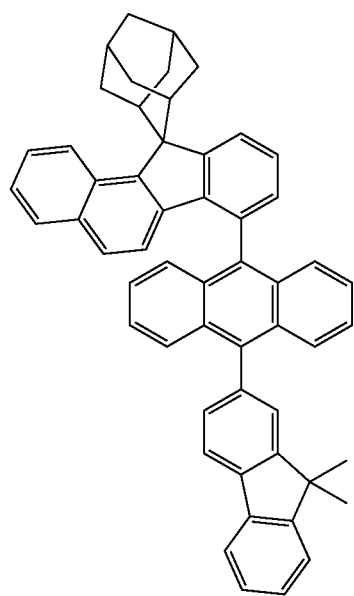

70
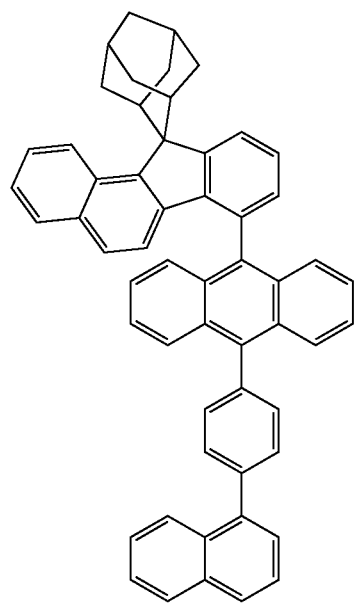
71
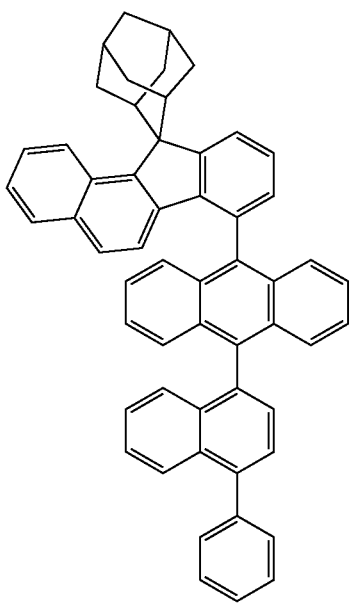
72
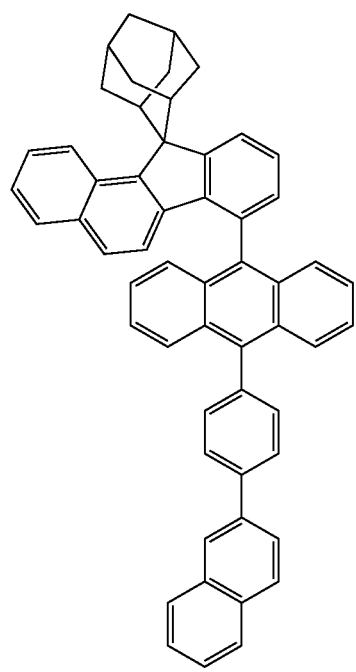
73
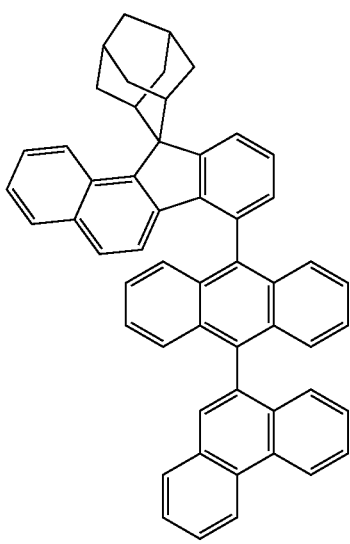

-continued
74
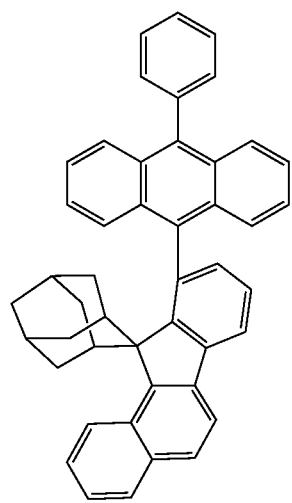
75
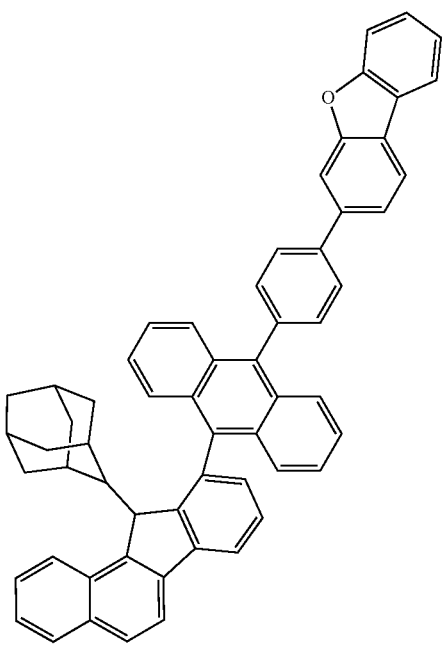
76
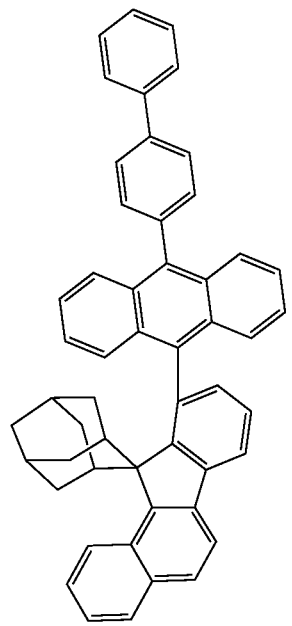
77
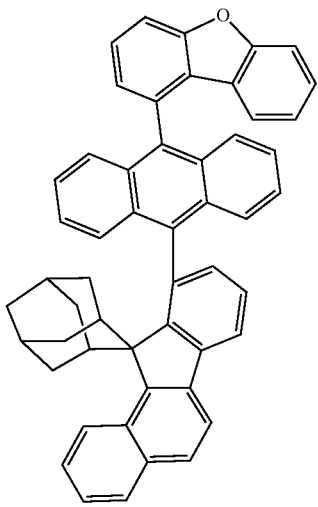

-continued
78 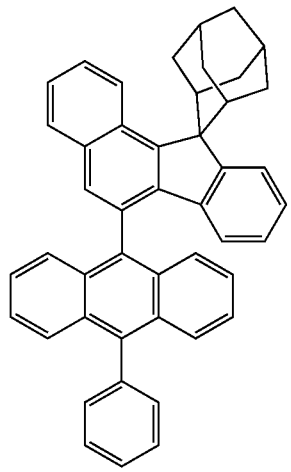
79 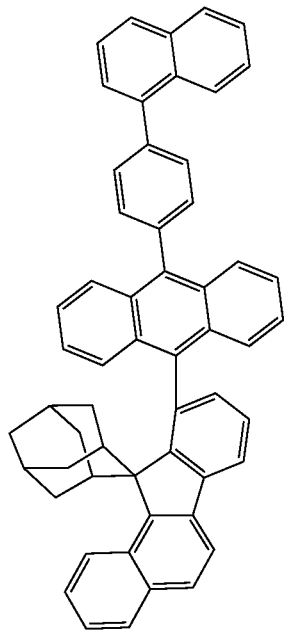
80 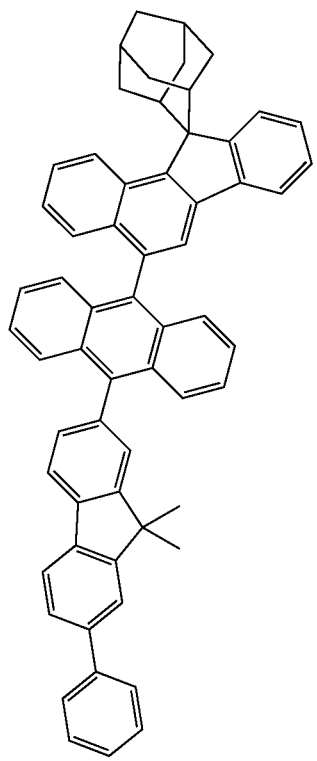
81 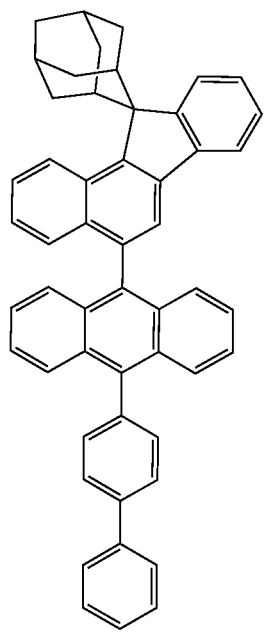

-continued
82
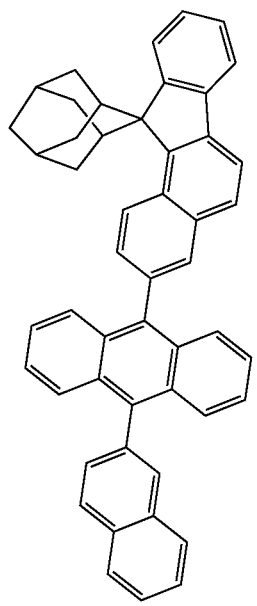
83
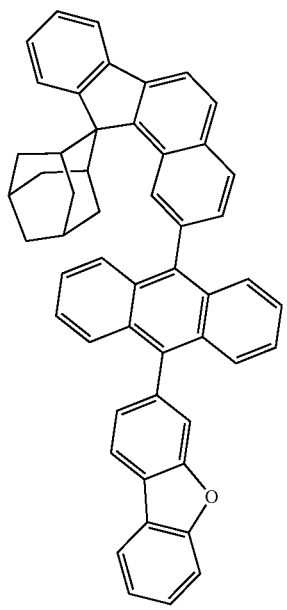
84
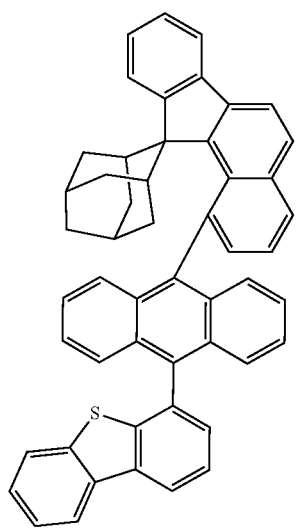
85
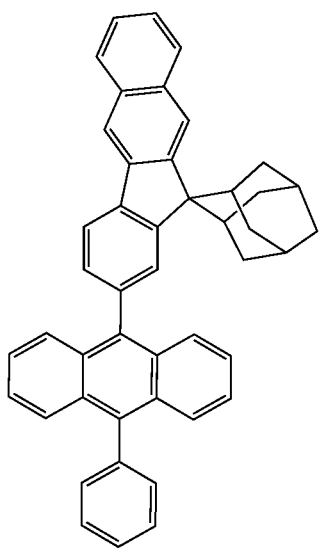

-continued
86
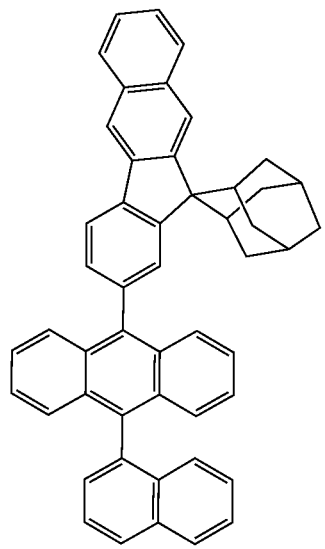
87
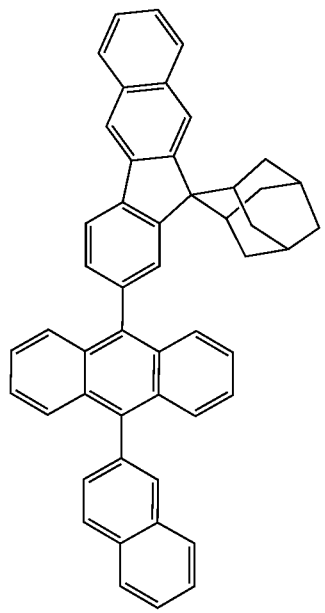
88
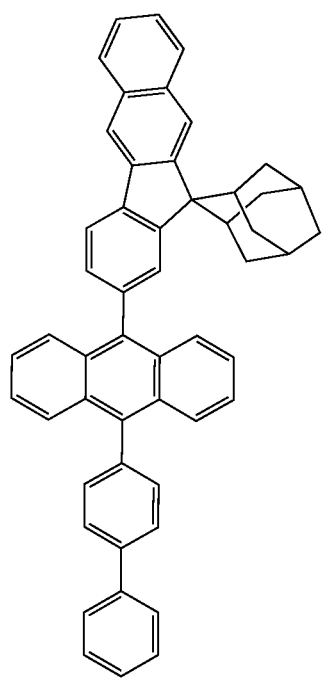
89
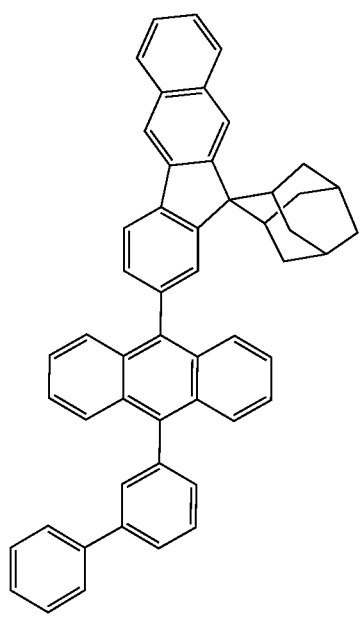

-continued
90
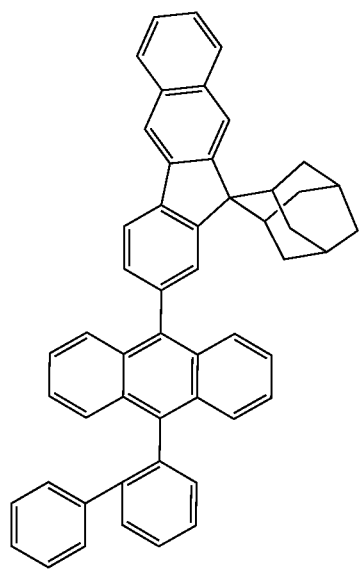
91
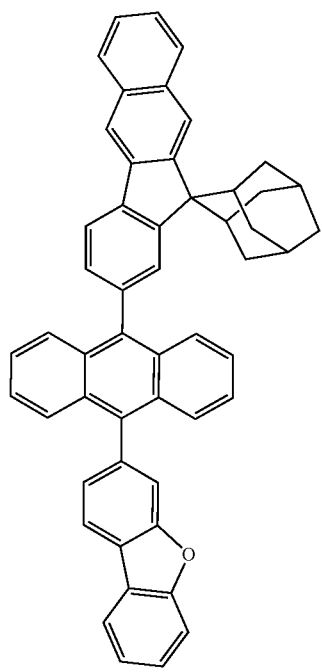
92
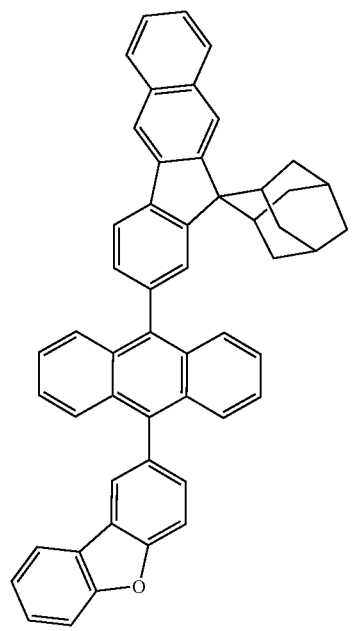
93
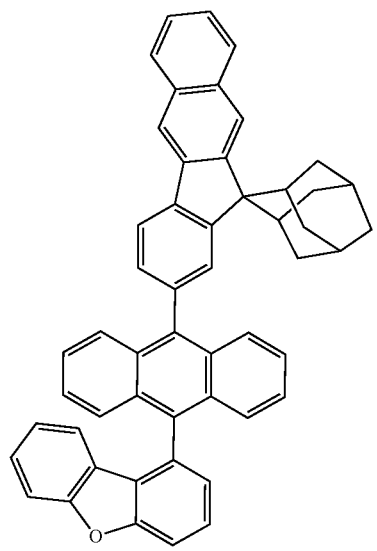

94
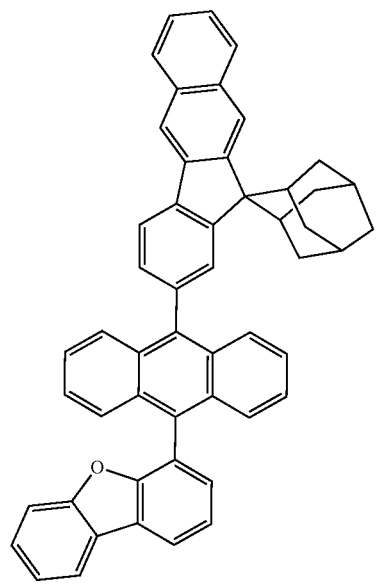
95
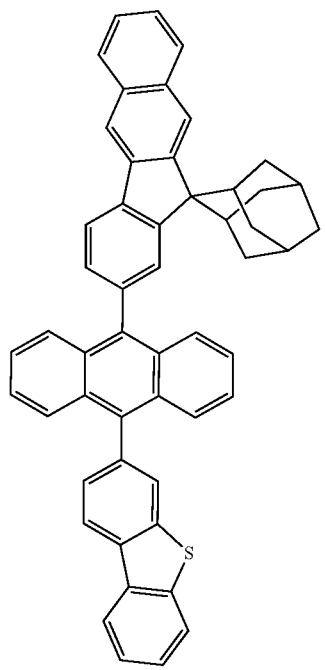
97
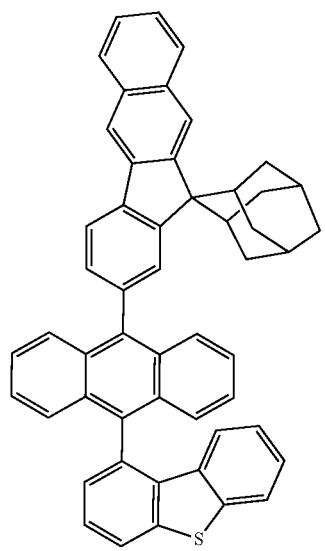
98
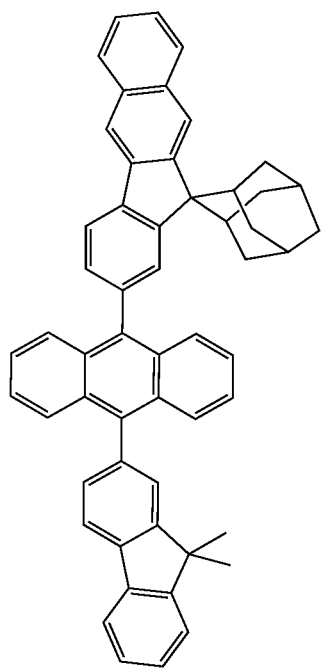

99
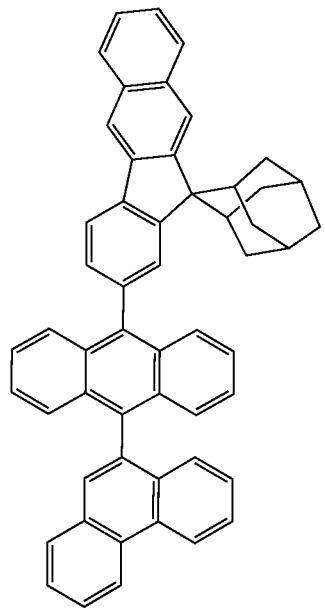
100
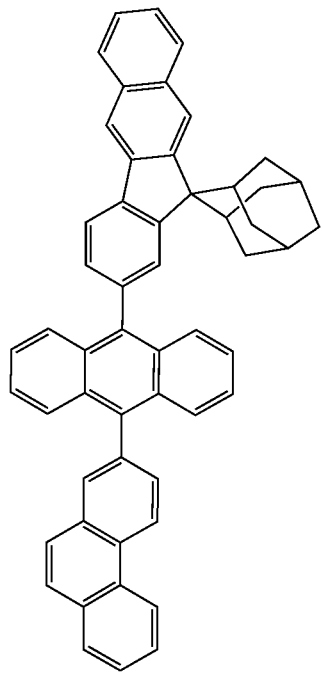
101
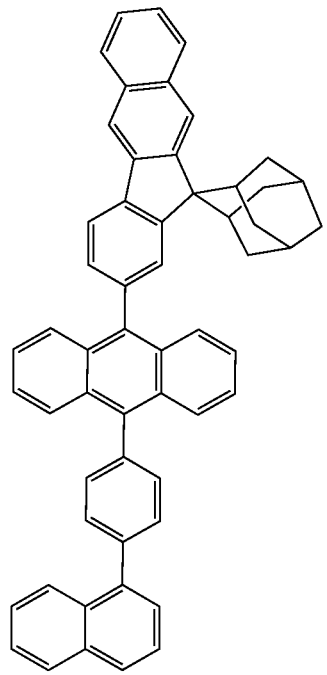
102
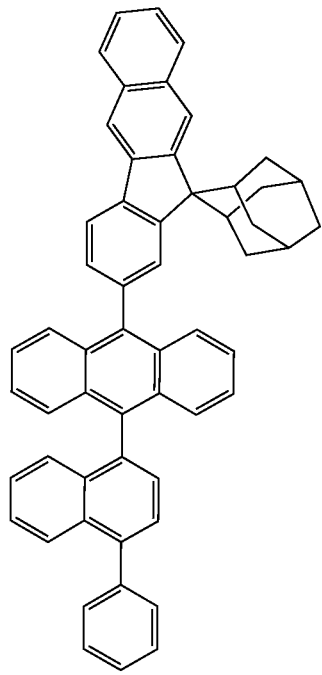

103
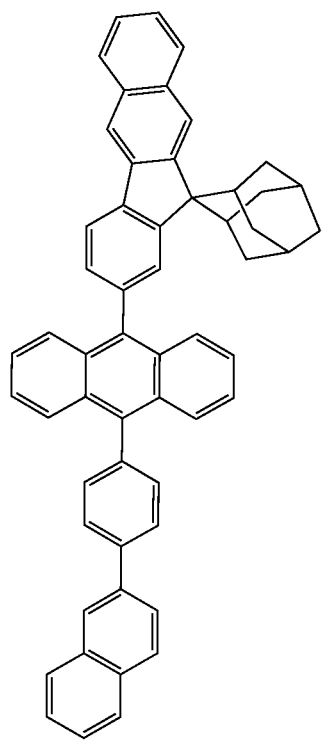
104
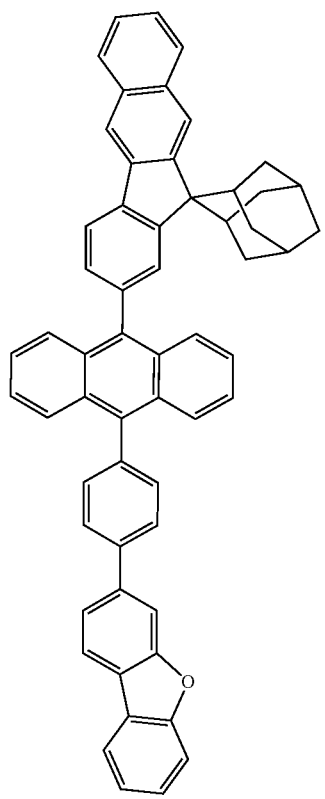
105
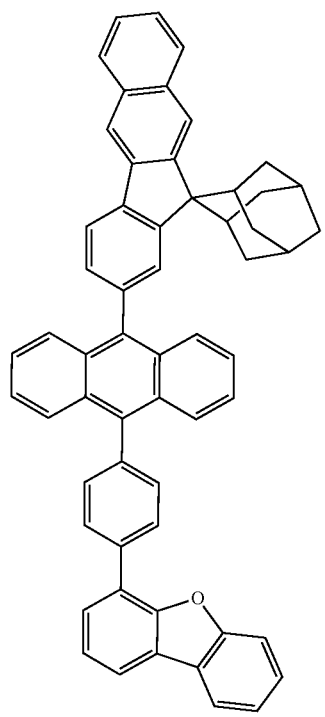
106
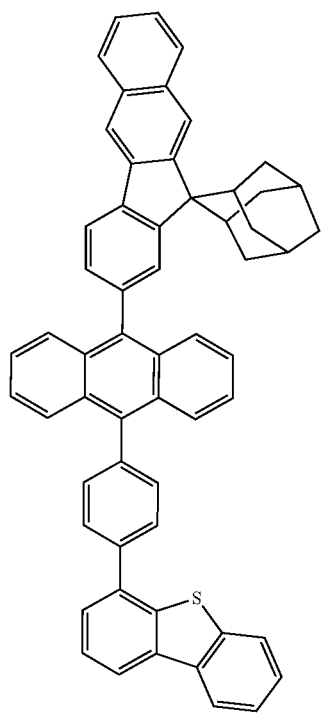

-continued
107
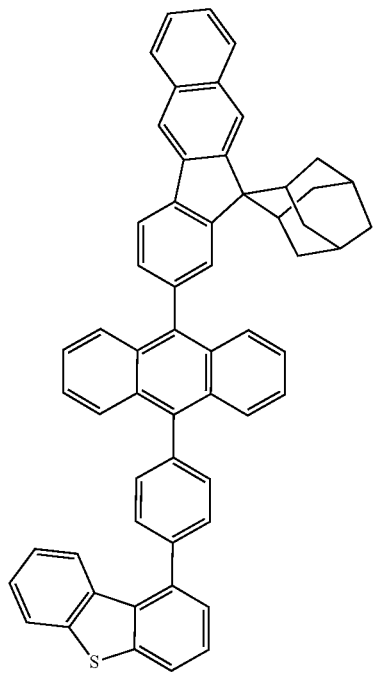
108
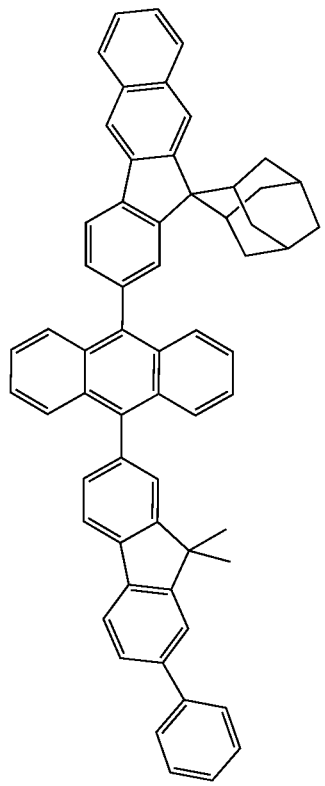
110
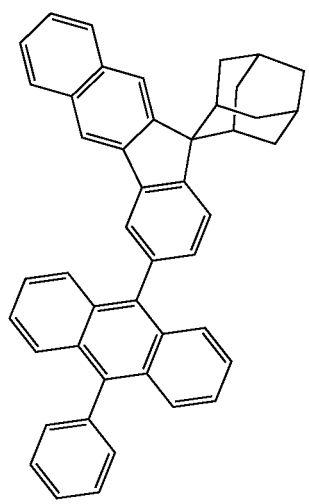
111

-continued
112 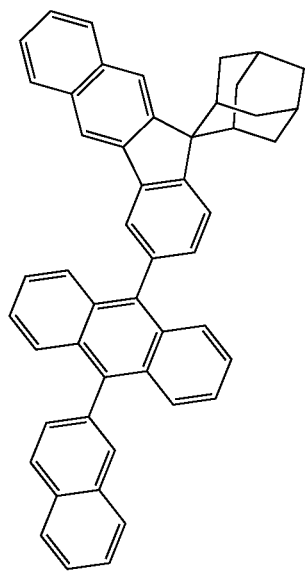
113 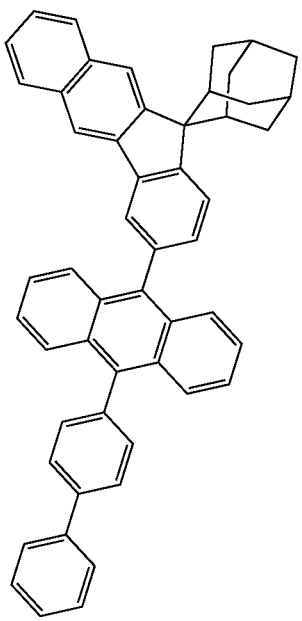
114 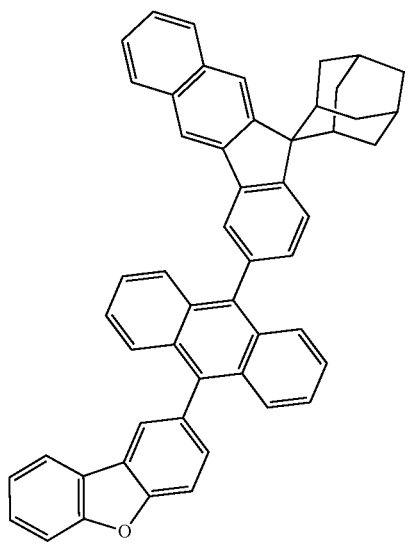
115 

-continued
116
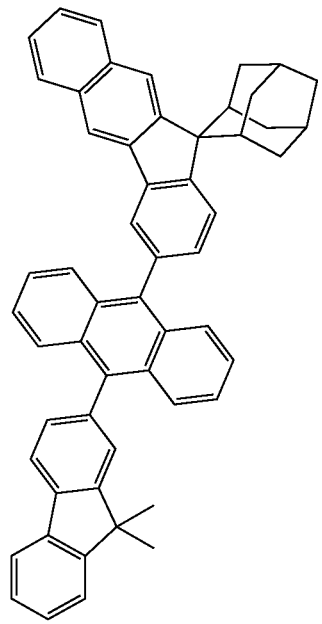
117
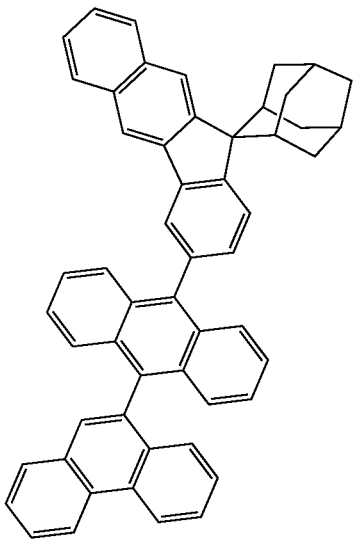
118
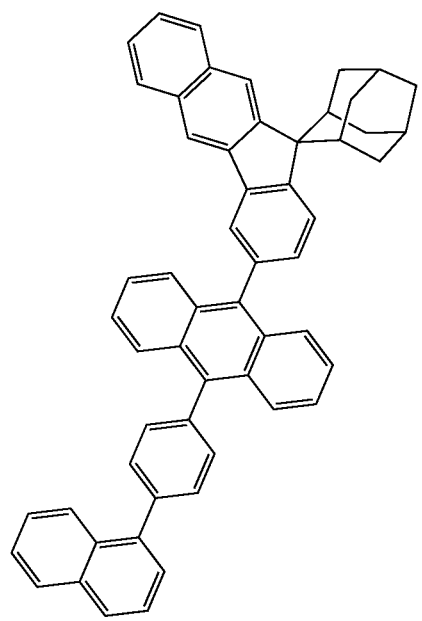
119
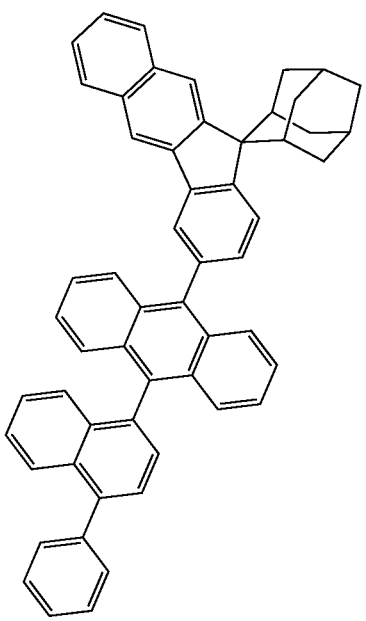

-continued
120
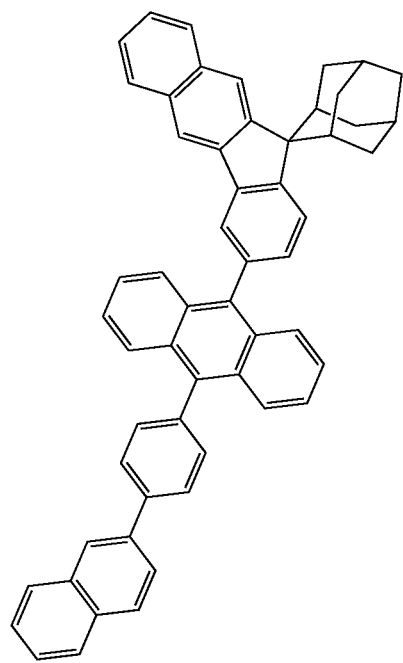
121
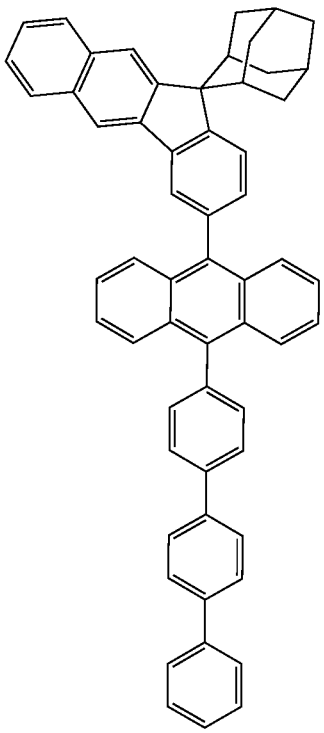
122
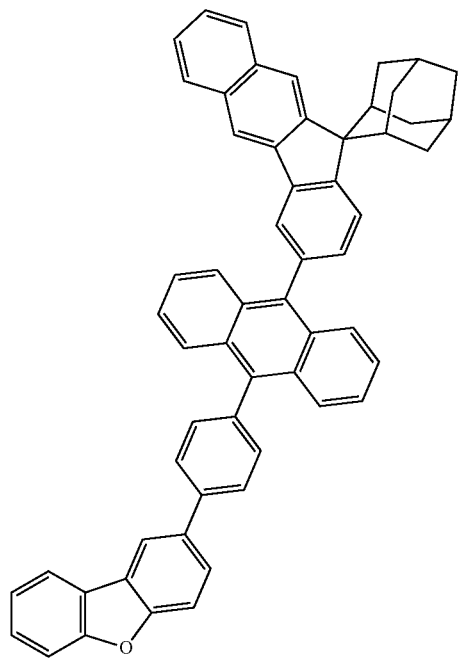
123
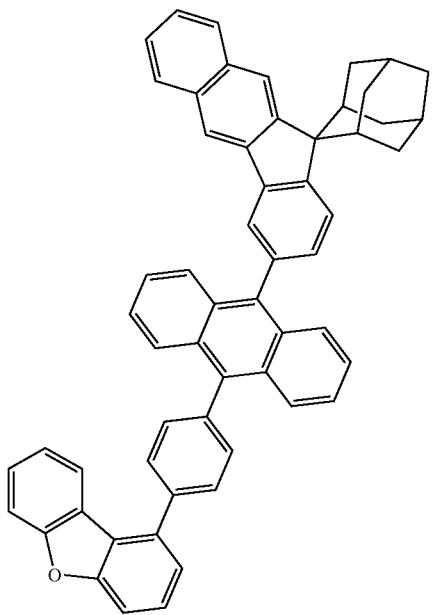

-continued
124
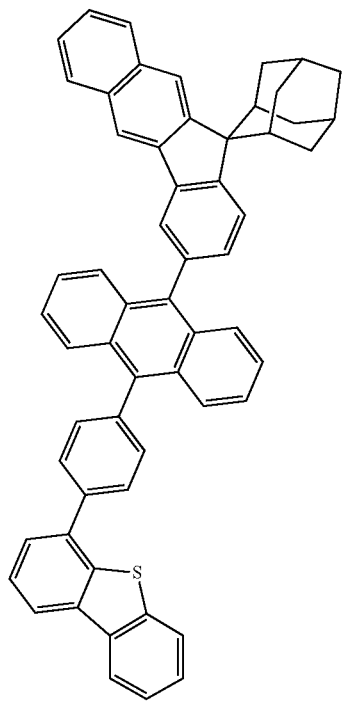
125
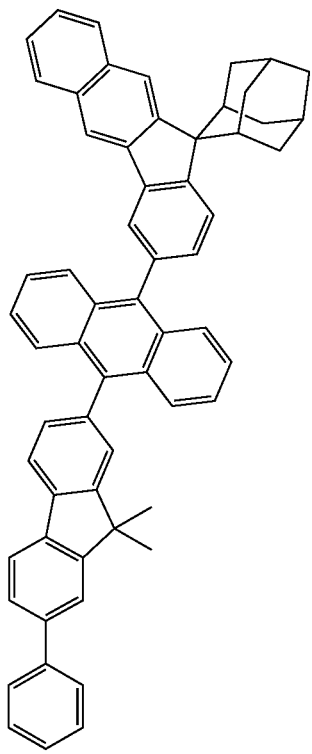
126
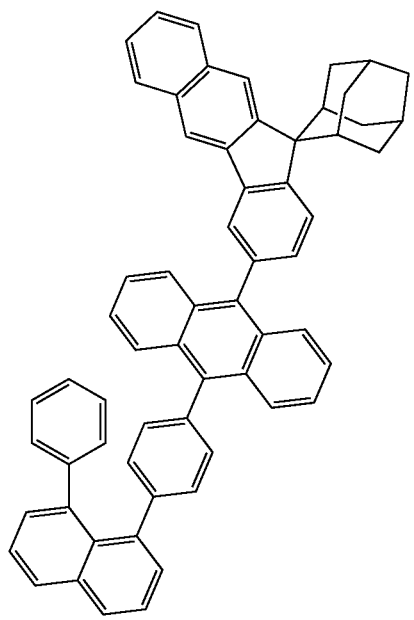
127
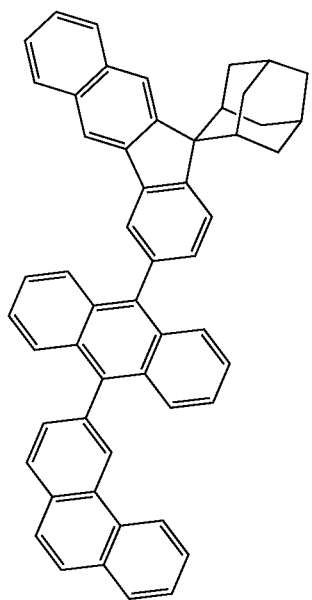

128
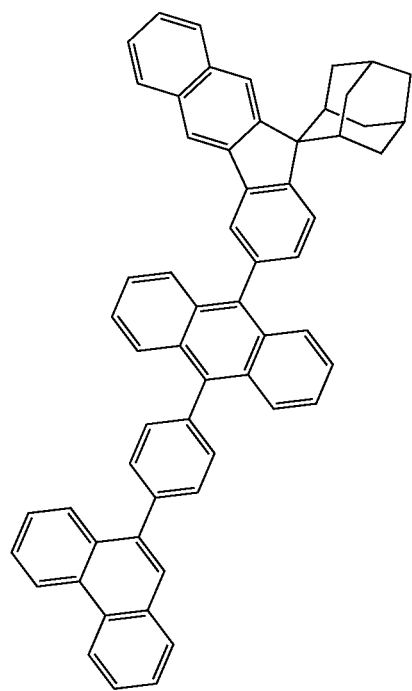
129
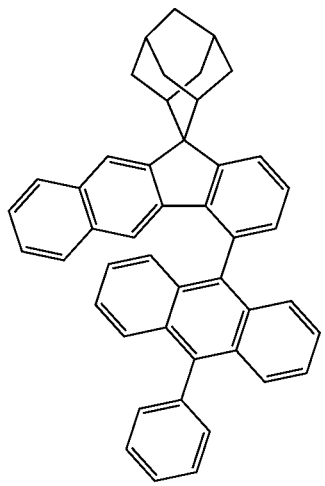
130
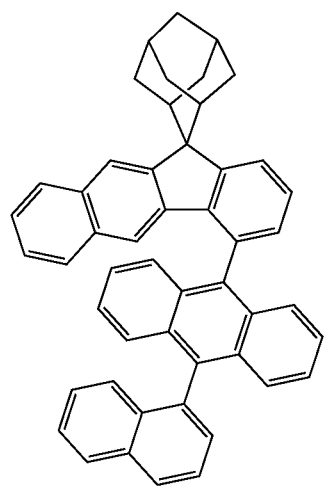
131
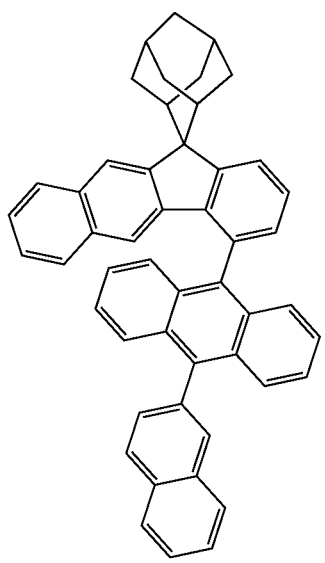

-continued
132
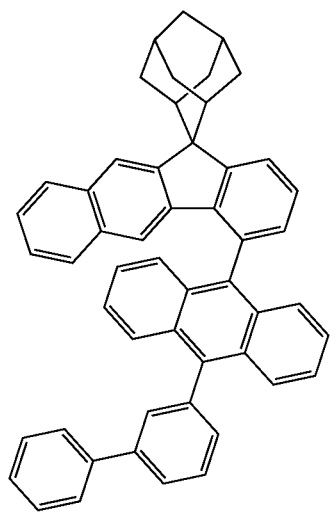
133
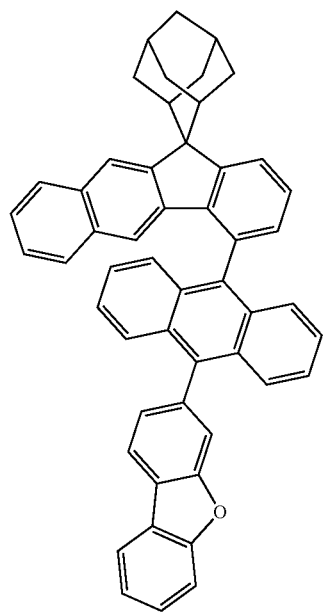
134
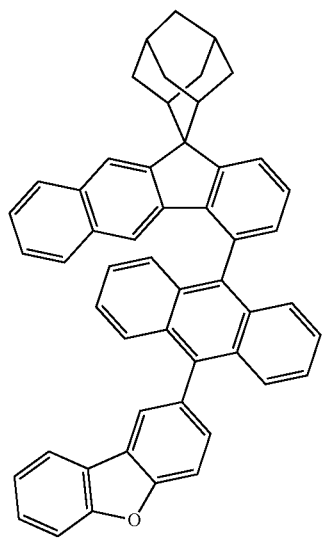
135
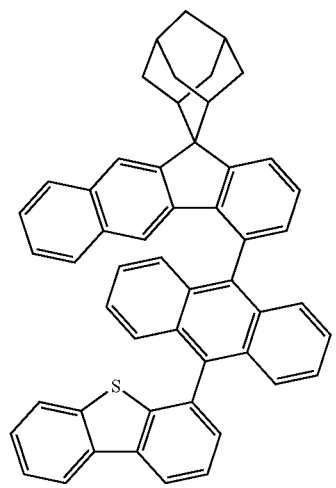

136
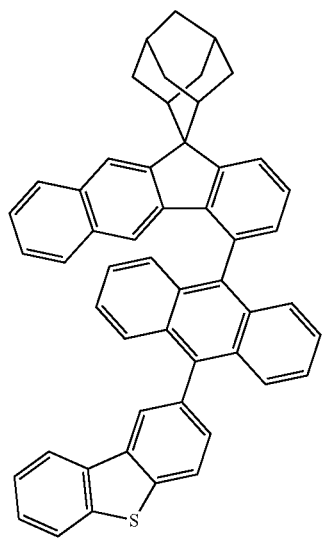
137
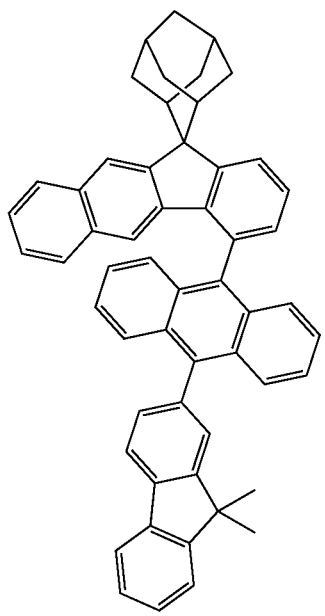
138
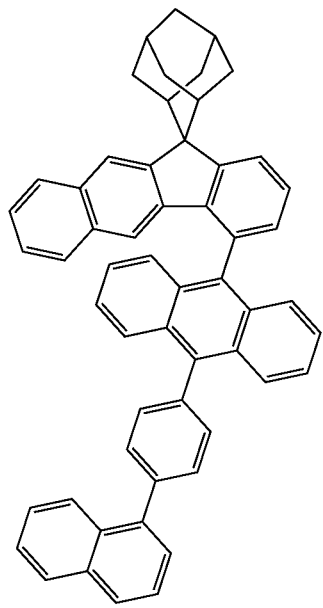
139
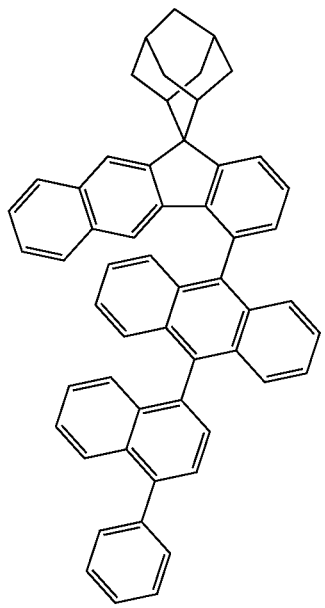

140
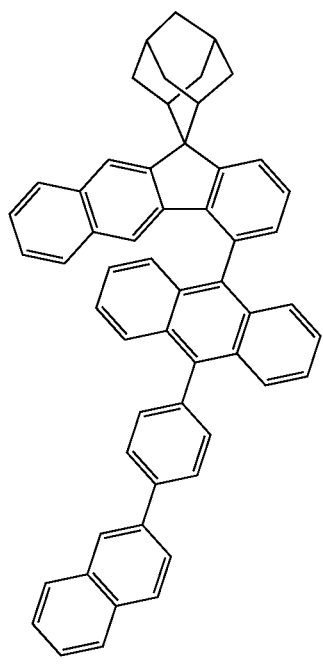
141
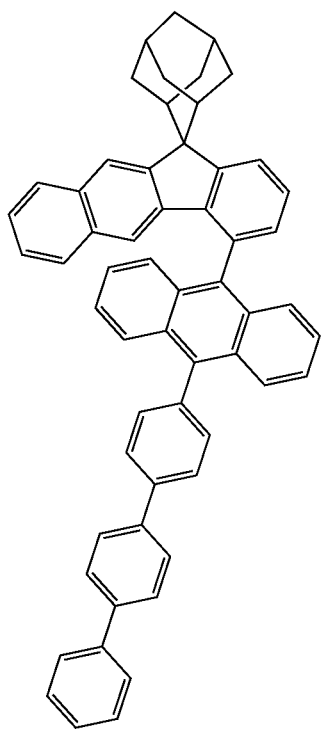
142
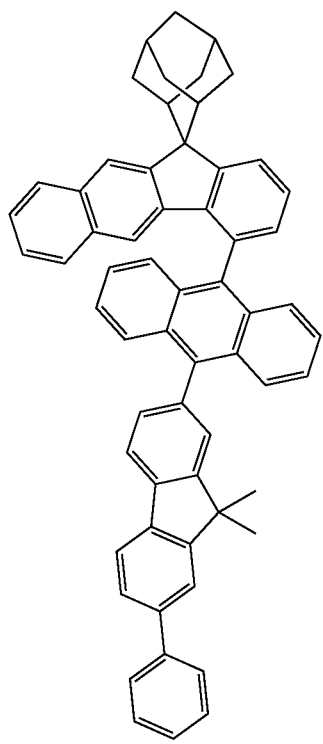
143
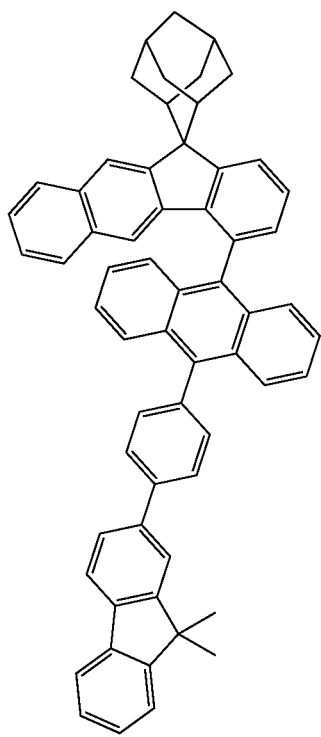

315
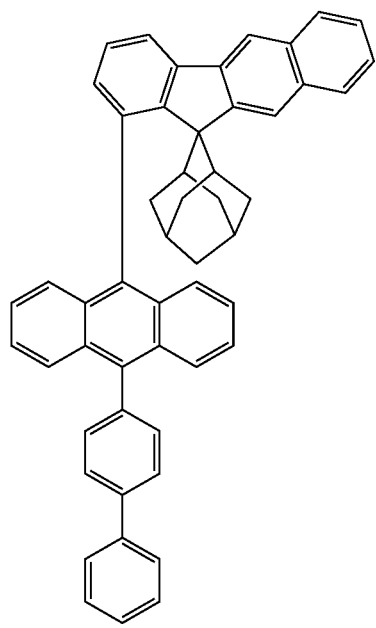
316
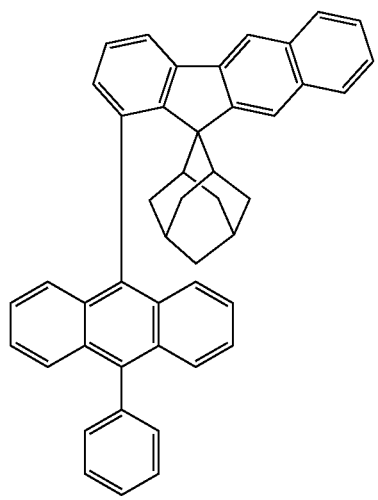
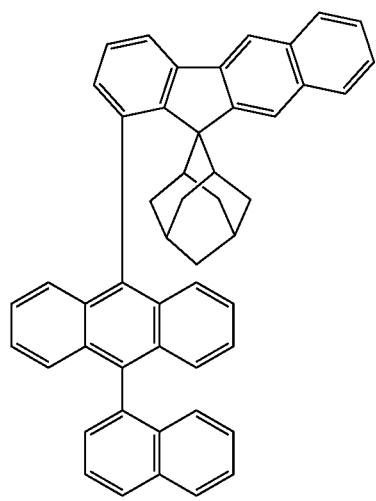
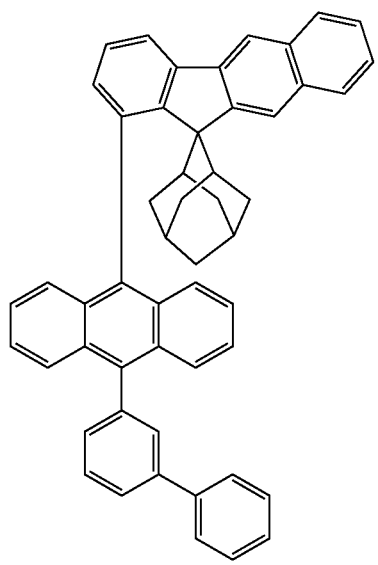

-continued
149
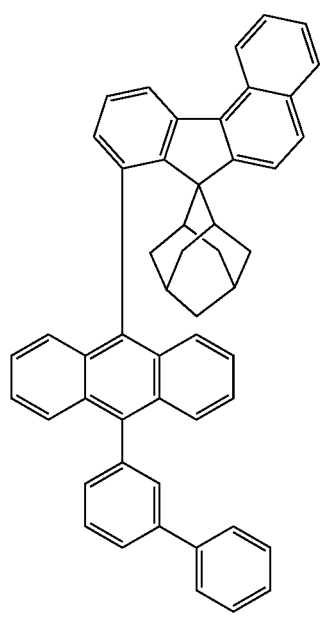
150
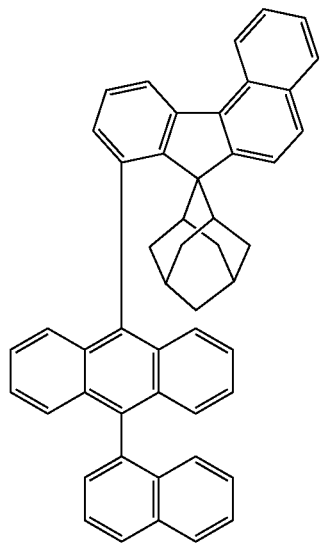
151
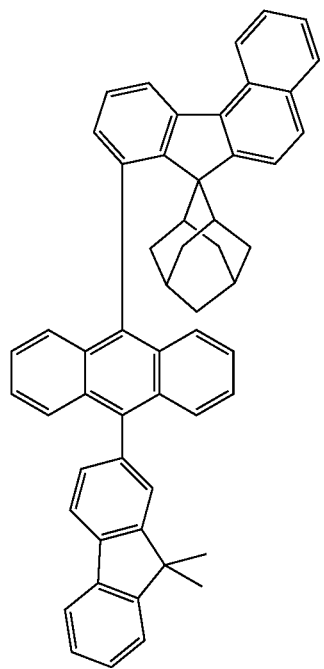
152
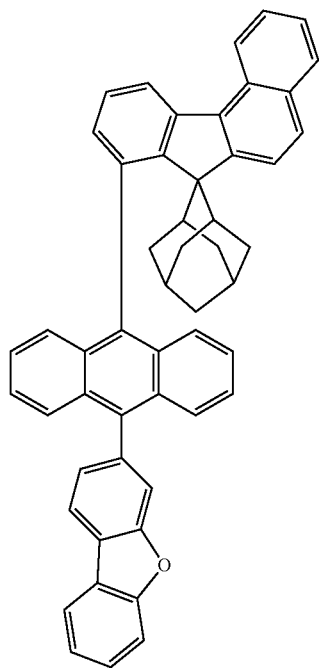

-continued
153
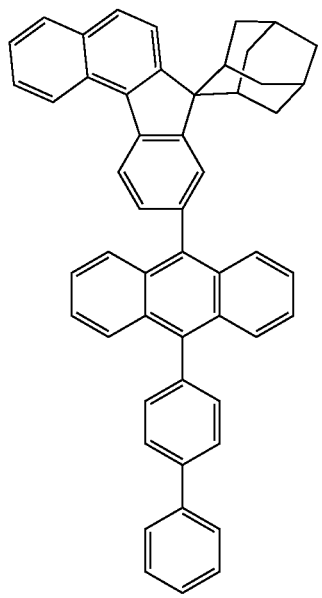
154
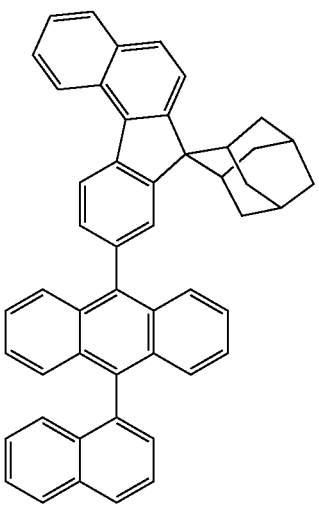
155
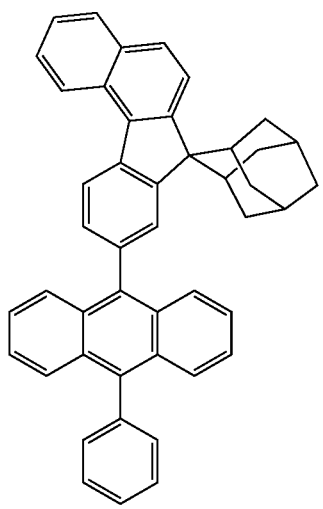
156
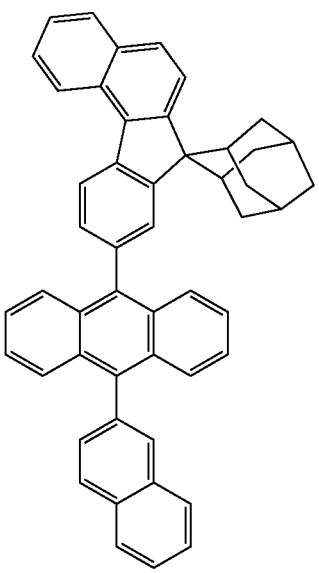

321
322
-continued
157
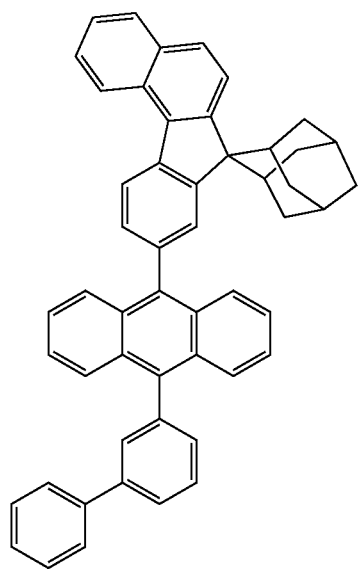
158
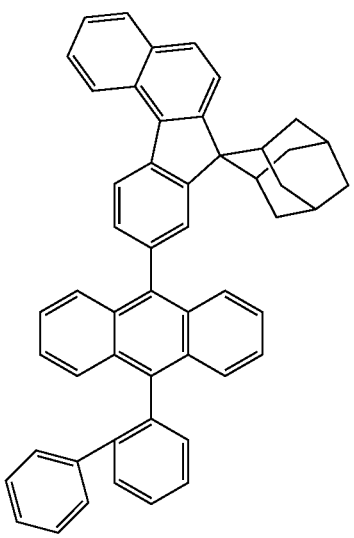
159
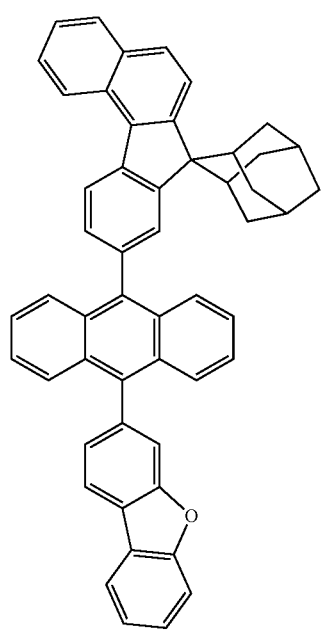
160
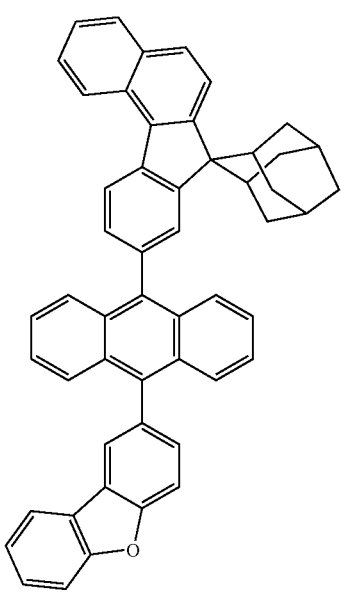

-continued
161
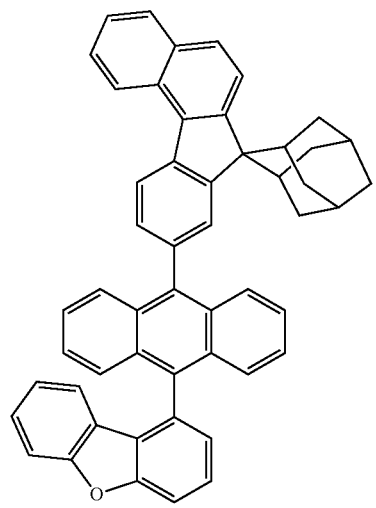
162
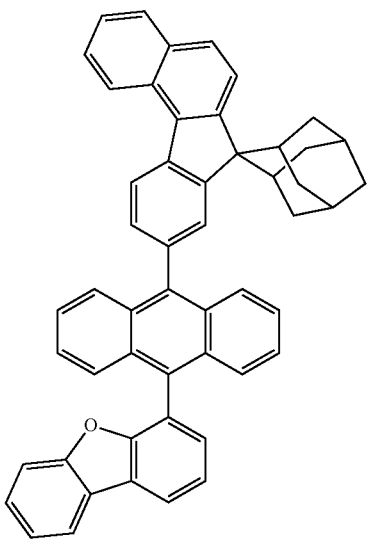
163
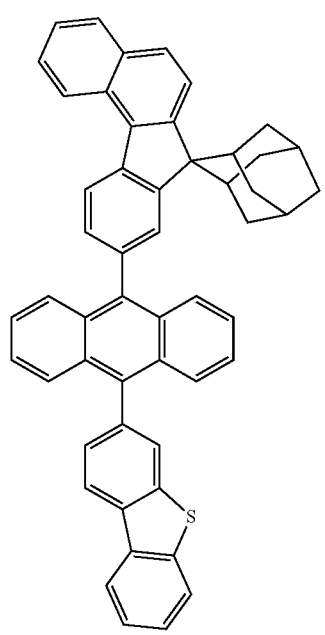
164
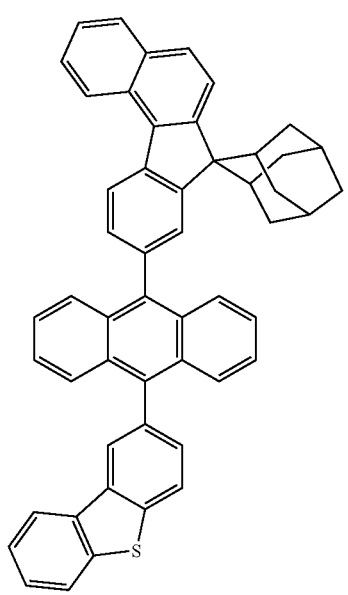

-continued
165
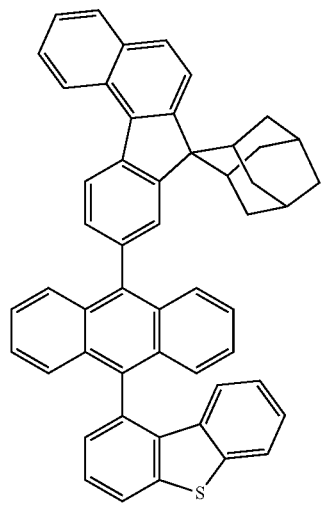
166
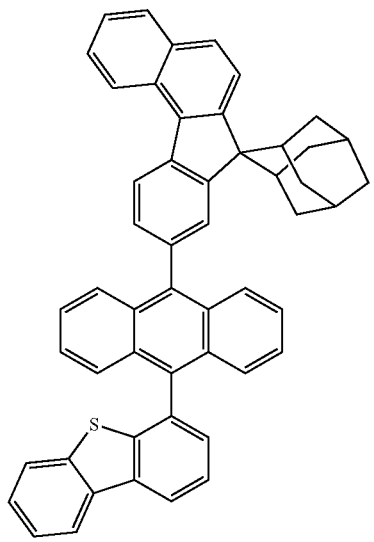
167
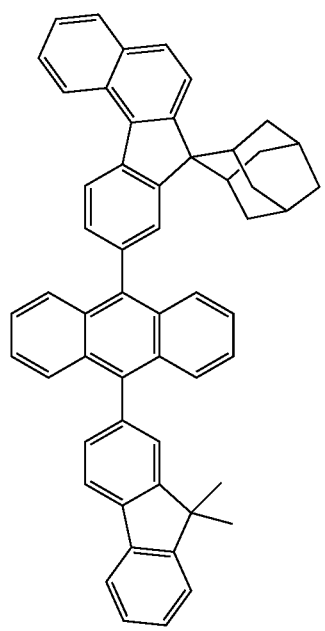
168
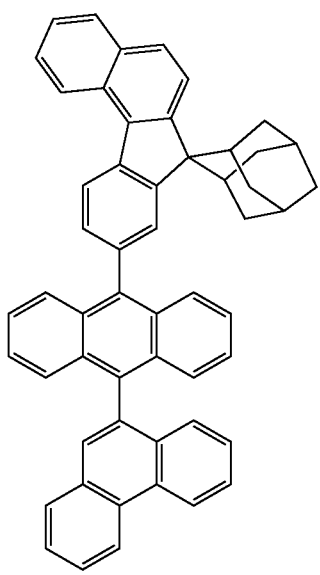

-continued
169
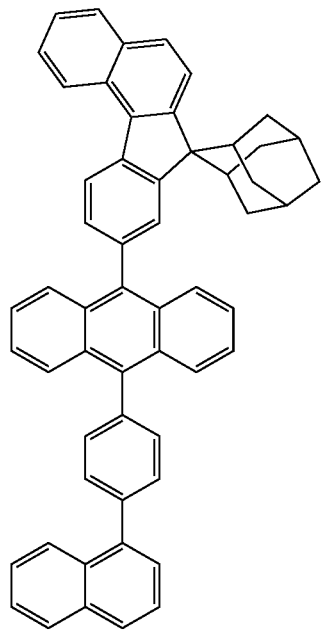
170
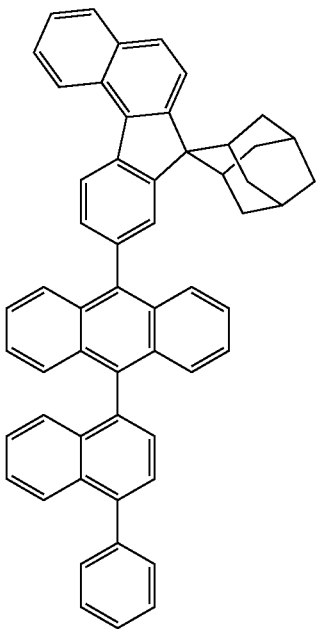
171
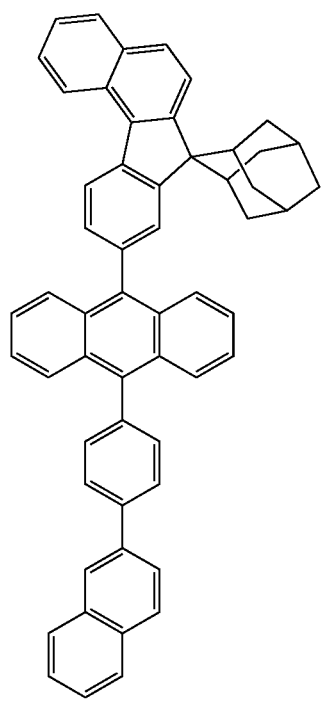
172
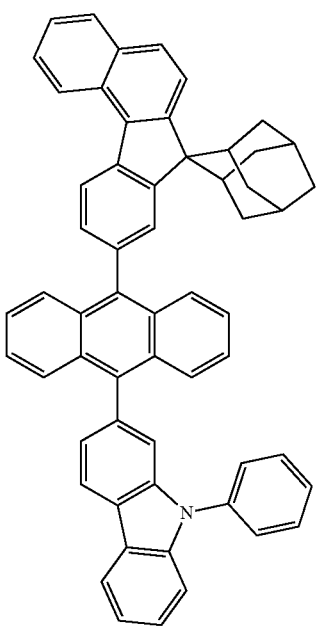

-continued
173 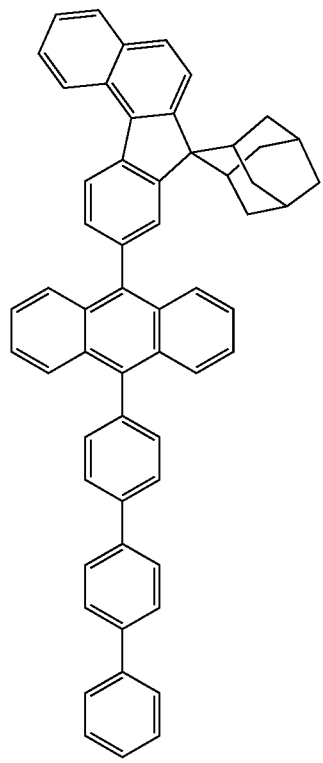
174 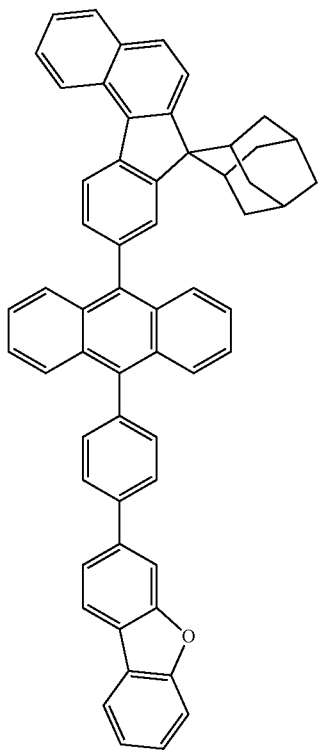
175 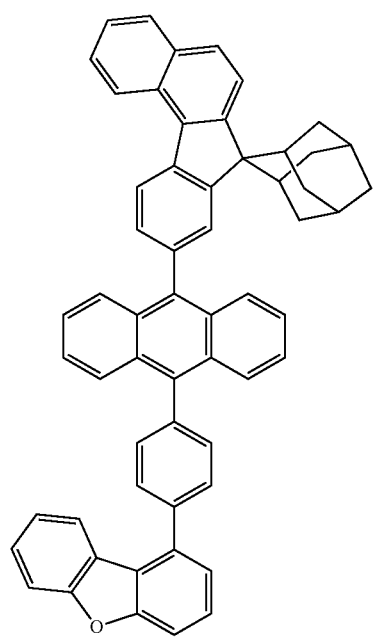
176 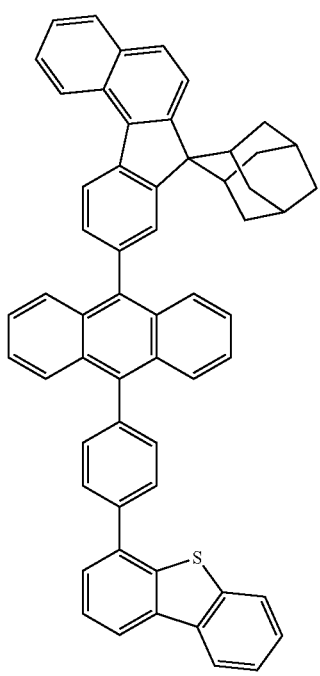

-continued
177
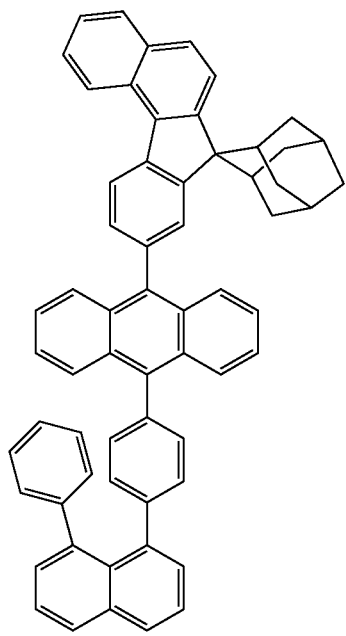
178
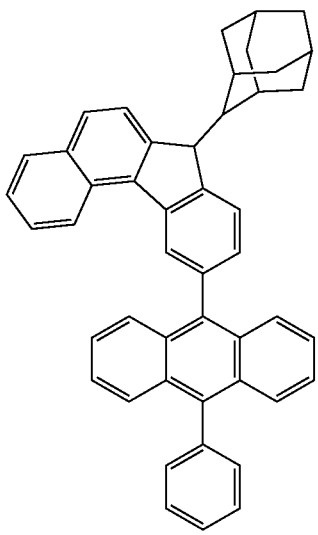
179
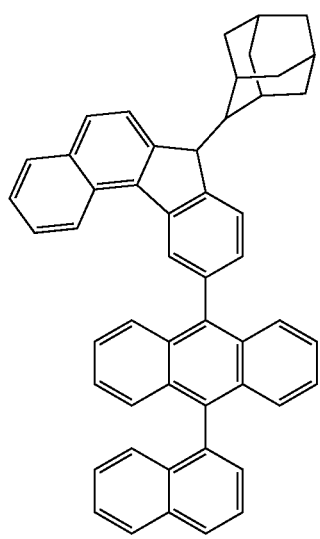
180
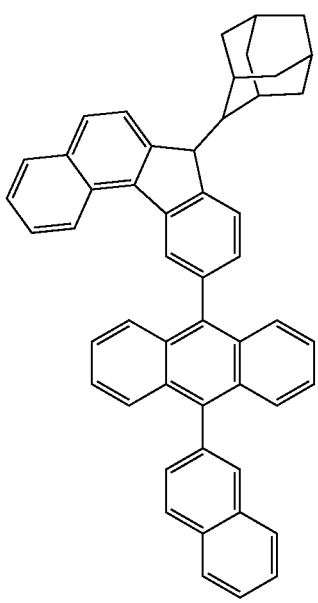

-continued
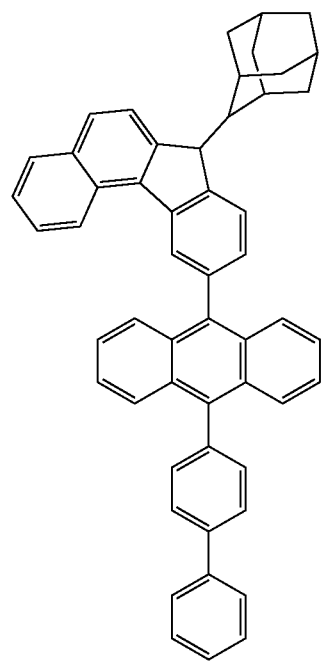
181
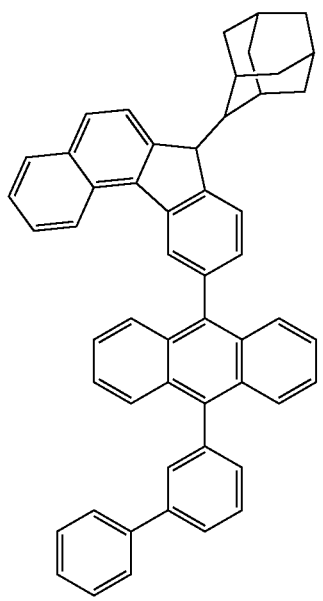
182
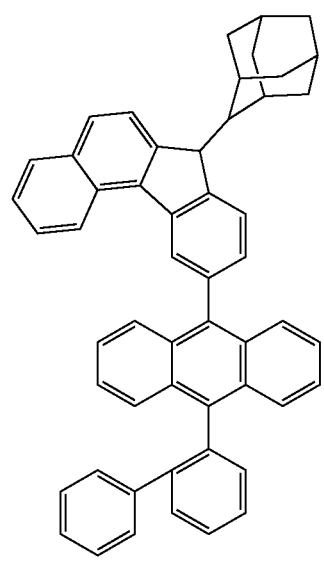
183
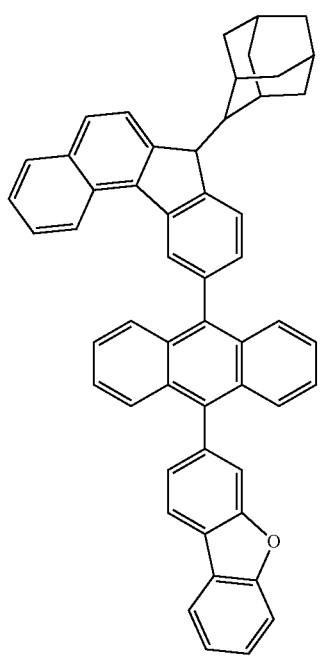
184

-continued
185
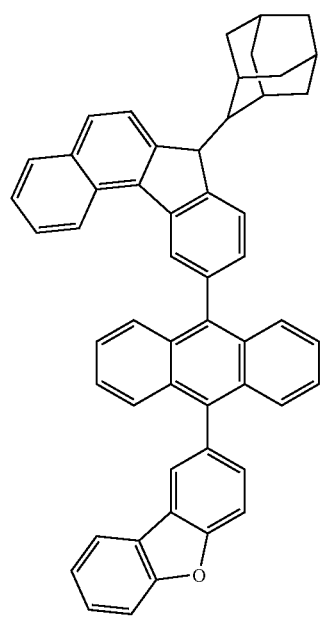
186
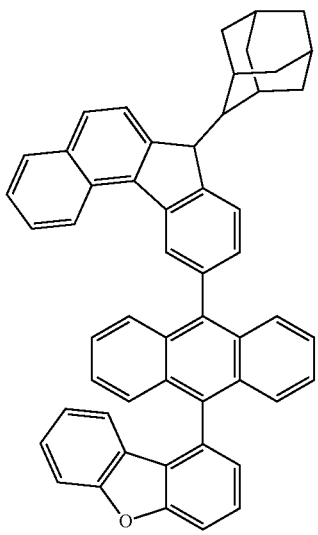
187
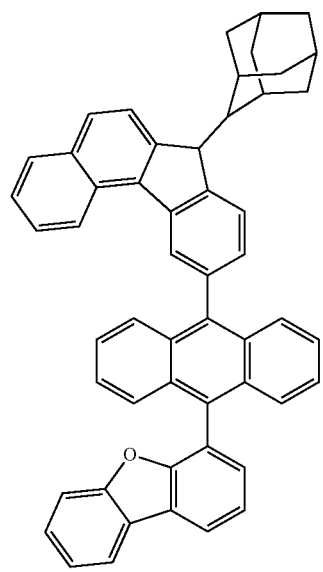
188
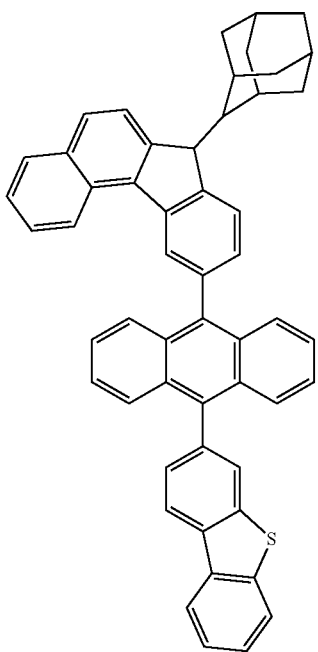

-continued
189
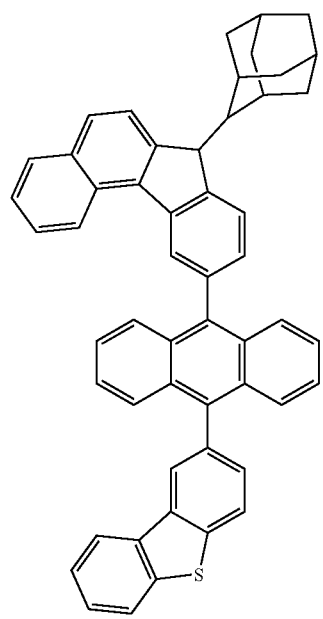
190
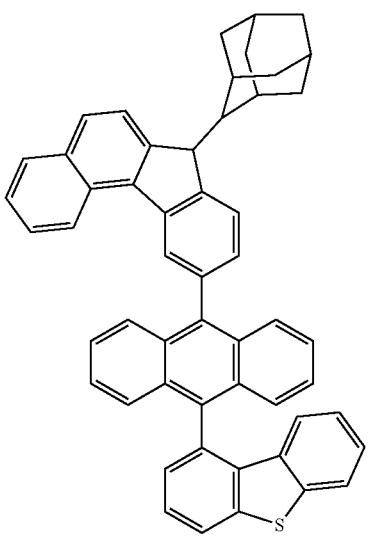
191
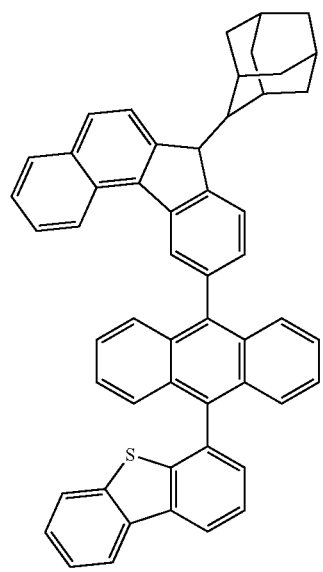
192
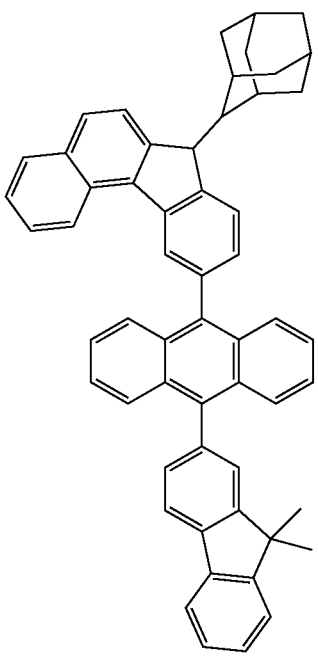

-continued
193 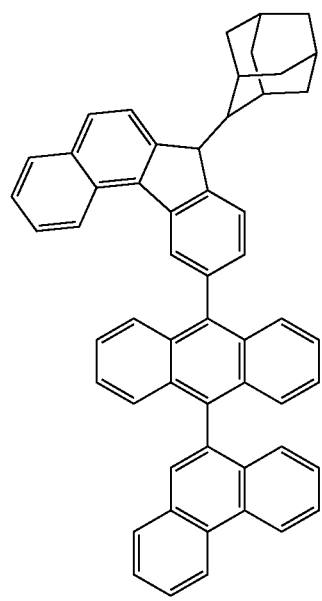
194 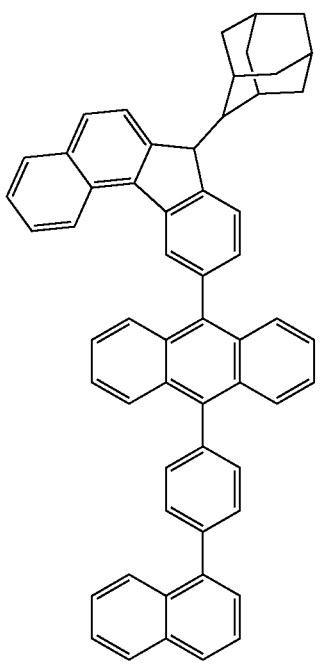
195 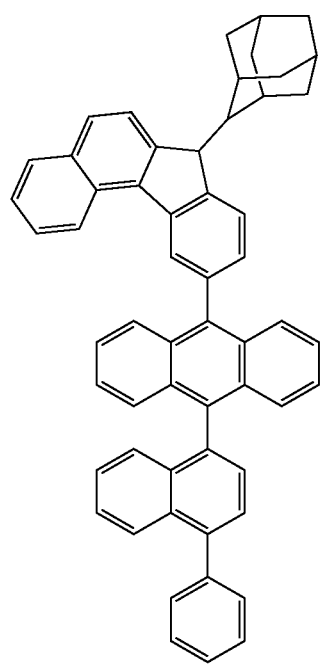
196 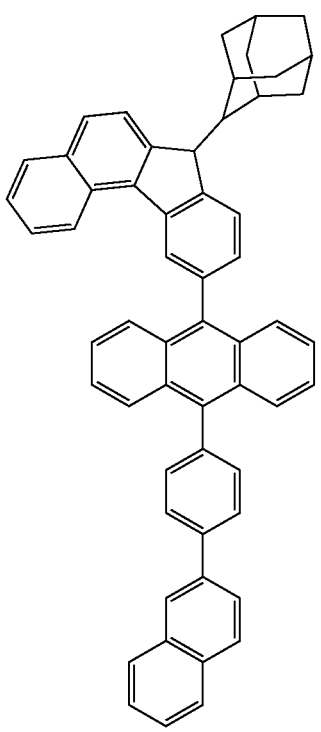

-continued
197
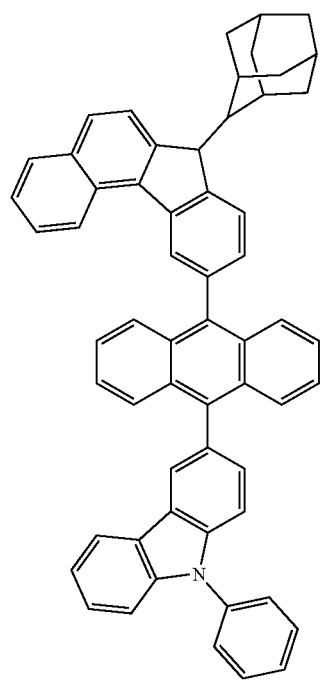
198
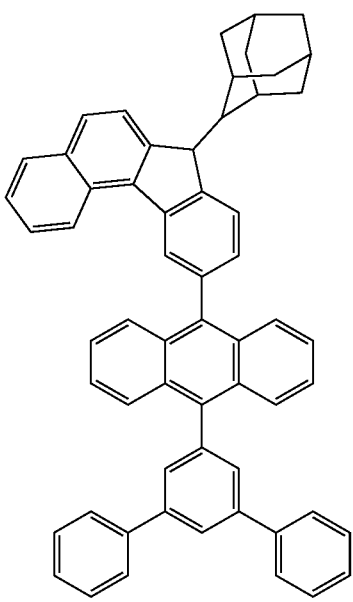
199
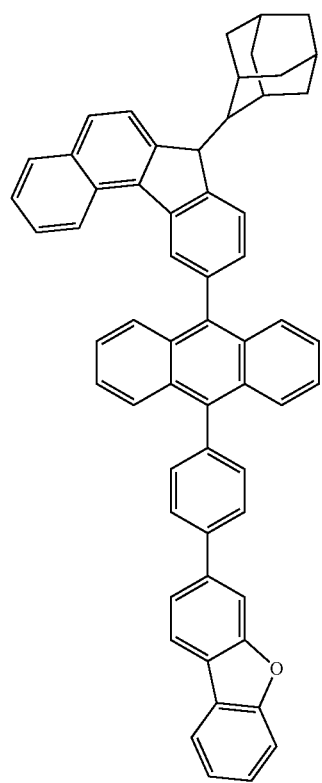
200
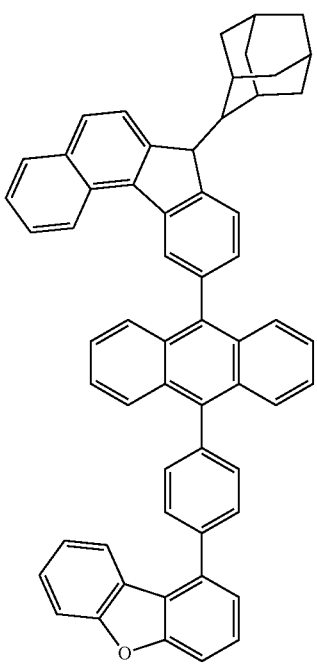

-continued
201
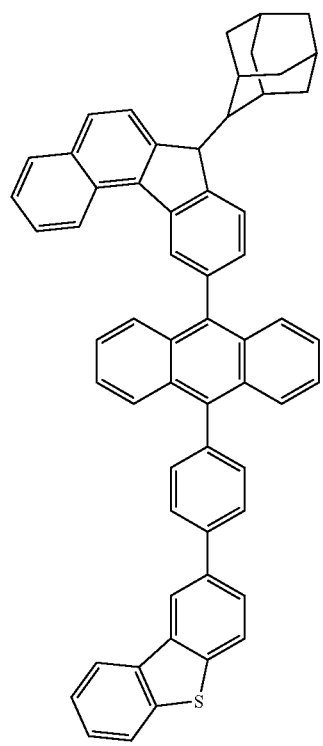
202
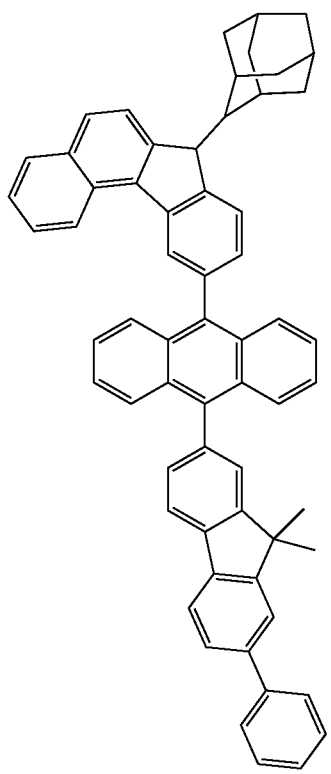
203
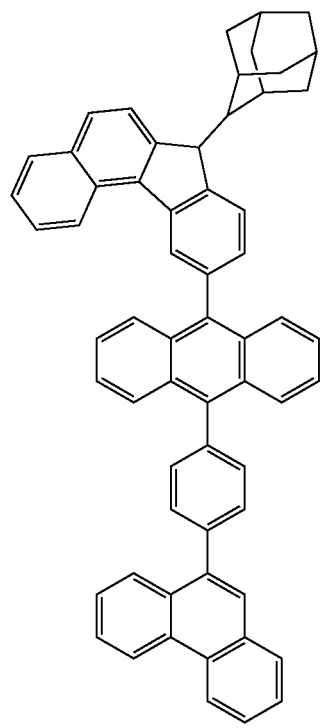
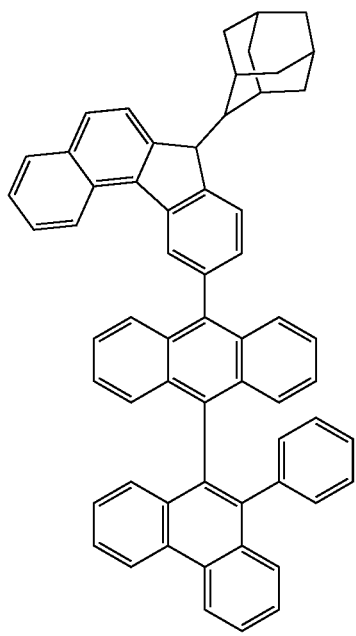

-continued
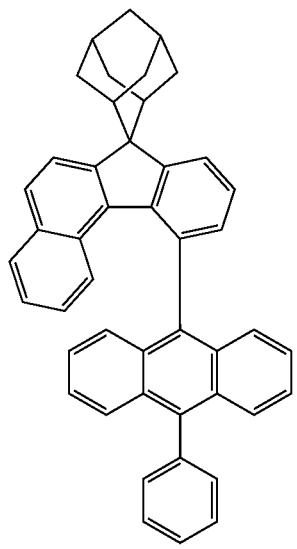
205
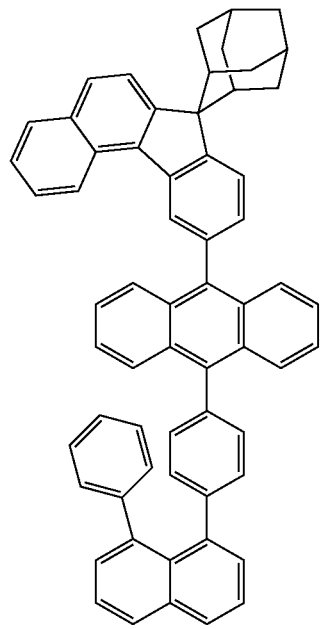
206
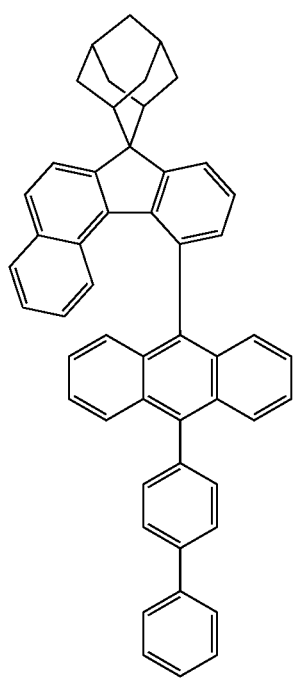
207

347
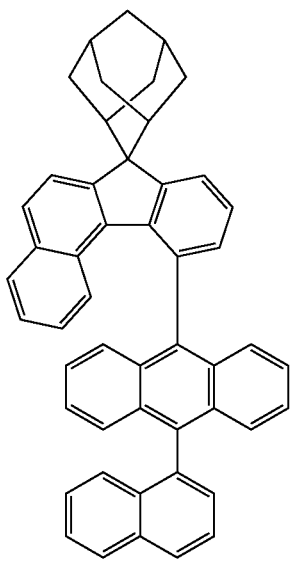
208
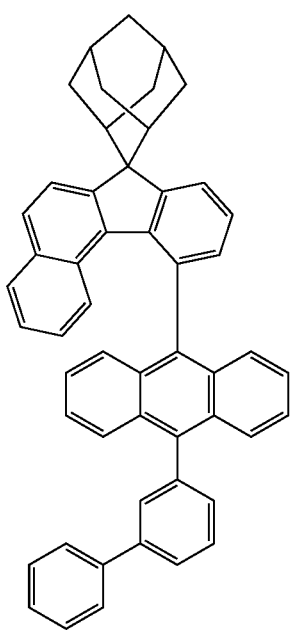
209
348
-continued
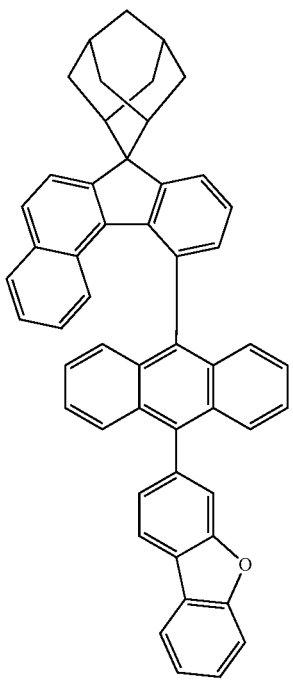
210
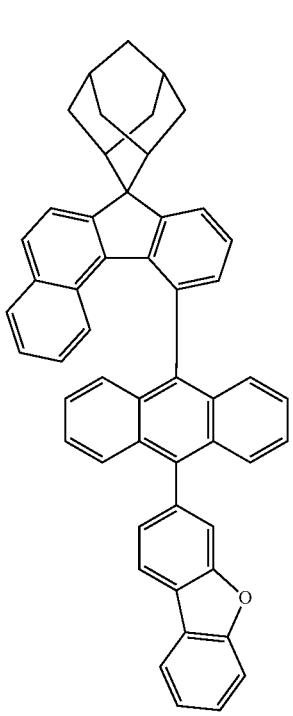
211

-continued
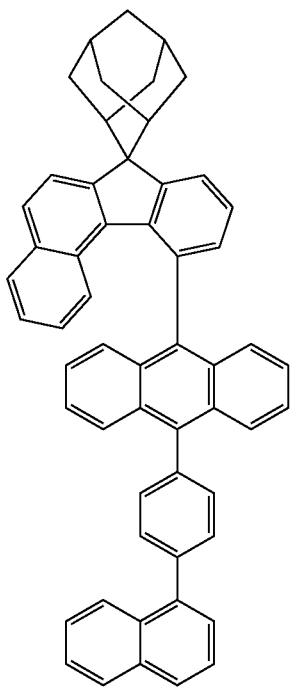
212
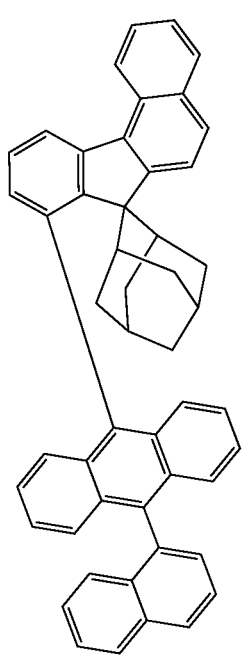
213
-continued
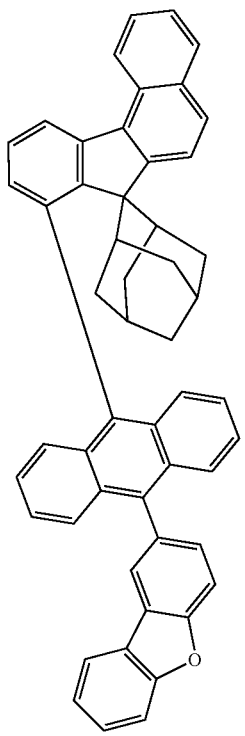
214
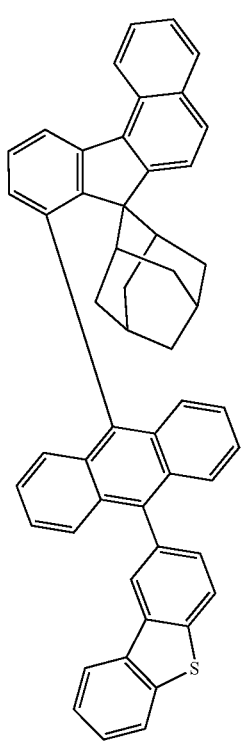
215

351
-continued
352
-continued
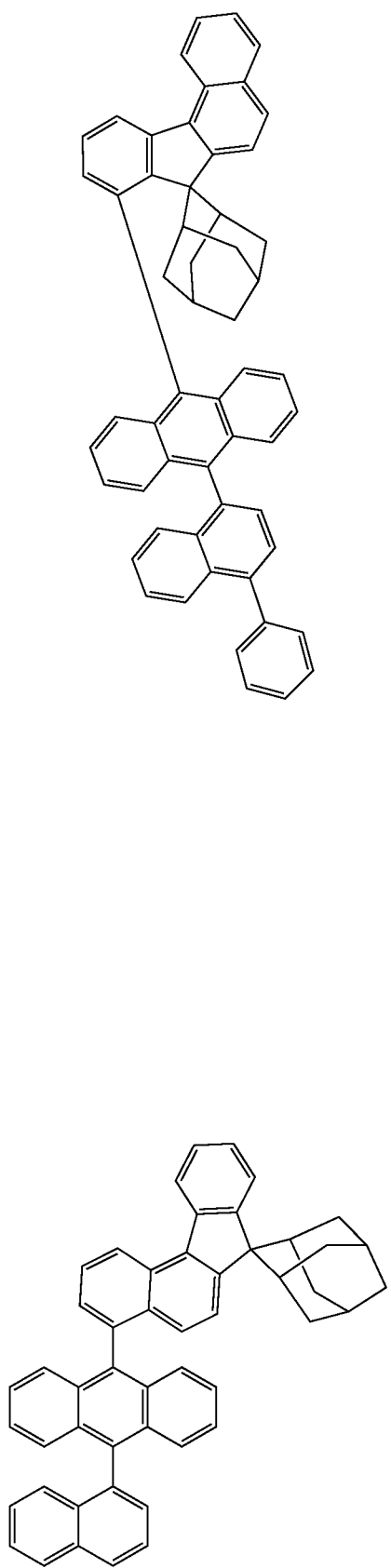
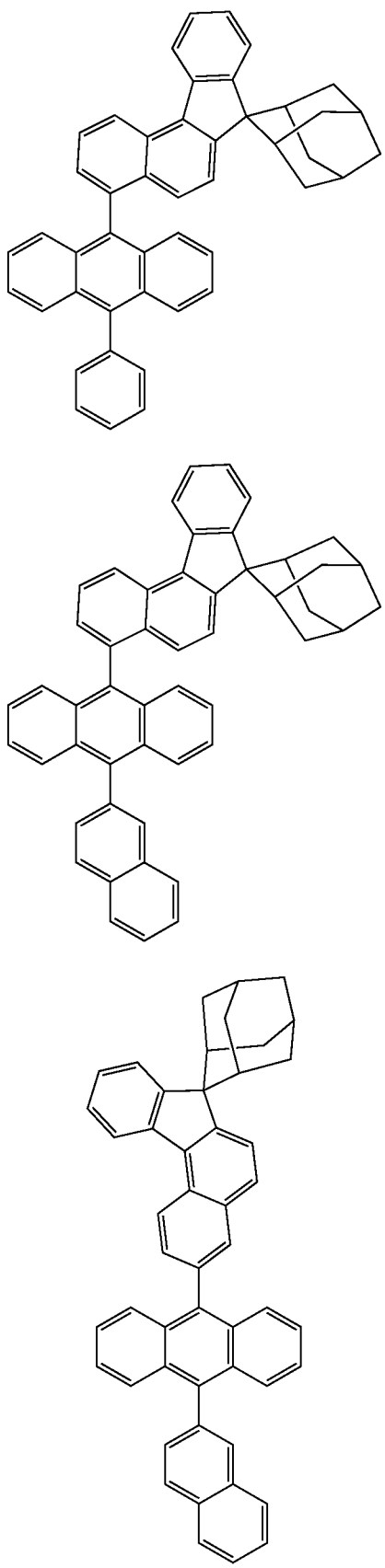

353
-continued
222
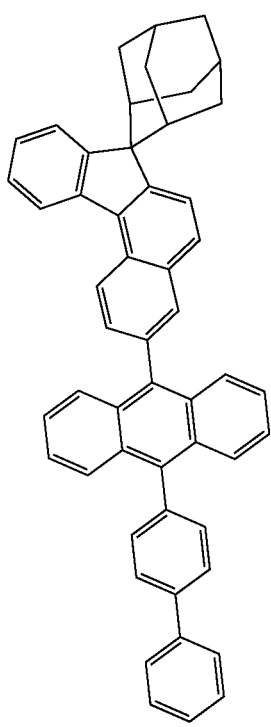
223
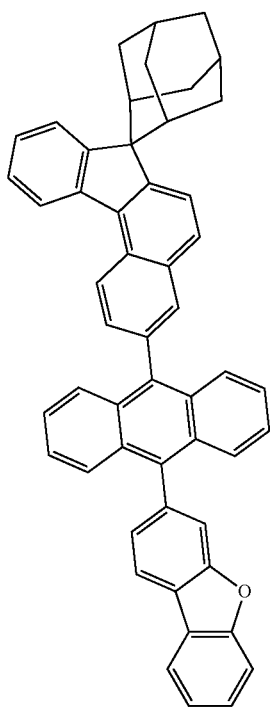
354
-continued
224
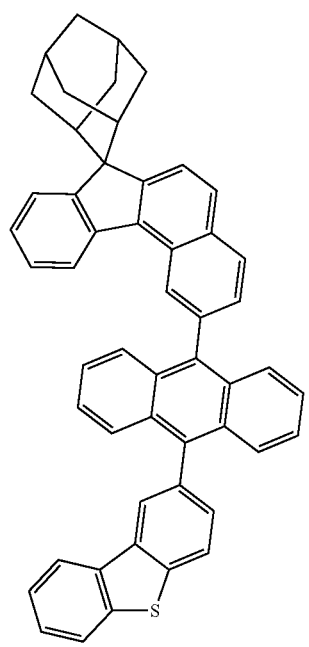
225
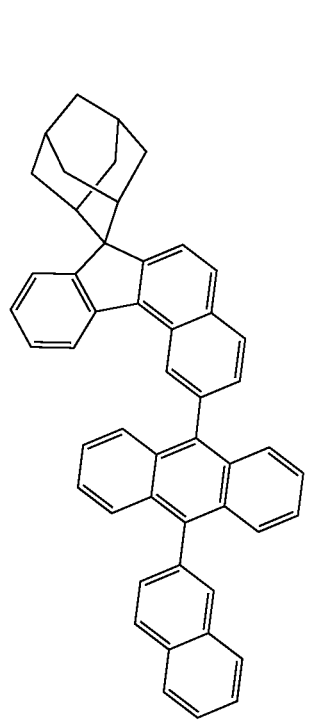

355
-continued
226
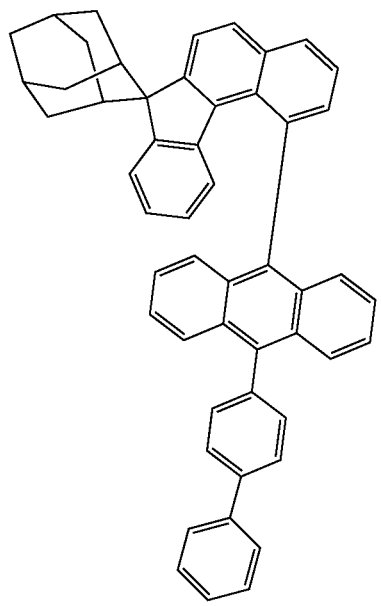
227
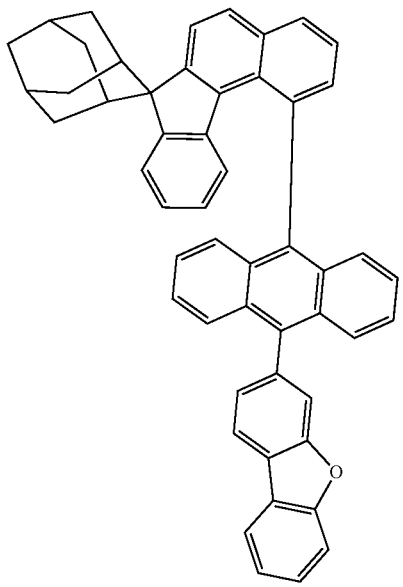
356
-continued
228
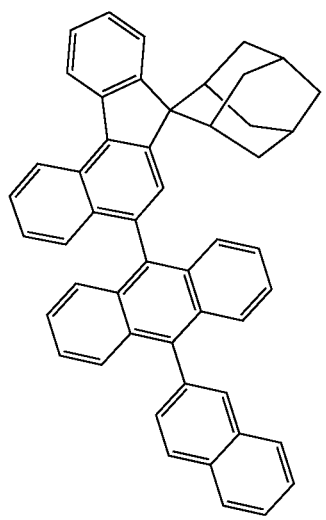
229
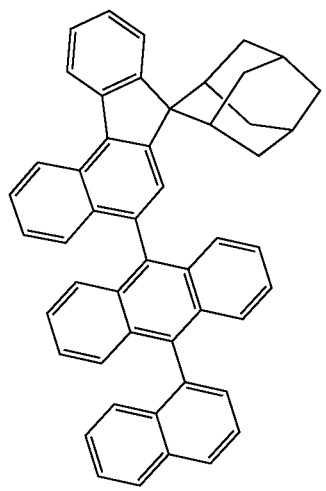
230
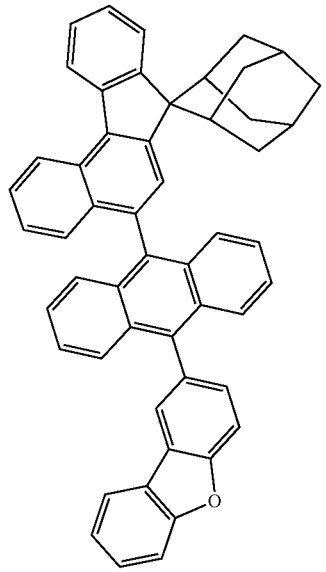

357
-continued
231
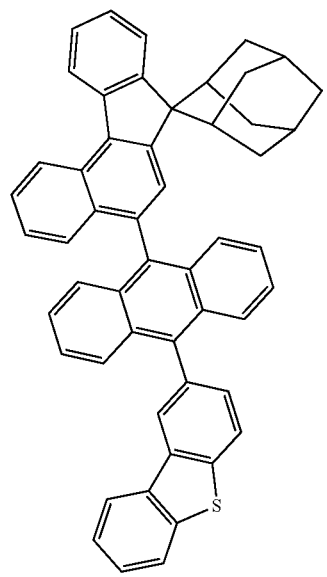
232
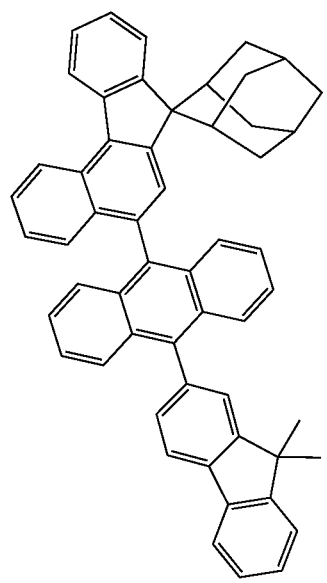
358
-continued
234
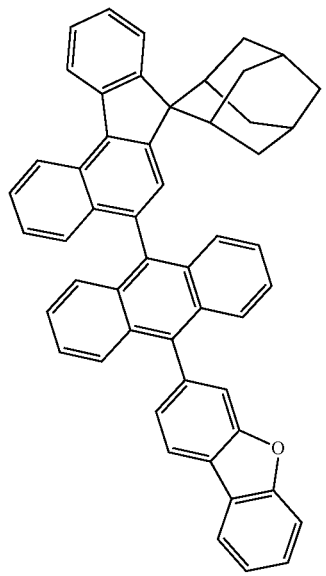
235
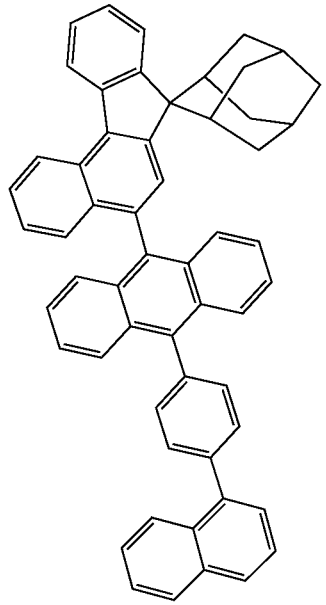

236
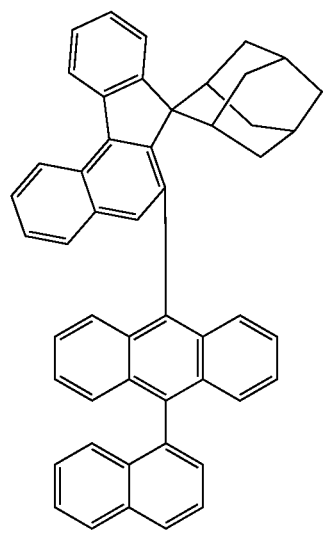
237
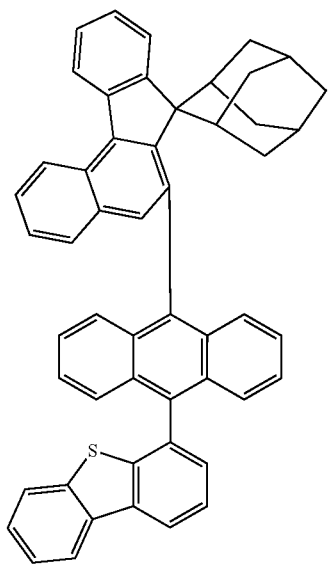
238
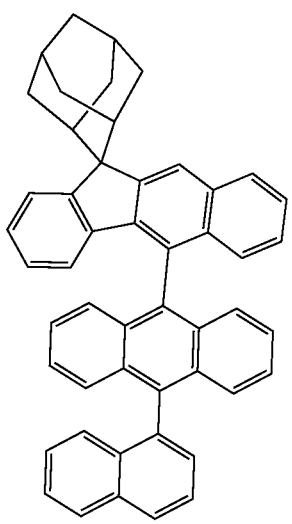
239
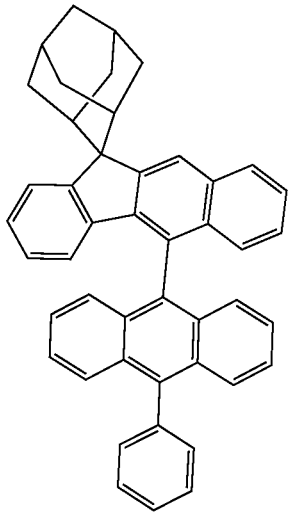
240

361
-continued
241
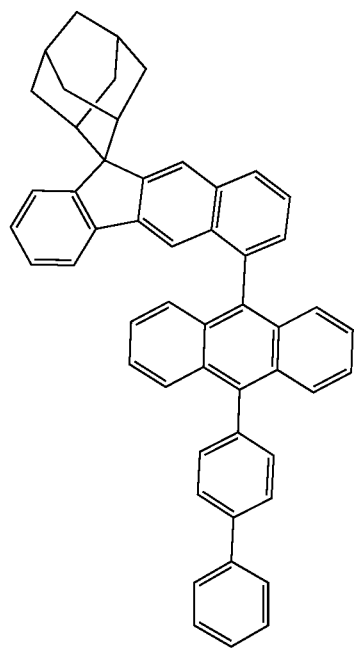
242
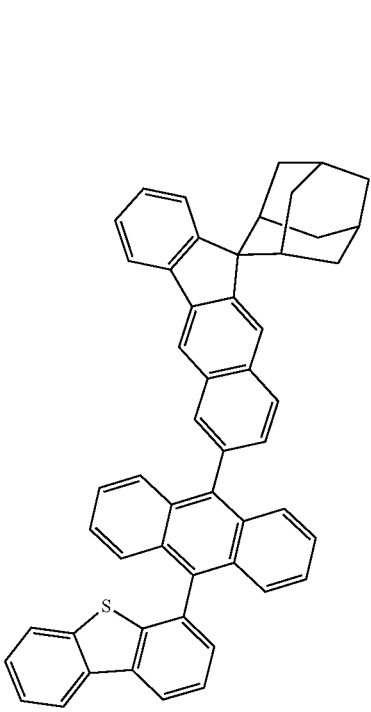
362
-continued
243
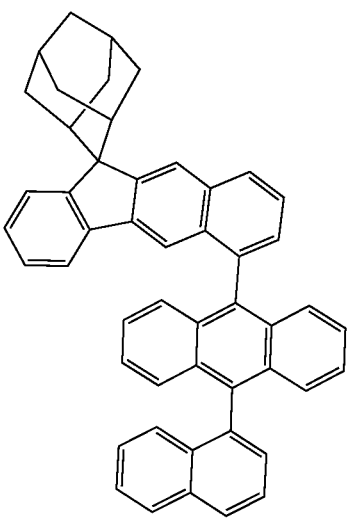
244
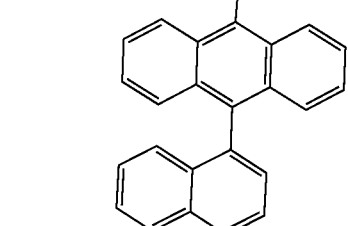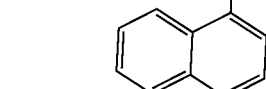

363
-continued
245
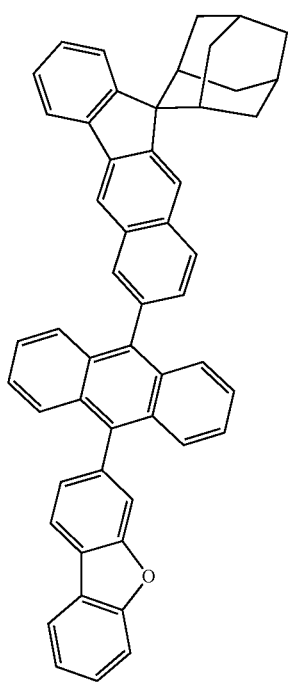
246
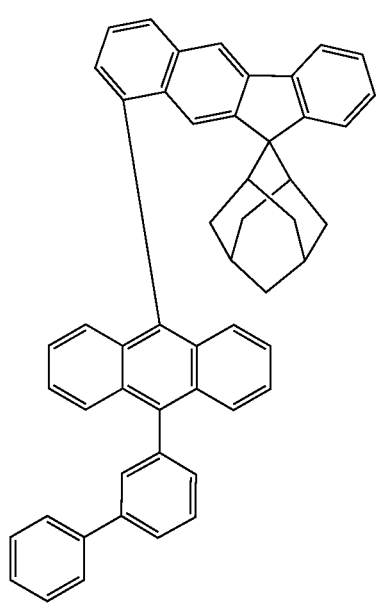
364
-continued
247
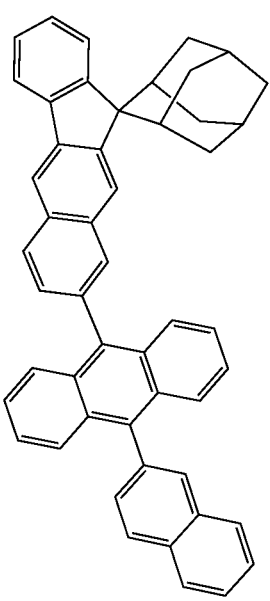
248
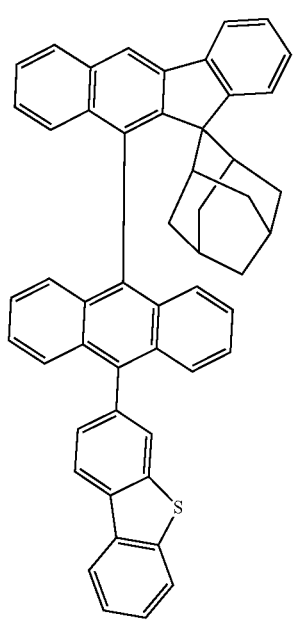

365
-continued
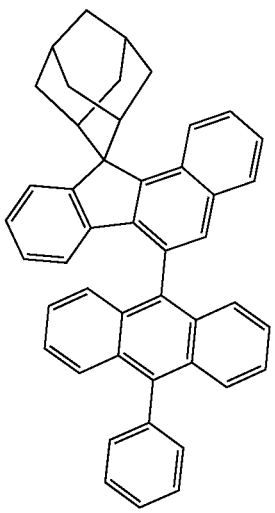
249
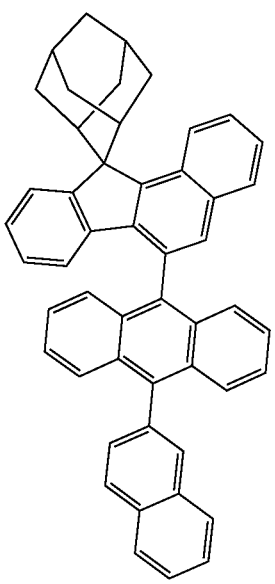
250
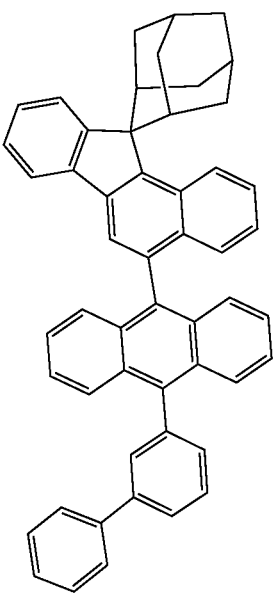
251
366
-continued
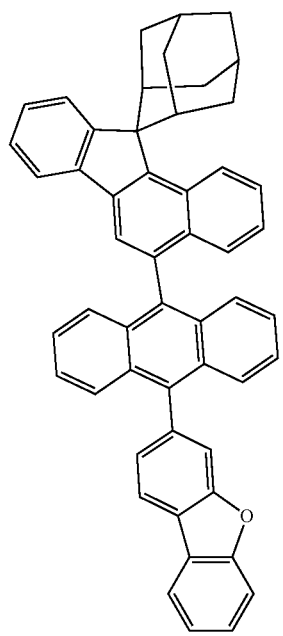
252
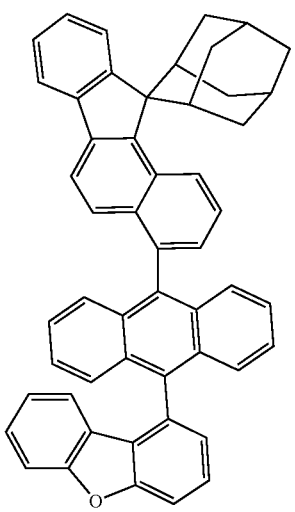
253

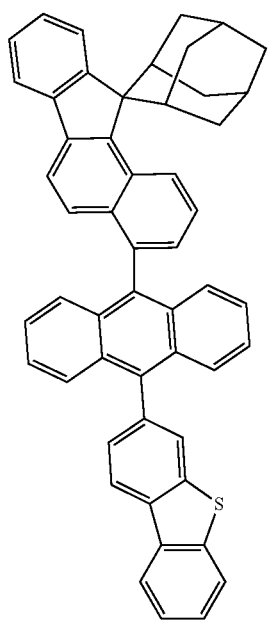
254
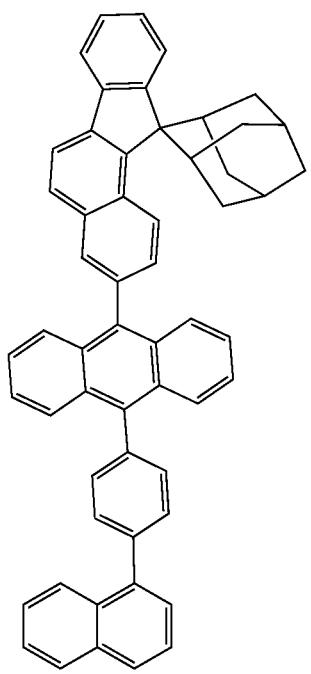
256
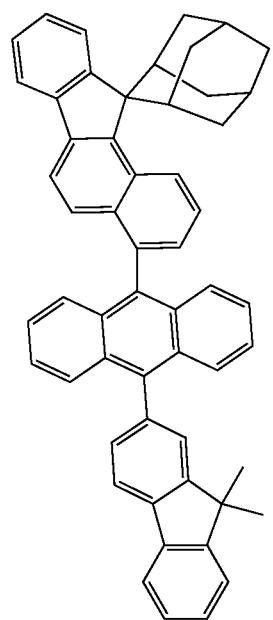
255
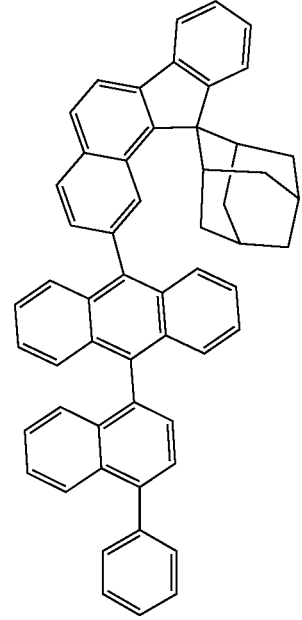
258

369
-continued
259
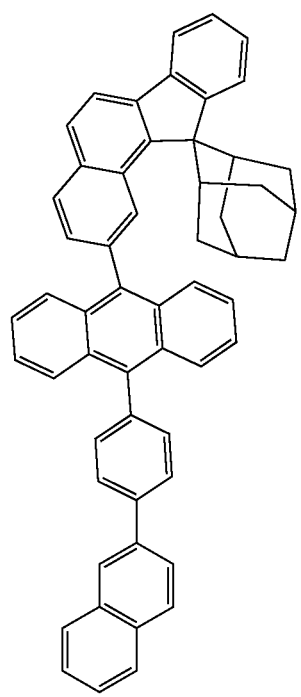
260
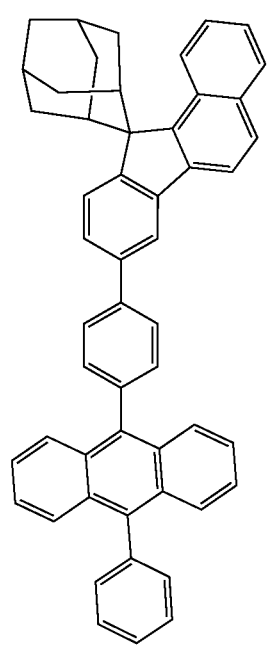
370
-continued
261
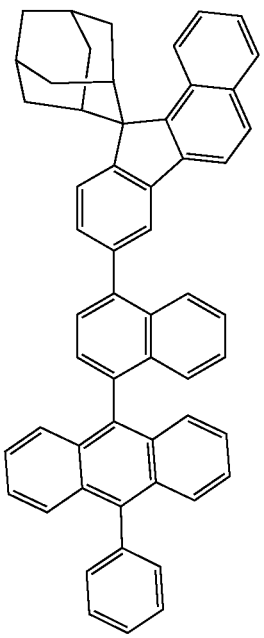
262
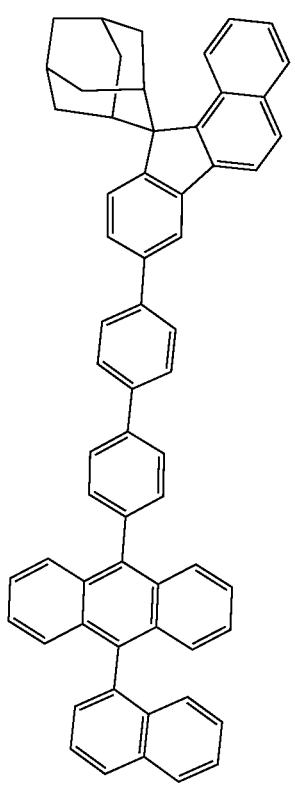

371
-continued
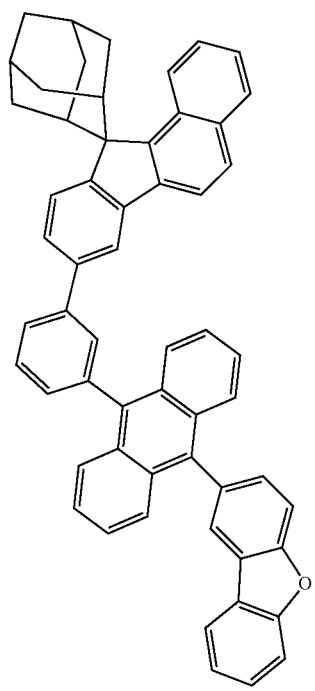
263
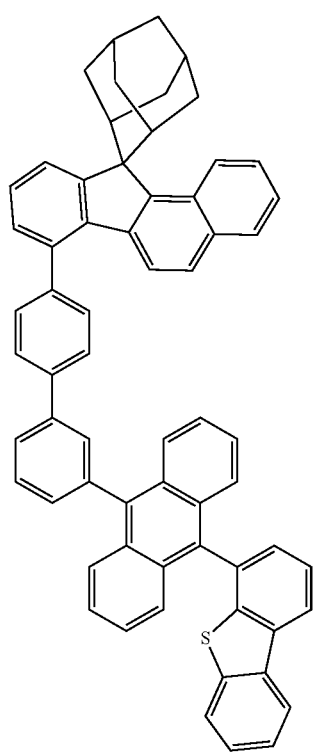
372
-continued
265
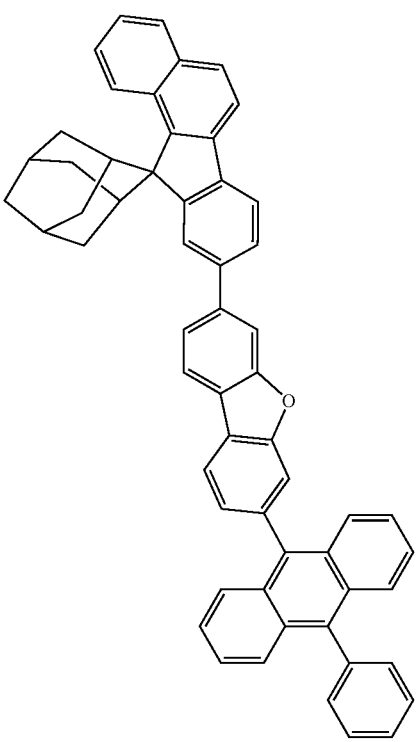
267

373
-continued
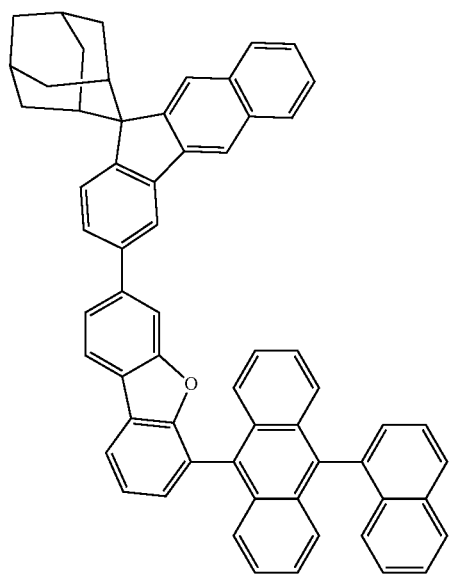
268
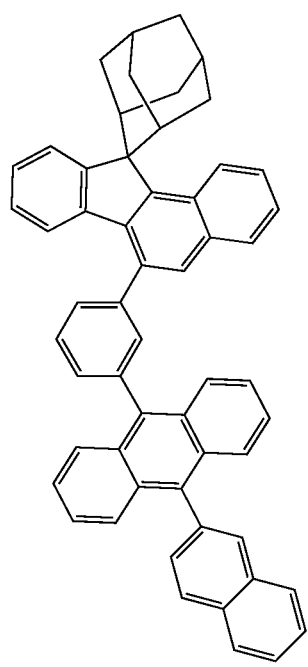
269
374
-continued
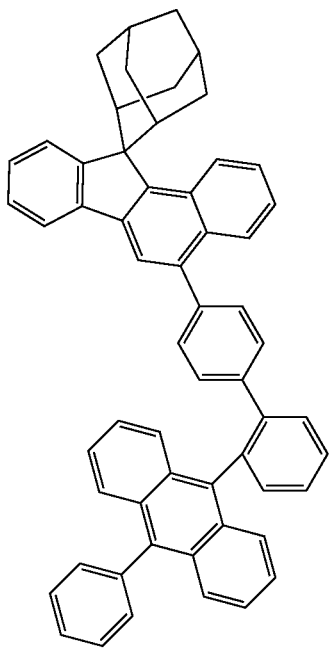
270
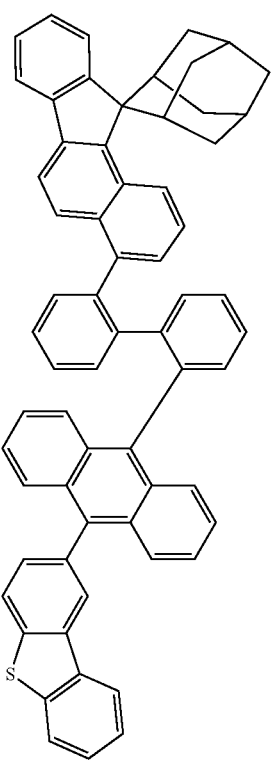
271

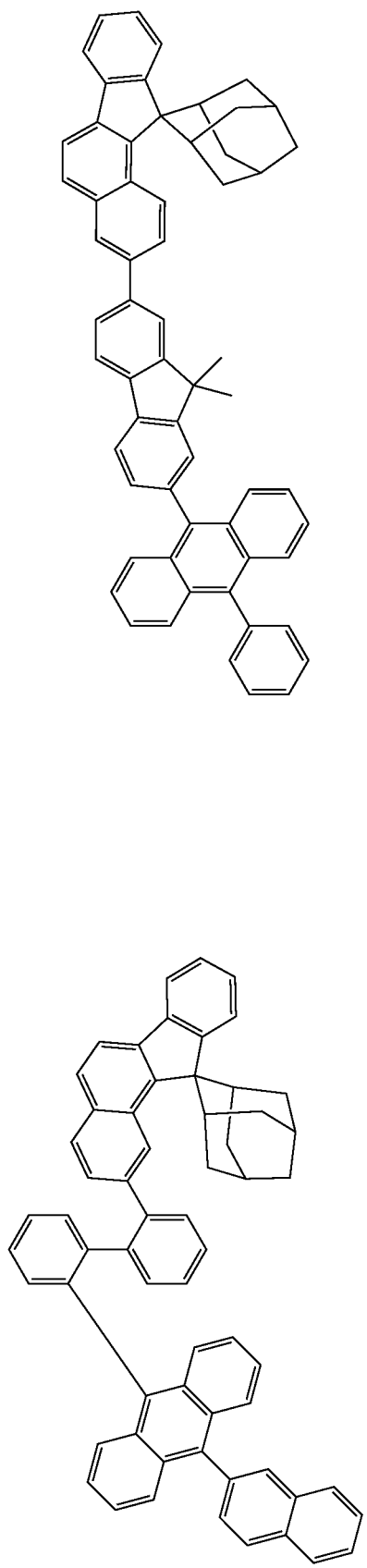
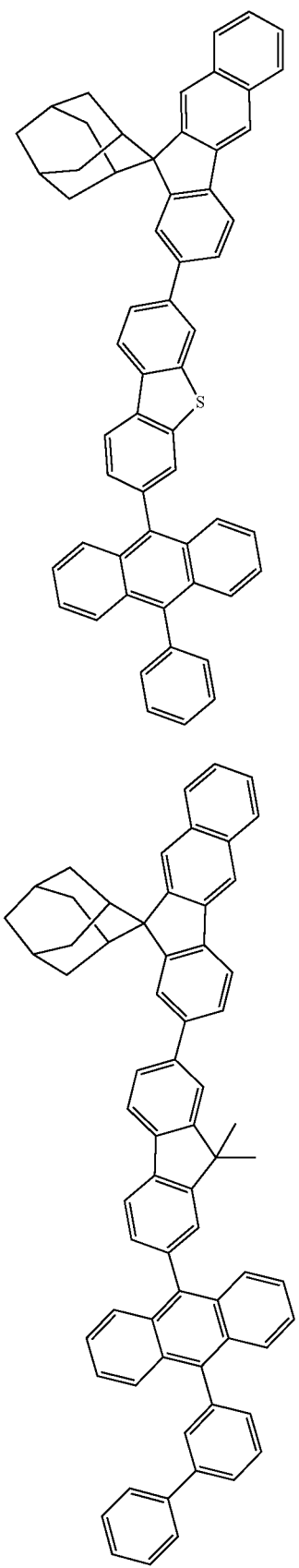

276
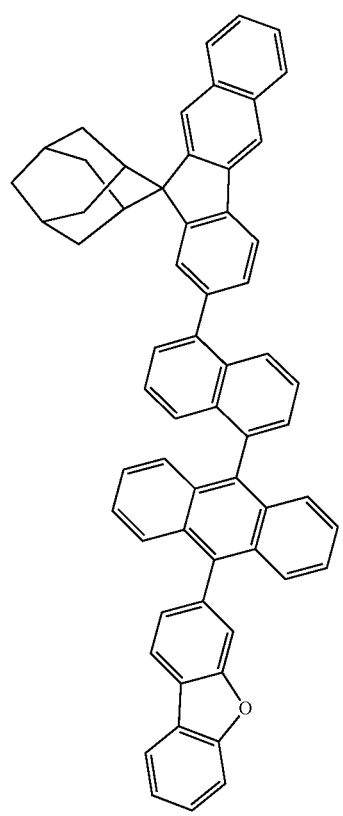
277
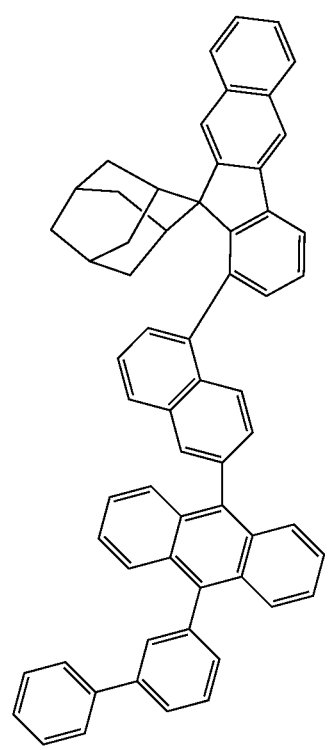
278
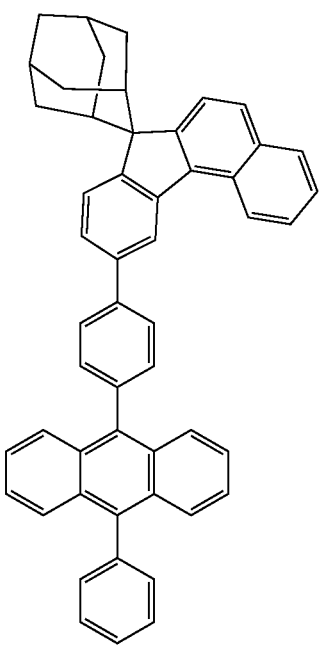
279
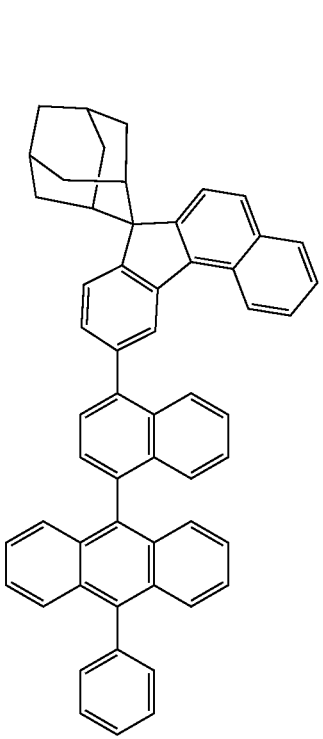

280
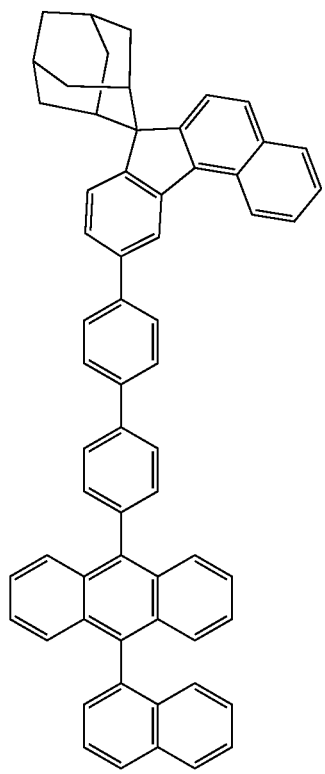
281
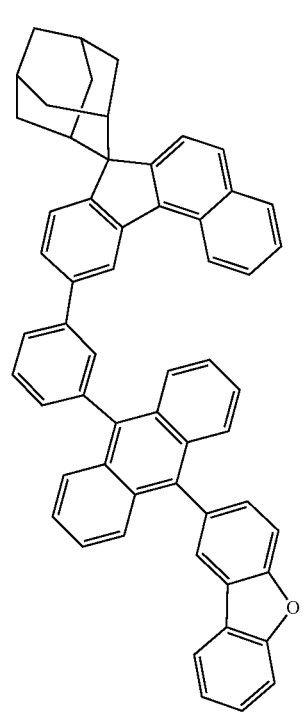
282
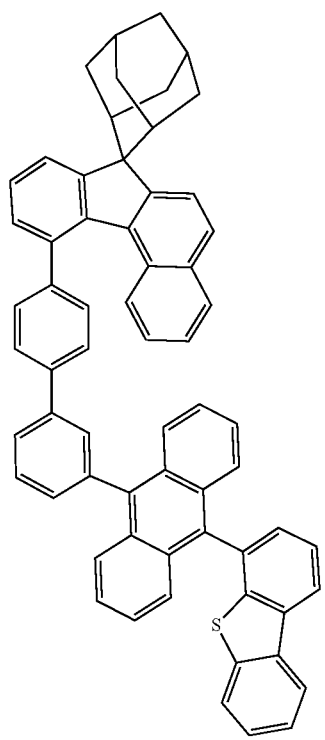
283
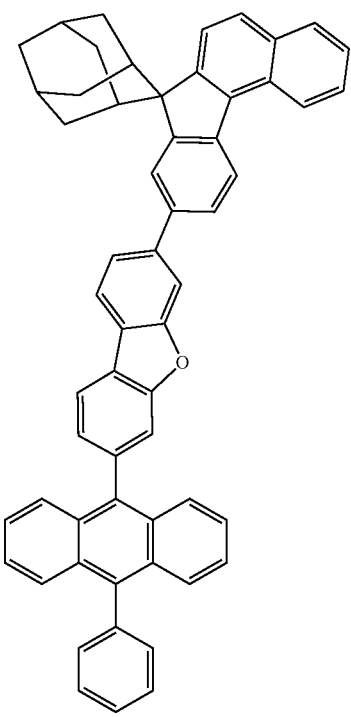

285
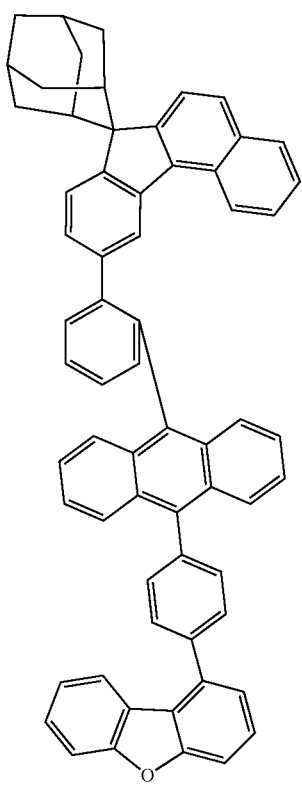
286
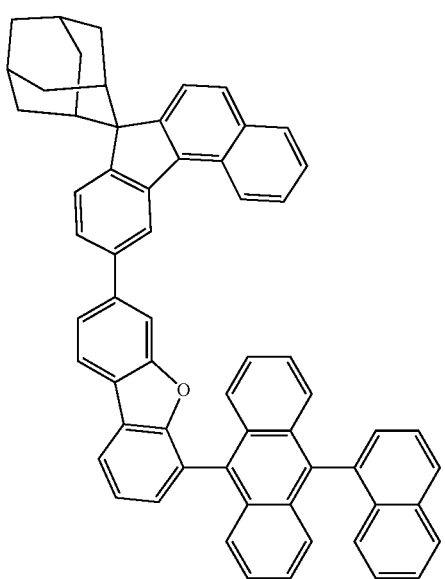
287
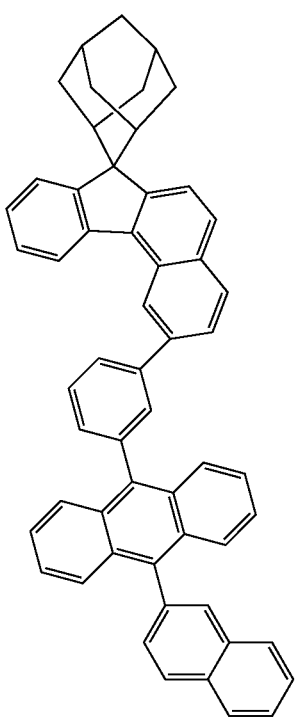
288

289
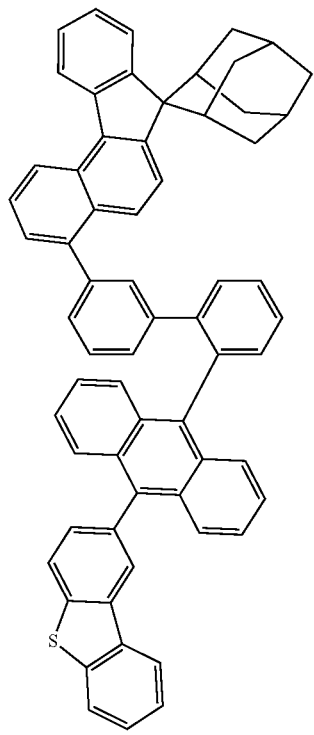
291
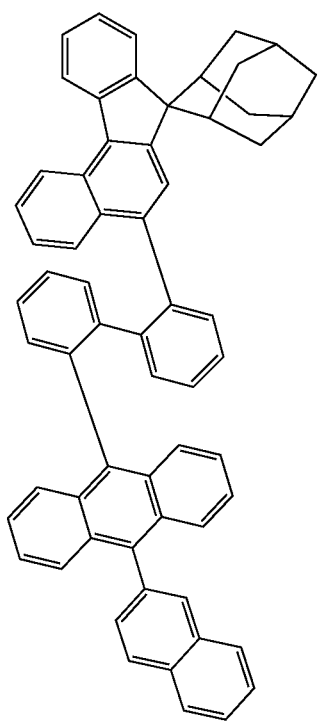
290
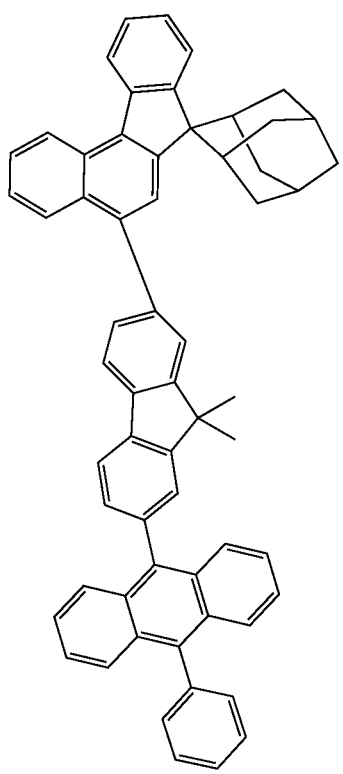
292
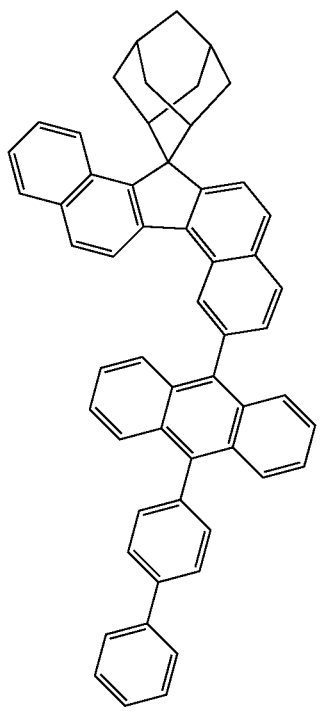

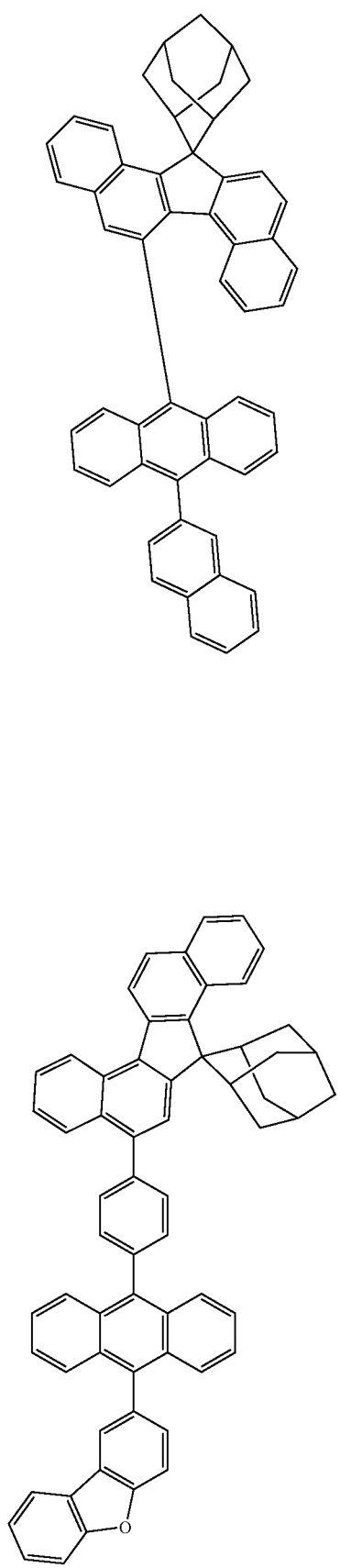
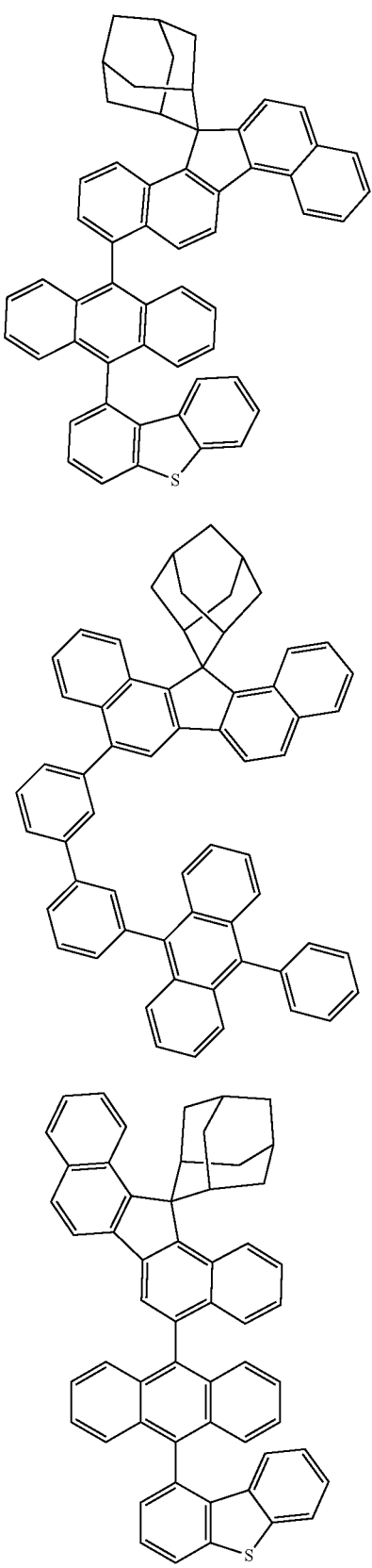

298
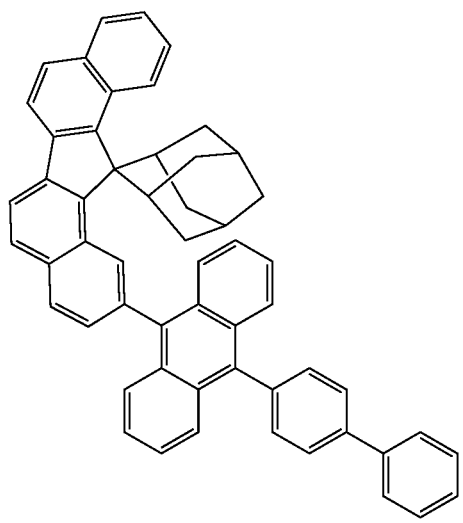
299
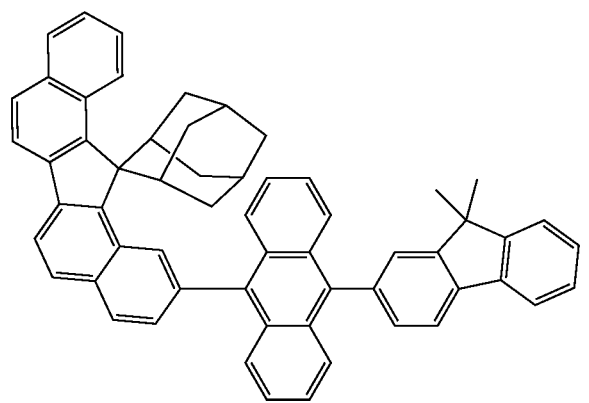
300
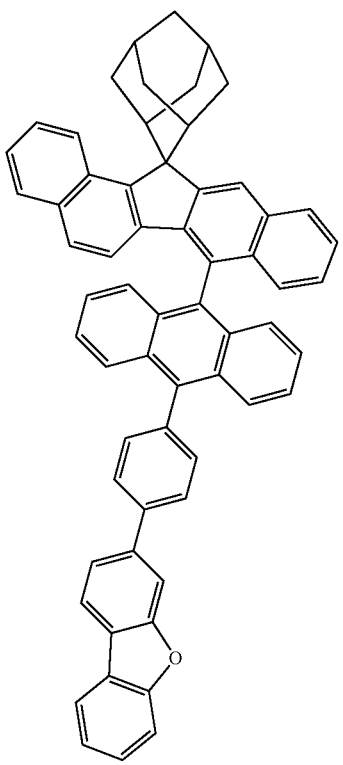
301

389
-continued
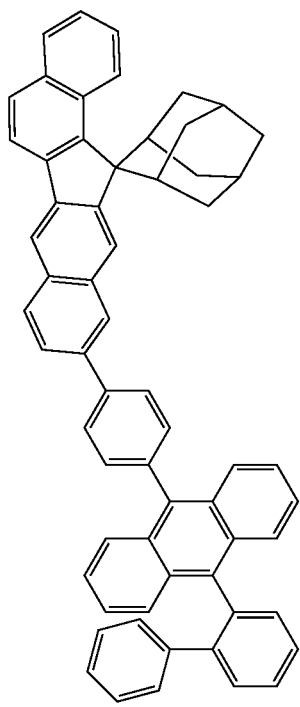
302
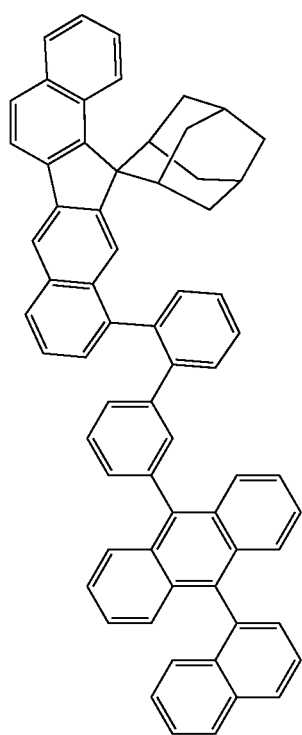
303
390
-continued
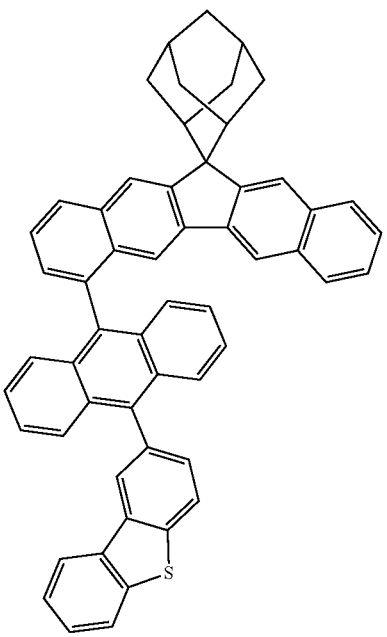
304
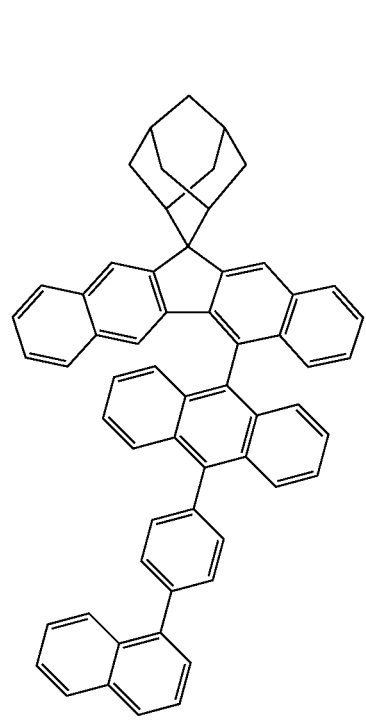
305

391
-continued
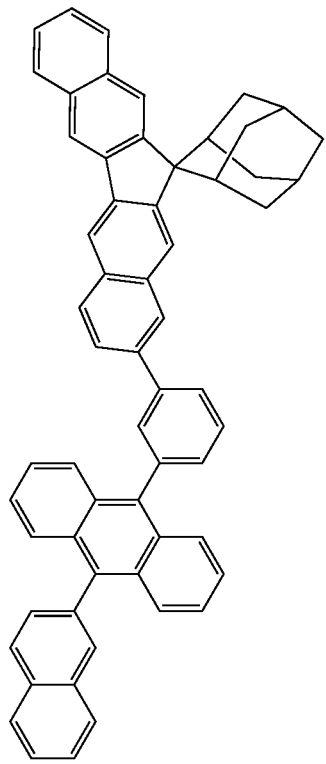
306
392
-continued
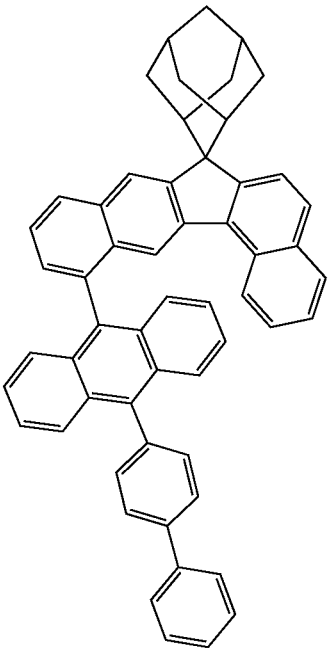
308
307
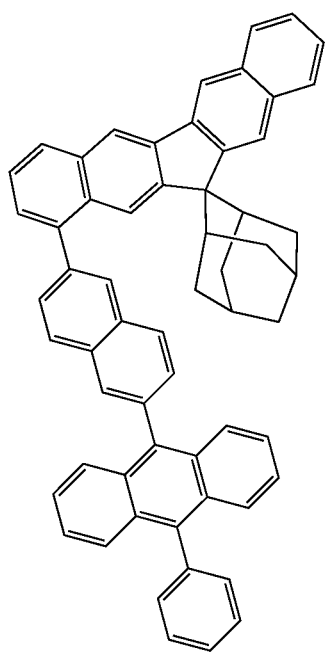
309
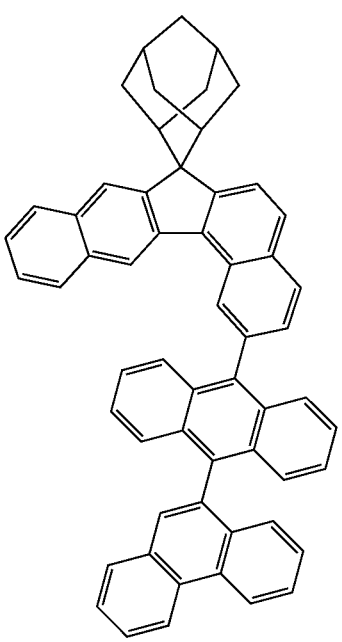

393
-continued
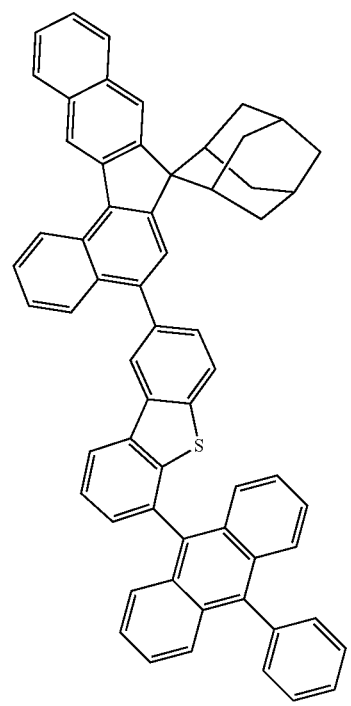
311
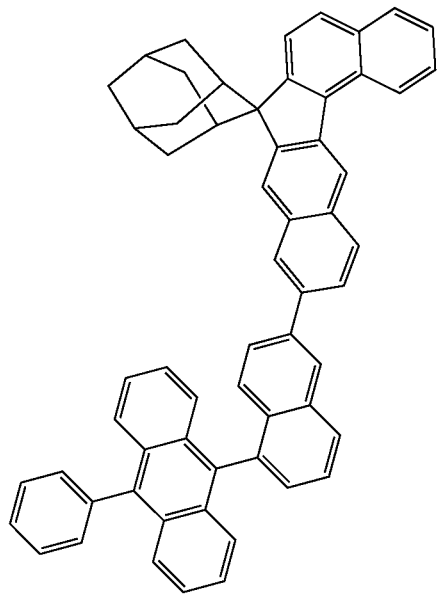
394
-continued
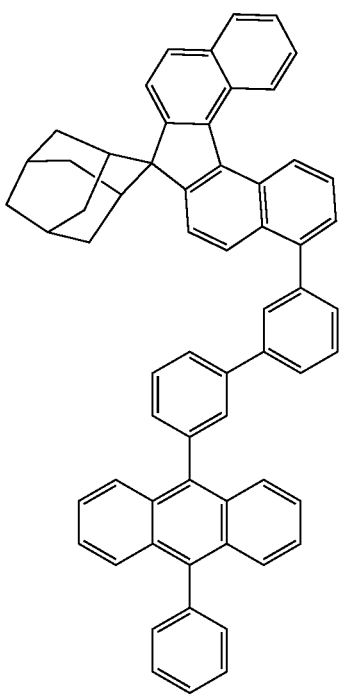
312
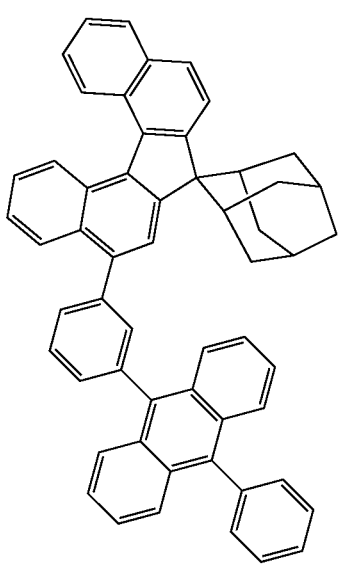
313